US010052364B2

(12) United States Patent
Karsenty et al.

(10) Patent No.: US 10,052,364 B2
(45) Date of Patent: Aug. 21, 2018

(54) OSTEOCALCIN AS A TREATMENT FOR COGNITIVE DISORDERS

(71) Applicant: THE TRUSTEES OF COLUMBIA UNIVERSITY IN THE CITY OF NEW YORK, New York, NY (US)

(72) Inventors: Gerard Karsenty, New York, NY (US); Franck Oury, New York, NY (US)

(73) Assignee: The Trustees of Columbia University in the City of New York, New York, NY (US)

(*) Notice: Subject to any disclaimer, the term of this patent is extended or adjusted under 35 U.S.C. 154(b) by 0 days.

(21) Appl. No.: 14/777,285

(22) PCT Filed: Mar. 14, 2014

(86) PCT No.: PCT/US2014/027404
§ 371 (c)(1),
(2) Date: Sep. 15, 2015

(87) PCT Pub. No.: WO2014/152497
PCT Pub. Date: Sep. 25, 2014

(65) Prior Publication Data

US 2016/0045571 A1 Feb. 18, 2016

Related U.S. Application Data

(60) Provisional application No. 61/794,006, filed on Mar. 15, 2013.

(51) Int. Cl.
*A61K 38/22* (2006.01)
*G01N 33/68* (2006.01)

(52) U.S. Cl.
CPC ......... *A61K 38/22* (2013.01); *G01N 33/6896* (2013.01); *G01N 2333/47* (2013.01); *G01N 2800/2814* (2013.01)

(58) Field of Classification Search
None
See application file for complete search history.

(56) References Cited

U.S. PATENT DOCUMENTS 4,059,589 A 11/1977 Scherberich et al.
4,250,088 A 2/1981 Yang
4,405,712 A 9/1983 Vande Woude et al.
4,426,330 A 1/1984 Sears
4,448,764 A 5/1984 Smith et al.
4,469,863 A 9/1984 Ts'o et al.
4,489,159 A 12/1984 Markussen
4,522,811 A 6/1985 Eppstein et al.
4,534,894 A 8/1985 Cerami et al.
4,534,899 A 8/1985 Sears
4,631,211 A 12/1986 Houghten
4,650,764 A 3/1987 Temin et al.
4,801,742 A 1/1989 Quirk et al.
4,946,778 A 8/1990 Ladner et al.
5,013,556 A 5/1991 Woodle et al.
5,034,506 A 7/1991 Summerton et al.
5,108,921 A 4/1992 Low et al.
5,213,804 A 5/1993 Martin et al.
5,216,141 A 6/1993 Benner
5,227,170 A 7/1993 Sullivan
5,235,033 A 8/1993 Summerton et al.
5,258,545 A 11/1993 Kurihara et al.
5,264,221 A 11/1993 Tagawa et al.
5,354,844 A 10/1994 Beug et al.
5,356,633 A 10/1994 Woodle et al.
5,395,619 A 3/1995 Zalipsky et al.
5,416,016 A 5/1995 Low et al.
5,417,978 A 5/1995 Tari et al.
5,386,023 A 7/1995 Sanghvi et al.
5,459,127 A 10/1995 Feigner et al.
5,462,854 A 10/1995 Coassin et al.
5,466,048 A 11/1995 Fowler et al.
5,469,854 A 11/1995 Unger et al.
5,512,295 A 4/1996 Kornberg et al.
5,521,291 A 5/1996 Curiel et al.
5,527,528 A 6/1996 Allen et al.
5,534,259 A 6/1996 Zalipsky et al.

(Continued)

FOREIGN PATENT DOCUMENTS

EP 0232262 A1 8/1987
EP 0464533 A1 6/1991

(Continued)

OTHER PUBLICATIONS

Umegaki, H. "Neurodegeneration in Diabetes Mellitus" Adv. Exp. Med. Biol (2012), vol. 724,pp. 258-265.
Ducy, Patricia et al., "Increased Bone Formation in Osteocalcin-Deficient Mice," Nature, vol. 382, pgs. 448-452, Aug. 1, 1996.
Ducy, Patricia et al., "Leptin Inhibits Bone Formation through a Hypothalamic Relay: A Central Control of Bone Mass," Cell, vol. 100, pp. 197-207, Jan. 21, 2000.
Poser, James W. et al., "Isolation and Sequence of the Vitamin K-Dependent Protein from human Bone," The Journal of Biological Chemistry, vol. 255, No. 18, pp. 8685-8691, Sep. 25, 1980.
Poser, James W: et al., "A Method for Decarboxylation of y-Carboxyglutamic Acid in Proteins," The Journal of Biological Chemistry, vol. 254, No. 2, pp. 431-436, Jan. 25, 1979.
Pogoda, Pia et al., "Leptin inhibits Bone Formation Not Only in Rodents, but Also in Sheep," Journal of Bone and Mineral Research, vol. 21, No. 10, pp. 1591-1598, Jul. 17, 2006.

(Continued)

*Primary Examiner* — Olga N Chernyshev
(74) *Attorney, Agent, or Firm* — Hunton Andrews Kurth LLP

(57) ABSTRACT

Methods and compositions for treating or preventing cognitive disorders in mammals, preferably humans, are provided. The methods generally involve modulation of the OST-PTP signaling pathway or the PTP-1B signaling pathway involving gamma-carboxylase and osteocalcin, e.g., by administration of undercarboxylated/uncarboxylated osteocalcin. Disorders amenable to treatment by the methods include, but are not limited to, cognitive loss due to neurodegeneration associated with aging, anxiety, depression, memory loss, learning difficulties, and cognitive disorders associated with food deprivation during pregnancy.

11 Claims, 42 Drawing Sheets

(56) References Cited

U.S. PATENT DOCUMENTS

| | | | |
|---|---|---|---|
| 5,543,152 | A | 8/1996 | Webb et al. |
| 5,543,158 | A | 8/1996 | Gref et al. |
| 5,547,932 | A | 8/1996 | Curiel et al. |
| 5,556,948 | A | 9/1996 | Tagawa et al. |
| 5,580,575 | A | 12/1996 | Unger et al. |
| 5,583,020 | A | 12/1996 | Sullivan |
| 5,591,721 | A | 1/1997 | Agrawal et al. |
| 5,595,756 | A | 1/1997 | Bally et al. |
| 5,602,240 | A | 2/1997 | De Mesmaeker et al. |
| 5,637,684 | A | 6/1997 | Cook et al. |
| 5,681,707 | A | 10/1997 | Hosoda et al. |
| 5,733,761 | A | 3/1998 | Treco et al. |
| 5,830,682 | A | 11/1998 | Moore |
| 6,270,985 | B1 | 8/2001 | Gottschalk et al. |
| 6,303,326 | B1 | 10/2001 | Felton et al. |
| 6,350,902 | B2 | 2/2002 | Hill et al. |
| 6,452,035 | B2 | 9/2002 | Dupont et al. |
| 6,511,958 | B1 | 1/2003 | Atkinson et al. |
| 6,514,514 | B1 | 2/2003 | Atkinson et al. |
| 6,560,471 | B1 | 5/2003 | Heller et al. |
| 6,828,151 | B2 | 12/2004 | Borchers et al. |
| 6,899,871 | B2 | 5/2005 | Kasahara et al. |
| 2003/0156302 | A1 | 8/2003 | Chaput et al. |
| 2003/0199615 | A1 | 10/2003 | Chaput et al. |
| 2004/0023390 | A1 | 2/2004 | Davidson et al. |
| 2004/0157864 | A1 | 8/2004 | Wu et al. |
| 2006/0052327 | A1 | 3/2006 | Liu et al. |
| 2006/0063699 | A1 | 3/2006 | Larsen |
| 2006/0257492 | A1 | 11/2006 | Wen et al. |
| 2006/0292670 | A1 | 12/2006 | Ting et al. |
| 2007/0059731 | A1 | 3/2007 | Kerppola |
| 2007/0099831 | A1 | 5/2007 | Morley |
| 2010/0105867 | A1 | 4/2010 | Ohnogi et al. |
| 2010/0190697 | A1 | 7/2010 | Karsenty et al. |
| 2013/0034572 | A1 | 2/2013 | Stanimirovic et al. |
| 2013/0034590 | A1 | 2/2013 | Uchegbu et al. |

FOREIGN PATENT DOCUMENTS

| | | | |
|---|---|---|---|
| WO | 87/01130 | A1 | 2/1987 |
| WO | 94/12650 | A2 | 6/1994 |
| WO | 95/31560 | A1 | 11/1995 |
| WO | 96/29411 | A1 | 9/1996 |
| WO | 99/15650 | A1 | 4/1999 |
| WO | 00/49162 | A2 | 8/2000 |
| WO | 2010033218 | A1 | 3/2010 |

OTHER PUBLICATIONS

Elefteriou, F. et al., "Serum Leptin Level is a Regulator of Bone Mass," PNAS, vol. 101, No. 9, pp. 3258-3263, Mar. 2, 2004.

Takeda, Shu et al., "Leptin Regulates Bone Fomratoin Via the Sympathetic Nervous System," Cell, vol. 111, pp. 305-317, Nov. 1, 2002.

Yadav, Vijay K. et al., "A Serotonin-Dependent Mechanism Explains the Leptin Regulation of Bone Mass, Appetite, and Energy Expenditure," Cell, vol. 138, pp. 976-989, Sep. 4, 2009.

Oury, Franck et al., "CREB Mediates Brain Serotonin Regulation of Bone Mass Through its Expression in Ventromedial hypothalamic Neurons," Genes & Development, vol. 24, pp. 2330-2342, 2010.

Lee, Na Kyung et al., "Endocrine Regulation of Energy Metabolism by the Skeleton," Cell, vol. 130, pp. 456-469, Aug. 10, 2007.

Lee, Kenneth et al., "Identification of a Developmentally Regulated Protein Tyrosine Phosphatase in Embryonic Stem Cells that is a Marker of Pluripotential Epiblast and Early Mesoderm," Mechanism of Development, vol. 59, pp. 153-164, 1996.

Lee, Allison Jane et al., "Measurement of Osteocalcin," Ann Clin Biochem, vol. 37, pp. 432-446, 2000.

Oury, Franck et al., "Endocrine Regulation of Male Fertility by the Skeleton," Cell, vol. 144, pp. 796-809, Mar. 4, 2011.

Charbonneau, Harry et al., "Human Placenta Protein-Tyrosine-Phosphatase: Amino Acid Sequence and Relationship to a Family of Receptor-Like Proteins," Proc. Natl. Acad. Sci., vol. 86, pp. 5252-5256, Jul. 1989.

Pi, Min et al., "GPRC6A null Mice Exhibit Osteopenia, Feminization and Metabolic Syndrome," PLoS One, vol. 3, No. 12, pp. 1-10, Dec. 2008.

Pi, Min et al., "Identification of a Novel Extracellular Cation-sensing G-protein-coupled Receptor," The Journal of Biological Chemistry, vol. 280, No. 48, pp. 40201-40209, Dec. 2, 2005.

Pi, Min et al., "GPRC6A Mediates the Non-Genomic Effects of Steroids," The Journal of Biological Chemistry, vol. 285, No. 51, pp. 39953-39964, Dec. 17, 2010.

Simon, Reyna J. et al., "Peptoids: A Modular Approach to Drug Discovery," Proc. Natl. Acad. Sci., vol. 89, pp. 9367-9371, Oct. 1992.

Houghten, Richard A., "General Method for the Rapid Solid-Phase Synthesis of Large numbers of Peptides: Specificity of Antigen-Antibody Interaction at the Level of Individual Amino Acids," Proc. Natl. Acad. Sci., vol. 82, pp. 5131-5135, Aug. 1985.

Karlin, Samuel et al., "Applications and Statistics for Multiple High-Scoring Segments in Molecular Sequences," Proc. Natl. Acad. Sci., vol. 90, pp. 5873-5877, Jun. 1993.

Johanson, Kyung et al., "Binding Interactions of human Interleukin 5 with Its Receptor . . .," The Journal of Biological Chemistry, vol. 270, No. 16, pp. 9456-9471, 1995.

Anderson, Kevin P, et al., "Inhibition of human Cytomegalovius Immediate-Early Gene Expression by an Antisense Oligonucleotide Complementary to Immediate-Early RNA," Antimicrobial Agents and Chemotherapy, vol. 40, No. 9, pp. 2004-2011, Sep. 1996.

Lu, Wei et al., "Cationic Albumin-Conjugated Pegylated Nanoparticles Allow Gene Delivery into Brain Tumors via Intravenous Administration," Cancer Res., vol. 66, No. 24, pp. 11878-11887, Dec. 15, 2006.

Robbins, Paul D., "Gene Therapy Protocols," Humana Press Inc. pp. 1-12, 1997.

Flotte, Terence R. et al., "Stable in vivo Expression of the Cystic Fibrosis Transmembrane Conductance Regulator with an Adeno-Associated Virus Vector," Proc. Natl, Acad. Sci., vol. 90, pp. 10613-10617, Nov. 1993.

Goodman, Stacey et al., "Recombinant Adeno-Associated Virus-Mediated Gene Transfer Into Hematopoietic Progenitor Cells," Blood, vol. 84, No. 5, pp. 1492-1500, Sep. 1, 1994.

Walsh, Christopher E. et al., "Regulated high Level Expression of a human y-Globin Gene Introduced into Erythroid Cells by an Adeno-Associated Virus Vector," Proc. Natl. Acad. Sci., vol. 89, pp. 7257-7261, Aug. 1992.

Lebkowski, Jane S. et al., "Adeno-Associated Virus: A Vector System for Efficient Introduction and Integration of DNA into a Variety of Mammalian Cell Types," Molecular and Cellular Biology, vol. 8, No. 10, pp. 3988-3996, Oct. 1988.

Samulski, Richard Jude et al., "Helper-Free Stocks of Recombinant Adeno-Associated Viruses: Normal Integration Does Not Require Viral Gene Expression," Journal of Virology, vol. 63, No. 9, pp. 3822-3828, Sep. 1989.

Zhou, Shang Zhen et al., "Adeno-Associated Virus 2-Mediated high Efficiency Gene Transfer into Immature and Mature Subsets of Hematopoietic Progenitor Cells in human Umbilical Cord Blood," Journal Exp. Med., vol. 179, pp. 1867-1875, Jun. 1994.

Hermonat, Paul L. et al., "Use of Adeno-Associated Virus as a Mammalian DNA Cloning Vector: Transduction of Neoycin Resistance into Mammalian Tissue Culture Cells," Proc. Natl. Acad. Sci., vol. 81, pp. 6466-6470, Oct. 1984.

Tratschin, Jon-Duri et al., "A Human Parvovirus, Adeno-Associated Virus, as a Eucaryotic Vector: transient Expression and Encapsidation of the Procaryotic Gene for Chloramphenicol Acetytransferase," Molecular and Cellular Biology, vol. 4, No. 10, pp. 2072-2081, Oct. 1984.

McLaughlin, Susan K. et al., "Adeno-Associated Virus General Transduction Vectors: Analysis of Proviral Structures," Journal of Virology, vol. 62, No. 6, pp. 1963-1973, Jun. 1988.

Wu, Min et al., "Packaging Cell Lines for Simian Foamy Virus Type 1 Vectors," Journal of Virology, vol. 73, No. 5, pp. 4498-4501, May 1999.

Poeschla, Eric et al., "Development of HIV Vectors for Anti-HIV Gene Therapy," Proc. Natl. Acad. Sci., vol. 93, pp. 11395-11399, Oct. 1996.

(56) References Cited

OTHER PUBLICATIONS

Srinivaskumar, Narasimhachar et al., "The Effect of Viral Regulatory Protein Expression on Gene Delivery by Human Immunodeficiency Virus Type 1 Vectors Produced in Stable Packaging Cell Lines," vol. 71, No. 8, Journal of Virology, pp. 5841-5848, Aug. 1997.

Kim, V. Narry et al., "Minimal Requirement for a Lentivirus Vector Based on Human Immunodeficiency Virus Type 1," Journal of Virology, vol. 72, No. 1, pp. 811-816, Jan. 1998.

Johnston, Julie C. et al., "Minimum Requirements of Efficient Transduction of Dividing and Nondividing Cells by Feline Immunodeficiency Virus Vectors," Journal of Virology, vol. 73, No. 6, pp. 4991-5000, Jun. 1999.

Johnston, James et al., "Productive Infection of human Peripheral Blood Mononuclear Cells by Feline Immunodeiciency Virus: Implications for Vector Development," Journal of Virology, vol. 73, No. 3, pp. 2491-2498, Mar. 1999.

Christiansen, B. et al., "Pharmacological Characterization of Mouse GPRC6A, an L-<-Amino-Acid Receptor modulated by Divalent Cations," British Journal of Pharmacology, vol. 150, pp. 798-807, 2007.

Sprinzl, Mathias et al., "Enzymatic Incorporation of ATP and CTP Analogues into the 3' End of tRNA," Eur. J. Biochem., vol. 81, pp. 579-589, 1977.

Letsinger, R.L. et al., "Effects of Pendant groups at Phosphorus on Binding Properties of d-ApA Analogues," Nucleic Acids Research, vol. 14, No. 8, pp. 3487-3499, 1986.

Sawai, Hiroaki, "Synthesis and Properties of Oligoadenylic Acids Containing 2'-5' Phosphoramide Linkage," Chemistry Letters, pp. 805-808, 1984.

Mag, Matthias et al., "Synthesis and Selective Cleavage of an Oligodeoxynucleotide containing a Bridged Internucleotide 5'-phiphorothioate Linkage,"Nucleic Acids Research, vol. 19, No. 7, pp. 1437-1441, Mar. 8, 1991.

Dempcy, Robert O. et al., "Synthesis of a Thymidyl Pentamer of Deoxyribonucleic Guanidine and Binding Studies with DNA Homopolynucleotides," Proc. Natl. Acad. Sci., vol. 92, pp. 6097-6101, Jun. 1995.

Bach, Helene et al., "Neuronal Tryptophan Hydroxylase Expression in BALB/cJ and C57B1/6J Mice," Journal of Neurochemistry, vol. 118, pp. 1067-1074, 2011.

Mayorga, Arthur J. et al., "Antidepressant-Like Behavioral Effects in 5-Hydroxytryptamine 1A and 5-Hydroxytryptamine 1B Receptor Mutant Mice," The Journal of Pharmacology and Experimental Therapeutics, vol. 298, No. 3, pp. 1101-1107, vol. 298, No. 3, May 26, 2001.

David, Denis J. et al., "Neurogenesis-Dependent and -Independent Effects of Fluoxetine in an Animal Model of Anxiety/Depression," Neuron, vol. 62, pp. 479-493, May 28, 2009.

D'Hooge, Rudi et al., "Neurocognitive and Psychotiform Behavioral Alterations and Enhanced Hippocampal Long-Term Potentiation in Transgenic Mice Displaying Neuropathological Features of Human~-Mannosidosis," The Journal of Neuroscience, vol. 25, No. 28, pp. 6539-6539, Jul. 13, 2005.

International Search Report and Written Opinion dated Oct. 6, 2014 for International Application No. PCT/US14/27404.

Hauschka, Peter V. et al., "Osteocalcin and Matrix Gla Protein: Vitamin K-Dependent Proteins in Bone," Physiological Reviews, vol. 69, No. 3, pp. 990-1047, Jul. 1989.

Price, Paul A. "Gla-Containing Proteins of Bone," Connective Tissue Research, vol. 21, pp. 51-60, 1989.

Ducy, Patrcia et al., "The Osteoblast: A Sophisticated Fibroblast under Central Surveillance," Science, vol. 289m pp. 1501-1504, Sep. 1, 2000.

Harada, Shun-Ichi et al., "Control of Osteoblast Function and Regulation of Bone Mass," Nature, vol. 423, pp. 349-355, May 15, 2003.

Garnero, Patrick et al., "Characterization of Immunoreactive Forms of Human Osteocalcin Generated in Vivo in in Vitro," Journal of Bone and Mineral Research, vol. 9, No. 2, pp. 255-264, 1994.

Taylor, Arch K. et al., "Multiple Osteocalcin Fragments in Human Urine and Serum as Detected by a Midmolecule Osteocalcin Radioimmunoassay*," Journal of Clinical Endocrinology and Metabolism, vol. 70, No. 2, pp. 467-472, 1990.

Bergh Van Den, Bea R.H. et al., "Antenatal Maternal Anxiety and Stress and the Neurobehavioural Development of the fetus and child: Links and Possible Mechanics. A Review," Neuroscience and Biobehavioral Reviews, vol. 29, pp. 237-258, 2005.

Goldstein, Barry J. "Regulation of Insulin Receptor Signaling by Protein-Tyrosine Dephosphorylation," Receptor, vol. 3, pp. 1-15, 1993.

Wellendorph, Petrine et al., "Molecular Cloning, Expression, and Sequence Analysis of GPRC6A, a Novel Family C G-protein-coupled Receptor," Gene. vol. 335, pgs. 37-46, 2004.

Osorio, Joana, "Excessive Maternal Weight Increases Risk of Infant Overgrowth," Nature Reviews Endocrinology, vol. 8, p. 624, 2012.

Lawlor, Debbie A. et al., "Maternal Adiposity-A Determinant of Perinatal and Offspring Outcomes," Nat. Rev. Endocrinla, vol. 8, pp. 679-288, Sep. 25, 2012.

Challis, John R.G. "Stress Responses in Children After Maternal Glucocorticoids," Nat. Rev. Endocrinol, vol. 8, pp. 629-630, Oct. 2, 2012.

Wadhwa, Pathik D. et al., "The Neurobiology of Stress in Human Pregnancy: Implications for Prematurity and Development of the Fetal Central Nervous System," Progress in Brain Research, vol. 133, pp. 131-142, 2001.

Weinstock, Marta et al., "The Long-Term Behavioural Consequences of Prenatal Stress," Neuroscience and Biobehavioral Reviews, vol. 32, pp. 1073-1086, 2008.

Adelman, John P. et al., "In Vitro Deletional Mutagenesis for Bacterial Production of the 20,000-Dalton Form of Human Pituitry Growth Hormone," DNA, vol. 2, No. 3, pp. 183-193, 1983.

Cho, Charles Y. et al., "An Unnatural Biopolymer," Science, vol. 261, pp. 1303-1305, Sep. 3, 1993.

Schumacher, Ton N.M. et al., "Identification of D-Peptide Ligands Through Mirror-Image Phage Display," Science, vol. 271, pp. 1854-1857, Mar. 29, 1996.

Brody, Edward N. et al., "The Use of Aptamers in Large Arrays for Molecular Diagnostics," Molecular Diagnosis, vol. 4, No. 4, pp. 381-388, Dec. 4, 1999.

Bowie, James U. et al., "Deciphering the Message in Protein Sequences: Tolerance to Amino Acid Substitutions," Science, vol. 247, pp. 1306-1310, Mar. 16, 1990.

Computer Analysis of Sequence Data Part I, Humana Press Inc. pp. 1-370, 1994.

Needleman, Saul B. et al., "A General Method Applicable to the Search for Similarities in the Amino Acid Sequences of two Proteins," J. Mol. Biol., vol. 48, pp. 443-453, 1970.

Molecular Reproduction and Development, Alan R. Less, Inc., pp. 146-147, 1989.

Bennett, Donald et al., "Kinetic Characterization of the Interaction of Biotinylated Human Interleukin 5 with an Fc Chimera of its Receptor . . .," Journal of Molecular Recognition, vol. 8, pp. 52-58, 1995.

Bentley, Michael D. et al., "Reductive Amination Using Poly(ethylene glycol) Acetaldehyde Hydrate Generated in Situ: Applications to Chitosan and Lysozyme," Journal of Pharmaceitical Sciences, vol. 87, No. 11, pp. 1446-1449, Nov. 1998.

Wold, Finn "Posttranslational Covalent Modifications: Perspectives and Prospectives" Academic Press, pp. 1-17, 1983.

Seifter, Sam et al., "Analysis for Protein Modifications and non-protein Cofactors," Methods in Enzymology, vol. 182, pp. 626-646, 1990.

Rattan, Suresh I.S. et al., "Protein Synthesis, Posttranslational Modifications, and Aging," Annals New York Academy of Sciences, vol. 663, pp. 48-62, 1992.

Bundgaard, Hans "Means to Enhance Penetration," Advanced Drug Delivery Reviews, vol. 8, pp. 1-38, 1992.

Huse, William D. et al., "Generation of a Large Combinatorial Library of the Immunoglobulin Repertoire in Phage Lambda," Research Article, Science 246, pp. 1275-1281, Dec. 8, 1989.

Agrawal, Sudhir et al., "Antisense Therapeutics," Next Generation Therapeutics, vol. 2, pp. 519-528, 1998.

(56) References Cited

OTHER PUBLICATIONS

Agrawal, Sudhir et al., "Pharmacokinetics of Oligonucleotides," Discussion, pp. 60-78, 1997.
Zhao, Qiuyan et al., "Cellular Distribution of Phosphorothioate Oligonucleotide Following Intravenous Administration in Mice," Antisense & Nucleic Acid Drug Development, vol. 8, pp. 451-458, 1998.
Elebashir, Sayda M. et al., "Duplexes of 21-Nucleotide RNAs Mediate RNA Interference in Cultured Mammalian Cells," nature, vol. 411, pp. 494-498, May 24, 2001.
Baulcombe, David C. "RNA as a Target and an Initiator of Post-Transcriptional Gene Silencing in Trangenic Plants," Plant Molecular Biology, vol. 32, pp. 79-88, 1996.
Timmons, Lisa et al., "Specific Interference by ingested dsRNA," Nature, vol. 395, p. 854, Oct. 29, 1998.
Wianny, Florence et al., "Specific Interference with Gene Function by Double-Stranded RNA in Early Mouse Development," Nature Cell Biology, vol. 2, pp. 70-75, Feb. 2000.
Svoboda, Petr et al., "Selective Reduction of Dormant Maternal mRNAs in Mouse Oocytes by RNA Interference," Development, vol. 127, pp. 4147-4156, 2000.
Pardridge, William M. "Drug Targeting to the Brain," Pharmaceutical Research, vol. 24, No. 9, pp. 1733-1744, Sep. 2007.
Beduneau, Arnaud et al., "Brain Targeting using Novel Lipid Nanovectos," Journal of Controlled Release, vol. 126, pp. 44-49, 2008.
Kreuter, Jorg et al., "Direct Evidence that Polysorbate-80-Coated Poly(Butylcyanoacrylate) Nanoparticles Deliver Drugs to the CNA via Specific Mechanisms Requiring Prior Binding of Drug to the Nanoparticles," Pharmaceutical Research, vol. 20, No. 3, pp. 409-416, Mar. 2003.
"Gene Therapy, Principles and Applications," Birkhauser Verlog, pp. 1-374, 1999.
"Current Topics in Microbology and Immunology," Springer-Verlag, pp. 1-183, Feb. 1992.
Laface, Drake et al., "Gene Transfer into Hematopoietic Progenitor Cells Mediated by an Adeno-Associated Virus Vector," Virology, vol. 162, pp. 483-486, 1988.
Zhou, Shang Zhen et al., "Adeno-Associated Virus 2-Mediated Gene Transfer in Murine Hematopoietic Progenitor Cells," Experimental Hematology, vol. 21, pp. 928-933, 1993.
Flotte, Terence et al., "Gene Expression from Adeno-Associated Virus Vectors in Airway Epithelial Cells," American Journal of Respratory Cell and Molecular Biology, vol. 7, pp. 350-356, 1992.
Kaplitt, Michael G. et al., "Long-Term Gene Expression and Phenotypic Correction using Adeno-Associated Virus Vectors in the Mammalian Brain," Nature Genetics, vol. 8, pp. 148-154, Oct. 1994.
Shelling, Andrew N. et al., "Targeted Integration of Transfected and infected Adeno-Associated Virus Vectors Containing the Neomycin Resistance Gene," Gene Theraphy, vol. 1, pp. 165-169, 1994.
"Blood," Journal of the American Society of Hematology, vol. 82, No. 10, pp. 347a, Nov. 15, 1993.
"Blood," Journal of the American Society of Hematology, vol. 82, No. 10, pp. 303a, Nov. 15, 1993.
Ohi, Seigo et al., "Construction and Replication of an Adeno-Associated Virus Expression Vector that Contains . . .," Gene, vol. 89, pp. 279-282, 1990.
Wei, Jing-Fang et al., "Expression of the Human Glucocerebrosidase and Arylsulfatase A Genes in Murine and Patient Primary Fibroblasts Transduced by an Adeno-Associated Virus Vector," Gene Therapy, vol. 1, pp. 261-268, 1994.
Naldini, Luigi et al., "In Vivo Gene Delivery and Stable Transduction of Nondividing Cells by a Lentiviral Vector," Science, vol. 272, pp. 263-267, Apr. 12, 1996.
Posechla, Eric M. et al., "Efficient Transduction of Nondividing Human Cells by Feline Immuniodeficieny Virus Lentiviral Vectors," Nature Medicine, vol. 4, No. 3, pp. 354-357, Mar. 1998.
Zufferey, Romain et al., "Multiply Attenuated Lentiviral Vector Achieves Effiicent Gene Delivery in Vivo," Nature Biotechnology, vol. 15, pp. 871-875, Sep. 1997.
Friedmann, Theodore "Progress Toward Human Gene Therapy," Science, vol. 244, pp. 1275-1281, Jun. 16, 1989.
Mulligan, Richard C. "The Basic Science of Gene Therapy," Science, vol. 260, pp. 926-932, May 14, 1993.
Crystal, Ronald G. "Transfer of Genes to Humans: Early Lessons and Obstacles to Success," Science, vol. 270, pp. 404-410, Oct. 20, 1995.
Morgan, Richard A. "Human Gene Therapy, BioPharm," vol. 6, No. 1, pp. 32-35, 1993.
Beaucage, Serge L. et al., "The Functionalization of Oligonucleotides Via Phosphoramidite Derivatives," Tetrahedron, vol. 49, No. 10, pp. 1925-1963, 1993.
Letsinger, Robert L. et al., "Phosphoramidate Analogs of Oligonucleotides," J. Org. Chem., vol. 35, No. 11, pp. 3800-3803, 1970.
Letsinger, Robert L. et al., "Cationic Oligonucleotides," J. Am. Chem. Soc. vol. 110, pp. 4470-4471, 1988.
Jung, Paul M. et al., "Hybridization of Alternating Cationic/Anionic Oligonucleotides to RNA Segments," Nucleosides & Nucleotides, vol. 13, Nos. 6 & 7, pp. 1597-1605, 1994.
Pauwels, R et al., "Biological Activity of New 2-5A Analogues," Chemica Scripta, vol. 26, pp. 141-145, 1986.
Mag, Matthias et al., "Synthesis and Selective Cleavage of an Oligodeoxynucleotide Containing a Bridged Internucleotide 5'-phosphorothioate Linkage," Nucleic Acids Research, vol. 19, No, 7, pp. 1437-1441, 1991.
Brill, Wolfgang K-D et al., "Synthesis of Oligodeoxynucleoside Phosphorodithioates via Thioamidotes," J. Am. Chem. Soc., vol. 111, pp. 2321-2322, 1989.
Egholm, Michael et al., "Peptide Nucleic Acids (ONA) Oligonucleotide Analogies with an Achiral Peptide Bakbone," J. Am. Chem. Soc., vol. 114, pp. 1895-1897, 1992.
Meier, Chris et al., "Peptide Nucleic Acids (PNAs)-Unusual Properties of Nonionic Oligonucleotide Analogues," Ange. Chem. int. Ed. Engl, vol. 31, No. 8, pp. 1008-1010, 1992.
Egholm, Michael et al., "PNA Hybridizes to Complementary Oligonucleotides Obeying the Watson-Crick Hydrogen-Bonding Rule," Nature, vol. 365, pp. 566-568, Oct. 7, 1993.
Carlsson, Christina et al., "Screening for Genetic Mutations," Nature, vol. 380, No. 6571, pp. 1-3, Mar. 21, 1996.
Kiedrowski, Gunter Von et al., "Parabolic Growth of a Self-Replicating Hexadeoxynucleotide Bearing a 3'-5'-Phosphoamidate Linage," Angew. Chem. Int. Ed. Engl. vol. 30, No. 4, pp. 423-426, 1991.
Mesmaeker, Alain De et al., "Novel Backbone replacements for Oligonucleotides," American Chemical Society, Chapter 2, pp. 24-39, Aug. 18, 1994.
"Carbohydrate Modifications in Antisense Research," ACS Symposium Series, American Chemical Society, San Diego, California, pp. 1-4, Mar. 13-17, 1994.
Maddry, Joseph A. et al., "Synthesis of Nonionic Oligonucleotide Analogues," American Chemical Society, pp. 40-51, Jul. 6, 1994.
Mesmaeker, Alain De et al., "Comparions of Rigid and Flexible Backbones in Antisense Oligonucleotides," Bioorganics & Medicinal Chemistry Letters, vol. 4, No. 3, pp. 395-398, 1994.
Gao, Xiaolian et al., "Unusual Conformation of a 3'-Thioformacetal Linkage in a DNA Duplex*," Journal of Biomolecular NMR, vol. 4, pp. 17-34, 1994.
Herdewijn, Piet et al., "Hexopyranosyl-Like Oligonucleotides," Laboratory of Medicinal Chemistry, Rega Institute Chapter 6, pp. 80-99, Aug. 8, 1994.
Rawls, Rebecca L. et al., "Optimistic About Antisense," Science/Technology, C&EN, pp. 35-39, Jun. 2, 1997.
Goeden, Nick et al., "Ex Vivo Perfusion of Mid-to-late-Gestation Mouse Placenta for Maternal-Fetal Interaction Studies During Pregnancy," Nature Protocols, vol. 8, No. 1, pp. 66-74, 2013.
Ferron, Mathieu et al., "Intermeittent Injections of Osteocalcin Improve Metabolism and Prevent Type 2 Diabetes in Mice," Bone, vol. 50, pp. 568-575, 2012.

(56) References Cited

OTHER PUBLICATIONS

Steru, Lucien et al., "The Tail Suspension Test: A New Method for Screening Antidepressants in Mice," Psychopharmacology, vol. 85, pp. 367-370, 1985.
Morris, R.G.M et al., "Place Navigation Impaired in Rats with Hippocampal Lesions," Nature, vol. 297, pp. 681-683, Jun. 1982.
Banks, William A. et al., "Leptin Enters the Brain by a Saturable System Independent of Insulin," Peptides, vol. 17, No. 2, pp. 305-311, 1996.
Friedman, Jeffrey M. et al., "Leptin andthe Regulation of Body Weight in Mammals," Nature, vol. 395, pp. 763-770, Oct. 22, 1998.
Crawley, Jacqueline N. "Exploratory Behavior Models of Anxiety in Mice," Neuroscience & Biobehavioral Reviews, vol. 9, pp. 37-44, 1985.
Holmes, A et al., "Behavioral Profile of Wild Mice in the Elevated Plus-Maze Test for Anxiety," Physiology & Behavior, vol. 71, pp. 509-516, 2000.
Lira, Alena et al., "Altered Depression-Related Behaviors and Functional Changes in the Dorsal Raphe Nucleus of Serotonin Transporter-Deficient Mice," Biol Psychiatry, vol. 54, pp. 960-971, 2003.
Sahay, Amar et al., "Increasing Adult Hippocampal Neurogenesis is Sufficient to Improve Pattern Separation," Nature, vol. 472, pp. 466-473, Apr. 28, 2011.
Cryan, John F. et al., "The Tail Suspension Test as a Model for Assessing Antidepressant Activity: Review of Pharmacological and Genetic Studies in Mice," Neuroscience and Biobehavioral Reviews, vol. 29, pp. 571-625, 2005.
Bonnin, Alexandre et al., "A Transient Placental Source of Serotonin for the Fetal Forebrain," Nature, vol. 472, pp. 347-352, Apr. 21, 2011.
Denny, Christine A. et al., "4-to 6-Week-Old Adult-Born Hippocampal Neurons Influence Novelty-Evoked Exploration and Contextual Fear Conditioning," Hippocampus, vol. 22, pp. 1188-1202, 2012.
"Oligonucleotides and Analogues, A Practical Approach," The Practical Approach Series, pp. 1-336, 1991.
"Remington, The Science and Practice of Pharmacy," 20th Edition, Philadelphia College of Pharmacy and Science pp. 1-2086, 2000.
"Design of Prodrugs," Elsevier, pp. 1-366, 1985.
"Sequence Analysis Primer," M Stockton Press, pp. 1-282, 1991.
"Sequence Analysis in Molecular Biology," Academic Press, Inc, pp. 1-197, 1987.
"Computational Molecular Biology, Sources and Methods for Sequence Analysis," Oxford, pp. 1-251, 1988.
"Biocomputing, Informatics and Genome Projects," Academic Press, Inc., pp. 1-344, 1993.
"The Development of Human Gene Therapy," Cold Spring Harbor Laboratory Press, pp. 1-735, 1999.
"A Textbook of Drug Design and Development," Harwood Academic Publishers, pp. 1-657, 1991.
Creighton, Thomas E. "Proteins, Structures and Molecular Principles," W.H. Freeman and Company, New York, pp. 1-522, 1940.
Creighton, Thomas E. "Proteins, Structures and Molecular Properties," 2nd Edition, W.H. Freeman and Company, New York, 1-519, 1940.
Ausubel, Frederick I et al., Current Protocols in Molecular Biology, pp. 1-16, 1992.
Ausubel, Frederick I et al., "Molecular Reproduction and Development," vol. 1, pp. 146-147, 1989.
Creighton, Thomas E., "Proteins, Structures and Molecular Properties," 2nd Edition, W.H. Freeman and Company, New York, 1993.
Hodgson, Clague P., "Retro-Vectors for Human Gene Therapy," Medical Intelligence Unit, Springer Verlag, 1996.
Muzyczka, N., "Current Topics in Microbiology and Immunology, Viral Expression Vectors," Springer-Verlag, vol. 158, pp. 1-183, 1992.
Flotte, Terence R. et al., "Gene Expression from Adeno-Associated Virus Vectors in Airway Epithelial Cells," American Journal of Respiratory Cell and Molecular Biology, vol. 7. pp. 349-356, 1992.
Russell, David W. et al., "Foamy Virus Vectors," Journal of Virology, vol. 70, No. 1, pp. 217-222, Jan. 1996.
Crowley, James J. et al., "Pharmacogenomic Evaluation of the Antidepressant Citalopram in the Mouse Tail Suspension Test," Neuropsychopharmacology, vol. 31, pp. 2433-2442.
Goeden, Nick et al., "Ex Vivo Perfusion of Mid-to-Late-Gestation Mouse Placenta for Maternal-Fetal Interaction Studies During Pregnancy," Nature Protocols, vol. 8, No. 1., pp. 66-74, 2013.
Ferron, Mathieu et al., "Insulin Signaling in Osteoblasts Integrates Bone Remodeling and Energy Metabolism," Cell, vol. 142, No. 2, pp. 296-308, Jul. 23, 2010.
"Current Protocols in Molecular Biology," John Wiley & Sons, Inc. vol. 1, pp. 1-16, Dec. 4, 2003.
"Analyze the Expression of any Gene," Retrieved from the Internet <URL:https://web.archive.org/web/20170401183635/http://www.sabiosciences.com/RT2PCR.php.>, [retrieved on Feb. 22, 2018].

| Osteocalcin (ng/mg) | |
|---|---|
| Serum | 0.00 |
| Bone | 0.00 |
| Cortex | 0.00 |
| Thal | 0.00 |
| Hypothal | 0.00 |
| Hindbrain | 0.00 |

Ocn-infusions in Ocn-/-

| Osteocalcin (ng/mg) | |
|---|---|
| Serum | 15.80 |
| Bone | 17.50 |
| Cortex | 0.00 |
| Thal | 11.65 |
| Hypothal | 9.20 |
| Hindbrain | 8.67 |

PBS-infusions in ob/ob

| Leptin (ng/ml) | |
|---|---|
| Serum | 0.00 |
| Cortex | 0.00 |
| Thal | 0.00 |
| Hypothal | 0.00 |
| Hindbrain | 0.00 |

Leptin-infusions in ob/ob

| Leptin (ng/ml) | |
|---|---|
| Serum | 10.42 |
| Cortex | 0.68 |
| Thal | 1.45 |
| Hypothal | 3.37 |
| Hindbrain | 3.63 |

WT-PBS-PUMP (n=7)
Osteocalcin-/--PBS-PUMP (n=7)
Osteocalcin-/--Osteocalcin-PUMP (n=7)

WT(n=9)

2.0 ± 0.4%

Ocn−/− from Ocn+/− mothers (n=3)

0.9 ± 0.2%

Ocn−/− from Ocn−/− mothers (n=10)

5.2 ± 0.4% ***

SEQUENCE LISTING

```
<160> NUMBER OF SEQ ID NOS: 19

<210> SEQ ID NO 1
<211> LENGTH: 498
<212> TYPE: DNA
<213> ORGANISM: Homo sapiens

<400> SEQUENCE: 1

cgcagccacc gagacaccat gagagccctc acactcctcg ccctattggc cctggccgca      60

ctttgcatcg ctggccaggc aggtgcgaag cccagcggtg cagagtccag caaaggtgca     120

gcctttgtgt ccaagcagga gggcagcgag gtagtgaaga gacccaggcg ctacctgtat     180

caatggctgg gagccccagt cccctacccg gatcccctgg agcccaggag ggaggtgtgt     240

gagctcaatc cggactgtga cgagttggct gaccacatcg gctttcagga ggcctatcgg     300

cgcttctacg gcccggtcta gggtgtcgct ctgctggcct ggccggcaac cccagttctg     360

ctcctctcca ggcacccttc tttcctcttc cccttgccct tgccctgacc tcccagccct     420

atggatgtgg ggtccccatc atcccagctg ctcccaaata aactccagaa gaggaatctg     480

aaaaaaaaaa aaaaaaaa                                                   498


<210> SEQ ID NO 2
<211> LENGTH: 100
<212> TYPE: PRT
<213> ORGANISM: Homo sapiens

<400> SEQUENCE: 2

Met Arg Ala Leu Thr Leu Leu Ala Leu Leu Ala Leu Ala Ala Leu Cys
1               5                   10                  15

Ile Ala Gly Gln Ala Gly Ala Lys Pro Ser Gly Ala Glu Ser Ser Lys
            20                  25                  30

Gly Ala Ala Phe Val Ser Lys Gln Glu Gly Ser Glu Val Val Lys Arg
        35                  40                  45

Pro Arg Arg Tyr Leu Tyr Gln Trp Leu Gly Ala Pro Val Pro Tyr Pro
    50                  55                  60

Asp Pro Leu Glu Pro Arg Arg Glu Val Cys Glu Leu Asn Pro Asp Cys
65                  70                  75                  80

Asp Glu Leu Ala Asp His Ile Gly Phe Gln Glu Ala Tyr Arg Arg Phe
                85                  90                  95

Tyr Gly Pro Val
            100


<210> SEQ ID NO 3
<211> LENGTH: 494
<212> TYPE: DNA
<213> ORGANISM: Mus musculus
```

<400> SEQUENCE: 3

```
agaacagaca agtcccacac agcagcttgg cccagaccta gcagacacca tgaggaccat      60
ctttctgctc actctgctga ccctggctgc gctctgtctc tctgacctca cagatgccaa     120
gcccagcggc cctgagtctg acaaagcctt catgtccaag caggagggca ataaggtagt     180
gaacagactc cggcgctacc ttggagcctc agtccccagc ccagatcccc tggagcccac     240
ccgggagcag tgtgagctta accctgcttg tgacgagcta tcagaccagt atggcttgaa     300
gaccgcctac aaacgcatct atggtatcac tatttaggac ctgtgctgcc ctaaagccaa     360
actctggcag ctcggctttg gctgctctcc gggacttgat cctccctgtc ctctctctct     420
gccctgcaag tatggatgtc acagcagctc caaaataaag ttcagatgag gaagtgcaaa     480
aaaaaaaaaa aaaa                                                       494
```

<210> SEQ ID NO 4
<211> LENGTH: 470
<212> TYPE: DNA
<213> ORGANISM: Mus musculus

<400> SEQUENCE: 4

```
gaacagacaa gtcccacaca gcagcttggt gcacacctag cagacaccat gaggaccctc      60
tctctgctca ctctgctggc cctggctgcg ctctgtctct ctgacctcac agatcccaag     120
cccagcggcc ctgagtctga caaagccttc atgtccaagc aggagggcaa taaggtagtg     180
aacagactcc ggcgctacct tggagcctca gtccccagcc cagatcccct ggagcccacc     240
cgggagcagt gtgagcttaa ccctgcttgt gacgagctat cagaccagta tggcttgaag     300
accgcctaca aacgcatcta cggtatcact atttaggacc tgtgctgccc taaagccaaa     360
ctctggcagc tcggctttgg ctgctctccg ggacttgatc ctccctgtcc tctctctctg     420
ccctgcaagt atggatgtca cagcagctcc aaaataaagt tcagatgagg               470
```

<210> SEQ ID NO 5
<211> LENGTH: 95
<212> TYPE: PRT
<213> ORGANISM: Mus musculus

<400> SEQUENCE: 5

```
Met Arg Thr Leu Ser Leu Leu Thr Leu Leu Ala Leu Ala Ala Leu Cys
1               5                   10                  15

Leu Ser Asp Leu Thr Asp Pro Lys Pro Ser Gly Pro Glu Ser Asp Lys
            20                  25                  30

Ala Phe Met Ser Lys Gln Glu Gly Asn Lys Val Val Asn Arg Leu Arg
        35                  40                  45

Arg Tyr Leu Gly Ala Ser Val Pro Ser Pro Asp Pro Leu Glu Pro Thr
    50                  55                  60

Arg Glu Gln Cys Glu Leu Asn Pro Ala Cys Asp Glu Leu Ser Asp Gln
65                  70                  75                  80

Tyr Gly Leu Lys Thr Ala Tyr Lys Arg Ile Tyr Gly Ile Thr Ile
                85                  90                  95
```

<210> SEQ ID NO 6
<211> LENGTH: 3176
<212> TYPE: DNA
<213> ORGANISM: Homo sapiens

<400> SEQUENCE: 6

```
gtgacccacc tgcctcctcc gcagagcaat ggcggtgtct gccgggtccg cgcggacctc      60
```

```
gcccagctca gataaagtac agaaagacaa ggctgaactg atctcagggc ccaggcagga    120
cagccgaata gggaaactct tgggttttga gtggacagat ttgtccagtt ggcggaggct    180
ctgaatcgac caacggaccc tgcaagctta gctgtctttc gttttctttt tgggttcttg    240
atggtgctag acattcccca ggagcggggg ctcagctctc tggaccggaa gggctggatg    300
tgtgccgctt ccccttgctg gatgccctac gcccactgcc atgtatcttg tctacaccat    360
catgtttctg gggcactgg gcatgatgct taccggataa gctgtgtgtt attcctgctg    420
ccatactggt atgtgtttct cctggacaag acatcatgga acaaccactc ctatctgtat    480
gggttgttgg cctttcagct gatgcaaacc actactggtc tgtggacggt ctgctgaatg    540
cccataggag gtgccccttt ggaactatgc agtgctccgt ggccagatct tcattgtgta    600
cttcattgcg ggtgtgaaaa agctggatgc agactgggtt gaaggctatt ccatggaata    660
tttgtcccgg cactggctct tcagtccctt caaactgctg ttgtctgagg agctgactag    720
cctgctggtc gtgcactggg gtgggctgct gcttgacctc tcagctggtt tcctgctctt    780
ttttgatgtc tcaagatcca ttggcctgtt ctttgtgtcc tacttccact gcatgaattc    840
ccagcttttc agcattggta tgttctccta cgtcatgctg gccagcagcc ctctcttctg    900
ctcccctgag tggcctcgga agctggtgtc ctactgcccc cgaaggttgc aacaactgtt    960
gcccctcaag gcagcccctc agcccagtgt ttcctgtgtg tataagagga gccggggcaa   1020
aagtggccag aagccagggc tgcgccatca gctgggagct gccttcaccc tgctctacct   1080
cctggagcag ctattcctgc cctattctca ttttctcacc cagggctata acaactggac   1140
aaatgggctg tatggctatt cctgggacat gatggtgcac tcccgctccc accagcacgt   1200
gaagatcacc taccgtgatg gccgcactgg cgaactgggc taccttaacc ctggggtatt   1260
tacacagagt cggcgatgga aggatcatgc agacatgctg aagcaatatg ccacttgcct   1320
gagccgcctg cttcccaagt ataatgtcac tgagccccag atctactttg atatttgggt   1380
ctccatcaat gaccgcttcc agcagaggat tttgaccct cgtgtggaca tcgtgcaggc   1440
cgcttggtca ccctttcagc gcacatcctg ggtgcaacca ctcttgatgg acctgtctcc   1500
ctggagggcc aagttacagg aaatcaagag cagcctagac aaccacactg aggtggtctt   1560
cattgcagat ttccctggac tgcacttgga gaattttgtg agtgaagacc tgggcaacac   1620
tagcatccag ctgctgcagg gggaagtgac tgtggagctt gtggcagaac agaagaacca   1680
gactcttcga gagggagaaa aaatgcagtt gcctgctggt gagtaccata aggtgtatac   1740
gacatcacct agcccttctt gctacatgta cgtctatgtc aacactacag agcttgcact   1800
ggagcaagac ctggcatatc tgcaagaatt aaaggaaaag gtggagaatg gaagtgaaac   1860
agggcctcta cccccagagc tgcagcctct gttggaaggg gaagtaaaag gggccctga   1920
gccaacacct ctggttcaga cctttcttag acgccaacaa aggctccagg agattgaacg   1980
ccggcgaaat actcctttcc atgagcgatt cttccgcttc ttgttgcgaa agctctatgt   2040
ctttcgccgc agcttcctga tgacttgtat ctcacttcga aatctgatat taggccgtcc   2100
ttccctggag cagctggccc aggaggtgac ttatgcaaac ttgagaccct ttgaggcagt   2160
tggagaactg aatccctcaa acacggattc ttcacattct aatcctcctg agtcaaatcc   2220
tgatcctgtc cactcagagt tctgaagggg gccagatgtt gggtgcagat gtagaagcag   2280
ccagtcacag acccattcta tgcaatggac atttatttga aaaaaattct caaaagtttt   2340
ttttttttt ttgggggggc ggggttctaa agctgttttt aactccgaga ttacaactta   2400
```

```
gaggaaccaa ggaaataaag caaataagat ttaacaaccc aagattaaga ggccaggaag   2460

aggttagacg caatgtgaaa ctgtcctcct aggataaggt ttaaagtggc tttttggggg   2520

ctgggtgccg tggctcacgc ctgtaatccc agcattttgg gaggctgagg tgggcagatc   2580

acttgaggcc aggagttcga gaccagcctg gccaacatgg caaaacccct tctctactaa   2640

aaatacaaaa attagccaga cgtggtggtg ggtgcctgta atccaactac ccaggaggct   2700

gaggcatgag aatcgcttgg gcccaggagg tggaggttgc agtgagccga gatcgagcca   2760

ctgcactcct gggcaacaga gcaagacttc gtctcaaaat aaataaataa agtggctctt   2820

ggggaaaagc aatttaatgt accacgatga atagctaact gttcccaagt gtttgctatg   2880

tgcaacacac cgcgtgagca gtgttacctg cattattaca ttaggctgag aggtaaaata   2940

atttgcccga agacatacag ctagtgacga atggactgat ggtttgaact taacgtctat   3000

ttgacttaag gtcctgcacc ctgccacttg taattttcag aatcactgat aatctgaaat   3060

aatgcagctt aaaacatgtt ttcttaatta aaagtataaa aaaaaaaaaa aaaaaaaaaa   3120

aaaaaaaaaa aaaaaaaaaa aaaaaaaaaa aaaaaaaaaa aaaaaaaaaa aaaaaa       3176


<210> SEQ ID NO 7
<211> LENGTH: 758
<212> TYPE: PRT
<213> ORGANISM: Homo sapiens

<400> SEQUENCE: 7

Met Ala Val Ser Ala Gly Ser Ala Arg Thr Ser Pro Ser Ser Asp Lys
1               5                   10                  15

Val Gln Lys Asp Lys Ala Glu Leu Ile Ser Gly Pro Arg Gln Asp Ser
            20                  25                  30

Arg Ile Gly Lys Leu Leu Gly Phe Glu Trp Thr Asp Leu Ser Ser Trp
        35                  40                  45

Arg Arg Leu Val Thr Leu Leu Asn Arg Pro Thr Asp Pro Ala Ser Leu
    50                  55                  60

Ala Val Phe Arg Phe Leu Phe Gly Phe Leu Met Val Leu Asp Ile Pro
65                  70                  75                  80

Gln Glu Arg Gly Leu Ser Ser Leu Asp Arg Lys Tyr Leu Asp Gly Leu
                85                  90                  95

Asp Val Cys Arg Phe Pro Leu Leu Asp Ala Leu Arg Pro Leu Pro Leu
            100                 105                 110

Asp Trp Met Tyr Leu Val Tyr Thr Ile Met Phe Leu Gly Ala Leu Gly
        115                 120                 125

Met Met Leu Gly Leu Cys Tyr Arg Ile Ser Cys Val Leu Phe Leu Leu
    130                 135                 140

Pro Tyr Trp Tyr Val Phe Leu Leu Asp Lys Thr Ser Trp Asn Asn His
145                 150                 155                 160

Ser Tyr Leu Tyr Gly Leu Leu Ala Phe Gln Leu Thr Phe Met Asp Ala
                165                 170                 175

Asn His Tyr Trp Ser Val Asp Gly Leu Leu Asn Ala His Arg Arg Asn
            180                 185                 190

Ala His Val Pro Leu Trp Asn Tyr Ala Val Leu Arg Gly Gln Ile Phe
        195                 200                 205

Ile Val Tyr Phe Ile Ala Gly Val Lys Lys Leu Asp Ala Asp Trp Val
    210                 215                 220

Glu Gly Tyr Ser Met Glu Tyr Leu Ser Arg His Trp Leu Phe Ser Pro
225                 230                 235                 240
```

```
Phe Lys Leu Leu Leu Ser Glu Glu Leu Thr Ser Leu Leu Val Val His
                245                 250                 255

Trp Gly Gly Leu Leu Leu Asp Leu Ser Ala Gly Phe Leu Leu Phe Phe
            260                 265                 270

Asp Val Ser Arg Ser Ile Gly Leu Phe Phe Val Ser Tyr Phe His Cys
        275                 280                 285

Met Asn Ser Gln Leu Phe Ser Ile Gly Met Phe Ser Tyr Val Met Leu
    290                 295                 300

Ala Ser Ser Pro Leu Phe Cys Ser Pro Glu Trp Pro Arg Lys Leu Val
305                 310                 315                 320

Ser Tyr Cys Pro Arg Arg Leu Gln Gln Leu Leu Pro Leu Lys Ala Ala
                325                 330                 335

Pro Gln Pro Ser Val Ser Cys Val Tyr Lys Arg Ser Arg Gly Lys Ser
            340                 345                 350

Gly Gln Lys Pro Gly Leu Arg His Gln Leu Gly Ala Ala Phe Thr Leu
        355                 360                 365

Leu Tyr Leu Leu Glu Gln Leu Phe Leu Pro Tyr Ser His Phe Leu Thr
    370                 375                 380

Gln Gly Tyr Asn Asn Trp Thr Asn Gly Leu Tyr Gly Tyr Ser Trp Asp
385                 390                 395                 400

Met Met Val His Ser Arg Ser His Gln His Val Lys Ile Thr Tyr Arg
                405                 410                 415

Asp Gly Arg Thr Gly Glu Leu Gly Tyr Leu Asn Pro Gly Val Phe Thr
            420                 425                 430

Gln Ser Arg Arg Trp Lys Asp His Ala Asp Met Leu Lys Gln Tyr Ala
        435                 440                 445

Thr Cys Leu Ser Arg Leu Leu Pro Lys Tyr Asn Val Thr Glu Pro Gln
    450                 455                 460

Ile Tyr Phe Asp Ile Trp Val Ser Ile Asn Asp Arg Phe Gln Gln Arg
465                 470                 475                 480

Ile Phe Asp Pro Arg Val Asp Ile Val Gln Ala Ala Trp Ser Pro Phe
                485                 490                 495

Gln Arg Thr Ser Trp Val Gln Pro Leu Leu Met Asp Leu Ser Pro Trp
            500                 505                 510

Arg Ala Lys Leu Gln Glu Ile Lys Ser Ser Leu Asp Asn His Thr Glu
        515                 520                 525

Val Val Phe Ile Ala Asp Phe Pro Gly Leu His Leu Glu Asn Phe Val
    530                 535                 540

Ser Glu Asp Leu Gly Asn Thr Ser Ile Gln Leu Leu Gln Gly Glu Val
545                 550                 555                 560

Thr Val Glu Leu Val Ala Glu Gln Lys Asn Gln Thr Leu Arg Glu Gly
                565                 570                 575

Glu Lys Met Gln Leu Pro Ala Gly Glu Tyr His Lys Val Tyr Thr Thr
            580                 585                 590

Ser Pro Ser Pro Ser Cys Tyr Met Tyr Val Tyr Val Asn Thr Thr Glu
        595                 600                 605

Leu Ala Leu Glu Gln Asp Leu Ala Tyr Leu Gln Glu Leu Lys Glu Lys
    610                 615                 620

Val Glu Asn Gly Ser Glu Thr Gly Pro Leu Pro Pro Glu Leu Gln Pro
625                 630                 635                 640

Leu Leu Glu Gly Glu Val Lys Gly Gly Pro Glu Pro Thr Pro Leu Val
                645                 650                 655

Gln Thr Phe Leu Arg Arg Gln Gln Arg Leu Gln Glu Ile Glu Arg Arg
```

```
            660                 665                 670

Arg Asn Thr Pro Phe His Glu Arg Phe Phe Arg Phe Leu Leu Arg Lys
        675                 680                 685

Leu Tyr Val Phe Arg Arg Ser Phe Leu Met Thr Cys Ile Ser Leu Arg
    690                 695                 700

Asn Leu Ile Leu Gly Arg Pro Ser Leu Glu Gln Leu Ala Gln Glu Val
705                 710                 715                 720

Thr Tyr Ala Asn Leu Arg Pro Phe Glu Ala Val Gly Glu Leu Asn Pro
                725                 730                 735

Ser Asn Thr Asp Ser Ser His Ser Asn Pro Pro Glu Ser Asn Pro Asp
            740                 745                 750

Pro Val His Ser Glu Phe
        755
```

<210> SEQ ID NO 8
<211> LENGTH: 2905
<212> TYPE: DNA
<213> ORGANISM: Mus musculus

<400> SEQUENCE: 8

```
agacagcaag tctaagtctg gaggttccac tgggtccgac ctggctgcag agaggctcac     60

ctgtccctgc agtcatggct gtgcaccgcg gctccgcact ggttgctccc gcctcagata    120

aagtacagaa aaacaagtct gcacagacat caggactgaa acagggcagc cgaatggaga    180

aaattttagg gtttgaatgg acagatttat ctagctggca gagtgtcgtg accctgctta    240

acaaaccaac ggaccctgca aacctggctg tctttcgttt tctctttgct ttcttgatgc    300

tgctggacat tccccaggaa cgcggcctta gctccctgga ccgaaaatac ttggatgggc    360

tggatgtgtg ccgtttcccc ttgctggatg ccttgcgccc actgccactg gactggatgt    420

atcttgtcta caccatcatg tttctggggg cactgggcat gatgctgggg ctatgctacc    480

ggctaagctg tgtgttattc ctgctaccgt actggtacgt gtttctcctg gacaagactt    540

cgtggaacaa tcactcctat ctgtatggtt tgttggcctt tcagttgaca ttcatggatg    600

caaaccacta ctggtctgtg gatggcttgc tgaatgcccg aaagaagaat gctcacgtgc    660

ccctttggaa ctacacagtt ctgcgtggcc agatcttcat cgtgtacttc atcgcgggtg    720

tgaagaagct cgatgctgac tgggttgggg gctactccat ggagcacctg tcccggcact    780

ggctcttcag tcccttcaag ctggtgttgt cggaggagct gacaagcctg ctggtagtac    840

actggtgtgg gcttctcctt gacctctcgg ctggcttcct gctcttcttt gatgcctcca    900

gacccgtcgg cctgttcttc gtgtcctact ttcactgcat gaactcgcag ctcttcagca    960

tcgggatgtt ccctatgtc atgctggcca gcagccctct cttctgctca gctgaatggc   1020

ctcggaagtt ggtagcccga tgcccgaaaa ggctgcaaga gctgctgccc accaaagccg   1080

ctcctcggcc tagtgcttcc tgtgtgtata agaggtcccg gggcaaagct ggcccgaagc   1140

ccgggctgcg ccaccagctg ggagccatct tcaccctgct ctacctccta gagcagctct   1200

tcctgcccta ttcccacttc ctgacccagg gttacaataa ctggacaaat gggctgtatg   1260

gctattcctg ggacatgatg gtgcactccc gctcccacca gcacgtaaag atcacctacc   1320

gcgacggcct cacgggcgag ctaggctacc ttaaccctgg ggtattcaca cagagccggc   1380

gatggaagga tcatgcagac atgctgaagc aatatgccac ttgcctgagc ctcctgcttc   1440

ccaagtacaa tgtcactgag ccccagatct actttgatat ttgggtctcc atcaatgacc   1500

gcttccagca gaggcttttt gaccctcgtg tggacatcgt gcaggctgtc tggtccccct   1560
```

```
tccagcgcac accttgggtg cagccactct tgatggattt atctccctgg aggaccaagt   1620

tacaggatat taagagcagt ctggacaacc acaccgaggt ggtcttcatt gcagatttcc   1680

ctgggcttca cttggagaat tttgtgagtg aagacctggg caacactagc atccagctgc   1740

tgcagggaga agtcaccgtg gaattggtgg cagaacagaa aaatcagact cttcaagaag   1800

gagagaaaat gcagttgcct gctggagagt accataaagt ctatactgta tcatctagtc   1860

cttcctgcta catgtacgtc tatgtcaaca ctacagaggt cgcactggag caagacctgg   1920

catatctgca agaattaaag gagaaggtgg agaacggaag tgaaacaggg cccctgcctc   1980

cagaacttca gcctcttttg gaaggggaag taaaaggggg ccctgagcca acacctctgg   2040

tccaaacttt tctcagacga cagaggaagc tccaagaaat tgaacgcagg cgaaatagcc   2100

ctttccatga gcgatttctc cgcttcgtgc tgcgaaagct ctacgtcttt cgacgcagct   2160

tcctgatgac tcgaatttca ctccgaaacc tgctattagg ccgcccttcc ctagagcaac   2220

tagcccaaga ggtgacatat gcaaacttgc gaccatttga accagttgat gagtcaagtg   2280

cttcaaacac agattcttca aatcacccgt cagagccaga ttctgagcat gttcactctg   2340

agttctgagg gatgtacaga tgctctgtgc agatgtgggg gcagcctgtt ataggcttat   2400

tgtctacgca aagaacatat ttttggagaa aaatgatatg ggacaggctt tcacagtaca   2460

gcccaggctg gcctcaaact catggttggt ccctctgctt cagcctgttt tgtaattaca   2520

tagtatcacc aaacctagtt gcttttccct ttacattttt tccccttata agttctttaa   2580

aattatagct tacatttttt cttttttctt tttttttttt ttgtattttt tctttgtcaa   2640

gacaggtctc tctctgtgta gcactggctg tcctggaact cactctgtag tccaggctgg   2700

cctccaactc agaaattctc ctgcctctgc ctcccaagtg ctgggattaa aggtgtgtgc   2760

caccacgccc cactgggctt ttagttttta tagacaagat ttctccatgt agaccagacc   2820

agctctcctg agtgctgaaa ttaaaggcac gggacatcac tacctggctt tcttattaaa   2880

cttgttttag tggtctcaac aaaaa                                         2905
```

<210> SEQ ID NO 9
<211> LENGTH: 757
<212> TYPE: PRT
<213> ORGANISM: Mus musculus

<400> SEQUENCE: 9

```
Met Ala Val His Arg Gly Ser Ala Leu Val Ala Pro Ala Ser Asp Lys
1               5                   10                  15

Val Gln Lys Asn Lys Ser Ala Gln Thr Ser Gly Leu Lys Gln Gly Ser
            20                  25                  30

Arg Met Glu Lys Ile Leu Gly Phe Glu Trp Thr Asp Leu Ser Ser Trp
        35                  40                  45

Gln Ser Val Val Thr Leu Leu Asn Lys Pro Thr Asp Pro Ala Asn Leu
    50                  55                  60

Ala Val Phe Arg Phe Leu Phe Ala Phe Leu Met Leu Leu Asp Ile Pro
65                  70                  75                  80

Gln Glu Arg Gly Leu Ser Ser Leu Asp Arg Lys Tyr Leu Asp Gly Leu
                85                  90                  95

Asp Val Cys Arg Phe Pro Leu Leu Asp Ala Leu Arg Pro Leu Pro Leu
            100                 105                 110

Asp Trp Met Tyr Leu Val Tyr Thr Ile Met Phe Leu Gly Ala Leu Gly
        115                 120                 125
```

```
Met Met Leu Gly Leu Cys Tyr Arg Leu Ser Cys Val Leu Phe Leu Leu
    130                 135                 140

Pro Tyr Trp Tyr Val Phe Leu Leu Asp Lys Thr Ser Trp Asn Asn His
145                 150                 155                 160

Ser Tyr Leu Tyr Gly Leu Leu Ala Phe Gln Leu Thr Phe Met Asp Ala
                165                 170                 175

Asn His Tyr Trp Ser Val Asp Gly Leu Leu Asn Ala Arg Lys Lys Asn
            180                 185                 190

Ala His Val Pro Leu Trp Asn Tyr Thr Val Leu Arg Gly Gln Ile Phe
        195                 200                 205

Ile Val Tyr Phe Ile Ala Gly Val Lys Lys Leu Asp Ala Asp Trp Val
    210                 215                 220

Gly Gly Tyr Ser Met Glu His Leu Ser Arg His Trp Leu Phe Ser Pro
225                 230                 235                 240

Phe Lys Leu Val Leu Ser Glu Glu Leu Thr Ser Leu Leu Val Val His
                245                 250                 255

Trp Cys Gly Leu Leu Leu Asp Leu Ser Ala Gly Phe Leu Leu Phe Phe
            260                 265                 270

Asp Ala Ser Arg Pro Val Gly Leu Phe Phe Val Ser Tyr Phe His Cys
        275                 280                 285

Met Asn Ser Gln Leu Phe Ser Ile Gly Met Phe Pro Tyr Val Met Leu
    290                 295                 300

Ala Ser Ser Pro Leu Phe Cys Ser Ala Glu Trp Pro Arg Lys Leu Val
305                 310                 315                 320

Ala Arg Cys Pro Lys Arg Leu Gln Glu Leu Leu Pro Thr Lys Ala Ala
                325                 330                 335

Pro Arg Pro Ser Ala Ser Cys Val Tyr Lys Arg Ser Arg Gly Lys Ala
            340                 345                 350

Gly Pro Lys Pro Gly Leu Arg His Gln Leu Gly Ala Ile Phe Thr Leu
        355                 360                 365

Leu Tyr Leu Leu Glu Gln Leu Phe Leu Pro Tyr Ser His Phe Leu Thr
    370                 375                 380

Gln Gly Tyr Asn Asn Trp Thr Asn Gly Leu Tyr Gly Tyr Ser Trp Asp
385                 390                 395                 400

Met Met Val His Ser Arg Ser His Gln His Val Lys Ile Thr Tyr Arg
                405                 410                 415

Asp Gly Leu Thr Gly Glu Leu Gly Tyr Leu Asn Pro Gly Val Phe Thr
            420                 425                 430

Gln Ser Arg Arg Trp Lys Asp His Ala Asp Met Leu Lys Gln Tyr Ala
        435                 440                 445

Thr Cys Leu Ser Leu Leu Leu Pro Lys Tyr Asn Val Thr Glu Pro Gln
    450                 455                 460

Ile Tyr Phe Asp Ile Trp Val Ser Ile Asn Asp Arg Phe Gln Gln Arg
465                 470                 475                 480

Leu Phe Asp Pro Arg Val Asp Ile Val Gln Ala Val Trp Ser Pro Phe
                485                 490                 495

Gln Arg Thr Pro Trp Val Gln Pro Leu Leu Met Asp Leu Ser Pro Trp
            500                 505                 510

Arg Thr Lys Leu Gln Asp Ile Lys Ser Ser Leu Asp Asn His Thr Glu
        515                 520                 525

Val Val Phe Ile Ala Asp Phe Pro Gly Leu His Leu Glu Asn Phe Val
    530                 535                 540

Ser Glu Asp Leu Gly Asn Thr Ser Ile Gln Leu Leu Gln Gly Glu Val
```

```
545                 550                 555                 560

Thr Val Glu Leu Val Ala Glu Gln Lys Asn Gln Thr Leu Gln Glu Gly
                565                 570                 575

Glu Lys Met Gln Leu Pro Ala Gly Glu Tyr His Lys Val Tyr Thr Val
            580                 585                 590

Ser Ser Ser Pro Ser Cys Tyr Met Tyr Val Tyr Val Asn Thr Thr Glu
        595                 600                 605

Val Ala Leu Glu Gln Asp Leu Ala Tyr Leu Gln Glu Leu Lys Glu Lys
    610                 615                 620

Val Glu Asn Gly Ser Glu Thr Gly Pro Leu Pro Pro Glu Leu Gln Pro
625                 630                 635                 640

Leu Leu Glu Gly Glu Val Lys Gly Gly Pro Glu Pro Thr Pro Leu Val
                645                 650                 655

Gln Thr Phe Leu Arg Arg Gln Arg Lys Leu Gln Glu Ile Glu Arg Arg
            660                 665                 670

Arg Asn Ser Pro Phe His Glu Arg Phe Leu Arg Phe Val Leu Arg Lys
        675                 680                 685

Leu Tyr Val Phe Arg Arg Ser Phe Leu Met Thr Arg Ile Ser Leu Arg
    690                 695                 700

Asn Leu Leu Leu Gly Arg Pro Ser Leu Glu Gln Leu Ala Gln Glu Val
705                 710                 715                 720

Thr Tyr Ala Asn Leu Arg Pro Phe Glu Pro Val Asp Glu Ser Ser Ala
                725                 730                 735

Ser Asn Thr Asp Ser Ser Asn His Pro Ser Glu Pro Asp Ser Glu His
            740                 745                 750

Val His Ser Glu Phe
        755
```

<210> SEQ ID NO 10
<211> LENGTH: 5555
<212> TYPE: DNA
<213> ORGANISM: Mus musculus

<400> SEQUENCE: 10

```
ggctgtggga gagcagaaga ggagctggaa gagcagccta caacagctgt cgggagggac      60

cagggctagt tcacacttgg aagctgggat gccaggaccg gccctcctgc ctctctcggt     120

ctccatcggc ctcctggtca gctcactcca cactgagacg attctgaagt aagatgctcc     180

tggctcctca cagactctgc tacaagagac agagtgaagt gtccccaggg ctcagagcct     240

ttgactctgc tccttccctt cccacggctg agttggcaca ggagcacctg ggtgagctgc     300

accagactta agaagatgag gcccctgatt ctgttagctg ccctcctctg gctccaggac     360

tctttggccc aggaagatgt atgctcatcc ttggatggga gcccagacag gcagggtgga     420

ggtccacctc tgagtgtgaa cgtcagcagc cgcggaaagc ctaccagcct gtttctgagc     480

tgggtagctg cagagccagg tggatttgac tatgccctct gcctcagggc tatgaacttg     540

tcgggttttc cagaagggca acagctccaa gctcatacca acgagtccag ctttgagttc     600

catggcctgg tgccagggag tcgctaccag ctggaactga ctgtcctaag accctgttgg     660

cagaatgtca caattaccct cactgctcga actgccccta cagtggtccg tggactgcaa     720

ctgcatagca ctgggagccc agccagcctg gaagcctcat ggagcgatgc ctctggggat     780

caagacagct atcaacttct cctctaccac ccggaatccc acactctggc atgtaatgtc     840

tctgtgtccc ctgacaccct gtcttacaat tttggtgacc tcttgccagg tagtcagtat     900
```

-continued

```
gtcttggagg ttatcacctg ggctggcagt ctccatgcga agactagcat cctccaatgg    960
acagagcctg tccctcctga tcacctaaca ctgcgtgcct tgggtaccag tagcctgcaa   1020
gccttctgga acagctctga aggggccacc tggtttcacc tgatacttac agacctccta   1080
gagggtacca acctgaccaa agtggtcaga caaggcatct caacccacac cttccttcgc   1140
ctgtctccgg gtacacctta ccagctgaag atctgtgctg ctgctgggcc ccaccagatt   1200
tggggaccca atgccactga gtggacctat ccctcttacc catctgacct ggtgctgacc   1260
cccttatgga atgagctctg ggcaagctgg aaggcagggc agggagcccg ggatggctat   1320
gtactgaagt taagtgggcc agtggagaat acaactactc tgggtcctga ggagtgcaac   1380
gctgtcttcc cagggcccct gcctccagga cactacactt tggggctgag ggttctagct   1440
ggaccttatg atgcctgggt agagggcagt atctggctgg ctgaatctgc tgctcgtccc   1500
atggaggtcc ctggtgccag actgtggcta gaaggactgg aagctactaa gcaacctggg   1560
agacgggcgc tgctctattc tgttgatgcc ccaggcctcc tagggaacat ctctgtgtct   1620
tctggtgcca ctcatgtcac cttctgtggc ttggtacccg gagcgcacta cagggtggac   1680
attgcctcat ccatgggaga catcactcag agcctcacag gctacacaag tcccctgcca   1740
ccacagtctc tggagatcat cagccggaac agcccatctg acctgactat cggttgggct   1800
ccagcaccag ggcagatgga aggttataag gtcacctggc atcaggatgg cagccagagg   1860
tcacctggcg accttgttga cttgggccct gacatttcga gcctgactct gaaatctctg   1920
gtacctggtt cctgctacac cgtgtcagca tgggcctggt ctgggaacct cagctctgac   1980
tctcagaaga ttcacagttg cacccgtccc gctcctccca ccaacctgag cctgggcttt   2040
gcccaccagc ctgcaacact gagggcttcc tggtgtcacc caccgggtgg cagggatgcc   2100
tttcagttac ggctttacag gctgaggccc ctgacactgg aaagtgagaa gatcctatcc   2160
caggaggccc agaacttctc ctgggcccag ctgcctgcag gctatgaatt ccaggtacag   2220
ctgtctacct tgtgggggtc ggaggagagc ggcagtgcca acaccacagg ctggacaccc   2280
ccctcagctc ctacattggt aaatgtgacc agtgaagccc ccacccagct ccacgtatcc   2340
tgggtccacg ctgctgggga ccggagcagc taccaagtga ccctatacca ggagagcact   2400
cggacagcca ccagcattgt ggggcccaag gcagacagca caagcttttg ggggtttgact  2460
cctggcacta agtacaaggt ggaagccatc tcctgggctg ggcccctta cactgcagca    2520
gccaacgttt ctgcttggac ctacccactc acacccaatg agctgctcgc ctctatgcag   2580
gcaggcagtg ctgtggttaa cctggcctgg cccagtggtc ccttggggca agggacatgc   2640
catgcccaac tctcagatgc tggacacctt tcatgggagc aaccgctgtc gctaggccaa   2700
gacctcctca tgctaaggaa tcttatacca ggacatacgg tttcattgtc tgtgaagtgt   2760
cgggcaggac cactccaggc ctccactcac cccctggtgc tgtctgtaga gcctggccct   2820
gtggaagatg tgttctgtca acctgaggcc acctacctgt ccctgaactg gacgatgcct   2880
actggagatg tggctgtctg tctggtggag gtagagcagc tggtgccagg agggagcgct   2940
cattttgtct tccaggtcaa cacctcggag gatgcacttc tgctgcccaa cttgacgccc   3000
accacttctt accgccttag cctcactgtg ctgggtggga atcgccagtg gagccgggcg   3060
gttaccctgg tgtgcactac ttctgctgag gtttggcacc ccccagagct agctgaggcc   3120
ccccaggtgg agctggggac agggatgggt gtgacagtca cacgtggcat gtttggtaaa   3180
gatgacgggc agatccagtg gtatggcata attgccacca tcaacatgac actggcccag   3240
ccttcccagg aagccatcaa ccacacatgg tatgaccact actatagagg acatgactcc   3300
```

```
tacctggctc tcctgttccc aaaccccttc tacccagagc cttgggctgt gccaagatcc   3360
tggacagtac ctgtgggtac agaggactgt gacaacaccc aggagatatg caatgggcat   3420
ctcaagccag gcttccagta taggttcagc attgcagcct ttagtaggct cagctctcca   3480
gagaccatcc tggccttctc cgccttctca gagcctcagg ctagcatctc tctggtggcc   3540
atgcccctga cagttatgat ggggactgtg gtgggctgca tcatcattgt gtgtgcagtg   3600
ctatgcttgt tgtgccggcg gcgcctgaag ggaccaaggt cagagaagaa tggcttttcc   3660
caggagttga tgccttacaa cctgtggcgg acccatcggc ccatccccag ccatagcttc   3720
cggcagagct atgaggccaa gagtgcacgt gcacaccagg ccttcttcca ggaatttgag   3780
gagctgaagg aggtgggcaa ggaccagccc agactagagg ctgagcatcc tgccaacatc   3840
accaagaacc ggtacccaca cgtgctacct tatgaccact ccagggtcag gctgacccag   3900
ctatcaggag agcctcattc tgactacatc aatgccaact tcatcccagg ctatagccac   3960
ccacaggaga tcattgccac ccaggggcct ctcaaaaaga cggtcgagga cttctggcgg   4020
ttggtgtggg agcagcaagt ccacgtgatc atcatgctaa ctgtgggcat ggagaatggg   4080
cgggtactgt gtgagcacta ctggccagtc aactccacgc ctgtcaccca cggtcacatc   4140
accacccacc tcctggcaga ggaatctgag gacgagtgga ccaggaggga attccagctg   4200
cagcacggtg cagagcaaaa acagaggcgc gtgaagcagc tgcagttcac gacctggcca   4260
gaccacagtg tccccgaggc tcccagctct ctgctcgctt ttgtggaact ggtgcaggag   4320
gaggtgaagg caactcaggg caaggggccc atcctggtgc attgcagtgc gggtgtgggc   4380
aggacaggca cctttgtggc tctcttaccg gctgttcgac aactagagga agaacaggtg   4440
gtcgatgtgt tcaacactgt gtacatactc cggctgcacc ggcccctcat gatccagacc   4500
ttgagtcaat acatcttcct gcacagctgc ctgctgaaca agattctgga agggccctct   4560
gacgcctcag actccggccc catccctgtg atgaattttg cacaagcttg tgccaagagg   4620
gcagccaatg ccaatgccgg tttcttgaag gagtacaggc tcctgaagca ggccatcaag   4680
gatgagactg gctctctgct gccctctcct gactataatc agaacagcat cgcctcctgt   4740
catcattctc aggagcagtt ggccctggtg gaggagagcc ctgctgataa catgctggca   4800
gcctcgctct tccctggtgg gccgtctggt cgcgaccatg tggtgctgac tggctcggcc   4860
ggaccaaagg aactctggga aatggtgtgg gaacatggcg cctatgtgct tgtctccctg   4920
ggtctgcctg ataccaagga gaagccacaa gacatctggc caatggagat gcagcctatt   4980
gtcacagaca tggtgacagt gcacagagtg gctgagagca acacagctgg ctggcccagt   5040
accctcatca gagttataca tggggacagt gggacggaaa ggcaggttca atgcctgcag   5100
tttccacact gcgagactgg gagtgagctc ccagctaaca ccctactgac cttccttgat   5160
gctgtgggcc agtgctgctc ccggggcaat agcaagaagc cagggaccct gctcagtcac   5220
tccagcaagg tcacaaacca gctgagcacc ttcttggcta tggaacagct gctacagcaa   5280
gcagggaccg agcgcacagt ggatgtcttc agtgtggccc tgaagcagac acaggcctgt   5340
ggccttaaga ccccaacgct ggagcagtat atctacctct acaactgtct gaacagcgca   5400
ttgaggaaca ggctgccccg agctaggaag tgaccttgcc ctgctaggca tcacgttcca   5460
gcaatccacc caggcctggc ttccccagga gaacagatct attcggcctc acgctgtcaa   5520
agggcagagt ctgggaataa agggtaaatc tcgag                              5555
```

<210> SEQ ID NO 11

```
<211> LENGTH: 1705
<212> TYPE: PRT
<213> ORGANISM: Mus musculus

<400> SEQUENCE: 11

Met Arg Pro Leu Ile Leu Leu Ala Ala Leu Leu Trp Leu Gln Asp Ser
1               5                   10                  15

Leu Ala Gln Glu Asp Val Cys Ser Ser Leu Asp Gly Ser Pro Asp Arg
            20                  25                  30

Gln Gly Gly Gly Pro Pro Leu Ser Val Asn Val Ser Ser Arg Gly Lys
        35                  40                  45

Pro Thr Ser Leu Phe Leu Ser Trp Val Ala Ala Glu Pro Gly Gly Phe
    50                  55                  60

Asp Tyr Ala Leu Cys Leu Arg Ala Met Asn Leu Ser Gly Phe Pro Glu
65                  70                  75                  80

Gly Gln Gln Leu Gln Ala His Thr Asn Glu Ser Ser Phe Glu Phe His
                85                  90                  95

Gly Leu Val Pro Gly Ser Arg Tyr Gln Leu Glu Leu Thr Val Leu Arg
            100                 105                 110

Pro Cys Trp Gln Asn Val Thr Ile Thr Leu Thr Ala Arg Thr Ala Pro
        115                 120                 125

Thr Val Val Arg Gly Leu Gln Leu His Ser Thr Gly Ser Pro Ala Ser
    130                 135                 140

Leu Glu Ala Ser Trp Ser Asp Ala Ser Gly Asp Gln Asp Ser Tyr Gln
145                 150                 155                 160

Leu Leu Leu Tyr His Pro Glu Ser His Thr Leu Ala Cys Asn Val Ser
                165                 170                 175

Val Ser Pro Asp Thr Leu Ser Tyr Asn Phe Gly Asp Leu Leu Pro Gly
            180                 185                 190

Ser Gln Tyr Val Leu Glu Val Ile Thr Trp Ala Gly Ser Leu His Ala
        195                 200                 205

Lys Thr Ser Ile Leu Gln Trp Thr Glu Pro Val Pro Pro Asp His Leu
    210                 215                 220

Thr Leu Arg Ala Leu Gly Thr Ser Ser Leu Gln Ala Phe Trp Asn Ser
225                 230                 235                 240

Ser Glu Gly Ala Thr Trp Phe His Leu Ile Leu Thr Asp Leu Leu Glu
                245                 250                 255

Gly Thr Asn Leu Thr Lys Val Val Arg Gln Gly Ile Ser Thr His Thr
            260                 265                 270

Phe Leu Arg Leu Ser Pro Gly Thr Pro Tyr Gln Leu Lys Ile Cys Ala
        275                 280                 285

Ala Ala Gly Pro His Gln Ile Trp Gly Pro Asn Ala Thr Glu Trp Thr
    290                 295                 300

Tyr Pro Ser Tyr Pro Ser Asp Leu Val Leu Thr Pro Leu Trp Asn Glu
305                 310                 315                 320

Leu Trp Ala Ser Trp Lys Ala Gly Gln Gly Ala Arg Asp Gly Tyr Val
                325                 330                 335

Leu Lys Leu Ser Gly Pro Val Glu Asn Thr Thr Thr Leu Gly Pro Glu
            340                 345                 350

Glu Cys Asn Ala Val Phe Pro Gly Pro Leu Pro Pro Gly His Tyr Thr
        355                 360                 365

Leu Gly Leu Arg Val Leu Ala Gly Pro Tyr Asp Ala Trp Val Glu Gly
    370                 375                 380

Ser Ile Trp Leu Ala Glu Ser Ala Ala Arg Pro Met Glu Val Pro Gly
```

```
385                 390                 395                 400

Ala Arg Leu Trp Leu Glu Gly Leu Glu Ala Thr Lys Gln Pro Gly Arg
                405                 410                 415

Arg Ala Leu Leu Tyr Ser Val Asp Ala Pro Gly Leu Leu Gly Asn Ile
            420                 425                 430

Ser Val Ser Ser Gly Ala Thr His Val Thr Phe Cys Gly Leu Val Pro
        435                 440                 445

Gly Ala His Tyr Arg Val Asp Ile Ala Ser Ser Met Gly Asp Ile Thr
    450                 455                 460

Gln Ser Leu Thr Gly Tyr Thr Ser Pro Leu Pro Pro Gln Ser Leu Glu
465                 470                 475                 480

Ile Ile Ser Arg Asn Ser Pro Ser Asp Leu Thr Ile Gly Trp Ala Pro
                485                 490                 495

Ala Pro Gly Gln Met Glu Gly Tyr Lys Val Thr Trp His Gln Asp Gly
            500                 505                 510

Ser Gln Arg Ser Pro Gly Asp Leu Val Asp Leu Gly Pro Asp Ile Ser
        515                 520                 525

Ser Leu Thr Leu Lys Ser Leu Val Pro Gly Ser Cys Tyr Thr Val Ser
    530                 535                 540

Ala Trp Ala Trp Ser Gly Asn Leu Ser Ser Asp Ser Gln Lys Ile His
545                 550                 555                 560

Ser Cys Thr Arg Pro Ala Pro Pro Thr Asn Leu Ser Leu Gly Phe Ala
                565                 570                 575

His Gln Pro Ala Thr Leu Arg Ala Ser Trp Cys His Pro Pro Gly Gly
            580                 585                 590

Arg Asp Ala Phe Gln Leu Arg Leu Tyr Arg Leu Arg Pro Leu Thr Leu
        595                 600                 605

Glu Ser Glu Lys Ile Leu Ser Gln Glu Ala Gln Asn Phe Ser Trp Ala
    610                 615                 620

Gln Leu Pro Ala Gly Tyr Glu Phe Gln Val Gln Leu Ser Thr Leu Trp
625                 630                 635                 640

Gly Ser Glu Glu Ser Gly Ser Ala Asn Thr Thr Gly Trp Thr Pro Pro
                645                 650                 655

Ser Ala Pro Thr Leu Val Asn Val Thr Ser Glu Ala Pro Thr Gln Leu
            660                 665                 670

His Val Ser Trp Val His Ala Ala Gly Asp Arg Ser Ser Tyr Gln Val
        675                 680                 685

Thr Leu Tyr Gln Glu Ser Thr Arg Thr Ala Thr Ser Ile Val Gly Pro
    690                 695                 700

Lys Ala Asp Ser Thr Ser Phe Trp Gly Leu Thr Pro Gly Thr Lys Tyr
705                 710                 715                 720

Lys Val Glu Ala Ile Ser Trp Ala Gly Pro Leu Tyr Thr Ala Ala Ala
                725                 730                 735

Asn Val Ser Ala Trp Thr Tyr Pro Leu Thr Pro Asn Glu Leu Leu Ala
            740                 745                 750

Ser Met Gln Ala Gly Ser Ala Val Val Asn Leu Ala Trp Pro Ser Gly
        755                 760                 765

Pro Leu Gly Gln Gly Thr Cys His Ala Gln Leu Ser Asp Ala Gly His
    770                 775                 780

Leu Ser Trp Glu Gln Pro Leu Ser Leu Gly Gln Asp Leu Leu Met Leu
785                 790                 795                 800

Arg Asn Leu Ile Pro Gly His Thr Val Ser Leu Ser Val Lys Cys Arg
                805                 810                 815
```

```
Ala Gly Pro Leu Gln Ala Ser Thr His Pro Leu Val Leu Ser Val Glu
            820                 825                 830

Pro Gly Pro Val Glu Asp Val Phe Cys Gln Pro Glu Ala Thr Tyr Leu
        835                 840                 845

Ser Leu Asn Trp Thr Met Pro Thr Gly Asp Val Ala Val Cys Leu Val
    850                 855                 860

Glu Val Glu Gln Leu Val Pro Gly Gly Ser Ala His Phe Val Phe Gln
865                 870                 875                 880

Val Asn Thr Ser Glu Asp Ala Leu Leu Leu Pro Asn Leu Thr Pro Thr
                885                 890                 895

Thr Ser Tyr Arg Leu Ser Leu Thr Val Leu Gly Gly Asn Arg Gln Trp
            900                 905                 910

Ser Arg Ala Val Thr Leu Val Cys Thr Thr Ser Ala Glu Val Trp His
        915                 920                 925

Pro Pro Glu Leu Ala Glu Ala Pro Gln Val Glu Leu Gly Thr Gly Met
    930                 935                 940

Gly Val Thr Val Thr Arg Gly Met Phe Gly Lys Asp Asp Gly Gln Ile
945                 950                 955                 960

Gln Trp Tyr Gly Ile Ile Ala Thr Ile Asn Met Thr Leu Ala Gln Pro
                965                 970                 975

Ser Gln Glu Ala Ile Asn His Thr Trp Tyr Asp His Tyr Tyr Arg Gly
            980                 985                 990

His Asp Ser Tyr Leu Ala Leu Leu  Phe Pro Asn Pro Phe  Tyr Pro Glu
        995                 1000                1005

Pro Trp  Ala Val Pro Arg Ser  Trp Thr Val Pro Val  Gly Thr Glu
    1010                1015                1020

Asp Cys  Asp Asn Thr Gln Glu  Ile Cys Asn Gly His  Leu Lys Pro
    1025                1030                1035

Gly Phe  Gln Tyr Arg Phe Ser  Ile Ala Ala Phe Ser  Arg Leu Ser
    1040                1045                1050

Ser Pro  Glu Thr Ile Leu Ala  Phe Ser Ala Phe Ser  Glu Pro Gln
    1055                1060                1065

Ala Ser  Ile Ser Leu Val Ala  Met Pro Leu Thr Val  Met Met Gly
    1070                1075                1080

Thr Val  Val Gly Cys Ile Ile  Ile Val Cys Ala Val  Leu Cys Leu
    1085                1090                1095

Leu Cys  Arg Arg Arg Leu Lys  Gly Pro Arg Ser Glu  Lys Asn Gly
    1100                1105                1110

Phe Ser  Gln Glu Leu Met Pro  Tyr Asn Leu Trp Arg  Thr His Arg
    1115                1120                1125

Pro Ile  Pro Ser His Ser Phe  Arg Gln Ser Tyr Glu  Ala Lys Ser
    1130                1135                1140

Ala Arg  Ala His Gln Ala Phe  Phe Gln Glu Phe Glu  Glu Leu Lys
    1145                1150                1155

Glu Val  Gly Lys Asp Gln Pro  Arg Leu Glu Ala Glu  His Pro Ala
    1160                1165                1170

Asn Ile  Thr Lys Asn Arg Tyr  Pro His Val Leu Pro  Tyr Asp His
    1175                1180                1185

Ser Arg  Val Arg Leu Thr Gln  Leu Ser Gly Glu Pro  His Ser Asp
    1190                1195                1200

Tyr Ile  Asn Ala Asn Phe Ile  Pro Gly Tyr Ser His  Pro Gln Glu
    1205                1210                1215
```

```
Ile Ile  Ala Thr Gln Gly Pro  Leu Lys Lys Thr Val  Glu Asp Phe
    1220                 1225                 1230

Trp Arg  Leu Val Trp Glu Gln  Gln Val His Val Ile  Ile Met Leu
    1235                 1240                 1245

Thr Val  Gly Met Glu Asn Gly  Arg Val Leu Cys Glu  His Tyr Trp
    1250                 1255                 1260

Pro Val  Asn Ser Thr Pro Val  Thr His Gly His Ile  Thr Thr His
    1265                 1270                 1275

Leu Leu  Ala Glu Glu Ser Glu  Asp Glu Trp Thr Arg  Arg Glu Phe
    1280                 1285                 1290

Gln Leu  Gln His Gly Ala Glu  Gln Lys Gln Arg Arg  Val Lys Gln
    1295                 1300                 1305

Leu Gln  Phe Thr Thr Trp Pro  Asp His Ser Val Pro  Glu Ala Pro
    1310                 1315                 1320

Ser Ser  Leu Leu Ala Phe Val  Glu Leu Val Gln Glu  Glu Val Lys
    1325                 1330                 1335

Ala Thr  Gln Gly Lys Gly Pro  Ile Leu Val His Cys  Ser Ala Gly
    1340                 1345                 1350

Val Gly  Arg Thr Gly Thr Phe  Val Ala Leu Leu Pro  Ala Val Arg
    1355                 1360                 1365

Gln Leu  Glu Glu Glu Gln Val  Val Asp Val Phe Asn  Thr Val Tyr
    1370                 1375                 1380

Ile Leu  Arg Leu His Arg Pro  Leu Met Ile Gln Thr  Leu Ser Gln
    1385                 1390                 1395

Tyr Ile  Phe Leu His Ser Cys  Leu Leu Asn Lys Ile  Leu Glu Gly
    1400                 1405                 1410

Pro Ser  Asp Ala Ser Asp Ser  Gly Pro Ile Pro Val  Met Asn Phe
    1415                 1420                 1425

Ala Gln  Ala Cys Ala Lys Arg  Ala Ala Asn Ala Asn  Ala Gly Phe
    1430                 1435                 1440

Leu Lys  Glu Tyr Arg Leu Leu  Lys Gln Ala Ile Lys  Asp Glu Thr
    1445                 1450                 1455

Gly Ser  Leu Leu Pro Ser Pro  Asp Tyr Asn Gln Asn  Ser Ile Ala
    1460                 1465                 1470

Ser Cys  His His Ser Gln Glu  Gln Leu Ala Leu Val  Glu Glu Ser
    1475                 1480                 1485

Pro Ala  Asp Asn Met Leu Ala  Ala Ser Leu Phe Pro  Gly Gly Pro
    1490                 1495                 1500

Ser Gly  Arg Asp His Val Val  Leu Thr Gly Ser Ala  Gly Pro Lys
    1505                 1510                 1515

Glu Leu  Trp Glu Met Val Trp  Glu His Gly Ala Tyr  Val Leu Val
    1520                 1525                 1530

Ser Leu  Gly Leu Pro Asp Thr  Lys Glu Lys Pro Gln  Asp Ile Trp
    1535                 1540                 1545

Pro Met  Glu Met Gln Pro Ile  Val Thr Asp Met Val  Thr Val His
    1550                 1555                 1560

Arg Val  Ala Glu Ser Asn Thr  Ala Gly Trp Pro Ser  Thr Leu Ile
    1565                 1570                 1575

Arg Val  Ile His Gly Asp Ser  Gly Thr Glu Arg Gln  Val Gln Cys
    1580                 1585                 1590

Leu Gln  Phe Pro His Cys Glu  Thr Gly Ser Glu Leu  Pro Ala Asn
    1595                 1600                 1605

Thr Leu  Leu Thr Phe Leu Asp  Ala Val Gly Gln Cys  Cys Ser Arg
```

```
    1610                1615                1620

Gly Asn  Ser Lys Lys Pro Gly  Thr Leu Leu Ser His  Ser Ser Lys
    1625                1630                1635

Val Thr  Asn Gln Leu Ser Thr  Phe Leu Ala Met Glu  Gln Leu Leu
    1640                1645                1650

Gln Gln  Ala Gly Thr Glu Arg  Thr Val Asp Val Phe  Ser Val Ala
    1655                1660                1665

Leu Lys  Gln Thr Gln Ala Cys  Gly Leu Lys Thr Pro  Thr Leu Glu
    1670                1675                1680

Gln Tyr  Ile Tyr Leu Tyr Asn  Cys Leu Asn Ser Ala  Leu Arg Asn
    1685                1690                1695

Arg Leu  Pro Arg Ala Arg Lys
    1700                1705


<210> SEQ ID NO 12
<211> LENGTH: 49
<212> TYPE: PRT
<213> ORGANISM: Homo sapiens

<400> SEQUENCE: 12

Tyr Leu Tyr Gln Trp Leu Gly Ala Pro Val Pro Tyr Pro Asp Pro Leu
1               5                   10                  15

Glu Pro Arg Arg Glu Val Cys Glu Leu Asn Pro Asp Cys Asp Glu Leu
            20                  25                  30

Ala Asp His Ile Gly Phe Gln Glu Ala Tyr Arg Arg Phe Tyr Gly Pro
        35                  40                  45

Val


<210> SEQ ID NO 13
<211> LENGTH: 49
<212> TYPE: PRT
<213> ORGANISM: Homo sapiens
<220> FEATURE:
<221> NAME/KEY: MOD_RES
<222> LOCATION: (17)..(17)
<223> OTHER INFORMATION: Any amino acid or amino acid analog
<220> FEATURE:
<221> NAME/KEY: MOD_RES
<222> LOCATION: (21)..(21)
<223> OTHER INFORMATION: Any amino acid or amino acid analog
<220> FEATURE:
<221> NAME/KEY: MOD_RES
<222> LOCATION: (24)..(24)
<223> OTHER INFORMATION: Any amino acid or amino acid analog
<220> FEATURE:
<223> OTHER INFORMATION: See specification as filed for detailed
      description of substitutions and preferred embodiments

<400> SEQUENCE: 13

Tyr Leu Tyr Gln Trp Leu Gly Ala Pro Val Pro Tyr Pro Asp Pro Leu
1               5                   10                  15

Xaa Pro Arg Arg Xaa Val Cys Xaa Leu Asn Pro Asp Cys Asp Glu Leu
            20                  25                  30

Ala Asp His Ile Gly Phe Gln Glu Ala Tyr Arg Arg Phe Tyr Gly Pro
        35                  40                  45

Val


<210> SEQ ID NO 14
<211> LENGTH: 5446
<212> TYPE: DNA
<213> ORGANISM: Rattus norvegicus
```

<400> SEQUENCE: 14

```
agaacagcct acaacagctg ccttccggga gggaccaggc tagttcacac ttggaagttg     60
ggatgccagg agcagccttc tgtcttccga ggccttcctg ggtctcctgg tcagctcatt    120
ccacactgag atgattctaa agaaagatcc tcacacagac tctgctggaa gaaacaaagt    180
gaagtgtccc cagactttat caggatgagg cccctgattc tgttagctgc cctcctctgg    240
ctccagggct tttggccga ggacgacgca tgctcatcct tggaagggag cccagacagg    300
cagggtggag gtccacttct gagtgtgaac gtcagtagcc atggaaagtc taccagcctg    360
tttctgagct gggtagctgc agagctgggc ggatttgact atgccctcag cctcaggagt    420
gtgaactcct caggttctcc agaagggcaa cagctccagg ctcacacaaa tgagtccggc    480
tttgagttcc atggcctggt gccagggagt cgctaccagc taaaactgac tgtcctaaga    540
ccctgttggc agaatgtcac aattaccctc actgcccgaa ctgccccgac agtggtccgt    600
ggactgcagc tgcatagcgc tgggagccca gccaggctgg aagcctcgtg gagtgatgcc    660
cctggagatc aagacagcta ccaacttctc ctctaccacc tggaatccca aactctggca    720
tgcaatgtct ctgtgtcccc tgacaccctg tcttacagtt ttggcgacct tttgccaggt    780
actcagtatg tcttggaggt tatcacctgg gctggcagtc tccatgcgaa gactagtatc    840
ctccagtgga cagagcctgt ccctcctgat cacctagcac tacgtgcctt gggtaccagt    900
agcctgcaag ccttctggaa cagctctgaa ggggccacct cgtttcacct gatgctcaca    960
gacctcctcg gggcaccaa cacgactgcg gtgatcagac aaggggtctc gacccacacc   1020
tttcttcacc tatctccggg tacacctcat gagctgaaga tttgtgcttc tgctgggccc   1080
caccagatct ggggacccag tgccaccgag tggacctatc cctcttaccc atctgacctg   1140
gtgctgactc ccttacggaa tgagctctgg gccagctgga aggcagggct gggagcccgg   1200
gacggctatg tactgaagtt aagtgggcca atggagagta cgtctaccct gggcccggaa   1260
gagtgcaatg cagtcttccc agggcccctg cctccgggac actacacttt gcagctgaag   1320
gttctagctg gaccttatga tgcctgggtg gagggcagta cctggctggc tgaatctgct   1380
gcccttccca gggaggtccc tggtgccaga ctgtggctag atggactgga agcttccaag   1440
cagcctggga gacgggcgct actctattct gacgatgccc caggctccct agggaacatc   1500
tctgtgccct ctggtgccac tcacgtcatt ttctgtggcc tggtacctgg agcccactat   1560
agggtggaca ttgcctcatc cacgggggac atctctcaga gcatctcagg ctatacaagt   1620
cccctgccac cgcagtcact ggaggtcatc agcaggagca gcccatctga cctgactatt   1680
gcttggggtc cagcaccagg gcagctggaa ggttataagg ttacctggca tcaggatggc   1740
agccagaggt ctcctggcga ccttgttgac ttgggccctg acactttgag cctgactctg   1800
aaatctctgg tacccggctc ctgctacacc gtgtcagcat gggcctgggc cgggaacctc   1860
gactctgact ctcagaagat tcacagctgc acccgccccg ctcctcccac caacctgagt   1920
ctgggctttg cccaccagcc tgcggcactg aaggcttcct ggtatcaccc accgggtggc   1980
agggatgcct ttcacttacg gctttacagg ctgaggcctc tgacactgga aagtgagaag   2040
gtcctacctc gggaggccca gaacttctcc tgggcccagc tgactgcagg ctgtgagttc   2100
caggtacagc tgtctacctt gtgggggtct gagagaagca gcagtgccaa cgccacaggc   2160
tggacacccc cttcagctcc tacactggta aacgtgacca gcgatgctcc tacccagctc   2220
caagtatcct gggcccacgt tcctgggggc cggagccgct accaagtgac cctataccag   2280
gagagtaccc ggacagccac cagcatcatg ggcccaagg aagatggcac gagcttttg   2340
```

```
ggtttgactc ctggcactaa gtacaaggtg gaagtcatct cctgggctgg gcccctctac   2400

actgcagcag ccaacgtttc tgcctggacc tacccactca tacccaatga gctgctcgtg   2460

tcaatgcagg caggcagtgc tgtggttaac ctggcctggc ccagtggtcc cctggggcaa   2520

ggggcatgcc acgcccaact ctcagatgct ggacacctct catgggagca acccctgaaa   2580

ctaggccaag agctcttcat gctaagggat ctcacaccag gacataccat ctcgatgtca   2640

gtgaggtgtc gggcagggcc gctccaggcc tctacgcacc ttgtggtgct gtctgtggag   2700

cctggccctg tggaagatgt gctctgtcat ccagaggcca cctacctggc cctgaactgg   2760

acgatgcctg ctggagacgt ggatgtctgt ctggtggtgg tagagcggct ggtgccggga   2820

gggggcactc attttgtctt ccaggtcaac acctcagggg atgctcttct gttgcccaac   2880

ttgatgccca ccacttctta ccgccttagc ctcaccgttc tgggcaggaa tagtcggtgg   2940

agccgggcgg tttccctggt gtgcagtact tctgctgagg cttggcaccc cccagagcta   3000

gctgagcccc cccaggtgga gctggggaca gggatgggtg tgacagtcat gcgtggcatg   3060

tttggtaaag atgacgggca gatccagtgg tatggcataa ttgccaccat caacatgacg   3120

ctggcccagc cttcccggga agccatcaat tacacatggt atgaccacta ctatagagga   3180

tgtgagtcct tcctggctct cctgttccca aaccccttct acccagagcc ttgggctggg   3240

ccaagatcct ggacagtacc tgtgggtact gaggactgtg acaacaccca agagatatgc   3300

aatgggcgtc tcaagtcagg cttccagtat aggttcagcg ttgtggcctt tagtaggctc   3360

aacactccag agaccatcct cgccttctcg gccttctcag agccccgggc cagcatctct   3420

ctggcgatca ttcccctgac agttatgctg gggggctgtgg tgggcagcat tgtcattgtg   3480

tgtgcagtgc tatgcttgct ccgctggcgg tgcctgaagg gaccaagatc agagaaggat   3540

ggcttttcca aggagctgat gccttacaac ctgtggcgga cccatcggcc tatccccatc   3600

catagcttcc ggcagagcta tgaggccaag agcgcacatg cacaccagac cttcttccag   3660

gaatttgagg agttgaagga ggtaggcaag gaccagcccc gactagaggc tgagcatccg   3720

gacaacatca tcaagaaccg gtacccacac gtgctgccct atgaccactc cagggtcagg   3780

ctgacccagc taccaggaga gcctcattct gactacatca atgccaactt catcccaggc   3840

tatagccaca cacaggagat cattgccacc caggggcctc tcaaaaagac gctagaggac   3900

ttctggcggt tggtatggga gcagcaagtc cacgtgatca tcatgctgac tgtgggcatg   3960

gagaacgggc gggtactgtg tgagcactac tggccagcca actccacgcc tgttactcac   4020

ggtcacatca ccatccacct cctggcagag gagcctgagg atgagtggac caggagggaa   4080

ttccagctgc agcacggtac cgagcaaaaa cagaggcgag tgaagcagct gcagttcact   4140

acctggccag accacagtgt cccggaggct cccagctctc tgctcgcttt tgtagaactg   4200

gtacaggagc aggtgcaggc cactcagggc aagggaccca tcctggtgca ttgcagtgct   4260

ggcgtgggga ggacaggcac ctttgtggct ctcttgcggc tactgcgaca actagaggaa   4320

gagaaggtgg ccgatgtgtt caacactgtg tacatactcc ggttgcaccg gcccctcatg   4380

atccagaccc tgagtcaata catcttcctg cacagttgcc tgctgaacaa gattctggaa   4440

gggccccctg acagctccga ctccggcccc atctctgtga tggattttgc acaggcttgt   4500

gccaagaggg cagccaacgc caatgctggt ttcttgaagg agtacaagct cctgaagcag   4560

gccatcaagg atgggactgg ctctctgctg ccccctcctg actacaatca gaacagcatt   4620

gtctcccgtc gtcattctca ggagcagttc gccctggtgg aggagtgccc tgaggatagc   4680
```

```
atgctggaag cctcactctt ccctggtggt ccgtctggtt gtgatcatgt ggtgctgact   4740

ggctcagccg gaccaaagga actctgggaa atggtgtggg agcatgatgc ccatgtgctc   4800

gtctccctgg gcctgcctga taccaaggag aagccaccag acatctggcc agtggagatg   4860

cagcctattg tcacagacat ggtgacagtg cacagagtgt ctgagagcaa cacaacaact   4920

ggctggccca gcaccctctt cagagtcata cacggggaga gtggaaagga aaggcaggtt   4980

caatgcctgc aatttccatg ctctgagtct gggtgtgagc tcccagctaa caccctactg   5040

accttccttg atgctgtggg ccagtgctgc ttccggggca agagcaagaa gccagggacc   5100

ctgctcagcc actccagcaa aaacacaaac cagctgggca ccttcttggc tatggaacag   5160

ctgttacagc aagcagggac agagcgcaca gtggacgtct tcaatgtggc cctgaagcag   5220

tcacaggcct gcggccttat gaccccaaca ctggagcagt atatctacct ctacaactgt   5280

ctgaacagcg cactgctgaa cgggctgccc agagctggga agtggcctgc gccctgctag   5340

gcgtcatgtt ccagcaaatc cacccaggcc tgacttccct aggagagtgg atccaccggg   5400

cctcacactg tccaagggca gagtccagga ataaagagac atggtc                  5446
```

```
<210> SEQ ID NO 15
<211> LENGTH: 1711
<212> TYPE: PRT
<213> ORGANISM: Rattus norvegicus

<400> SEQUENCE: 15

Met Arg Pro Leu Ile Leu Leu Ala Ala Leu Leu Trp Leu Gln Gly Phe
1               5                   10                  15

Leu Ala Glu Asp Asp Ala Cys Ser Ser Leu Glu Gly Ser Pro Asp Arg
            20                  25                  30

Gln Gly Gly Gly Pro Leu Leu Ser Val Asn Val Ser Ser His Gly Lys
        35                  40                  45

Ser Thr Ser Leu Phe Leu Ser Trp Val Ala Ala Glu Leu Gly Gly Phe
    50                  55                  60

Asp Tyr Ala Leu Ser Leu Arg Ser Val Asn Ser Ser Gly Ser Pro Glu
65                  70                  75                  80

Gly Gln Gln Leu Gln Ala His Thr Asn Glu Ser Gly Phe Glu Phe His
                85                  90                  95

Gly Leu Val Pro Gly Ser Arg Tyr Gln Leu Lys Leu Thr Val Leu Arg
            100                 105                 110

Pro Cys Trp Gln Asn Val Thr Ile Thr Leu Thr Ala Arg Thr Ala Pro
        115                 120                 125

Thr Val Val Arg Gly Leu Gln Leu His Ser Ala Gly Ser Pro Ala Arg
    130                 135                 140

Leu Glu Ala Ser Trp Ser Asp Ala Pro Gly Asp Gln Asp Ser Tyr Gln
145                 150                 155                 160

Leu Leu Leu Tyr His Leu Glu Ser Gln Thr Leu Ala Cys Asn Val Ser
                165                 170                 175

Val Ser Pro Asp Thr Leu Ser Tyr Ser Phe Gly Asp Leu Leu Pro Gly
            180                 185                 190

Thr Gln Tyr Val Leu Glu Val Ile Thr Trp Ala Gly Ser Leu His Ala
        195                 200                 205

Lys Thr Ser Ile Leu Gln Trp Thr Glu Pro Val Pro Pro Asp His Leu
    210                 215                 220

Ala Leu Arg Ala Leu Gly Thr Ser Ser Leu Gln Ala Phe Trp Asn Ser
225                 230                 235                 240
```

```
Ser Glu Gly Ala Thr Ser Phe His Leu Met Leu Thr Asp Leu Leu Gly
                245                 250                 255

Gly Thr Asn Thr Thr Ala Val Ile Arg Gln Gly Val Ser Thr His Thr
            260                 265                 270

Phe Leu His Leu Ser Pro Gly Thr Pro His Glu Leu Lys Ile Cys Ala
        275                 280                 285

Ser Ala Gly Pro His Gln Ile Trp Gly Pro Ser Ala Thr Glu Trp Thr
    290                 295                 300

Tyr Pro Ser Tyr Pro Ser Asp Leu Val Leu Thr Pro Leu Arg Asn Glu
305                 310                 315                 320

Leu Trp Ala Ser Trp Lys Ala Gly Leu Gly Ala Arg Asp Gly Tyr Val
                325                 330                 335

Leu Lys Leu Ser Gly Pro Met Glu Ser Thr Ser Thr Leu Gly Pro Glu
            340                 345                 350

Glu Cys Asn Ala Val Phe Pro Gly Pro Leu Pro Pro Gly His Tyr Thr
        355                 360                 365

Leu Gln Leu Lys Val Leu Ala Gly Pro Tyr Asp Ala Trp Val Glu Gly
    370                 375                 380

Ser Thr Trp Leu Ala Glu Ser Ala Ala Leu Pro Arg Glu Val Pro Gly
385                 390                 395                 400

Ala Arg Leu Trp Leu Asp Gly Leu Glu Ala Ser Lys Gln Pro Gly Arg
                405                 410                 415

Arg Ala Leu Leu Tyr Ser Asp Asp Ala Pro Gly Ser Leu Gly Asn Ile
            420                 425                 430

Ser Val Pro Ser Gly Ala Thr His Val Ile Phe Cys Gly Leu Val Pro
        435                 440                 445

Gly Ala His Tyr Arg Val Asp Ile Ala Ser Ser Thr Gly Asp Ile Ser
    450                 455                 460

Gln Ser Ile Ser Gly Tyr Thr Ser Pro Leu Pro Pro Gln Ser Leu Glu
465                 470                 475                 480

Val Ile Ser Arg Ser Ser Pro Ser Asp Leu Thr Ile Ala Trp Gly Pro
                485                 490                 495

Ala Pro Gly Gln Leu Glu Gly Tyr Lys Val Thr Trp His Gln Asp Gly
            500                 505                 510

Ser Gln Arg Ser Pro Gly Asp Leu Val Asp Leu Gly Pro Asp Thr Leu
        515                 520                 525

Ser Leu Thr Leu Lys Ser Leu Val Pro Gly Ser Cys Tyr Thr Val Ser
    530                 535                 540

Ala Trp Ala Trp Ala Gly Asn Leu Asp Ser Asp Ser Gln Lys Ile His
545                 550                 555                 560

Ser Cys Thr Arg Pro Ala Pro Pro Thr Asn Leu Ser Leu Gly Phe Ala
                565                 570                 575

His Gln Pro Ala Ala Leu Lys Ala Ser Trp Tyr His Pro Pro Gly Gly
            580                 585                 590

Arg Asp Ala Phe His Leu Arg Leu Tyr Arg Leu Arg Pro Leu Thr Leu
        595                 600                 605

Glu Ser Glu Lys Val Leu Pro Arg Glu Ala Gln Asn Phe Ser Trp Ala
    610                 615                 620

Gln Leu Thr Ala Gly Cys Glu Phe Gln Val Gln Leu Ser Thr Leu Trp
625                 630                 635                 640

Gly Ser Glu Arg Ser Ser Ser Ala Asn Ala Thr Gly Trp Thr Pro Pro
                645                 650                 655

Ser Ala Pro Thr Leu Val Asn Val Thr Ser Asp Ala Pro Thr Gln Leu
```

```
            660                 665                 670

Gln Val Ser Trp Ala His Val Pro Gly Gly Arg Ser Arg Tyr Gln Val
        675                 680                 685

Thr Leu Tyr Gln Glu Ser Thr Arg Thr Ala Thr Ser Ile Met Gly Pro
    690                 695                 700

Lys Glu Asp Gly Thr Ser Phe Leu Gly Leu Thr Pro Gly Thr Lys Tyr
705                 710                 715                 720

Lys Val Glu Val Ile Ser Trp Ala Gly Pro Leu Tyr Thr Ala Ala Ala
                725                 730                 735

Asn Val Ser Ala Trp Thr Tyr Pro Leu Ile Pro Asn Glu Leu Leu Val
            740                 745                 750

Ser Met Gln Ala Gly Ser Ala Val Val Asn Leu Ala Trp Pro Ser Gly
        755                 760                 765

Pro Leu Gly Gln Gly Ala Cys His Ala Gln Leu Ser Asp Ala Gly His
    770                 775                 780

Leu Ser Trp Glu Gln Pro Leu Lys Leu Gly Gln Glu Leu Phe Met Leu
785                 790                 795                 800

Arg Asp Leu Thr Pro Gly His Thr Ile Ser Met Ser Val Arg Cys Arg
                805                 810                 815

Ala Gly Pro Leu Gln Ala Ser Thr His Leu Val Val Leu Ser Val Glu
            820                 825                 830

Pro Gly Pro Val Glu Asp Val Leu Cys His Pro Glu Ala Thr Tyr Leu
        835                 840                 845

Ala Leu Asn Trp Thr Met Pro Ala Gly Asp Val Asp Val Cys Leu Val
    850                 855                 860

Val Val Glu Arg Leu Val Pro Gly Gly Gly Thr His Phe Val Phe Gln
865                 870                 875                 880

Val Asn Thr Ser Gly Asp Ala Leu Leu Leu Pro Asn Leu Met Pro Thr
                885                 890                 895

Thr Ser Tyr Arg Leu Ser Leu Thr Val Leu Gly Arg Asn Ser Arg Trp
            900                 905                 910

Ser Arg Ala Val Ser Leu Val Cys Ser Thr Ser Ala Glu Ala Trp His
        915                 920                 925

Pro Pro Glu Leu Ala Glu Pro Pro Gln Val Glu Leu Gly Thr Gly Met
    930                 935                 940

Gly Val Thr Val Met Arg Gly Met Phe Gly Lys Asp Asp Gly Gln Ile
945                 950                 955                 960

Gln Trp Tyr Gly Ile Ile Ala Thr Ile Asn Met Thr Leu Ala Gln Pro
                965                 970                 975

Ser Arg Glu Ala Ile Asn Tyr Thr Trp Tyr Asp His Tyr Tyr Arg Gly
            980                 985                 990

Cys Glu Ser Phe Leu Ala Leu Leu  Phe Pro Asn Pro Phe  Tyr Pro Glu
        995                 1000                1005

Pro Trp  Ala Gly Pro Arg Ser  Trp Thr Val Pro Val  Gly Thr Glu
    1010                 1015                 1020

Asp Cys  Asp Asn Thr Gln Glu  Ile Cys Asn Gly Arg  Leu Lys Ser
    1025                 1030                 1035

Gly Phe  Gln Tyr Arg Phe Ser  Val Val Ala Phe Ser  Arg Leu Asn
    1040                 1045                 1050

Thr Pro  Glu Thr Ile Leu Ala  Phe Ser Ala Phe Ser  Glu Pro Arg
    1055                 1060                 1065

Ala Ser  Ile Ser Leu Ala Ile  Ile Pro Leu Thr Val  Met Leu Gly
    1070                 1075                 1080
```

```
Ala Val  Val Gly Ser Ile Val  Ile Val Cys Ala Val  Leu Cys Leu
    1085                 1090                 1095

Leu Arg  Trp Arg Cys Leu Lys  Gly Pro Arg Ser Glu  Lys Asp Gly
    1100                 1105                 1110

Phe Ser  Lys Glu Leu Met Pro  Tyr Asn Leu Trp Arg  Thr His Arg
    1115                 1120                 1125

Pro Ile  Pro Ile His Ser Phe  Arg Gln Ser Tyr Glu  Ala Lys Ser
    1130                 1135                 1140

Ala His  Ala His Gln Thr Phe  Phe Gln Glu Phe Glu  Glu Leu Lys
    1145                 1150                 1155

Glu Val  Gly Lys Asp Gln Pro  Arg Leu Glu Ala Glu  His Pro Asp
    1160                 1165                 1170

Asn Ile  Ile Lys Asn Arg Tyr  Pro His Val Leu Pro  Tyr Asp His
    1175                 1180                 1185

Ser Arg  Val Arg Leu Thr Gln  Leu Pro Gly Glu Pro  His Ser Asp
    1190                 1195                 1200

Tyr Ile  Asn Ala Asn Phe Ile  Pro Gly Tyr Ser His  Thr Gln Glu
    1205                 1210                 1215

Ile Ile  Ala Thr Gln Gly Pro  Leu Lys Lys Thr Leu  Glu Asp Phe
    1220                 1225                 1230

Trp Arg  Leu Val Trp Glu Gln  Gln Val His Val Ile  Ile Met Leu
    1235                 1240                 1245

Thr Val  Gly Met Glu Asn Gly  Arg Val Leu Cys Glu  His Tyr Trp
    1250                 1255                 1260

Pro Ala  Asn Ser Thr Pro Val  Thr His Gly His Ile  Thr Ile His
    1265                 1270                 1275

Leu Leu  Ala Glu Glu Pro Glu  Asp Glu Trp Thr Arg  Arg Glu Phe
    1280                 1285                 1290

Gln Leu  Gln His Gly Thr Glu  Gln Lys Gln Arg Arg  Val Lys Gln
    1295                 1300                 1305

Leu Gln  Phe Thr Thr Trp Pro  Asp His Ser Val Pro  Glu Ala Pro
    1310                 1315                 1320

Ser Ser  Leu Leu Ala Phe Val  Glu Leu Val Gln Glu  Gln Val Gln
    1325                 1330                 1335

Ala Thr  Gln Gly Lys Gly Pro  Ile Leu Val His Cys  Ser Ala Gly
    1340                 1345                 1350

Val Gly  Arg Thr Gly Thr Phe  Val Ala Leu Leu Arg  Leu Leu Arg
    1355                 1360                 1365

Gln Leu  Glu Glu Glu Lys Val  Ala Asp Val Phe Asn  Thr Val Tyr
    1370                 1375                 1380

Ile Leu  Arg Leu His Arg Pro  Leu Met Ile Gln Thr  Leu Ser Gln
    1385                 1390                 1395

Tyr Ile  Phe Leu His Ser Cys  Leu Leu Asn Lys Ile  Leu Glu Gly
    1400                 1405                 1410

Pro Pro  Asp Ser Ser Asp Ser  Gly Pro Ile Ser Val  Met Asp Phe
    1415                 1420                 1425

Ala Gln  Ala Cys Ala Lys Arg  Ala Ala Asn Ala Asn  Ala Gly Phe
    1430                 1435                 1440

Leu Lys  Glu Tyr Lys Leu Leu  Lys Gln Ala Ile Lys  Asp Gly Thr
    1445                 1450                 1455

Gly Ser  Leu Leu Pro Pro Pro  Asp Tyr Asn Gln Asn  Ser Ile Val
    1460                 1465                 1470
```

```
Ser Arg  Arg His Ser Gln Glu  Gln Phe Ala Leu Val  Glu Glu Cys
    1475                 1480                 1485

Pro Glu  Asp Ser Met Leu Glu  Ala Ser Leu Phe Pro  Gly Gly Pro
    1490                 1495                 1500

Ser Gly  Cys Asp His Val Val  Leu Thr Gly Ser Ala  Gly Pro Lys
    1505                 1510                 1515

Glu Leu  Trp Glu Met Val Trp  Glu His Asp Ala His  Val Leu Val
    1520                 1525                 1530

Ser Leu  Gly Leu Pro Asp Thr  Lys Glu Lys Pro Pro  Asp Ile Trp
    1535                 1540                 1545

Pro Val  Glu Met Gln Pro Ile  Val Thr Asp Met Val  Thr Val His
    1550                 1555                 1560

Arg Val  Ser Glu Ser Asn Thr  Thr Thr Gly Trp Pro  Ser Thr Leu
    1565                 1570                 1575

Phe Arg  Val Ile His Gly Glu  Ser Gly Lys Glu Arg  Gln Val Gln
    1580                 1585                 1590

Cys Leu  Gln Phe Pro Cys Ser  Glu Ser Gly Cys Glu  Leu Pro Ala
    1595                 1600                 1605

Asn Thr  Leu Leu Thr Phe Leu  Asp Ala Val Gly Gln  Cys Cys Phe
    1610                 1615                 1620

Arg Gly  Lys Ser Lys Lys Pro  Gly Thr Leu Leu Ser  His Ser Ser
    1625                 1630                 1635

Lys Asn  Thr Asn Gln Leu Gly  Thr Phe Leu Ala Met  Glu Gln Leu
    1640                 1645                 1650

Leu Gln  Gln Ala Gly Thr Glu  Arg Thr Val Asp Val  Phe Asn Val
    1655                 1660                 1665

Ala Leu  Lys Gln Ser Gln Ala  Cys Gly Leu Met Thr  Pro Thr Leu
    1670                 1675                 1680

Glu Gln  Tyr Ile Tyr Leu Tyr  Asn Cys Leu Asn Ser  Ala Leu Leu
    1685                 1690                 1695

Asn Gly  Leu Pro Arg Ala Gly  Lys Trp Pro Ala Pro  Cys
    1700                 1705                 1710
```

<210> SEQ ID NO 16
<211> LENGTH: 3247
<212> TYPE: DNA
<213> ORGANISM: Homo sapiens

<400> SEQUENCE: 16

```
gggcgggcct cggggctaag agcgcgacgc ctagagcggc agacggcgca gtgggccgag     60

aaggaggcgc agcagccgcc ctggcccgtc atggagatgg aaaaggagtt cgagcagatc    120

gacaagtccg ggagctgggc ggccatttac caggatatcc gacatgaagc cagtgacttc    180

ccatgtagag tggccaagct tcctaagaac aaaaaccgaa ataggtacag agacgtcagt    240

ccctttgacc atagtcggat taaactacat caagaagata atgactatat caacgctagt    300

ttgataaaaa tggaagaagc ccaaaggagt tacattctta cccagggccc tttgcctaac    360

acatgcggtc acttttggga gatggtgtgg gagcagaaaa gcaggggtgt cgtcatgctc    420

aacagagtga tggagaaagg ttcgttaaaa tgcgcacaat actggccaca aaaagaagaa    480

aaagagatga tctttgaaga cacaaatttg aaattaacat tgatctctga agatatcaag    540

tcatattata cagtgcgaca gctagaattg gaaaacctta caacccaaga aactcgagag    600

atcttacatt tccactatac cacatggcct gactttggag tccctgaatc accagcctca    660

ttcttgaact tcttttcaa agtccgagag tcagggtcac tcagcccgga gcacgggccc    720
```

```
gttgtggtgc actgcagtgc aggcatcggc aggtctggaa ccttctgtct ggctgatacc    780
tgcctcctgc tgatggacaa gaggaaagac ccttcttccg ttgatatcaa gaaagtgctg    840
ttagaaatga ggaagtttcg gatggggttg atccagacag ccgaccagct gcgcttctcc    900
tacctggctg tgatcgaagg tgccaaattc atcatggggg actcttccgt gcaggatcag    960
tggaaggagc tttcccacga ggacctggag cccccacccg agcatatccc cccacctccc   1020
cggccaccca aacgaatcct ggagccacac aatgggaaat gcagggagtt cttcccaaat   1080
caccagtggg tgaaggaaga gacccaggag gataaagact gccccatcaa ggaagaaaaa   1140
ggaagcccct taaatgccgc accctacggc atcgaaagca tgagtcaaga cactgaagtt   1200
agaagtcggg tcgtgggggg aagtcttcga ggtgcccagg ctgcctcccc agccaaaggg   1260
gagccgtcac tgcccgagaa ggacgaggac catgcactga gttactggaa gcccttcctg   1320
gtcaacatgt gcgtggctac ggtcctcacg gccggcgctt acctctgcta caggttcctg   1380
ttcaacagca acacatagcc tgaccctcct ccactccacc tccacccact gtccgcctct   1440
gcccgcagag cccacgcccg actagcaggc atgccgcggt aggtaagggc cgccggaccg   1500
cgtagagagc cgggccccgg acggacgttg gttctgcact aaaacccatc ttccccggat   1560
gtgtgtctca cccctcatcc ttttactttt tgccccttcc actttgagta ccaaatccac   1620
aagccatttt ttgaggagag tgaaagagag taccatgctg gcggcgcaga gggaaggggc   1680
ctacacccgt cttggggctc gccccaccca gggctccctc ctggagcatc ccaggcggcg   1740
cacgccaaca gcccccccct tgaatctgca gggagcaact ctccactcca tatttattta   1800
aacaattttt tccccaaagg catccatagt gcactagcat ttcttgaacc caataatgta   1860
ttaaaatttt ttgatgtcag ccttgcatca agggctttat caaaaagtac aataataaat   1920
cctcaggtag tactgggaat ggaaggcttt gccatgggcc tgctgcgtca gaccagtact   1980
gggaaggagg acggttgtaa gcagttgtta tttagtgata ttgtgggtaa cgtgagaaga   2040
tagaacaatg ctataatata taatgaacac gtgggtattt aataagaaac atgatgtgag   2100
attactttgt cccgcttatt ctcctccctg ttatctgcta gatctagttc tcaatcactg   2160
ctcccccgtg tgtattagaa tgcatgtaag gtcttcttgt gtcctgatga aaaatatgtg   2220
cttgaaatga gaaactttga tctctgctta ctaatgtgcc ccatgtccaa gtccaacctg   2280
cctgtgcatg acctgatcat tacatggctg tggttcctaa gcctgttgct gaagtcattg   2340
tcgctcagca atagggtgca gttttccagg aataggcatt tgctaattcc tggcatgaca   2400
ctctagtgac ttcctggtga ggcccagcct gtcctggtac agcagggtct tgctgtaact   2460
cagacattcc aagggtatgg gaagccatat tcacacctca cgctctggac atgatttagg   2520
gaagcaggga cacccccgc cccccacctt tgggatcagc ctccgccatt ccaagtcaac   2580
actcttcttg agcagaccgt gatttggaag agaggcacct gctggaaacc acacttcttg   2640
aaacagcctg ggtgacggtc ctttaggcag cctgccgccg tctctgtccc ggttcacctt   2700
gccgagagag gcgcgtctgc cccaccctca aaccctgtgg ggcctgatgg tgctcacgac   2760
tcttcctgca aagggaactg aagacctcca cattaagtgg ctttttaaca tgaaaaacac   2820
ggcagctgta gctcccgagc tactctcttg ccagcatttt cacattttgc ctttctcgtg   2880
gtagaagcca gtacagagaa attctgtggt gggaacattc gaggtgtcac cctgcagagc   2940
tatggtgagg tgtggataag gcttaggtgc caggctgtaa gcattctgag ctggcttgtt   3000
gtttttaagt cctgtatatg tatgtagtag tttgggtgtg tatatatagt agcatttcaa   3060
```

```
aatggacgta ctggtttaac ctcctatcct tggagagcag ctggctctcc accttgttac   3120

acattatgtt agagaggtag cgagctgctc tgctatatgc cttaagccaa tatttactca   3180

tcaggtcatt attttttaca atggccatgg aataaaccat ttttacaaaa ataaaaacaa   3240

aaaaagc                                                             3247


<210> SEQ ID NO 17
<211> LENGTH: 435
<212> TYPE: PRT
<213> ORGANISM: Homo sapiens

<400> SEQUENCE: 17

Met Glu Met Glu Lys Glu Phe Glu Gln Ile Asp Lys Ser Gly Ser Trp
1               5                   10                  15

Ala Ala Ile Tyr Gln Asp Ile Arg His Glu Ala Ser Asp Phe Pro Cys
            20                  25                  30

Arg Val Ala Lys Leu Pro Lys Asn Lys Asn Arg Asn Arg Tyr Arg Asp
        35                  40                  45

Val Ser Pro Phe Asp His Ser Arg Ile Lys Leu His Gln Glu Asp Asn
    50                  55                  60

Asp Tyr Ile Asn Ala Ser Leu Ile Lys Met Glu Glu Ala Gln Arg Ser
65                  70                  75                  80

Tyr Ile Leu Thr Gln Gly Pro Leu Pro Asn Thr Cys Gly His Phe Trp
                85                  90                  95

Glu Met Val Trp Glu Gln Lys Ser Arg Gly Val Val Met Leu Asn Arg
            100                 105                 110

Val Met Glu Lys Gly Ser Leu Lys Cys Ala Gln Tyr Trp Pro Gln Lys
        115                 120                 125

Glu Glu Lys Glu Met Ile Phe Glu Asp Thr Asn Leu Lys Leu Thr Leu
    130                 135                 140

Ile Ser Glu Asp Ile Lys Ser Tyr Tyr Thr Val Arg Gln Leu Glu Leu
145                 150                 155                 160

Glu Asn Leu Thr Thr Gln Glu Thr Arg Glu Ile Leu His Phe His Tyr
                165                 170                 175

Thr Thr Trp Pro Asp Phe Gly Val Pro Glu Ser Pro Ala Ser Phe Leu
            180                 185                 190

Asn Phe Leu Phe Lys Val Arg Glu Ser Gly Ser Leu Ser Pro Glu His
        195                 200                 205

Gly Pro Val Val Val His Cys Ser Ala Gly Ile Gly Arg Ser Gly Thr
    210                 215                 220

Phe Cys Leu Ala Asp Thr Cys Leu Leu Leu Met Asp Lys Arg Lys Asp
225                 230                 235                 240

Pro Ser Ser Val Asp Ile Lys Lys Val Leu Leu Glu Met Arg Lys Phe
                245                 250                 255

Arg Met Gly Leu Ile Gln Thr Ala Asp Gln Leu Arg Phe Ser Tyr Leu
            260                 265                 270

Ala Val Ile Glu Gly Ala Lys Phe Ile Met Gly Asp Ser Ser Val Gln
        275                 280                 285

Asp Gln Trp Lys Glu Leu Ser His Glu Asp Leu Glu Pro Pro Pro Glu
    290                 295                 300

His Ile Pro Pro Pro Pro Arg Pro Pro Lys Arg Ile Leu Glu Pro His
305                 310                 315                 320

Asn Gly Lys Cys Arg Glu Phe Phe Pro Asn His Gln Trp Val Lys Glu
                325                 330                 335
```

-continued

```
Glu Thr Gln Glu Asp Lys Asp Cys Pro Ile Lys Glu Glu Lys Gly Ser
            340                 345                 350

Pro Leu Asn Ala Ala Pro Tyr Gly Ile Glu Ser Met Ser Gln Asp Thr
        355                 360                 365

Glu Val Arg Ser Arg Val Val Gly Gly Ser Leu Arg Gly Ala Gln Ala
    370                 375                 380

Ala Ser Pro Ala Lys Gly Glu Pro Ser Leu Pro Glu Lys Asp Glu Asp
385                 390                 395                 400

His Ala Leu Ser Tyr Trp Lys Pro Phe Leu Val Asn Met Cys Val Ala
                405                 410                 415

Thr Val Leu Thr Ala Gly Ala Tyr Leu Cys Tyr Arg Phe Leu Phe Asn
            420                 425                 430

Ser Asn Thr
        435


<210> SEQ ID NO 18
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ala Gly Leu Tyr Ser Thr Val Leu Met Gly Arg Pro Ser
1               5                   10


<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Leu Val Ser Thr Val Leu Met Gly Asn
1               5                   10
```

OSTEOCALCIN AS A TREATMENT FOR COGNITIVE DISORDERS

CROSS REFERENCE TO RELATED APPLICATIONS

This application is a 371 of International Patent Application No. PCT/US2014/027404, which claims the benefit of priority to U.S. Provisional Patent Application Ser. No. 61/794,006, filed Mar. 15, 2013, the disclosures of which are incorporated herein by reference in their entirety.

STATEMENT OF GOVERNMENT INTEREST

This invention was made with Government support under Grant No. AR045548 awarded by the National Institutes of Health. The government has certain rights in this invention.

FIELD OF THE INVENTION

The present invention is directed to methods and compositions for treating or preventing cognitive disorders in mammals. Such cognitive disorders include, but are not limited to, cognitive loss due to neurodegeneration associated with aging, anxiety, depression, memory loss, learning difficulties, and cognitive disorders associated with food deprivation during pregnancy.

BACKGROUND OF THE INVENTION

Osteocalcin, one of the very few osteoblast-specific proteins, has several features of a hormone. For instance, it is synthesized as a pre-pro-molecule and is secreted in the general circulation (Hauschka et al., 1989, Physiol. Review 69:990-1047; Price, 1989, Connect. Tissue Res. 21:51-57 (discussion 57-60)). Because of their exquisite cell-specific expression, the osteocalcin genes have been intensively studied to identify osteoblast-specific transcription factors and to define the molecular bases of bone physiology (Ducy et al., 2000, Science 289:1501-1504; Harada & Rodan, 2003, Nature 423:349-355).

Osteocalcin is the most abundant non-collagenous protein found associated with the mineralized bone matrix and it is currently being used as a biological marker for clinical assessment of bone turnover. Osteocalcin is a small (46-50 amino acid residues) bone specific protein that contains 3 gamma-carboxylated glutamic acid residues in its primary structure. The name osteocalcin (osteo, Greek for bone; calc, Latin for lime salts; in, protein) derives from the protein's ability to bind $Ca^{2+}$ and its abundance in bone. Osteocalcin undergoes a peculiar posttranslational modification whereby glutamic acid residues are carboxylated to form gamma-carboxyglutamic acid (Gla) residues; hence osteocalcin's other name, bone Gla protein (Hauschka et al., 1989, Physiol. Review 69:990-1047).

Mature human osteocalcin contains 49 amino acids with a predicted molecular mass of 5,800 kDa (Poser et al., 1980, J. Biol. Chem. 255:8685-8691). Osteocalcin is synthesized primarily by osteoblasts and ondontoblasts and comprises 15 to 20% of the non-collagenous protein of bone. Poser et al., 1980, J. Biol. Chem. 255:8685-8691 showed that mature osteocalcin contains three carboxyglutamic acid residues which are formed by posttranslational vitamin K-dependent modification of glutamic acid residues. The carboxylated Gla residues are at positions 17, 21 and 24 of mature human osteocalcin. Some human osteocalcin has been shown to contain only 2 Gla residues (Poser & Price, 1979, J. Biol. Chem. 254:431-436).

Osteocalcin has several features of a hormone. Ducy et al., 1996, Nature 382:448-452 demonstrated that mineralized bone from aging osteocalcin-deficient mice was two times thicker than that of wild-t e. It was shown that the absence of osteocalcin led to an increase in bone formation without impairing bone resorption and did not affect mineralization. Multiple immunoreactive forms of human osteocalcin have been discovered in circulation (Garnero et al., 1994, J. Bone Miner. Res. 9:255-264) and also in urine (Taylor et al., 1990, J. Clin. Endocrin. Metab. 70:467-472). Fragments of human osteocalcin can be produced either during osteoclastic degradation of bone matrix or as the result of the catabolic breakdown of the circulating protein after synthesis by osteoblasts.

The identification in recent years of novel organs influencing bone physiology expanded the spectrum of questions studied in skeletal biology. An example of this is the regulation of bone mass accrual by the brain that was first revealed by studying the mechanisms whereby the adipocyte-derived hormone leptin decreases bone mass accrual in all species tested (Ducy et al., 2000, Cell 100:197-207; Pogoda et al., 2006, J. Bone and Mineral Res. 21:1591-1599; Elefteriou et al., 2004, Proceedings of the National Academy of Sciences of the United States of America 101:3258-3263; Vaira et al., 2012, Neuroscience Biobehavioral Rev. 29:237-258). The use of cell-specific gene deletion models revealed widespread evidence that leptin signals in brainstem neurons to prevent synthesis of serotonin, a neurotransmitter that decreases the activity of the sympathetic nervous system, an inhibitor of bone mass accrual (Takeda et al., 2002, Cell 111:305-317; Yadav et al., 2009, Cell 138:976-989; Oury et al., 2010, Genes & Development 24:2330-2342, Genes Dev. 24:2330-2342). What underlines best the importance of this function of brain-derived serotonin is the fact that selective serotonin reuptake inhibitors (SSRIs) that increase the local concentrations of serotonin in the brain (Gardier et al., 1996, Fundamental Clin. Pharmacol. 10:16-27) have deleterious effects on bone mass in humans.

A second development of significance in skeletal biology has been the demonstration that bone is an endocrine organ secreting at least two hormones. One of them, osteocalcin, is made by the osteoblast, the bone forming cell, and promotes several functions apparently unrelated to bone health such as energy expenditure, insulin secretion, insulin sensitivity, and, in males, testosterone synthesis (Lee et al., 2007, Cell 130:456-469; Oury et al., 2011, Cell 144:796-809). The latter function occurs following the binding of osteocalcin to a specific receptor, gprc6a, on Leydig cells (Oury et al., 2011, Cell 144:796-809).

OST-PTP is the protein encoded by the Esp gene. The Esp gene was originally named for embryonic stem (ES) cell phosphatase and it has also been called the Ptprv gene in mice. (Lee et al, 1996, Mech. Dev. 59:153-164). Because of its bone and testicular localization, the gene product of Esp is often referred to as osteoblast testicular protein tyrosine phosphatase (OST-PTP). OST-PTP is a large, 1,711 amino acid-long protein that includes three distinct domains. OST-PTP has a 1,068 amino-acid long extracellular domain containing multiple fibronectin type III repeats.

Esp expression is restricted to ES cells, the gonads, and the skeleton. In the gonads, Esp is specifically expressed in Sertoli cells of the testis and coelomic epithelial cells of the ovaries. During development, Esp is initially expressed in the apical ectodermal ridge of the limbs. Later during embryonic development and after birth, its expression becomes restricted to pre-osteoblasts and osteoblasts (i.e., Runx2-positive cells) of the perichondrium and periosteum.

Protein tyrosine phosphatase-1B (PTP-1B) is an ~50 kd intracellular protein present in abundant amounts in various human tissues (Charbonneau et al., 1989, Proc. Natl. Acad. Sci. USA 86:5252-5256; Goldstein, 1993, Receptor 3:1-15).

Gprc6a is a receptor that belongs to the C family of GPCRs (Wellendorph and Brauner-Osborne, 2004, Gene 335:37-46) and has been proposed to be a receptor for amino acids or for calcium in the presence of osteocalcin as a cofactor, and for androgens (Pi et al., 2008, PLoS One.3: e3858; Pi et al., 2005, J. Biol. Chem. 280:40201-40209; Pi et al., 2010, J. Biol. Chem. 285:39953-39964).

Embryonic development is affected by a variety of environmental signals. In particular, both clinical outcome studies and experimental evidence gathered in model organisms concur to indicate that the mother's health during pregnancy is an important determinant of embryonic development (Osorio et al., 2012, Nature Rev. Endocrinol. 8:624; Lawlor et al., 2012, Nature Rev. Endocrinol. 8:679-688; Challis et al., 2012, Nature Rev. Endocrinol. 8:629-630). By definition, any direct maternal influence on vertebrate embryonic development occurs through the placenta, an organ allowing the transfer of circulating molecules from the mother to the embryo. To date however, molecules either made in the placenta or by the mother, crossing the placenta and that would affect development of the brain of the pup, have not been identified. This is an important question considering that a growing number of epidemiological studies suggest that maternal health may also be a risk factor for neurologic and psychiatric diseases in the offspring (Wadhwa et al., 2001, Prog. Brain Res. 133:131-142; Van den Bergh et al., 2005, Neurosci. Biobehavioral Rev. 29:237-258; Weinstock, 2008, Neurosci. Biobehavioral Rev. 32:1073-1086).

SUMMARY OF THE INVENTION

The present invention provides methods of treating or preventing cognitive disorders in mammals comprising administering to a mammal in need of treatment for or prevention of a cognitive disorder a pharmaceutical composition comprising a therapeutically effective amount of undercarboxylated/uncarboxylated osteocalcin and a pharmaceutically acceptable carrier or excipient. In certain embodiments, the mammal is a human and the osteocalcin is human osteocalcin. In certain embodiments, the cognitive disorder is selected from the group consisting of cognitive loss due to neurodegeneration associated with aging, anxiety, depression, memory loss, learning difficulties, and cognitive disorders associated with food deprivation during pregnancy. In certain embodiments, the cognitive disorder is anxiety due to aging, depression due to aging, memory loss due to aging, or learning difficulties due to aging.

The present invention also provides methods of treating cognitive disorders in mammals comprising administering to a mammal in need of treatment for a cognitive disorder a pharmaceutical composition comprising an agent that modulates the OST-PTP signaling pathway or the PTP-1B signaling pathway, wherein the agent reduces OST-PTP phosphorylase expression or activity or reduces PTP-1B phosphorylase expression or activity, reduces gamma-carboxylase expression or activity, or increases the level of undercarboxylated/uncarboxylated osteocalcin, wherein the pharmaceutical composition comprises the agent in an amount that produces an effect in a mammal selected from the group consisting of lessening of cognitive loss due to neurodegeneration associated with aging, lessening of anxiety, lessening of depression, lessening of memory loss, learning difficulties, and lessening of cognitive disorders associated with food deprivation during pregnancy.

In certain embodiments, the mammal is a human.

In certain embodiments, the agent is undercarboxylated/uncarboxylated osteocalcin. In certain embodiments, the agent is human undercarboxylated/uncarboxylated osteocalcin.

In certain embodiments, the agent inhibits the expression or activity of OST-PTP, inhibits the expression or activity of PTP-1B, inhibits the expression or activity of gamma-carboxylase, inhibits phosphorylation of gamma-carboxylase, inhibits carboxylation of osteocalcin, or decarboxylates osteocalcin. In certain embodiments, the agent is selected from the group consisting of a small molecule, an antibody, or a nucleic acid.

In certain embodiments where the agent is undercarboxylated/uncarboxylated osteocalcin, at least one of the glutamic acids in the undercarboxylated/uncarboxylated osteocalcin at the positions corresponding to positions 17, 21 and 24 of mature human osteocalcin is not carboxylated. In certain embodiments, all three of the glutamic acids in the undercarboxylated/uncarboxylated osteocalcin at the positions corresponding to positions 17, 21 and 24 of mature human osteocalcin are not carboxylated.

In certain embodiments, the undercarboxylated/uncarboxylated osteocalcin is a preparation of undercarboxylated/uncarboxylated osteocalcin in which more than about 20% of the total Glu residues at the positions corresponding to positions 17, 21 and 24 of mature human osteocalcin in the preparation are not carboxylated. In certain embodiments, the undercarboxylated/uncarboxylated osteocalcin shares at least 80% amino acid sequence identity with mature human osteocalcin when the undercarboxylated/uncarboxylated osteocalcin and mature human osteocalcin are aligned for maximum sequence homology. In certain embodiments, the undercarboxylated/uncarboxylated osteocalcin shares about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, or about 98% amino acid sequence identity with mature human osteocalcin when the undercarboxylated/uncarboxylated osteocalcin and mature human osteocalcin are aligned for maximum sequence homology. In certain embodiments, the undercarboxylated/uncarboxylated osteocalcin differs at 1, 2, 3, 4, 5, 6, 7, 8, 9, or 10 amino acid residues from mature human osteocalcin.

In certain embodiments, at least one of the glutamic acids in the undercarboxylated/uncarboxylated osteocalcin at the positions corresponding to positions 17, 21 and 24 of mature human osteocalcin is not carboxylated. In certain embodiments, all three of the glutamic acids in the undercarboxylated/uncarboxylated osteocalcin at the positions corresponding to positions 17, 21 and 24 of mature human osteocalcin are not carboxylated.

In certain embodiments, the undercarboxylated/uncarboxylated osteocalcin is a polypeptide selected from the group consisting of:

(a) a fragment comprising mature human osteocalcin missing the last 10 amino acids from the C-terminal end;

(b) a fragment comprising mature human osteocalcin missing the first 10 amino acids from the N-terminal end;

(c) a fragment comprising amino acids 62-90 of SEQ ID NO:2;

(d) a fragment comprising amino acids 1-36 of mature human osteocalcin;

(e) a fragment comprising amino acids 13-26 of mature human osteocalcin;

(f) a fragment comprising amino acids 13-46 of mature human osteocalcin; and (g) variants of the above.

In certain embodiments, the pharmaceutical composition comprises a small molecule selected from the group consisting of warfarin, vitamin K inhibitors, and biologically active fragments or variants thereof. In a preferred embodiment, the small molecule is warfarin. In another preferred embodiment, the agent is a small molecule that increases the activity or expression of osteocalcin.

In certain embodiments, the pharmaceutical composition comprises an antibody or antibody fragment that binds to and inhibits the activity of OST-PTP, PTP-1B, or gamma-carboxylase. Preferably, the antibody or antibody fragment is a monoclonal antibody. In certain embodiments, the antibody or antibody fragment binds to the extracellular domain of OST-PTP or PTP-1B. In preferred embodiments, the OST-PTP is human OST-PTP or the PTP-1B is human PTP-1B. In certain embodiments, the OST-PTP is the mouse OST-PTP of SEQ ID NO:11 or an OST-PTP having an amino acid sequence that is substantially homologous or identical to SEQ ID NO:11. In certain embodiments, the OST-PTP is an OST-PTP having an amino acid sequence that is at least 70% homologous or identical to SEQ ID NO:11. In certain embodiments, the PTP-1B is human PTP-1B of SEQ ID NO:17 or a PTP-1B having an amino acid sequence that is substantially homologous or identical to SEQ ID NO:17. In certain embodiments, the PTP-1B is a PTP-1B having an amino acid sequence that is at least 70%, at least 80%, at least 90%, at least 95%, or at least 98% homologous or identical to SEQ ID NO:17.

In certain embodiments, the pharmaceutical composition comprises a nucleic acid that inhibits the expression or activity of OST-PTP, PTP-1B, or gamma-carboxylase. In certain embodiments, the nucleic acid is an antisense oligonucleotide or a small interfering RNA (siRNA). In certain embodiments, the nucleic acid is an isolated nucleic acid that is selected from the group consisting of an antisense DNA, antisense RNA, and siRNA, which nucleic acid is sufficiently complementary to SEQ ID NO:10 or a sequence that is substantially homologous or identical to SEQ ID NO:10 to permit specific hybridization to SEQ ID NO:10 or a sequence that is substantially homologous or identical to SEQ ID NO:10, and wherein the hybridization prevents or reduces expression of OST-PTP in osteoblasts. In certain embodiments, the nucleic acid is an isolated nucleic acid that is selected from the group consisting of an antisense DNA, antisense RNA, and siRNA, which nucleic acid is sufficiently complementary to SEQ ID NO:16 or a sequence that is substantially homologous or identical to SEQ ID NO:16 to permit specific hybridization to SEQ ID NO:16 or a sequence that is substantially homologous or identical to SEQ ID NO:16, and wherein the hybridization prevents or reduces expression of PTP-1B in osteoblasts.

In certain embodiments, the pharmaceutical composition comprises about 0.5 mg to about 5 g, about 1 mg to about 1 g, about 5 mg to about 750 mg, about 10 mg to about 500 mg, about 20 mg to about 250 mg, or about 25 mg to about 200 mg, of the agent. In certain embodiments, the pharmaceutical composition comprises an agent that is formulated into a controlled release preparation. In certain embodiments, the pharmaceutical composition comprises an agent that is chemically modified to prolong its half life in the human body.

In certain embodiments, the pharmaceutical composition for treating a cognitive disorder in mammals comprises an undercarboxylated/uncarboxylated osteocalcin polypeptide comprising an amino acid sequence (SEQ ID NO: 13)

$YLYQWLGAPVPYPDPLX_1PRRX_2VCX_3LNPDCDELADHIGFQEAYRRFYGPV$ wherein $X_1$, $X_2$ and $X_3$ are each independently selected from an amino acid or amino acid analog, with the proviso that if $X_1$, $X_2$ and $X_3$ are each glutamic acid, then $X_1$ is not carboxylated, or less than 50 percent of $X_2$ is carboxylated, and/or less than 50 percent of $X_3$ is carboxylated, or said osteocalcin polypeptide comprises an amino acid sequence that is different from SEQ. ID. NO:13 at 1 to 7 positions other than $X_1$, $X_2$ and $X_3$; and/or wherein said amino acid sequence can include one or more amide backbone substitutions.

In certain embodiments, the osteocalcin polypeptide of SEQ. ID. NO:13 is a fusion protein. In certain embodiments, the arginine at position 43 of SEQ. ID. NO:13 is replaced with an amino acid or amino acid analog that reduces susceptibility of the osteocalcin polypeptide to proteolytic degradation. In certain embodiments, the arginine at position 44 of SEQ. ID. NO:13 is replaced with β-dimethyl-arginine. In certain embodiments, the osteocalcin polypeptide is a retroenantiomer of uncarboxylated human osteocalcin (1-49).

The present invention also provides a method of treating a cognitive disorder in mammals by modulating the OST-PTP signaling pathway or the PTP-1B signaling pathway, the method comprising administering an agent that reduces OST-PTP phosphorylase activity or reduces PTP-1B phosphorylase activity, reduces gamma-carboxylase activity, or increases undercarboxylated/uncarboxylated osteocalcin, wherein the agent is administered in an amount that produces an effect in a mammal selected from the group consisting of lessening of cognitive loss due to neurodegeneration associated with aging, lessening of anxiety, lessening of depression, lessening of memory loss, lessening of learning difficulties, and lessening of cognitive disorders associated with food deprivation during pregnancy.

In certain embodiments, the patient has or is at risk for a cognitive disorder selected from the group consisting of cognitive loss due to neurodegeneration associated with aging, anxiety, depression, memory loss, learning difficulties, and cognitive disorders associated with food deprivation during pregnancy.

The present invention provides a use of an agent that reduces OST-PTP phosphorylase activity, reduces PTP-1B phosphorylase activity, reduces gamma-carboxylase activity, and/or increases undercarboxylated/uncarboxylated osteocalcin as a medicament for treating or preventing a cognitive disorder, preferably cognitive loss due to neurodegeneration associated with aging, anxiety, depression, memory loss, learning difficulties, or cognitive disorders associated with food deprivation during pregnancy.

In certain embodiments, the agent inhibits phosphorylation of gamma-carboxylase. In certain embodiments, the agent increases the level of undercarboxylated/uncarboxylated osteocalcin. In certain embodiments, the agent increases the ratio of undercarboxylated/uncarboxylated osteocalcin compared to carboxylated osteocalcin. In certain embodiments, the agent inhibits carboxylation of osteocalcin. In certain embodiments, the agent decarboxylates osteocalcin.

In certain embodiments of the use described above, the agent is undercarboxylated/uncarboxylated osteocalcin. Thus, the present invention provides undercarboxylated/uncarboxylated osteocalcin for use in the treatment or prevention of a cognitive disorder in mammals. In particular embodiments, the cognitive disorder is selected from the group consisting of cognitive loss due to neurodegeneration associated with aging, anxiety, depression, memory loss, learning difficulties, and cognitive disorders associated with food deprivation during pregnancy. In certain embodiments, the cognitive disorder is anxiety due to aging, depression due to aging, memory loss due to aging, or learning difficulties due to aging.

In certain embodiments of the use described above, the undercarboxylated/uncarboxylated osteocalcin lessens cognitive loss due to neurodegeneration associated with aging, lessens anxiety, lessens depression, lessens memory loss, improves learning, or lessens cognitive disorders associated with food deprivation during pregnancy. In certain embodiments, at least one of the glutamic acids in the undercarboxylated/uncarboxylated osteocalcin at the positions corresponding to positions 17, 21 and 24 of mature human osteocalcin is not carboxylated. In certain embodiments, all three of the glutamic acids in the undercarboxylated/uncarboxylated osteocalcin at the positions corresponding to positions 17, 21 and 24 of mature human osteocalcin are not carboxylated. In certain embodiments, the undercarboxylated/uncarboxylated osteocalcin is a preparation of undercarboxylated/uncarboxylated osteocalcin in which more than about 20% of the total Glu residues at the positions corresponding to positions 17, 21 and 24 of mature human osteocalcin in the preparation are not carboxylated. In certain embodiments, the undercarboxylated/uncarboxylated osteocalcin shares about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, or about 98% amino acid sequence identity with mature human osteocalcin when the undercarboxylated/uncarboxylated osteocalcin and mature human osteocalcin are aligned for maximum sequence homology. In certain embodiments, the undercarboxylated/uncarboxylated osteocalcin differs at 1, 2, 3, 4, 5, 6, 7, 8, 9, or 10 amino acid residues from mature human osteocalcin.

In certain embodiments of the use described above, the agent is selected from the group consisting of a small molecule, an antibody, or a nucleic acid.

In certain embodiments of the use described above, the agent is a small molecule that inhibits the expression or activity of OST-PTP, PTP-1B, or gamma-carboxylase. In certain embodiments, the agent is a small molecule selected from the group consisting of warfarin, vitamin K inhibitors, and biologically active fragments or variants thereof. In a preferred embodiment, the small molecule is warfarin. In another preferred embodiment, the agent is a small molecule that increases the activity or expression of osteocalcin.

The present invention provides the use of an undercarboxylated/uncarboxylated osteocalcin polypeptide, or mimetic thereof, for the manufacture of a medicament for treatment of a cognitive disorder in mammals. In certain embodiments, the disorder is selected from the group consisting of cognitive loss due to neurodegeneration associated with aging, anxiety, depression, memory loss, learning difficulties, and cognitive disorders associated with food deprivation during pregnancy.

The present invention also provides the use of an agent that reduces OST-PTP phosphorylase activity, reduces PTP-1B phosphorylase activity, reduces gamma-carboxylase activity, and/or increases undercarboxylated/uncarboxylated osteocalcin for the manufacture of a medicament for treatment of a cognitive disorder in mammals. In certain embodiments, the disorder is selected from the group consisting of cognitive loss due to neurodegeneration associated with aging, anxiety, depression, memory loss, learning difficulties, and cognitive disorders associated with food deprivation during pregnancy.

DETAILED DESCRIPTION OF THE INVENTION

Figure 1A:
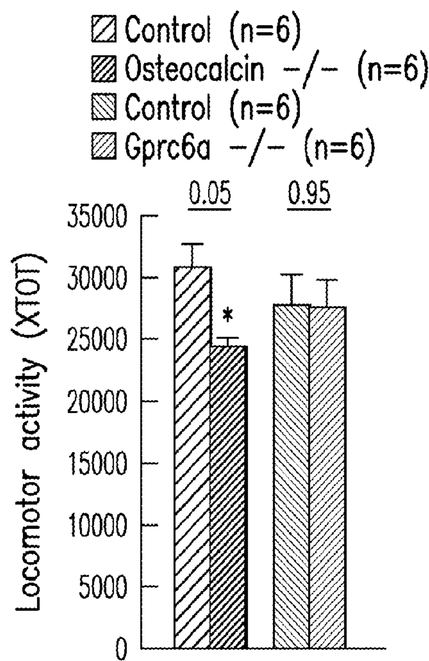
FIG. 1. Osteocalcin affects the biosynthesis of neurotransmitters. (A-B) Measure of (A) total activity (XTOT) and (B) ambulatory activity (AMBX), in Osteocalcin$^{-/-}$ (n=6) and Gprc6a$^{-/-}$ (n=6) mice, during 12 hr light and dark phases over a period of three days. Mutant mice were compared to their respective WT (n=6) littermates. (C) Video tracking of an open field paradigm test performed in Osteocalcin$^{-/-}$, Gprc6a$^{-/-}$ and WT littermate mice. (D-G) HPLC analysis of (D) serotonin, (E) GABA, (F) dopamine, and (G) norepinephrine contents in various parts of Osteocalcin$^{-/-}$ (n=15) and controls (n=15) brains. (H) Quantitative PCR analysis of Tryptophan hydroxylase-2 (Tph2), Glutamate decarboxylase-1 (GAD1), Glutamate decarboxylase-2 (GAD2), Tyrosine hydroxylase (Th) and Aromatic L-amino acid decarboxylase (Ddc) expression levels in the brainstem and midbrain of Osteocalcin$^{-/-}$ (n=13), Gprc6a$^{-/-}$ (n=5) and control (n=11) mice. Error bars represent SEM. Student's T-test is represented on the top of the bars.

The present invention is based in part on the discovery of a previously unknown biochemical pathway linking osteocalcin and cognitive processes in mammals. The present inventors have discovered that osteocalcin crosses the blood-brain barrier, binds to and signals in neurons of the brainstem, inhibits GABA, and favors serotonin and dopamine synthesis by increasing the activity of enzymes involved in the synthesis of serotonin and dopamine. These effects lead to beneficial effects on cognitive functions such as memory, learning, anxiety, depression as well as to beneficial effects on neurodegeneration associated with aging.

The present invention is also based in part on the observation that maternally-derived osteocalcin crosses the placenta and prevents neuronal apoptosis in mouse embryos. Uncarboxylated osteocalcin injections in Osteocalcin$^{-/-}$ mouse mothers throughout pregnancy prevent this neuronal apoptosis. These observations indicate that osteocalcin is a critical regulator of neuronal apoptosis and that administration of undercarboxylated/uncarboxylated osteocalcin may be useful in the treatment or prevention of diseases where neuronal apoptosis plays an important role.

Moreover, direct administration of undercarboxylated/uncarboxylated osteocalcin to the brains of adult Osteocalcin$^{-/-}$ mice (mice completely lacking osteocalcin expression) rescued defects in anxiety, depression, learning, and memory in the mice. Since undercarboxylated/uncarboxylated osteocalcin can cross the blood/brain barrier, this result indicates that administration of undercarboxylated/uncarboxylated osteocalcin in such a manner as to increase the blood concentration of undercarboxylated/uncarboxylated osteocalcin in a mammal should provide beneficial effects on cognitive functions relating to anxiety, depression, learning, and memory.

In view of the observations described above, it may be concluded that osteocalcin regulates cognitive functions such as anxiety, depression, learning, and memory. Thus, certain aspects of the invention are directed to the therapeutic use of undercarboxylated/uncarboxylated osteocalcin, as well as fragments and variants thereof, to treat or prevent disorders related to cognition in mammals. It is known that aging is frequently associates with mild to severe cognitive impairment. Aging is also associated with loss of bone mass. Since bone osteoblasts are a major source of osteocalcin, the findings disclosed herein support the use of osteocalcin to treat cognitive disorders associated with aging. In certain embodiments, the disorder is increased anxiety, increased depression, decreased memory, or decreased learning ability that occurs as a result of aging.

"Cognitive disorders" include conditions characterized by temporary or permanent loss, either total or partial, of the ability to learn, memorize, solve problems, process information, reason correctly, or recall information. In certain embodiments of the invention, the cognitive disorder arises as a result of the normal aging process. In other embodiments, the cognitive disorder is the result of such factors as injury to the brain, specific neurodegenerative disease (e.g., Alzheimer's disease, Parkinson's disease, Huntington's disease, amyotrophic lateral sclerosis), vascular conditions (e.g., stroke, ischemia), tumors or infections in the brain. When the cognitive disorder is memory loss, the loss may occur in short term or long term memory. Cognitive disorders also include various forms of dementia.

Preventing a disorder related to cognition in mammals means actively intervening as described herein prior to overt onset of the disorder to prevent or minimize the extent of the disorder or slow its course of development.

Treating a disorder related to cognition in mammals means actively intervening after onset of the disorder to slow down, ameliorate symptoms of, minimize the extent of, or reverse the disorder in a patient who is known or suspected of having the disorder.

A "patient" is a mammal, preferably a human, but can also be a companion animal such as dogs or cats, or farm animals such as horses, cattle, pigs, or sheep. In certain embodiments, the patient is a human who is more than 50, 55, 60, 65, 70, 75, or 80 years old. In certain embodiments, the patient is a human who is between 50 and 80 years old, between 55 and 75 years old, or between 60 and 70 years old. In certain embodiments, the patient is a human who is between 50 and 55 years old, between 55 and 60 years old, between 65 and 70 years old, between 70 and 75 years old, between 75 and 80 years old, between 80 and 85 years old, or between 85 and 90 years old.

A patient in need of treatment or prevention for a cognitive disorder includes a patient known or suspected of having or being at risk of developing a cognitive disorder. Such a patient in need of treatment could be, e.g., a mammal known to have low undercarboxylated/uncarboxylated levels. Patients in need of treatment or prevention by the methods of the present invention include patients who are known to be in need of therapy to increase serum undercarboxylated/uncarboxylated levels in order to treat or prevent a cognitive disorder. In some embodiments, such patients might include mammals who have been identified as having a serum undercarboxylated/uncarboxylated level that is about 5%, about 15%, or about 50% lower than the serum undercarboxylated/uncarboxylated level in normal subjects.

A patient in need of treatment or prevention for a cognitive disorder by the methods of the present invention does not include a patient being administered the therapeutic agents described herein where the patient is being administered the therapeutic agents only for a purpose other than to treat or prevent a cognitive disorder. Thus, e.g., a patient in need of treatment or prevention for a cognitive disorder by the methods of the present invention does not include a patient being treated with osteocalcin only for the purpose of treating a bone mass disease, metabolic syndrome, glucose intolerance, type 1 diabetes, type 2 diabetes, atherosclerosis, or obesity. Nor does it include a patient being treated with osteocalcin only for the purpose of causing an increase in glucose tolerance, an increase in insulin production, an increase insulin sensitivity, an increase in pancreatic beta-cell proliferation, an increase in adiponectin serum level, a reduction of oxidized phospholipids, a regression of atherosclerotic plaques, a decrease in inflammatory protein biosynthesis, a reduction in plasma cholesterol, a reduction in vascular smooth muscle cell (VSMC) proliferation and number, or a decrease in the thickness of arterial plaque. A patient in need of treatment or prevention for a cognitive disorder by the methods of the present invention also does not include a patient being treated with osteocalcin that is not undercarboxylated/uncarboxylated osteocalcin.

In certain embodiments, the methods of the present invention comprise the step of identifying a patient in need of therapy for a cognitive disorder. Thus, the present invention provides a method comprising:

(a) identifying a patient in need of therapy for a cognitive disorder;

(b) administering to the patient a therapeutically effective amount of undercarboxylated/uncarboxylated osteocalcin or an agent that modulates the OST-PTP signaling pathway or the PTP-1B signaling pathway, wherein the agent reduces OST-PTP phosphorylase expression or activity, reduces PTP-1B phosphorylase expression or activity, or reduces gamma-carboxylase expression or activity.

The present invention is also based on the observation that gamma-carboxylase carboxylates osteocalcin, thereby producing carboxylated osteocalcin. This provides the opportunity to modulate the degree of carboxylation of the osteocalcin used in the methods of the present invention by modulating the activity of gamma-carboxylase. In particular, this provides the opportunity to lower the degree of carboxylation of the osteocalcin used in the methods of the present invention, thus providing undercarboxylated/uncarboxylated osteocalcin for use in the methods of the present invention. Therefore, certain aspects of the invention are directed to the therapeutic use of agents that inhibit the activity of gamma-carboxylase to treat or prevent a cognitive disorder in mammals.

The present invention is further based on the observation that OST-PTP activates gamma-carboxylase through dephosphorylation. As indicated above, activation of gamma-carboxylase leads to carboxylation of osteocalcin. This provides the opportunity to indirectly modulate the degree of carboxylation of the osteocalcin used in the methods of the present invention by modulating the activity of OST-PTP (which will then modulate the activity of gamma-carboxylase). Therefore certain aspects of the invention are directed to the therapeutic use of agents that inhibit the activity of OST-PTP to treat or prevent a cognitive disorder in mammals.

The present invention is further based on the observation that, in humans, PTP-1B activates gamma-carboxylase through dephosphorylation. As indicated above, activation of gamma-carboxylase leads to carboxylation of osteocalcin. This provides the opportunity to indirectly modulate the degree of carboxylation of the osteocalcin used in the methods of the present invention by modulating the activity of PTP-1B in humans (which will then modulate the activity of gamma-carboxylase). Therefore certain aspects of the invention are directed to the therapeutic use in humans of agents that inhibit the activity of PTP-1B to treat or prevent a cognitive disorder in humans.

Other aspects of the invention are directed to diagnostic methods based on detection of the level of undercarboxylated/uncarboxylated osteocalcin in a patient, which level is associated with disorders related to cognition in mammals.

In one aspect, the method of diagnosing a cognitive disorder in a patient comprises (i) determining a patient level of undercarboxylated/uncarboxylated osteocalcin in a biological sample taken from the patient (ii) comparing the patient level of undercarboxylated/uncarboxylated osteocalcin and a control level of undercarboxylated/uncarboxylated osteocalcin, and (iii) if the patient level is significantly lower than the control level, then diagnosing the patient as having, or being at risk for, the cognitive disorder. A further step may then be to inform the patient or the patient's healthcare provider of the diagnosis.

Other aspects of the invention are directed to diagnostic methods based on detection of decreased ratios of undercarboxylated/uncarboxylated vs carboxylated osteocalcin. Such ratios may be associated with disorders related to cognition in mammals. In one aspect, the method of diagnosing a disorder related to cognition in a patient comprises (i) determining a patient ratio of undercarboxylated/uncarboxylated vs. carboxylated osteocalcin in a biological sample taken from the patient (ii) comparing the patient ratio of undercarboxylated/uncarboxylated vs carboxylated osteocalcin and a control ratio of undercarboxylated/uncarboxylated vs carboxylated osteocalcin, and (iii) if the patient ratio is significantly lower than the control ratio, then the patient is diagnosed has having, or being at risk for, the disorder related to cognition. A further step may then be to inform the patient or the patient's healthcare provider of the diagnosis.

Pharmaceutical Compositions for Use in the Methods of the Invention

The present invention provides pharmaceutical compositions for use in the treatment of a cognitive disorder in mammals comprising an agent for modulating the OST-PTP signaling pathway or for modulating the PTP-1B signaling pathway, which pathways involve gamma-carboxylase and osteocalcin. In particular embodiments, the agent inhibits OST-PTP phosphorylase activity, inhibits PTP-1B phosphorylase activity reduces gamma-carboxylase activity, and/or increases undercarboxylated/uncarboxylated osteocalcin. In particular embodiments, the agent decarboxylates osteocalcin. The agent may be selected from the group consisting of small molecules, polypeptides, antibodies, and nucleic acids. The pharmaceutical compositions of the invention provide an amount of the agent effective to treat or prevent a cognitive disorder in mammals. In certain embodiments, the pharmaceutical composition provides an amount of the agent effective to treat or prevent neurodegeneration associated with aging, anxiety, depression, memory loss, learning difficulties, and cognitive disorders associated with food deprivation during pregnancy.

In certain embodiments, the pharmaceutical compositions for use in the methods of the invention may function to increase serum undercarboxylated/uncarboxylated osteocalcin serum levels.

In particular embodiments of the invention, therapeutic agents that may be administered in the methods of the present invention include undercarboxylated osteocalcin; uncarboxylated osteocalcin; or inhibitors that reduce the expression or activity of gamma-carboxylase, PTP-1B, or OST-PTP (e.g., antibodies, small molecules, antisense nucleic acids or siRNA). The pharmaceutical agents may also include agents that decarboxylate osteocalcin.

The therapeutic agents are generally administered in an amount sufficient to lessen cognitive loss due to neurodegeneration associated with aging, lessen anxiety, lessen depression, lessen memory loss, improve learning, or lessen cognitive disorders associated with food deprivation during pregnancy.

In certain embodiments, the pharmaceutical compositions comprising undercarboxylated/uncarboxylated osteocalcin are administered together with another therapeutic agent that is known to be useful for treating cognitive disorders in mammals. Examples of such other therapeutic agents include monoamine oxidase B inhibitors such as selegiline; vasodilators such as nicerogoline and vinpocetine; phosphatidylserine; propentofyline; anticholinesterases (cholinesterase inhibitors) such as tacrine, galantamine, rivastigmine, vinpocetine, donepezil (ARICEPT® (donepezil hydrochloride)), metrifonate, and physostigmine; lecithin; choline cholinomimetics such as milameline and xanomeline; ionotropic N-methyl-D-aspartate (NMDA) receptor antagonists such as memantine; anti-inflammatory drugs such as prednisolone, diclofenac, indomethacin, propentofyline, naproxen, rofecoxin, ibruprofen and suldinac; metal chelating agents such as cliquinol; *Ginkgo biloba*; bisphosophonates; selective oestrogen receptor modulators such as raloxifene and estrogen; beta and gamma secretase inhibitors; cholesterol-lowering drugs such as statins; calcitonin; risedronate; alendronate; and combinations thereof.

In some embodiments, the undercarboxylated/uncarboxylated osteocalcin and the other therapeutic agent that is known to be useful for treating cognitive disorders in mammals are present in the same pharmaceutical composition. In other embodiments, the undercarboxylated/uncarboxylated osteocalcin and the other therapeutic agent that is known to be useful for treating cognitive disorders in mammals are administered in separate pharmaceutical compositions.

In other embodiments, undercarboxylated/uncarboxylated osteocalcin is the only active pharmaceutical ingredient present in the pharmaceutical compositions of the present invention.

Biologically active fragments or variants of the therapeutic agents are also within the scope of the present invention. By "biologically active" is meant capable of modulating the OST-PTP signaling pathway or the PTP-1B signaling pathway involving gamma-carboxylase and osteocalcin. "Biologically active" may also mean reducing the expression of OST-PTP or its ability to dephosphorylate gamma-carboxylase and reducing the expression of gamma-carboxylase or its ability to carboxylate osteocalcin, or decarboxylating carboxylated osteocalcin thereby leading to increased levels of undercarboxylated/uncarboxylated osteocalcin.

"Biologically active" also means reducing the expression of PTP-1B or its ability to dephosphorylate gamma-carboxylase and reducing the expression of gamma-carboxylase or its ability to carboxylate osteocalcin, or decarboxylating carboxylated osteocalcin thereby leading to increased levels of undercarboxylated/uncarboxylated osteocalcin.

"Biologically active" also refers to fragments or variants of osteocalcin that retain the ability of undercarboxylated/uncarboxylated osteocalcin to treat or prevent a cognitive disorder in mammals.

"Biologically active" also means capable of producing at least one effect in a mammal selected from the group consisting of lessening of cognitive loss due to neurodegeneration associated with aging, lessening of anxiety, lessening of depression, lessening of memory loss, improving learning, and lessening of cognitive disorders associated with food deprivation during pregnancy.

Pharmaceutical Compositions Comprising Undercarboxylated/Uncarboxylated Osteocalcin In a specific embodiment of the invention, pharmaceutical compositions comprising undercarboxylated/uncarboxylated osteocalcin are provided for use in treating or preventing a cognitive disorder in a mammal.

"Undercarboxylated osteocalcin" means osteocalcin in which one or more of the Glu residues at positions Glu17, Glu21, and Glu24 of the amino acid sequence of the mature human osteocalcin having 49 amino acids, or at the positions corresponding to Glu17, Glu21 and Glu24 in other forms of osteocalcin, are not carboxylated. Undercarboxylated osteocalcin includes "uncarboxylated osteocalcin," i.e., osteocalcin in which all three of the glutamic acid residues at positions 17, 21, and 24 are not carboxylated. Preparations of osteocalcin are considered to be "undercarboxylated osteocalcin" if more than about 10% of the total Glu residues at positions Glu17, Glu21, and Glu24 (taken together) in mature osteocalcin (or the corresponding Glu residues in other forms) of the preparation are not carboxylated. In particular preparations of undercarboxylated osteocalcin, more than about 20%, more than about 30%, more than about 40%, more than about 50%, more than about 60%, more than about 70%, more than about 80%, more than about 90%, more than about 95%, or more than about 99% of the total Glu residues at positions Glu17, Glu21, and Glu24 in mature osteocalcin (or the corresponding Glu residues in other forms) of the preparation are not carboxylated. In particularly preferred embodiments, essentially all of the Glu residues at positions Glu17, Glu21 and Glu24 in mature osteocalcin (or the corresponding Glu residues in other forms) of the preparation are not carboxylated.

"Undercarboxylated/uncarboxylated osteocalcin" is used herein to refer collectively to undercarboxylated and uncarboxylated osteocalcin.

Human osteocalcin cDNA (SEQ ID NO:1) encodes a mature osteocalcin protein represented by the last 49 amino acids of SEQ ID NO:2 (i.e., positions 52-100) with a predicted molecular mass of 5,800 kDa (Poser et al., 1980, J. Biol. Chem. 255:8685-8691). SEQ ID NO:2 is the prepro-sequence of human osteocalcin encoded by SEQ ID NO:1 and mature human osteocalcin (SEQ ID NO:12) is the processed product of SEQ ID NO:2. In this application, the amino acid positions of mature human osteocalcin are referred to. It will be understood that the amino acid positions of mature human osteocalcin correspond to those of SEQ ID NO:2 as follows: position 1 of mature human osteocalcin corresponds to position 52 of SEQ ID NO:2; position 2 of mature human osteocalcin corresponds to position 53 of SEQ ID NO:2, etc. In particular, positions 17, 21, and 24 of mature human osteocalcin correspond to positions 68, 72, and 75, respectively, of SEQ ID NO:2.

When positions in two amino acid sequences correspond, it is meant that the two positions align with each other when the two amino acid sequences are aligned with one another to provide maximum homology between them. This same concept of correspondence also applies to nucleic acids.

For example, in the two amino acid sequences AGLYSTVLMGRPS (SEQ ID NO:18) and GLVSTVLMGN (SEQ ID NO:19), positions 2-11 of the first sequence correspond to positions 1-10 of the second sequence, respectively. Thus, position 2 of the first sequence corresponds to position 1 of the second sequence; position 4 of the first sequence corresponds to position 3 of the second sequence; etc. It should be noted that a position in one sequence may correspond to a position in another sequence, even if the positions in the two sequences are not occupied by the same amino acid.

"Osteocalcin" includes the mature protein and further includes biologically active fragments derived from full-length osteocalcin (SEQ ID NO:2) or the mature protein, including various domains, as well as variants as described herein.

In one embodiment of the present invention, the pharmaceutical compositions for use in the methods of the invention comprise a mammalian uncarboxylated osteocalcin. In a preferred embodiment of the invention, the compositions for use in the methods of the invention comprise human uncarboxylated osteocalcin having the amino acid sequence of SEQ ID NO:2, or portions thereof, and encoded for by the nucleic acid of SEQ ID NO:1, or portions thereof. In some embodiments, the compositions for use in the methods of the invention may comprise one or more of the human osteocalcin fragments described herein.

In a preferred embodiment of the invention, the compositions for use in the methods of the invention comprise human uncarboxylated osteocalcin having the amino acid sequence of SEQ ID NO:12.

In a specific embodiment, the present invention provides pharmaceutical compositions comprising human undercarboxylated osteocalcin which does not contain a carboxylated glutamic acid at one or more of positions corresponding to positions 17, 21, and 24 of mature human osteocalcin. A preferred form of osteocalcin for use in the methods of the present invention is mature human osteocalcin wherein at least one of the glutamic acid residues at positions 17, 21, and 24 is not carboxylated. In certain embodiments, the glutamic acid residue at position 17 is not carboxylated. Preferably, all three of the glutamic acid residues at positions 17, 21, and 24 are not carboxylated. The amino acid sequence of mature human osteocalcin is shown in SEQ. ID. NO:12.

The primary sequence of osteocalcin is highly conserved among species and it is one of the ten most abundant proteins in the human body, suggesting that its function is preserved throughout evolution. Conserved features include 3 Gla residues at positions 17, 21, and 24 and a disulfide bridge between Cys23 and Cys29. In addition, most species contain a hydroxyproline at position 9. The N-terminus of osteocalcin shows highest sequence variation in comparison to other parts of the molecule. The high degree of conservation of human and mouse osteocalcin underscores the relevance of the mouse as an animal model for the human, in both healthy and diseased states, and validates the therapeutic and diagnostic use of osteocalcin to treat or prevent disorders related to cognition in humans based on the experimental data derived from the mouse model disclosed herein.

The present invention also includes the use of polypeptide fragments of osteocalcin. Fragments can be derived from the full-length, naturally occurring amino acid sequence of osteocalcin (e.g., SEQ. ID. NO:2). Fragments may also be derived from mature osteocalcin (e.g., SEQ. ID. NO:12). The invention also encompasses fragments of the variants of osteocalcin described herein. A fragment can comprise an amino acid sequence of any length that is biologically active.

Preferred fragments of osteocalcin include fragments containing Glu17, Glu21, and Glu24 of the mature protein. Also preferred are fragments of the mature protein missing the last 10 amino acids from the C-terminal end of the mature protein. Also preferred are fragments missing the first 10 amino acids from the N-terminal end of the mature protein. Also preferred is a fragment of the mature protein missing both the last 10 amino acids from the C-terminal end and the first 10 amino acids from the N-terminal end. Such a fragment comprises amino acids 62-90 of SEQ ID NO:2.

Other preferred fragments of osteocalcin for the pharmaceutical compositions of the invention described herein include polypeptides comprising, consisting of, or consisting essentially of, the following sequences of amino acids:

positions 1-19 of mature human osteocalcin
positions 20-43 of mature human osteocalcin
positions 20-49 of mature human osteocalcin
positions 1-43 of mature human osteocalcin
positions 1-42 of mature human osteocalcin
positions 1-41 of mature human osteocalcin
positions 1-40 of mature human osteocalcin
positions 1-39 of mature human osteocalcin
positions 1-38 of mature human osteocalcin
positions 1-37 of mature human osteocalcin
positions 1-36 of mature human osteocalcin
positions 1-35 of mature human osteocalcin
positions 1-34 of mature human osteocalcin
positions 1-33 of mature human osteocalcin
positions 1-32 of mature human osteocalcin
positions 1-31 of mature human osteocalcin
positions 1-30 of mature human osteocalcin
positions 1-29 of mature human osteocalcin
positions 2-49 of mature human osteocalcin
positions 2-45 of mature human osteocalcin
positions 2-40 of mature human osteocalcin
positions 2-35 of mature human osteocalcin
positions 2-30 of mature human osteocalcin
positions 2-25 of mature human osteocalcin
positions 2-20 of mature human osteocalcin
positions 4-49 of mature human osteocalcin
positions 4-45 of mature human osteocalcin
positions 4-40 of mature human osteocalcin
positions 4-35 of mature human osteocalcin
positions 4-30 of mature human osteocalcin
positions 4-25 of mature human osteocalcin
positions 4-20 of mature human osteocalcin
positions 8-49 of mature human osteocalcin
positions 8-45 of mature human osteocalcin
positions 8-40 of mature human osteocalcin
positions 8-35 of mature human osteocalcin
positions 8-30 of mature human osteocalcin
positions 8-25 of mature human osteocalcin
positions 8-20 of mature human osteocalcin
positions 10-49 of mature human osteocalcin
positions 10-45 of mature human osteocalcin
positions 10-40 of mature human osteocalcin
positions 10-35 of mature human osteocalcin
positions 10-30 of mature human osteocalcin
positions 10-25 of mature human osteocalcin
positions 10-20 of mature human osteocalcin
positions 6-34 of mature human osteocalcin
positions 6-35 of mature human osteocalcin
positions 6-36 of mature human osteocalcin
positions 6-37 of mature human osteocalcin
positions 6-38 of mature human osteocalcin
positions 7-34 of mature human osteocalcin
positions 7-35 of mature human osteocalcin
positions 7-36 of mature human osteocalcin
positions 7-37 of mature human osteocalcin
positions 7-38 of mature human osteocalcin
positions 7-30 of mature human osteocalcin
positions 7-25 of mature human osteocalcin
positions 7-23 of mature human osteocalcin
positions 7-21 of mature human osteocalcin positions 7-19 of mature human osteocalcin
positions 7-17 of mature human osteocalcin
positions 8-30 of mature human osteocalcin
positions 8-25 of mature human osteocalcin
positions 8-23 of mature human osteocalcin
positions 8-21 of mature human osteocalcin
positions 8-19 of mature human osteocalcin
positions 8-17 of mature human osteocalcin
positions 9-30 of mature human osteocalcin
positions 9-25 of mature human osteocalcin
positions 9-23 of mature human osteocalcin
positions 9-21 of mature human osteocalcin
positions 9-19 of mature human osteocalcin
positions 9-17 of mature human osteocalcin Especially preferred is a fragment comprising positions 1-36 of mature human osteocalcin. Another preferred fragment is a fragment comprising positions 20-49 of mature human osteocalcin. Other fragments can be designed to contain Pro13 to Tyr76 or Pro13 to Asn26 of mature human osteocalcin. Additionally, fragments containing the cysteine residues at positions 23 and 29 of mature human osteocalcin, and capable of forming a disulfide bond between those two cysteines, are useful.

Fragments can be discrete (not fused to other amino acids or polypeptides) or can be within a larger polypeptide. Further, several fragments can be comprised within a single larger polypeptide. In one embodiment, a fragment designed for expression in a host can have heterologous pre- and pro-polypeptide regions fused to the amino terminus of the osteocalcin fragment and/or an additional region fused to the carboxyl terminus of the fragment.

Also provided for use in the compositions and methods of the present invention are variants of osteocalcin and the osteocalcin fragments described above. "Variants" refers to osteocalcin peptides that contain modifications in their amino acid sequences such as one or more amino acid substitutions, additions, deletions and/or insertions but that are still biologically active. In some instances, the antigenic and/or immunogenic properties of the variants are not substantially altered, relative to the corresponding peptide from which the variant was derived. Such modifications may be readily introduced using standard mutagenesis techniques, such as oligonucleotide directed site-specific mutagenesis as taught, for example, by Adelman et al., 1983, DNA 2:183, or by chemical synthesis. Variants and fragments are not mutually exclusive terms. Fragments also include peptides that may contain one or more amino acid substitutions, additions, deletions and/or insertions such that the fragments are still biologically active.

One particular type of variant that is within the scope of the present invention is a variant in which one of more of the positions corresponding to positions 17, 21, and 24 of mature human osteocalcin is occupied by an amino acid that is not glutamic acid. In some embodiments, the amino acid that is not glutamic acid is also not aspartic acid. Such variants are versions of undercarboxylated osteocalcin because at least one of the three positions corresponding to positions 17, 21, and 24 of mature human osteocalcin is not carboxylated glutamic acid, since at least one of those positions is not occupied by glutamic acid.

In particular embodiments, the present invention provides osteocalcin variants comprising the amino acid sequence (SEQ. ID. NO: 13)
YLYQWLGAPV PYPDPL$X_1$PRR $X_2$VC$X_3$LNPDCD ELADHIGFQE

AYRRFYGPV wherein $X_1$, $X_2$ and $X_3$ are each independently selected from an amino acid or amino acid analog, with the proviso that if $X_1$, $X_2$ and $X_3$ are each glutamic acid, then $X_1$ is not carboxylated, or less than 50 percent of $X_2$ is carboxylated, and/or less than 50 percent of $X_3$ is carboxylated.

In certain embodiments, the osteocalcin variants comprise an amino acid sequence that is different from SEQ. ID. NO:13 at 1 to 7 positions other than $X_1$, $X_2$ and $X_3$.

In other embodiments, the osteocalcin variants comprise an amino acid sequence that includes one or more amide backbone substitutions.

Fully functional variants typically contain only conservative variation or variation in non-critical residues or in non-critical regions. Functional variants can also contain substitutions of similar amino acids, which results in no change, or an insignificant change, in function. Alternatively, such substitutions may positively or negatively affect function to some degree. The activity of such functional osteocalcin variants can be determined using assays such as those described herein.

Variants can be naturally-occurring or can be made by recombinant means, or chemical synthesis, to provide useful and novel characteristics for undercarboxylated/uncarboxylated osteocalcin. For example, the variant osteocalcin polypeptides may have reduced immunogenicity, increased serum half-life, increased bioavailability, and/or increased potency. In particular embodiments, serum half-life is increased by substituting one or more of the native Arg residues at positions 19, 20, 43, and 44 of mature osteocalcin with another amino acid or an amino acid analog, e.g., β-dimethyl-arginine. Such substitutions can be combined with the other changes in the native amino acid sequence of osteocalcin described herein.

Provided for use in the pharmaceutical compositions and methods of the present invention are variants that are also derivatives of the osteocalcin and osteocalcin fragments described above. Derivatization is a technique used in chemistry which transforms a chemical compound into a product of similar chemical structure, called derivative. Generally, a specific functional group of the compound participates in the derivatization reaction and transforms the compound to a derivate of different reactivity, solubility, boiling point, melting point, aggregate state, functional activity, or chemical composition. Resulting new chemical properties can be used for quantification or separation of the derivatized compound or can be used to optimize the derivatized compound as a therapeutic agent. The well-known techniques for derivatization can be applied to the above-described osteocalcin and osteocalcin fragments. Thus, derivatives of the osteocalcin and osteocalcin fragments described above will contain amino acids that have been chemically modified in some way so that they differ from the natural amino acids.

Provided also are osteocalcin mimetics. "Mimetic" refers to a synthetic chemical compound that has substantially the same structural and functional characteristics of a naturally or non-naturally occurring osteocalcin polypeptide, and includes, for instance, polypeptide- and polynucleotide-like polymers having modified backbones, side chains, and/or bases. Peptide mimetics are commonly used in the pharmaceutical industry as non-peptide drugs with properties analogous to those of the template peptide. Generally, mimetics are structurally similar (i.e., have the same shape) to a paradigm polypeptide that has a biological or pharmacological activity, but one or more polypeptide linkages are replaced. The mimetic can be either entirely composed of synthetic, non-natural analogues of amino acids or is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity.

By way of examples that can be adapted to osteocalcin by those skilled in the art: Cho et al., 1993, Science 261:1303-1305 discloses an "unnatural biopolymer" consisting of chiral aminocarbonate monomers substituted with a variety of side chains, synthesis of a library of such polymers, and screening for binding affinity to a monoclonal antibody. Simon et al., 1992, Proc. Natl. Acad. Sci. 89:9367-9371 discloses a polymer consisting of N-substituted glycines ("peptoids") with diverse side chains. Schumacher et al, 1996, Science 271:1854-1857 discloses D-peptide ligands identified by screening phage libraries of L-peptides against proteins synthesized with D-amino acids and then synthesizing a selected L-peptide using D-amino acids. Brody et al., 1999, Mol. Diagn. 4:381-8 describes generation and screening of hundreds to thousands of aptamers.

A particular type of osteocalcin variant within the scope of the invention is an osteocalcin mimetic in which one or more backbone amides is replaced by a different chemical structure or in which one or more amino acids are replaced by an amino acid analog. In a particular embodiment, the osteocalcin mimetic is a retroenantiomer of uncarboxylated human osteocalcin.

Osteocalcin, as well as its fragments and variants, is optionally produced by chemical synthesis or recombinant methods and may be produced as a modified osteocalcin molecule (i.e., osteocalcin fragments or variants) as described herein. Osteocalcin polypeptides can be produced by any conventional means (Houghten, 1985, Proc. Natl. Acad. Sci. USA 82:5131-5135). Simultaneous multiple peptide synthesis is described in U.S. Pat. No. 4,631,211 and can also be used. When produced recombinantly, osteocalcin may be produced as a fusion protein, e.g., a GST-osteocalcin fusion protein.

Undercarboxylated/uncarboxylated osteocalcin molecules that can be used in the methods of the invention include proteins substantially homologous to human osteocalcin, including proteins derived from another organism, i.e., an ortholog of human osteocalcin. One particular ortholog is mouse osteocalcin. Mouse osteocalcin gene 1 cDNA is SEQ ID NO:3; mouse osteocalcin gene 2 cDNA is SEQ ID NO:4; the amino acid sequence of mouse osteocalcin gene 1 and gene 2 is SEQ ID NO:5.

As used herein, two proteins are substantially homologous when their amino acid sequences are at least about 70-75% homologous. Typically the degree of homology is at least about 80-85%, and most typically at least about 90-95%, 97%, 98% or 99% or more. "Homology" between two amino acid sequences or nucleic acid sequences can be determined by using the algorithms disclosed herein. These algorithms can also be used to determine percent identity between two amino acid sequences or nucleic acid sequences.

In a specific embodiment of the invention, the undercarboxylated/uncarboxylated osteocalcin is an osteocalcin molecule sharing at least 80% homology with the human osteocalcin of SEQ ID:2 or a portion of SEQ ID:2 that is at least 8 amino acids long. In another embodiment, the undercarboxylated/uncarboxylated osteocalcin is an osteocalcin molecule sharing at least 80%, at least 90%, at least 95%, or at least 97% amino acid sequence identity with the human osteocalcin of SEQ ID:2 or a portion of SEQ ID:2 that is at least 8 amino acids long. Homologous sequences include those sequences that are substantially identical. In preferred embodiments, the homology or identity is over the entire length of mature human osteocalcin.

To determine the percent homology or percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). Preferably, the length of a reference sequence aligned for comparison purposes is at least 30%, preferably at least 40%, more preferably at least 50%, even more preferably at least 60%, and even more preferably at least 70%, 80%, or 90% or more of the length of the sequence that the reference sequence is compared to. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The invention also encompasses polypeptides having a lower degree of identity but which have sufficient similarity so as to perform one or more of the same functions performed by undercarboxylated/uncarboxylated osteocalcin. Similarity is determined by considering conserved amino acid substitutions. Such substitutions are those that substitute a given amino acid in a polypeptide by another amino acid of like characteristics. Conservative substitutions are likely to be phenotypically silent. Guidance concerning which amino acid changes are likely to be phenotypically silent may be found in Bowie et al., 1990, Science 247: 1306-1310.

Examples of conservative substitutions are the replacements, one for another, among the hydrophobic amino acids Ala, Val, Leu, and Ile; interchange of the hydroxyl residues Ser and Thr; exchange of the acidic residues Asp and Glu; substitution between the amide residues Asn and Gln; exchange of the basic residues Lys, His and Arg; replacements among the aromatic residues Phe, Trp and Tyr; exchange of the polar residues Gln and Asn; and exchange of the small residues Ala, Ser, Thr, Met, and Gly.

The comparison of sequences and determination of percent identity and homology between two osteocalcin polypeptides can be accomplished using a mathematical algorithm. See, for example, Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H G., eds., Humana Press, New Jersey, 1994; Sequence Analysis in Molecular Biology, van Heinje, G., Academic Press, 1987; and Sequence Analysis Primer, Gribskov, M. and Devereux, J., eds., M Stockton Press, New York, 1991. A non-limiting example of such a mathematical algorithm is described in Karlin et al., 1993, Proc. Natl. Acad. Sci. USA 90:5873-5877.

The percent identity or homology between two osteocalcin amino acid sequences may be determined using the Needleman et al., 1970, J. Mol. Biol. 48:444-453 algorithm.

A substantially homologous osteocalcin, according to the present invention, may also be a polypeptide encoded by a nucleic acid sequence capable of hybridizing to the human osteocalcin nucleic acid sequence under highly stringent conditions, e.g., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. (Ausubel et al., eds., 1989, Current Protocols in Molecular Biology, Vol. I, Green Publishing Associates, Inc., and John Wiley & sons, Inc., New York, at p. 2.10.3) and encoding a functionally equivalent gene product; or under less stringent conditions, such as moderately stringent conditions, e.g., washing in 0.2×SSC/0.1% SDS at 42° C. (Ausubel et al., 1989 supra), yet which still encodes a biologically active undercarboxylated/uncarboxylated osteocalcin.

A substantially homologous osteocalcin according to the present invention may also be a polypeptide encoded by a nucleic acid sequence capable of hybridizing to a sequence having at least 70-75%, typically at least about 80-85%, and most typically at least about 90-95%, 97%, 98% or 99% identity to the human osteocalcin nucleic acid sequence, under stringent conditions, e.g., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3) and encoding a functionally equivalent gene product; or under less stringent conditions, such as moderately stringent conditions, e.g., washing in 0.2×SSC/0.1% SDS at 42° C. (Ausubel et al., 1989 supra), yet which still encodes a biologically active undercarboxylated/uncarboxylated osteocalcin.

It will be understood that a biologically active fragment or variant of human osteocalcin may contain a different number of amino acids than native human osteocalcin. Accordingly, the position number of the amino acid residues corresponding to positions 17, 21, and 24 of mature human osteocalcin may differ in the fragment or variant. One skilled in the art would easily recognize such corresponding positions from a comparison of the amino acid sequence of the fragment or variant with the amino acid sequence of mature human osteocalcin.

Peptides corresponding to fusion proteins in which full length osteocalcin, mature osteocalcin, or an osteocalcin fragment or variant is fused to an unrelated protein or polypeptide are also within the scope of the invention and can be designed on the basis of the osteocalcin nucleotide and amino acid sequences disclosed herein. Such fusion proteins include fusions to an enzyme, fluorescent protein, or luminescent protein which provides a marker function. In a preferred embodiment of the invention, the fusion protein comprises fusion to a polypeptide capable of targeting the osteocalcin to a particular target cell or location in the body. For example, osteocalcin polypeptide sequences may be fused to a ligand molecule capable of targeting the fusion protein to a cell expressing the receptor for said ligand. In a particular embodiment, osteocalcin polypeptide sequences may be fused to a ligand capable of targeting the fusion protein to specific neurons in the brain of a mammal.

Osteocalcin can also be made as part of a chimeric protein for drug screening or use in making recombinant protein. These chimeric proteins comprise an osteocalcin peptide sequence linked to a heterologous peptide having an amino acid sequence not substantially homologous to the osteocalcin. The heterologous peptide can be fused to the N-terminus or C-terminus of osteocalcin or can be internally located. In one embodiment, the fusion protein does not affect osteocalcin function. For example, the fusion protein can be a GST-fusion protein in which the osteocalcin sequences are fused to the N- or C-terminus of the GST sequences. Other types of fusion proteins include, but are not limited to, enzymatic fusion proteins, for example beta-galactosidase fusions, yeast two-hybrid GAL-4 fusions, poly-His fusions and Ig fusions. Such fusion proteins, particularly poly-His fusions, can facilitate the purification of recombinant osteocalcin. In certain host cells (e.g., mammalian host cells), expression and/or secretion of a protein can be increased by using a heterologous signal sequence. Therefore, the fusion protein may contain a heterologous signal sequence at its N-terminus.

Those skilled in art would understand how to adapt well-known techniques for use with osteocalcin. For example, EP 0 464 533 discloses fusion proteins comprising various portions of immunoglobulin constant regions (Fc regions). The Fc region is useful in therapy and diagnosis and thus results, for example, in improved pharmacokinetic properties (see, e.g., EP 0 232 262). In drug discovery, for example, human proteins have been fused with Fc regions for the purpose of high-throughput screening assays to identify antagonists (Bennett et al., 1995, J. Mol. Recog. 8:52-58 and Johanson et al., 1995, J. Biol. Chem. 270:9459-9471). Thus, various embodiments of this invention also utilize soluble fusion proteins containing an osteocalcin polypeptide and various portions of the constant regions of heavy or light chains of immunoglobulins of various subclasses (e.g., IgG, IgM, lgA, IgE, lgB). Preferred as immunoglobulin is the constant part of the heavy chain of human IgG, particularly IgG1, where fusion takes place at the hinge region. For some uses, it is desirable to remove the Fc region after the fusion protein has been used for its intended purpose. In a particular embodiment, the Fc part can be removed in a simple way by a cleavage sequence, which is also incorporated and can be cleaved, e.g., with factor Xa.

A chimeric or fusion protein can be produced by standard recombinant DNA techniques. For example, DNA fragments coding for the different protein sequences can be ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., 1992, Current Protocols in Molecular Biology). Moreover, many expression vectors are commercially available that already encode a fusion moiety (e.g., a GST protein). An osteocalcin-encoding nucleic acid can be cloned into such an expression vector such that the fusion moiety is linked in-frame to osteocalcin.

Chimeric osteocalcin proteins can be produced in which one or more functional sites are derived from a different isoform, or from another osteocalcin molecule from another species. Sites also could be derived from osteocalcin-related proteins that occur in the mammalian genome but which have not yet been discovered or characterized.

Polypeptides often contain amino acids other than the 20 amino acids commonly referred to as the 20 naturally-occurring amino acids. Further, many amino acids, including the terminal amino acids, may be modified by natural processes, such as processing and other posttranslational modifications, or by chemical modification techniques well known in the art.

Accordingly, the osteocalcin polypeptides useful in the methods of the present invention also encompass derivatives which contain a substituted non-naturally occurring amino acid residue that is not one encoded by the genetic code, in which a substituent group is included, in which the mature polypeptide is fused with another compound, such as a compound to increase the half-life of the polypeptide (for example, polyethylene glycol), or in which the additional amino acids are fused to the osteocalcin polypeptide, such as a leader or secretory sequence or a sequence for purification of the osteocalcin polypeptide or a pro-protein sequence.

Undercarboxylated/uncarboxylated osteocalcin can be modified according to known methods in medicinal chemistry to increase its stability, half-life, uptake or efficacy. Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

In a specific embodiment of the invention, modifications may be made to the osteocalcin to reduce susceptibility to proteolysis at residue Arg43 as a means for increasing serum half life. Such modifications include, for example, the use of retroenantio isomers, D-amino acids, or other amino acid analogs.

Acylation of the N-terminal amino group can be accomplished using a hydrophilic compound, such as hydroorotic acid or the like, or by reaction with a suitable isocyanate, such as methylisocyanate or isopropylisocyanate, to create a urea moiety at the N-terminus. Other agents can also be N-terminally linked that will increase the duration of action of the osteocalcin derivative.

Reductive amination is the process by which ammonia is condensed with aldehydes or ketones to form imines which are subsequently reduced to amines. Reductive amination is a useful method for conjugating undercarboxylated/uncarboxylated osteocalcin and its fragments or variants to polyethylene glycol (PEG). Covalent linkage of PEG to undercarboxylated/uncarboxylated osteocalcin and its fragments and variants may result in conjugates with increased water solubility, altered bioavailability, pharmacokinetics, immunogenic properties, and biological activities. See, e.g., Bentley et al., 1998, J. Pharm. Sci. 87:1446-1449.

Several particularly common modifications that may be applied to undercarboxylated/uncarboxylated osteocalcin and its fragments and variants such as glycosylation, lipid attachment, sulfation, hydroxylation and ADP-ribosylation are described in most basic texts, such as Proteins-Structure and Molecular Properties, 2nd ed., T. E. Creighton, W. H. Freeman and Company, New York (1993). Many detailed reviews are available on this subject, such as by Wold, F., Posttranslational Covalent Modification of Proteins, B. C. Johnson, Ed., Academic Press, New York 1-12 (1983); Seifter et al., 1990, Meth. Enzymol. 182:626-646 and Rattan et al., 1992, Ann. New York Acad. Sci. 663:48-62.

As is also well known, polypeptides are not always entirely linear. For instance, polypeptides may be branched as a result of ubiquitination, and they may be circular, with or without branching, generally as a result of post-translation events, including natural processing events and events brought about by human manipulation which do not occur naturally. Circular, branched and branched circular polypeptides may be synthesized by non-translational natural processes and by synthetic methods. Well-known techniques for preparing such non-linear polypeptides may be adapted by those skilled in the art to produce non-linear osteocalcin polypeptides.

Modifications can occur anywhere in the undercarboxylated/uncarboxylated osteocalcin and its fragments and variants, including the peptide backbone, the amino acid side-chains and the amino or carboxyl termini. Blockage of the amino or carboxyl group in a polypeptide, or both, by a covalent modification, is common in naturally-occurring and synthetic polypeptides and may be applied to the undercarboxylated/uncarboxylated osteocalcin or its fragments and variants used in the present invention. For instance, the amino terminal residue of polypeptides made in *E. coli*, prior to proteolytic processing, almost invariably will be N-formylmethionine. Thus, the use of undercarboxylated/uncarboxylated osteocalcin and its fragments and variants with N-formylmethionine as the amino terminal residue are within the scope of the present invention.

A brief description of various protein modifications that come within the scope of this invention are set forth in the table below:

TABLE 1

| Protein Modification | Description |
|---|---|
| Acetylation | Acetylation of N-terminus or ε-lysines. Introducing an acetyl group into a protein, specifically, the substitution of an acetyl group for an active hydrogen atom.<br>A reaction involving the replacement of the hydrogen atom of a hydroxyl group with an acetyl group ($CH_3CO$) yields a specific ester, the acetate. Acetic anhydride is commonly used as an acetylating agent, which reacts with free hydroxyl groups.<br>Acylation may facilitate addition of other functional groups. A common reaction is acylation of e.g., conserved lysine residues with a biotin appendage. |

TABLE 1-continued

| Protein Modification | Description |
|---|---|
| ADP-ribosylation | Covalently linking proteins or other compounds via an arginine-specific reaction. |
| Alkylation | Alkylation is the transfer of an alkyl group from one molecule to another. The alkyl group may be transferred as an alkyl carbocation, a free radical or a carbanion (or their equivalents). Alkylation is accomplished by using certain functional groups such as alkyl electrophiles, alkyl nucleophiles or sometimes alkyl radicals or carbene acceptors. A common example is methylation (usually at a lysine or arginine residue). |
| Amidation | Reductive animation of the N-terminus. Methods for amidation of insulin are described in U.S. Pat. No. 4,489,159. |
| Carbamylation | Nigen et al. describes a method of carbamylating hemoglobin. |
| Citrullination | Citrullination involves the addition of citrulline amino acids to the arginine residues of a protein, which is catalyzed by peptidylarginine deaminase enzymes (PADs). This generally converts a positively charged arginine into a neutral citrulline residue, which may affect the hydrophobicity of the protein (and can lead to unfolding). |
| Condensation of amines with aspartate or glutamate | Such reactions, may be used, e.g., to attach a peptide to other proteins labels. |
| Covalent attachment of flavin | Flavin mononucleotide (FAD) may be covalently attached to serine and/or threonine residues. May be used, e.g., as a light-activated tag. |
| Covalent attachment of heme moiety | A heme moiety is generally a prosthetic group that consists of an iron atom contained in the center of a large heterocyclic organic ring, which is referred to as a porphyrin. The heme moiety may be used, e.g., as a tag for the peptide. |
| Attachment of a nucleotide or nucleotide derivative | May be used as a tag or as a basis for further derivatising a peptide. |
| Cross-linking | Cross-linking is a method of covalently joining two proteins. Cross-linkers contain reactive ends to specific functional groups (primary amines, sulfhydryls, etc.) on proteins or other molecules. Several chemical groups may be targets for reactions in proteins and peptides. For example, Ethylene glycol bis[succinimidylsuccinate, Bis[2-(succinimidooxycarbonyloxy)ethyl]sulfone, and Bis[sulfosuccinimidyl] suberate link amines to amines. |
| Cyclization | For example, cyclization of amino acids to create optimized delivery forms that are resistant to, e.g., aminopeptidases (e.g., formation of pyroglutamate, a cyclized form of glutamic acid). |
| Disulfide bond formation | Disulfide bonds in proteins are formed by thiol-disulfide exchange reactions, particularly between cysteine residues (e.g., formation of cystine). |
| Demethylation | See, e.g., U.S. Pat. No. 4,250,088 (Process for demethylating lignin). |
| Formylation | The addition of a formyl group to, e.g., the N-terminus of a protein. See, e.g., U.S. Pat. Nos. 4,059,589, 4,801,742, and 6,350,902. |
| Glycylation | The covalent linkage of one to more than 40 glycine residues to the tubulin C-terminal tail. |
| Glycosylation | Glycosylation may be used to add saccharides (or polysaccharides) to the hydroxy oxygen atoms of serine and threonine side chains (which is also known as O-linked Glycosylation). Glycosylation may also be used to add saccharides (or polysaccharides) to the amide nitrogen of asparagine side chains (which is also known as N-linked Glycosylation), e.g., via oligosaccharyl transferase. |
| GPI anchor formation | The addition of glycosylphosphatidylinositol to the C-terminus of a protein. GPI anchor formation involves the addition of a hydrophobic phosphatidylinositol group - linked through a carbohydrate containing linker (e.g., glucosamine and mannose linked to phosphoryl ethanolamine residue) - to the C-terminal amino acid of a protein. |

TABLE 1-continued

| Protein Modification | Description |
|---|---|
| Hydroxylation | Chemical process that introduces one or more hydroxyl groups (—OH) into a protein (or radical). Hydroxylation reactions are typically catalyzed by hydroxylases. Proline is the principal residue to be hydroxylated in proteins, which occurs at the $C^{\gamma}$ atom, forming hydroxyproline (Hyp). In some cases, proline may be hydroxylated at its $C^{\beta}$ atom. Lysine may also be hydroxylated on its $C^{\delta}$ atom, forming hydroxylysine (Hyl). These three reactions are catalyzed by large, multi-subunit enzymes known as prolyl 4-hydroxylase, prolyl 3-hydroxylase and lysyl 5-hydroxylase, respectively. These reactions require iron (as well as molecular oxygen and α-ketoglutarate) to carry out the oxidation, and use ascorbic acid to return the iron to its reduced state. |
| Iodination | See, e.g., U.S. Pat. No. 6,303,326 for a disclosure of an enzyme that is capable of iodinating proteins. U.S. Pat. No. 4,448,764 discloses, e.g., a reagent that may be used to iodinate proteins. |
| ISGylation | Covalently linking a peptide to the ISG15 (Interferon-Stimulated Gene 15) protein, for, e.g., modulating immune response. |
| Methylation | Reductive methylation of protein amino acids with formaldehyde and sodium cyanoborohydride has been shown to provide up to 25% yield of N-cyanomethyl (—$CH_2CN$) product. The addition of metal ions, such as $Ni^{2+}$, which complex with free cyanide ions, improves reductive methylation yields by suppressing by-product formation. The N-cyanomethyl group itself, produced in good yield when cyanide ion replaces cyanoborohydride, may have some value as a reversible modifier of amino groups in proteins. (Gidley et al.) Methylation may occur at the arginine and lysine residues of a protein, as well as the N- and C-terminus thereof. |
| Myristoylation | Myristoylation involves the covalent attachment of a myristoyl group (a derivative of myristic acid), via an amide bond, to the alpha-amino group of an N-terminal glycine residue. This addition is catalyzed by the N-myristoyltransferase enzyme. |
| Oxidation | Oxidation of cysteines.<br>Oxidation of N-terminal Serine or Threonine residues (followed by hydrazine or aminooxy condensations).<br>Oxidation of glycosylations (followed by hydrazine or aminooxy condensations). |
| Palmitoylation | Palmitoylation is the attachment of fatty acids, such as palmitic acid, to cysteine residues of proteins. Palmitoylation increases the hydrophobicity of a protein. |
| (Poly)glutamylation | Polyglutamylation occurs at the glutamate residues of a protein. Specifically, the gamma-carboxy group of a glutamate will form a peptide-like bond with the amino group of a free glutamate whose alpha-carboxy group may be extended into a polyglutamate chain. The glutamylation reaction is catalyzed by a glutamylase enzyme (or removed by a deglutamylase enzyme). Polyglutamylation has been carried out at the C-terminus of proteins to add up to about six glutamate residues. Using such a reaction, Tubulin and other proteins can be covalently linked to glutamic acid residues. |
| Phosphopantetheinylation | The addition of a 4'-phosphopantetheinyl group. |
| Phosphorylation | A process for phosphorylation of a protein or peptide by contacting a protein or peptide with phosphoric acid in the presence of a non-aqueous apolar organic solvent and contacting the resultant solution with a dehydrating agent is disclosed e.g., in U.S. Pat. No. 4,534,894. Insulin products are described to be amenable to this process. See, e.g., U.S. Pat. No. 4,534,894. Typically, phosphorylation occurs at the serine, threonine, and tyrosine residues of a protein. |
| Prenylation | Prenylation (or isoprenylation or lipidation) is the addition of hydrophobic molecules to a protein. Protein prenylation involves the transfer of either a farnesyl (linear grouping of three isoprene units) or a geranyl-geranyl moiety to C-terminal cysteine(s) of the target protein. |
| Proteolytic Processing | Processing, e.g., cleavage of a protein at a peptide bond. |
| Selenoylation | The exchange of, e.g., a sulfur atom in the peptide for selenium, using a selenium donor, such as selenophosphate. |

TABLE 1-continued

| Protein Modification | Description |
|---|---|
| Sulfation | Processes for sulfating hydroxyl moieties, particularly tertiary amines, are described in, e.g., U.S. Pat. No. 6,452,035. A process for sulphation of a protein or peptide by contacting the protein or peptide with sulphuric acid in the presence of a non-aqueous apolar organic solvent and contacting the resultant solution with a dehydrating agent is disclosed. Insulin products are described to be amenable to this process. See, e.g., U.S. Pat. No. 4,534,894. |
| SUMOylation | Covalently linking a peptide a SUMO (small ubiquitin-related Modifier) protein, for, e.g., stabilizing the peptide. |
| Transglutamination | Covalently linking other protein(s) or chemical groups (e.g., PEG) via a bridge at glutamine residues |
| tRNA-mediated addition of amino acids (e.g., arginylation) | For example, the site-specific modification (insertion) of an amino acid analog into a peptide. |
| Ubiquitination | The small peptide ubiquitin is covalently linked to, e.g., lysine residues of a protein. The ubiquitin-proteasome system can be used to carryout such reaction. See, e.g., U.S. 2007-0059731. |

The present invention also encompasses the use of prodrugs of undercarboxylated/uncarboxylated osteocalcin or derivative or variant thereof that can be produced by esterifying the carboxylic acid functions of the undercarboxylated/uncarboxylated osteocalcin or derivative or variant thereof with a lower alcohol, e.g., methanol, ethanol, propanol, isopropanol, butanol, etc. The use of prodrugs of the undercarboxylated/uncarboxylated osteocalcin or derivative or variant thereof that are not esters is also contemplated. For example, pharmaceutically acceptable carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters of the undercarboxylated/uncarboxylated osteocalcin or derivative or variant thereof are also contemplated. In some embodiments, the prodrugs will contain a biohydrolyzable moiety (e.g., a biohydrolyzable amide, biohydrolyzable carbamate, biohydrolyzable carbonate, biohydrolyzable ester, biohydrolyzable phosphate, or biohydrolyzable ureide analog). Guidance for the preparation of prodrugs of the undercarboxylated/uncarboxylated osteocalcin or derivative or variant thereof disclosed herein can be found in publications such as *Design of Prodrugs*, Bundgaard, A. Ed., Elsevier, 1985; *Design and Application of Prodrugs, A Textbook of Drug Design and Development*, Krosgaard-Larsen and H. Bundgaard, Ed., 1991, Chapter 5, pages 113-191; and Bundgaard, H., Advanced Drug Delivery Review, 1992, 8, pages 1-38.

To practice the methods of the present invention, it may be desirable to recombinantly express osteocalcin, e.g., by recombinantly expressing a cDNA sequence encoding osteocalcin. The cDNA sequence and deduced amino acid sequence of human osteocalcin is represented in SEQ ID NO:1 and SEQ ID NO:2. Osteocalcin nucleotide sequences may be isolated using a variety of different methods known to those skilled in the art. For example, a cDNA library constructed using RNA from a tissue known to express osteocalcin can be screened using a labeled osteocalcin probe. Alternatively, a genomic library may be screened to derive nucleic acid molecules encoding osteocalcin. Further, osteocalcin nucleic acid sequences may be derived by performing a polymerase chain reaction (PCR) using two oligonucleotide primers designed on the basis of known osteocalcin nucleotide sequences. The template for the reaction may be cDNA obtained by reverse transcription of mRNA prepared from cell lines or tissue known to express osteocalcin.

While the osteocalcin polypeptides and peptides can be chemically synthesized (e.g., see Creighton, 1983, Proteins: Structures and Molecular Principles, W.H. Freeman & Co., N.Y.), large polypeptides derived from osteocalcin and the full length osteocalcin itself may be advantageously produced by recombinant DNA technology using techniques well known in the art for expressing a nucleic acid. Such methods can be used to construct expression vectors containing the osteocalcin nucleotide sequences and appropriate transcriptional and translational control signals. These methods include, for example, in vitro recombinant DNA techniques, synthetic techniques, and in vivo genetic recombination. See, for example, the techniques described in Ausubel et al., 1989, supra.

A variety of host-expression vector systems may be utilized to express the osteocalcin nucleotide sequences. In a preferred embodiment, the osteocalcin peptide or polypeptide is secreted and may be recovered from the culture media.

Appropriate expression systems can be chosen to ensure that the correct modification, processing and subcellular localization of the osteocalcin protein occurs. To this end, bacterial host cells are useful for expression of osteocalcin, as such cells are unable to carboxylate osteocalcin.

The isolated osteocalcin can be purified from cells that naturally express it, e.g., osteoblasts, or purified from cells that naturally express osteocalcin but have been recombinantly modified to overproduce osteocalcin, or purified from cells that that do not naturally express osteocalcin but have been recombinantly modified to express osteocalcin. In a particular embodiment, a recombinant cell has been manipulated to activate expression of the endogenous osteocalcin gene. For example, International Patent Publications WO 99/15650 and WO 00/49162 describe a method of expressing endogenous genes termed random activation of gene expression (RAGE), which can be used to activate or increase expression of endogenous osteocalcin. The RAGE methodology involves non-homologous recombination of a regulatory sequence to activate expression of a downstream endogenous gene. Alternatively, International Patent Publications WO 94/12650, WO 95/31560, and WO 96/29411, as well as U.S. Pat. No. 5,733,761 and U.S. Pat. No. 6,270,985, describe a method of increasing expression of an endogenous gene that involves homologous recombination of a DNA construct that includes a targeting sequence, a regulatory sequence, an exon, and a splice-donor site. Upon homologous recombination, a downstream endogenous gene is expressed. The methods of expressing endogenous genes described in the foregoing patents are hereby expressly incorporated by reference herein.

In certain embodiments of methods of the present invention where the therapeutic agent is undercarboxylated/uncarboxylated osteocalcin or a derivative or variant thereof, the undercarboxylated/uncarboxylated osteocalcin or a derivative or variant thereof is administered to a patient in a dosage range of from about 0.5 μg/kg/day to about 100 mg/kg/day, from about 1 μg/kg/day to about 90 mg/kg/day, from about 5 μg/kg/day to about 85 mg/kg/day, from about 10 μg/kg/day to about 80 mg/kg/day, from about 20 μg/kg/day to about 75 mg/kg/day, from about 50 μg/kg/day to about 70 mg/kg/day, from about 150 μg/kg/day to about 65 mg/kg/day, from about 250 μg/kg/day to about 50 mg/kg/day, from about 500 μg/kg/day to about 50 mg/kg/day, from about 1 mg/kg/day to about 50 mg/kg/day, from about 5 mg/kg/day to about 40 mg/kg/day, from about 10 mg/kg/day to about 35 mg/kg/day, from about 15 mg/kg/day to about 30 mg/kg/day, from about 5 mg/kg/day to about 16 mg/kg/day, or from about 5 mg/kg/day to about 15 mg/kg/day.

In certain embodiments of methods of the present invention where the therapeutic agent is undercarboxylated/uncarboxylated osteocalcin or a derivative or variant thereof, the undercarboxylated/uncarboxylated osteocalcin or a derivative or variant thereof is administered to a patient in a dosage range of from about 0.5 μg/kg/day to about 100 μg/kg/day, from about 1 μg/kg/day to about 80 μg/kg/day, from about 3 μg/kg/day to about 50 μg/kg/day, or from about 3 μg/kg/day to about 30 μg/kg/day.

In certain embodiments of methods of the present invention where the therapeutic agent is undercarboxylated/uncarboxylated osteocalcin or a derivative or variant thereof, the undercarboxylated/uncarboxylated osteocalcin or a derivative or variant thereof is administered to a patient in a dosage range of from about 0.5 ng/kg/day to about 100 ng/kg/day, from about 1 ng/kg/day to about 80 ng/kg/day, from about 3 ng/kg/day to about 50 ng/kg/day, or from about 3 ng/kg/day to about 30 ng/kg/day.

Compositions Comprising Inhibitors of Gamma-Carboxylase, PTP-1B, and/or OST-PTP In certain embodiments of the invention, the pharmaceutical compositions useful in the method of the invention comprise an inhibitor that reduces the expression or activity of gamma-carboxylase, PTP-1B, or OST-PTP. Preferably, the biological activity of gamma-carboxylase, PTP-1B, or OST-PTP is inhibited. The inhibitors may be antibodies (monoclonal or polyclonal) or fragments of antibodies, small molecules, polypeptides or proteins, or nucleic acids (e.g., antisense DNA or RNA, siRNA).

In certain embodiments, the inhibitors reduce the activity of OST-PTP having the amino acid sequence of SEQ ID NO:11. In other embodiments, the inhibitors reduce the activity of an OST-PTP having an amino acid sequence that is substantially homologous or substantially identical, as previously described, to the amino acid sequence of SEQ ID NO:11.

In certain embodiments, the inhibitors reduce the activity of human PTP-1B having the amino acid sequence of SEQ ID NO:17. In other embodiments, the inhibitors reduce the activity of a PTP-1B having an amino acid sequence that is substantially homologous or substantially identical, as previously described, to the amino acid sequence of SEQ ID NO:17.

In certain embodiments, the inhibitors reduce the activity of human gamma-carboxylase having the amino acid sequence of SEQ ID NO:7. In other embodiments, the inhibitors reduce the activity of a gamma-carboxylase having an amino acid sequence that is substantially homologous or identical to SEQ ID NO:7.

Small Molecule Inhibitors of OST-PTP, PTP-1B, and Gamma-Carboxylase

In certain embodiments, the agent is a small molecule. By "small molecule" is meant organic compounds of molecular weight of more than 100 and less than about 2,500 daltons, and preferably less than 500 daltons. Such small molecules inhibit the biological activity of OST-PTP, PTP-1B, or gamma-carboxylase.

The small molecule inhibitors may comprise agents that act as inhibitors of vitamin K. Warfarin and other vitamin K inhibitors, including Coumadin and other derivatives, may be administered to patients who would benefit from inhibition of gamma-carboxylase in order to treat or prevent a cognitive disorder in mammals. In a specific embodiment of the invention, the small molecule warfarin may be used to inhibit the activity of gamma-carboxylase. Warfarin derivatives are exemplified by acenocoumarol, phenprocoumon and phenindione. Warfarin and other Coumadin derivatives block vitamin K-dependent gamma-carboxylation of osteocalcin, thus increasing the level of undercarboxylated/uncarboxylated osteocalcin.

Other inhibitors include thiol specific inhibitors of gamma-carboxylase. Cys and His residues of gamma-carboxylase are implicated in the carboxylase mechanism of gamma-carboxylase and it is observed that the enzyme is inhibited by thiol-specific inhibitors, such as N-ethylmaleimide (NEM) and mercurials such as p-hydroxymurcuribenzoate (pHMB). Additional non-limiting examples of these inhibitors include 5,5-dithiobis-(2-nitrobenzoic acid) (DTNB), 2-nitro-5-thiocyanobenzoic acid (NTCB), iodoacetamide (IA), N-phenylmaleimide (PheM), N-(1-pyrenyl) maleimide (PyrM), naphthalene-1,5-dimaleimide (NDM), N,N'-(1,2-phenylene) dimaleimide (oPDM), N,N'-1,4-phenylene dimaleimide (pPDM), N,N'-1,3-phenylene dimaleimide (mPDM), 1,1-(methylenedi-4,1-phenylene)bismaleimide (BM), 4-(N-maleimido)phenyltrimethylammonium (MPTM), N,N'-bis(3-maleimidopropionyl)-2-hydroxy-1,3-propanediamine (BMP), N-succinimidyl 3-(2-pyridyldithio) propionate, diethyl pyrocarbonate, p-chloromercuribenzene sulphonic acid and thiosulfinates. These inhibitors may also be provided as conjugate or derivative, such as with, e.g., BSA or aminodextran.

Antibody Inhibitors of OST-PTP, PTP-1B, and Gamma-Carboxylase

The present invention also provides compositions comprising an antibody or antibodies, as well as biologically active fragments or variants thereof, that are capable of binding to an epitope of OST-PTP, PTP-1B, or gamma-carboxylase polypeptides and inhibiting the activity of OST-PTP, PTP-1B, or gamma-carboxylase.

An antibody against OST-PTP that decreases its activity can be used therapeutically. In certain embodiments, the antibody against OST-PTP binds to the extracellular domain of OST-PTP.

In certain embodiments, the antibody against OST-PTP binds to an epitope in the mouse OST-PTP of SEQ ID NO:11 or an OST-PTP having an amino acid sequence that is substantially homologous or identical to SEQ ID NO:11. In other embodiments, the antibody against OST-PTP binds to an epitope in an OST-PTP having an amino acid sequence that is at least 70% homologous or identical to SEQ ID NO:11.

Human OST-PTP can be obtained by isolating the human ortholog of mouse OST-PTP (SEQ ID NO:10) or rat OST-PTP (SEQ ID NO:14) by methods known in the art. For example, one could prepare a cDNA library from human osteoblasts and identify human OST-PTP cDNA by hybridizing the cDNA clones from the library to a mouse probe. The mouse probe could be based on a portion of mouse OST-PTP (SEQ ID NO:10). Alternatively, PCR, using primers based on the mouse sequence, can be used to obtain the human OST-PTP gene.

An antibody against human PTP-1B that decreases its activity can be used therapeutically in the methods of the present invention. In certain embodiments, the antibody against human PTP-1B binds to the extracellular domain of human PTP-1B.

In certain embodiments, the antibody against human PTP-1B binds to an epitope in the human PTP-1B of SEQ ID NO:17 or an OST-PTP having an amino acid sequence that is substantially homologous or identical to SEQ ID NO:17. In other embodiments, the antibody against human PTP-1B binds to an epitope in a human PTP-1B having an amino acid sequence that is at least 70% homologous or identical to SEQ ID NO:17.

Gamma-carboxylase is an intracellular protein, so antibodies or fragments of antibodies against it are preferably used therapeutically when combined with technologies for delivering the antibodies, fragments or variants into the interior of target cells expressing gamma-carboxylase, e.g., osteoblasts. Antibodies or antibody fragments or variants against osteocalcin similarly can be used with technologies for delivering the antibodies or fragments into the interior of target cells and can also be used in diagnostics and drug screening assays.

In a particular embodiment, the present invention provides antibodies, fragments or variants of antibodies that recognize an epitope in OST-PTP that includes the amino acid at position 1316 of mouse OST-PTP or the corresponding position of human OST-PTP. In certain embodiments, these antibodies, fragments or variants of antibodies block or inhibit the ability of OST-PTP to activate gamma-carboxylase. In certain embodiments, use of these antibodies or fragments results in OST-PTP losing 50%, 60%, 70%, 80%, 90%, 95%, or essentially all of its ability to activate gamma-carboxylase.

The term "epitope" refers to an antigenic determinant on an antigen to which an antibody binds. Epitopes usually consist of chemically active surface groupings of molecules such as amino acids or sugar side chains, and typically have specific three-dimensional structural characteristics, as well as specific charge characteristics. Epitopes generally have at least five contiguous amino acids but some epitopes are formed by discontiguous amino acids that are brought together by the folding of the protein that contains them.

The terms "antibody" and "antibodies" include polyclonal antibodies, monoclonal antibodies, humanized or chimeric antibodies, single chain Fv antibody fragments, Fab fragments, and $F(ab')_2$ fragments. Polyclonal antibodies are heterogeneous populations of antibody molecules that are specific for a particular antigen, while monoclonal antibodies are homogeneous populations of antibodies to a particular epitope contained within an antigen. Monoclonal antibodies are particularly useful in the present invention.

Antibody fragments that have specific binding affinity for the polypeptide of interest (e.g., OST-PTP, PTP-1B, or gamma-carboxylase) can be generated by known techniques. Such antibody fragments include, but are not limited to, $F(ab')_2$ fragments that can be produced by pepsin digestion of an antibody molecule, and Fab fragments that can be generated by reducing the disulfide bridges of $F(ab')_2$ fragments. Alternatively, Fab expression libraries can be constructed. See, for example, Huse et al., 1989, Science 246:1275-1281. Single chain Fv antibody fragments are formed by linking the heavy and light chain fragments of the Fv region via an amino acid bridge (e.g., 15 to 18 amino acids), resulting in a single chain polypeptide. Single chain Fv antibody fragments can be produced through standard techniques, such as those disclosed in U.S. Pat. No. 4,946,778.

Once produced, antibodies or fragments thereof can be tested for recognition of the target polypeptide by standard immunoassay methods including, for example, enzyme-linked immunosorbent assay (ELISA) or radioimmunoassay assay (RIA). See, Short Protocols in Molecular Biology eds. Ausubel et al., Green Publishing Associates and John Wiley & Sons (1992).

The immunoassays, immunohistochemistry, RIA, IRMAs used herein are based on the generation of various antibodies, including those that specifically bind to osteocalcin, OST-PTP, PTP-1B, gamma-carboxylase, vitamin K, or their fragments or variants. Antibodies and methods of using antibodies to quantitate the amount of osteocalcin, in particular, in a sample are also described in U.S. Pat. No. 5,681,707. U.S. Pat. No. 5,681,707 discloses antibodies that bind to the N-terminal 20 amino acids, or the C-terminal 14 amino acids of osteocalcin. Anti-OST-PTP antibodies are commercially available.

In one embodiment, antibodies against OST-PTP, PTP-1B, or gamma-carboxylase that reduce its activity are useful in the treatment of a patient having a cognitive disorder.

Nucleic Acid Inhibitors of OST-PTP, PTP-1B, and Gamma-Carboxylase

Other embodiments of the present invention are directed to the use of antisense nucleic acids or small interfering RNA (siRNA) to reduce or inhibit expression and hence the biological activity of osteocalcin, OST-PTP, PTP-1B, and/or gamma-carboxylase. cDNA sequences encoding osteocalcin, OST-PTP, PTP-1B, and/or gamma-carboxylase are set forth herein. Based on these sequences, antisense DNA or RNA that hybridize sufficiently to the respective gene or mRNA encoding osteocalcin, OST-PTP, PTP-1B, and/or gamma-carboxylase to turn off or reduce expression can be readily designed and engineered, using methods known in the art.

In a specific embodiment of the invention, antisense or siRNA molecules for use in the methods of the present invention include those that bind under stringent conditions to the human gamma-carboxylase nucleic acid sequence of SEQ ID NO:6. In yet another embodiment of the invention, the antisense or siRNA molecules are those that that bind under stringent conditions to the OST-PTP nucleic acid sequence of SEQ ID NO:10, or sequences that are substantially homologous to SEQ ID NO:10.

In a specific embodiment of the invention, antisense or siRNA molecules for use in the methods of the present invention include those that bind under stringent conditions to the human PTP-1B nucleic acid sequence of SEQ ID NO:16, or sequences that are substantially homologous to SEQ ID NO:16.

Antisense-RNA and anti-sense DNA have been used therapeutically in mammals to treat various diseases. See for example Agrawal & Zhao, 1998, Curr. Opin. Chemical Biol. 2: 519-528; Agrawal & Zhao, 1997, CIBA Found. Symp. 209:60-78; and Zhao et al., 1998, Antisense Nucleic Acid Drug Dev. 8:451-458; the entire contents of which are hereby incorporated by reference as if fully set forth herein. Antisense oligodeoxyribonucleotides (antisense-DNA), oligoribonucleotides (antisense-RNA), and other polymeric antisense compounds (e.g., oligonucleotides composed of naturally-occurring nucleobases, sugars and covalent internucleoside linkages and non-naturally-occurring portions which function similarly) can base pair with a gene or its transcript. Anderson et al., 1996, Antimicrobiol. Agents Chemother. 40:2004-2011 and U.S. Pat. No. 6,828,151 describe methods for making and using antisense nucleic acids and their formulation, the entire contents of which are hereby incorporated by reference as if fully set forth herein. The disclosures of the foregoing publications can be adapted by those skilled in the art for use in the methods of the present invention.

Methods of making antisense nucleic acids are well known in the art. Further provided by the present invention are methods of modulating the expression of OST-PTP, PTP1B, and gamma-carboxylase genes and mRNA in cells or tissues by contacting the cells or tissues with one or more antisense compounds or compositions in order to treat or prevent a cognitive disorder in mammals. As used herein, the term "target nucleic acid" encompasses DNA encoding osteocalcin, OST-PTP, PTP-1B, or gamma-carboxylase and RNA (including pre-mRNA and mRNA) transcribed from such DNA. The specific hybridization of a nucleic acid oligomeric compound with its target nucleic acid interferes with the normal function of the target nucleic acid. This modulation of function of a target nucleic acid by compounds which specifically hybridize to it is generally referred to as "antisense." The functions of DNA to be interfered with include replication and transcription. The functions of RNA to be interfered with include all vital functions such as, for example, translocation of the RNA to the site of protein translation, translation of protein from the RNA, and catalytic activity which may be engaged in or facilitated by the RNA. The overall effect of such interference with target nucleic acid function is modulation of the expression of the protein encoded by the DNA or RNA. In the context of the present invention, "modulation" means reducing or inhibiting the expression of the gene or mRNA for osteocalcin, OST-PTP and/or gamma-carboxylase. DNA is the preferred antisense nucleic acid.

The targeting process includes determination of a site or sites within the target DNA or RNA encoding the osteocalcin, OST-PTP, PTP-1B, and/or gamma-carboxylase for the antisense interaction to occur such that the desired inhibitory effect is achieved. Within the context of the present invention, a preferred intragenic site is the region encompassing the translation initiation or termination codon of the open reading frame (ORF) of the mRNA for osteocalcin, OST-PTP, PTP-1B, or gamma-carboxylase, preferably human osteocalcin, OST-PTP, PTP-1B, or gamma-carboxylase. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine in eukaryotes. It is also known in the art that eukaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene. Routine experimentation will determine the optimal sequence of the antisense or siRNA.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites.

Once one or more target sites have been identified, nucleic acids are chosen which are sufficiently complementary to the target, i.e., hybridize sufficiently well and with sufficient specificity, to give the desired effect of inhibiting gene expression and transcription or mRNA translation.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of a nucleic acid is capable of hydrogen bonding with a nucleotide at the same position of a DNA or RNA molecule, then the nucleic acid and the DNA or RNA are considered to be complementary to each other at that position. The nucleic acid and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the nucleic acid and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of function, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

Antisense nucleic acids have been employed as therapeutic moieties in the treatment of disease states in animals and man. Antisense nucleic acid drugs, including ribozymes, have been safely and effectively administered to humans in numerous clinical trials. It is thus established that nucleic acids can be useful therapeutic modalities that can be configured to be useful in treatment regimes for treatment of cells, tissues and animals, especially humans, for example to regulate expression of osteocalcin, OST-PTP, PTP-1B, and/or gamma-carboxylase.

Nucleic acids in the context of this invention include "oligonucleotides," which refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense nucleic acids are a preferred form of antisense compound, the present invention comprehends other oligomeric antisense compounds, including but not limited to oligonucleotide mimetics. The antisense compounds in accordance with this invention preferably comprise from about 8 to about 50 nucleobases (i.e., from about 8 to about 50 linked nucleosides). Particularly preferred antisense compounds are antisense nucleic acids comprising from about 12 to about 30 nucleobases. Antisense compounds include ribozymes, external guide sequence (EGS) nucleic acids (oligozymes), and other short catalytic RNAs or catalytic nucleic acids which hybridize to the target nucleic acid and modulate its expression.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare nucleic acids such as the phosphorothioates and alkylated derivatives.

The antisense compounds of the present invention can be utilized for diagnostics, therapeutics, and prophylaxis and as research reagents and kits. For therapeutics, an animal, preferably a human, suspected of having a cognitive disease or disorder such as cognitive loss due to neurodegeneration associated with aging, anxiety, depression, memory loss, learning difficulties, and cognitive disorders associated with food deprivation during pregnancy, which can be treated by modulating the expression of osteocalcin, gamma-carboxylase, PTP-1B, or OST-PTP, is treated by administering antisense compounds in accordance with this invention. The compounds useful in the methods of the invention can be formulated into pharmaceutical compositions by adding an effective amount of an antisense compound to a suitable pharmaceutically acceptable diluent or carrier. The antisense compounds and methods of the present invention are useful prophylactically, e.g., to prevent or delay the appearance of cognitive loss due to neurodegeneration associated with aging, anxiety, depression, memory loss, learning difficulties, and cognitive disorders associated with food deprivation during pregnancy. The antisense compounds and methods of the invention are also useful to retard the progression of cognitive loss due to neurodegeneration associated with aging, anxiety, depression, memory loss, learning difficulties, and cognitive disorders associated with food deprivation during pregnancy.

The present invention also encompasses the use of siRNA to treat or prevent a cognitive disorder in mammals. U.S. Patent Application Publication No. 2004/0023390 (the entire contents of which are hereby incorporated by reference as if fully set forth herein) teaches that double-stranded RNA (dsRNA) can induce sequence-specific posttranscriptional gene silencing in many organisms by a process known as RNA interference (RNAi). However, in mammalian cells, dsRNA that is 30 base pairs or longer can induce sequence-nonspecific responses that trigger a shut-down of protein synthesis and even cell death through apoptosis. Recent work shows that RNA fragments are the sequence-specific mediators of RNAi (Elbashir et al., 2001, Nature 411:494-498). Interference of gene expression by these small interfering RNA (siRNA) is now recognized as a naturally occurring strategy for silencing genes in *C. elegans, Drosophila*, plants, and in mouse embryonic stem cells, oocytes and early embryos (Baulcombe, 1996, Plant Mol Biol. 32:79-88; Timmons & Fire, 1998, Nature 395:854; Wianny and Zernicka-Goetz, 2000, Nat Cell Biol. 2:70-75; Svoboda et al., 2000, Development 127:4147-4156).

In mammalian cell culture, a siRNA-mediated reduction in gene expression has been accomplished by transfecting cells with synthetic RNA nucleic acids (Elbashir et al., 2001, Nature 411:494-498). U.S. Patent Application Publication No. 2004/0023390, the entire contents of which are hereby incorporated by reference as if fully set forth herein, provides exemplary methods using a viral vector containing an expression cassette containing a pol II promoter operably-linked to a nucleic acid sequence encoding a small interfering RNA molecule (siRNA) targeted against a gene of interest.

As used herein, RNAi is the process of RNA interference. A typical mRNA produces approximately 5,000 copies of a protein. RNAi is a process that interferes with or significantly reduces the number of protein copies made by an mRNA, preferably encoding osteocalcin, OST-PTP, PTP-1B, or gamma-carboxylase. For example, a double-stranded short interfering RNA (siRNA) molecule is engineered to complement and match the protein-encoding nucleotide sequence of the target mRNA to be interfered with. In certain embodiments of the present invention, following intracellular delivery, the siRNA molecule associates with an RNA-induced silencing complex (RISC) and binds the target mRNA (such as mRNA encoding osteocalcin, gamma-carboxylase, PTP-1B or OST-PTP) through a base-pairing interaction and degrades it. The RISC remains capable of degrading additional copies of the targeted mRNA. Other forms of RNA such as short hairpin RNA and longer RNA molecules can be used in the methods of the present invention. Longer molecules cause cell death, for example by instigating apoptosis and inducing an interferon response. Cell death was the major hurdle to achieving RNAi in mammals because dsRNAs longer than 30 nucleotides activated defense mechanisms that resulted in non-specific degradation of RNA transcripts and a general shutdown of the host cell. Using from about 20 to about 29 nucleotide siRNAs to mediate gene-specific suppression in mammalian cells has apparently overcome this obstacle. These siRNAs are long enough to cause gene suppression but not of a length that induces an interferon response. In a specific embodiment of the present invention, the targets for suppression are osteocalcin mRNA, OST-PTP mRNA, PTP-1B mRNA, or gamma-carboxylase mRNA. siRNA molecules useful in the methods of the present invention include those sequences that bind under stringent conditions to the human PTP-1B sequence of SEQ ID:16, the human gamma-carboxylase sequence of SEQ ID:6, or the mouse OST-PTP sequence of SEQ ID NO:10. siRNA molecules useful in the methods of the present invention also include those sequences that bind under stringent conditions to nucleic acids that are 80%, 85%, 90%, or 95% homologous to SEQ ID NO:16, SEQ ID NO:6 or SEQ ID NO:10.

Formulation and Administration of Pharmaceutical Compositions

The present invention encompasses the use of the polypeptides, nucleic acids, antibodies, small molecules and other therapeutic agents described herein formulated in pharmaceutical compositions to administer to a subject. The therapeutic agents (also referred to as "active compounds") can be incorporated into pharmaceutical compositions suitable for administration to a subject, e.g., a human. Such compositions typically comprise the polypeptides, nucleic acids, antibodies, small molecules and a pharmaceutically acceptable carrier. Preferably, such compositions are non-pyrogenic when administered to humans.

The pharmaceutical compositions of the invention are administered in an amount sufficient to modulate the OST-PTP signaling pathway or the PTP-1B signaling pathway involving gamma-carboxylase and osteocalcin.

As used herein the language "pharmaceutically acceptable carrier" is intended to include any and all solvents, binders, diluents, disintegrants, lubricants, dispersion media, coatings, antibacterial and antifungal agents, isotonic and absorption delaying agents, and the like, compatible with pharmaceutical administration. The use of such media and agents for pharmaceutically active substances is well known in the art. As long as any conventional media or agent is compatible with the active compound, such media can be used in the compositions of the invention. Supplementary active compounds or therapeutic agents can also be incorporated into the compositions. A pharmaceutical composition of the invention is formulated to be compatible with its intended route of administration. Examples of routes of administration include parenteral, e.g., intravenous, intradermal, intranasal, subcutaneous, oral, inhalation, transdermal (topical), transmucosal, and rectal administration.

The term "administer" is used in its broadest sense and includes any method of introducing the compositions of the present invention into a subject. This includes producing polypeptides or polynucleotides in vivo as by transcription or translation of polynucleotides that have been exogenously introduced into a subject. Thus, polypeptides or nucleic acids produced in the subject from the exogenous compositions are encompassed in the term "administer."

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylene diamine tetra acetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where the therapeutic agents are water soluble) or dispersions and sterile powders for the extemporaneous preparation of sterile injectable solutions or dispersion. For intravenous administration, suitable carriers include physiological saline, bacteriostatic water, Cremophor EL® (BASF, Parsippany, N.J.) or phosphate buffered saline (PBS). In all cases, the composition must be sterile and should be fluid to the extent that easy syringability exists. It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., undercarboxylated/uncarboxylated osteocalcin protein or anti-OST-PTP antibody) in the required amount in an appropriate solvent with one or a combination of the ingredients enumerated above, as required, followed by filter sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yield a powder of the active ingredient plus any additional desired ingredient from a previously sterile-filtered solution thereof.

Oral compositions generally include an inert diluent or an edible carrier. They can be enclosed in gelatin capsules or compressed into tablets. Depending on the specific conditions being treated, pharmaceutical compositions of the present invention for treatment of cognitive disorders in mammals can be formulated and administered systemically or locally. Techniques for formulation and administration can be found in "Remington: The Science and Practice of Pharmacy" (20$^{th}$ edition, Gennaro (ed.) and Gennaro, Lippincott, Williams & Wilkins, 2000). For oral administration, the agent can be contained in enteric forms to survive the stomach or further coated or mixed to be released in a particular region of the GI tract by known methods. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, PRIMOGEL®, or corn starch; a lubricant such as magnesium stearate or STEROTES®; a glidant such as colloidal silicon dioxide; a sweetening agent such as sucrose or saccharin; or a flavoring agent such as peppermint, methyl salicylate, or orange flavoring.

For administration by inhalation, the compounds may be delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

If appropriate, the compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to particular cells with, e.g., monoclonal antibodies) can also be used as pharmaceutically acceptable carriers. These can be prepared according to methods known to those skilled in the art, for example, as described in U.S. Pat. No. 4,522,811.

It is especially advantageous to formulate oral or parenteral compositions in unit dosage form for ease of administration and uniformity of dosage. "Unit dosage form" as used herein refers to physically discrete units suited as unitary dosages for the subject to be treated; each unit containing a predetermined quantity of active compound calculated to produce the desired therapeutic effect in association with the required pharmaceutical carrier. The specification for the unit dosage forms of the invention are dictated by and directly dependent on the unique characteristics of the active compound and the particular therapeutic effect to be achieved, and the limitations inherent in the art of compounding such an active compound for the treatment of individuals.

As previously noted, the agent may be administered continuously by pump or frequently during the day for extended periods of time. In certain embodiments, the agent may be administered at a rate of from about 0.3-100 ng/hour, preferably about 1-75 ng/hour, more preferably about 5-50 ng/hour, and even more preferably about 10-30 ng/hour. The agent may be administered at a rate of from about 0.1-100 μg/hr, preferably about 1-75 μg/hr, more preferably about 5-50 μg/hr, and even more preferably about 10-30 μg/hr. It will also be appreciated that the effective dosage of antibody, protein, or polypeptide used for treatment may increase or decrease over the course of a particular treatment. Changes in dosage may result and become apparent from monitoring the level of undercarboxylated/uncarboxylated osteocalcin in a biological sample, preferably blood or serum.

In an embodiment of the invention, the agent can be delivered by subcutaneous, long-term, automated drug delivery using an osmotic pump to infuse a desired dose of the agent for a desired time. Insulin pumps are widely available and are used by diabetics to automatically deliver insulin over extended periods of time. Such insulin pumps can be adapted to deliver the agent for use in the methods of the present invention. The delivery rate of the agent can be readily adjusted through a large range to accommodate changing requirements of an individual (e.g., basal rates and bolus doses). New pumps permit a periodic dosing manner, i.e., liquid is delivered in periodic discrete doses of a small fixed volume rather than in a continuous flow manner. The overall liquid delivery rate for the device is controlled and adjusted by controlling and adjusting the dosing period. The pump can be coupled with a continuous monitoring device and remote unit, such as a system described in U.S. Pat. No. 6,560,471, entitled "Analyte Monitoring Device and Methods of Use." In such an arrangement, the hand-held remote unit that controls the continuous blood monitoring device could wirelessly communicate with and control both the blood monitoring unit and the fluid delivery device delivering therapeutic agents for use in the methods of the present invention.

In some embodiments of the present invention, routine experimentation may be used to determine the appropriate dosage value for each patient by monitoring the effect of the therapeutic agent on serum undercarboxylated/uncarboxylated osteocalcin levels. The agent can be administered once or multiple times per day. Serum undercarboxylated/uncarboxylated osteocalcin levels can be monitored before and during therapy to determine the appropriate amount of therapeutic agent to administer to raise serum undercarboxylated/uncarboxylated osteocalcin levels or bring serum undercarboxylated/uncarboxylated osteocalcin levels to normal and to maintain normal levels over extended periods of time. In a preferred embodiment, a patient is tested to determine if his serum undercarboxylated/uncarboxylated osteocalcin levels are significantly lower than normal levels (about 25% below) before administering treatment with the therapeutic agent. The frequency of administration may vary from a single dose per day to multiple doses per day. Preferred routes of administration include oral, intravenous and intraperitoneal, but other forms of administration may be chosen as well.

A “therapeutically effective amount” of a protein or polypeptide, small molecule, antibody, or nucleic acid is an amount that achieves the desired therapeutic result. For example, if a therapeutic agent is administered to treat or prevent a cognitive disorder in mammals, a therapeutically effective amount is an amount that ameliorates one or more symptoms of the disorder, or produces at least one effect selected from the group consisting of lessening of cognitive loss due to neurodegeneration associated with aging, lessening of anxiety, lessening of depression, lessening of memory loss, improving learning, and lessening of cognitive disorders associated with food deprivation during pregnancy.

A therapeutically effective amount of protein or polypeptide, small molecule or nucleic acid for use in the present invention typically varies and can be an amount sufficient to achieve serum therapeutic agent levels typically of between about 1 nanogram per milliliter and about 10 micrograms per milliliter in the subject, or an amount sufficient to achieve serum therapeutic agent levels of between about 1 nanogram per milliliter and about 7 micrograms per milliliter in the subject. Other preferred serum therapeutic agent levels include about 0.1 nanogram per milliliter to about 3 micrograms per milliliter, about 0.5 nanograms per milliliter to about 1 microgram per milliliter, about 1 nanogram per milliliter to about 750 nanograms per milliliter, about 5 nanograms per milliliter to about 500 nanograms per milliliter, and about 5 nanograms per milliliter to about 100 nanograms per milliliter.

The amount of therapeutic agent disclosed herein to be administered to a patient in the methods of the present invention can be determined by those skilled in the art through routine methods and may range from about 1 mg/kg/day to about 1,000 mg/kg/day, from about 5 mg/kg/day to about 750 mg/kg/day, from about 10 mg/kg/day to about 500 mg/kg/day, from about 25 mg/kg/day to about 250 mg/kg/day, from about 50 mg/kg/day to about 100 mg/kg/day, or other suitable amounts.

The amount of therapeutic agent disclosed herein to be administered to a patient in the methods of the present invention also may range from about 1 μg/kg/day to about 1,000 μg/kg/day, from about 5 μg/kg/day to about 750 μg/kg/day, from about 10 μg/kg/day to about 500 μg/kg/day, from about 25 μg/kg/day to about 250 μg/kg/day, or from about 50 μg/kg/day to about 100 μg/kg/day.

The amount of therapeutic agent disclosed herein to be administered to a patient in the methods of the present invention also may range from about 1 ng/kg/day to about 1,000 ng/kg/day, from about 5 ng/kg/day to about 750 ng/kg/day, from about 10 ng/kg/day to about 500 ng/kg/day, from about 25 ng/kg/day to about 250 ng/kg/day, or from about 50 ng/kg/day to about 100 ng/kg/day.

The skilled artisan will appreciate that certain factors may influence the dosage required to effectively treat a subject, including but not limited to the severity of the condition, previous treatments, the general health and/or age of the subject, and other disorders or diseases present.

Treatment of a subject with a therapeutically effective amount of a protein, polypeptide, nucleotide or antibody can include a single treatment or, preferably, can include a series of treatments.

In certain embodiments, treatment of a subject with undercarboxylated/uncarboxylated osteocalcin leads to undercarboxylated/uncarboxylated osteocalcin being about 10%, about 15%, about 20%, about 25%, about 30%, about 35%, about 40%, about 45%, or about 50% of the total osteocalcin in the blood of the patient.

It is understood that the appropriate dose of a small molecule agent depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, and the effect which the practitioner desires the small molecule to have. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of OST-PTP, PTP-1B, or gamma-carboxylase, a relatively low dose may be prescribed at first, with the dose subsequently increased until an appropriate response is obtained. In addition, it is understood that the specific dose level for any particular subject will depend upon a variety of factors including the activity of the specific compound employed, the age, body weight, general health, and diet of the subject, the time of administration, the route of administration, the rate of excretion, whether other drugs are being administered to the patient, and the degree of expression or activity to be modulated.

For prevention or treatment, a suitable subject can be an individual who is suspected of having, has been diagnosed as having, or is at risk of developing a cognitive disorder in mammals.

Suitable routes of administration of the pharmaceutical compositions useful in the methods of the present invention can include oral, intestinal, parenteral, transmucosal, transdermal, intramuscular, subcutaneous, transdermal, rectal, intramedullary, intrathecal, intravenous, intraventricular, intraatrial, intraaortal, intraarterial, or intraperitoneal administration. The pharmaceutical compositions useful in the methods of the present invention can be administered to the subject by a medical device, such as, but not limited to, catheters, balloons, implantable devices, biodegradable implants, prostheses, grafts, sutures, patches, shunts, or stents. In one preferred embodiment, the therapeutic agent (e.g., undercarboxylated/uncarboxylated osteocalcin) can be coated on a stent for localized administration to the target area. In this situation a slow release preparation of undercarboxylated/uncarboxylated osteocalcin, for example, is preferred.

The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations and that may be consulted by those skilled in the art for techniques useful for practicing the present invention include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

While uncarboxylated osteocalcin crosses the blood-brain barrier, certain derivatives, variants, or modified forms of osteocalcin may not. In embodiments of the invention utilizing a form of osteocalcin that does not cross the blood-brain barrier, one may take advantage of methods known in the art for transporting substances across the blood-brain barrier. For example, the methods disclosed in U.S. Patent Application Publication No. 2013/0034590 or U.S. Patent Application Publication No. 2013/0034572 may be used. The human insulin or transferrin receptor can be utilized by targeting these receptors with a monoclonal antibody-modified osteocalcin conjugate (Pardridge, 2007, Pharm. Res. 24:1733-1744; Beduneau et al., 2008, J. Control. Release 126:44-49). Surfactant coated poly(butylcyanoacrylate) nanoparticles containing modified osteocalcin my be used (Kreuter et al., 2003, Pharm. Res. 20:409-416). Alternatively, cationic carriers such as cationic albumin conjugated to pegylated nanoparticles containing modified osteocalcin may be used to deliver modified osteocalcin to the brain (Lu et al., 2006, Cancer Res. 66:11878-11887).

In yet another aspect of the invention, undercarboxylated/uncarboxylated osteocalcin is administered as a pharmaceutical composition with a pharmaceutically acceptable excipient. Exemplary pharmaceutical compositions for undercarboxylated/uncarboxylated osteocalcin include injections as solutions or injections as injectable self-setting or self-gelling mineral polymer hybrids.

Undercarboxylated/uncarboxylated osteocalcin may be administered using a porous crystalline biomimetic bioactive composition of calcium phosphate. See U.S. Pat. Nos. 5,830,682; 6,514,514; and 6,511,958 and U.S. Patent Application Publications Nos. 2006/0063699; 2006/0052327; 2003/199615; 2003/0158302; 2004/0157864; 2006/0292670; 2007/0099831 and 2006/0257492, all of which are incorporated herein in their entirety by reference.

Methods of Treatment

The present invention provides methods for modulating the level of undercarboxylated/uncarboxylated osteocalcin in mammals through modulating the OST-PTP signaling pathway or the PTP-1B signaling pathway for treating or preventing a variety of different cognitive disorders in mammals. In particular, the methods are used to inhibit OST-PTP phosphorylase activity, inhibit PTP-1B phosphorylase activity, reduce gamma-carboxylase activity, and/or increase undercarboxylated/uncarboxylated osteocalcin. According to the invention, the methods provide an amount of an agent effective to treat or prevent a cognitive disorder associated with the OST-PTP signaling pathway or the PTP-1B signaling pathway. The agent may be selected from the group consisting of small molecules, antibodies and nucleic acids. Such disorders include, but are not limited to, neurodegeneration associated with aging, anxiety, depression, memory loss, and cognitive disorders associated with food deprivation during pregnancy.

In certain embodiments, the methods comprise identifying a patient in need of treatment or prevention of neurodegeneration associated with aging, anxiety, depression, memory loss, learning difficulties, or cognitive disorders associated with food deprivation during pregnancy and then applying the methods disclosed herein to the patient.

In one embodiment of the invention, the method of treatment comprises administering to a patient in need thereof a therapeutically effective amount of undercarboxylated/uncarboxylated osteocalcin sufficient to raise the patient's blood level of undercarboxylated/uncarboxylated osteocalcin compared to the pretreatment patient level. Since undercarboxylated/uncarboxylated osteocalcin can cross the blood/brain barrier, this can lead to therapeutically effective levels of undercarboxylated/uncarboxylated osteocalcin in target areas of the brain. Preferably, the patient is a human. In another embodiment, the method of treatment comprises administering to a patient in need thereof a therapeutically effective amount of undercarboxylated/uncarboxylated osteocalcin sufficient to raise the ratio of undercarboxylated/uncarboxylated osteocalcin to total osteocalcin in the patient's blood compared to the pretreatment patient ratio.

In another aspect of the invention, a method is provided for treating or preventing a cognitive disorder in a mammal comprising administering to a mammal in need thereof undercarboxylated/uncarboxylated osteocalcin in a therapeutically effective amount that produces at least one effect selected from the group consisting of lessening of cognitive loss due to neurodegeneration associated with aging, lessening of anxiety, lessening of depression, lessening of memory loss, improving learning, and lessening of cognitive disorders associated with food deprivation during pregnancy, compared to pretreatment levels. Preferably, the mammal is a human.

In an embodiment of the invention, a method is provided for treating or preventing a cognitive disorder in a mammal comprising administering to a mammal in need of such treatment or prevention a therapeutically effective amount of an agent that reduces OST-PTP expression or activity in osteoblasts, or reduces PTP-1B expression or activity in osteoblasts, sufficient to produce at least one effect selected from the group consisting of lessening of cognitive loss due to neurodegeneration associated with aging, lessening of anxiety, lessening of depression, lessening of memory loss, improving learning, and lessening of cognitive disorders associated with food deprivation during pregnancy, compared to pretreatment levels. Preferably, the patient is a human.

The present invention is directed to methods (i) for treating or preventing a cognitive disorder in a mammal comprising administering to a mammal in need of such treatment or prevention in a therapeutically effective amount an agent that reduces gamma-carboxylase expression or activity in osteoblasts sufficient to produce at least one effect selected from the group consisting of lessening of cognitive loss due to neurodegeneration associated with aging, lessening of anxiety, lessening of depression, lessening of memory loss, improving learning, and lessening of cognitive disorders associated with food deprivation during pregnancy, compared to pretreatment levels comprising administering to the mammal in need of such treatment or prevention in a therapeutically effective amount an agent that reduces gamma-carboxylase expression or activity in osteoblasts sufficient to lessen cognitive loss due to neurodegeneration associated with aging, lessen anxiety, lessen depression, lessen memory loss, improve learning, and lessen cognitive disorders associated with food deprivation during pregnancy. Preferably, the mammal is a human. In an embodiment of the invention, the agent is an isolated nucleic acid that is selected from the group consisting of cDNA, antisense DNA, antisense RNA, and small interfering RNA, which nucleic acid is sufficiently complementary to the gene or mRNA encoding gamma-carboxylase to permit specific hybridization to the gene or mRNA, and wherein the hybridization prevents or reduces expression of gamma-carboxylase in osteoblasts. In another embodiment of the invention, the nucleic acid is conjugated to a phosphate group or other targeting ligand to facilitate uptake by osteoblasts.

In the methods described herein, it will be understood that "treating" a disease or disorder encompasses not only improving the disease or disorder or its symptoms but also retarding the progression of the disease or disorder or ameliorating the deleterious effects of the disease or disorder.

The present invention also encompasses the use of gene therapy for treatment of cognitive disorders in mammals. This can be accomplished by introducing a gene encoding osteocalcin or a biologically active fragment or variant thereof into a vector, and transfecting or infecting cells from a patient afflicted with the disorder or at a high risk of developing the disorder with the vector, according to various methods known in the art. The cells may be transfected or infected by ex vivo or by in vivo methods.

Methods of gene therapy known in the art can be adapted for use in the methods of the present invention. Adeno-associated virus (AAV) is one of the most promising vectors for gene therapy and may be used in the methods of the present invention. Conventional methods of gene transfer and gene therapy are described in, e.g., Gene Therapy: Principles and Applications, ed. T. Blackenstein, Springer Verlag, 1999; Gene Therapy Protocols (Methods in Molecular Medicine), ed. P. D. Robbins, Humana Press, 1997; and Retro-vectors for Human Gene Therapy, ed. C. P. Hodgson, Springer Verlag, 1996. AAV is an attractive vector system for human gene therapy because it is non-pathogenic for humans, it has a high frequency of integration, and it can infect non-dividing cells, thus making it useful for delivery of genes into mammalian cells both in tissue culture and in whole animals. See, e.g., Muzyczka, 1992, Curr. Top. Microbiol. Immunol., 158:97-129. Recent studies have demonstrated AAV to be a potentially useful vector for gene delivery. LaFace et al., 1998, Virology, 162:483-486; Zhou et al., 1993, Exp. Hematol. (NY), 21:928-933; Flotte et al., 1993, Proc. Natl. Acad. Sci. USA 90:10613-10617; and Walsh et al., 1994, Blood 84:1492-1500. Recombinant AAV vectors have been used successfully for in vitro and in vivo transduction of marker genes (Kaplitt et al., 1994, Nature Genetics, 8:148-154; Lebkowski et al., 1988, Mol. Cell. Biol. 8:3988-3996; Samulski et al., 1989, J. Virol., 63:3822-3828; Shelling & Smith, 1994, Gene Therapy 1:165-169; Yoder et al., 1994, Blood, 82:suppl. 1:347A; Zhou et al., 1994, J. Exp. Med., 179:1867-1875; Hermonat & Muzyczka, 1984, Proc. Natl. Acad. Sci. USA., 81:6466-6470; Tratschin et al., 1984, Mol. Cell. Biol., 4:2072-2081; McLaughlin et al., 1988, J. Virol., 62:1963-1973) as well as genes involved in human diseases (Flotte et al., 1992, Am. J. Respir. Cell Mol. Biol. 7:349-356; Luo et al., 1994, Blood, 82:suppl. 1,303A; Ohi et al., 1990, Gene, 89:279-282; Walsh et al., 1992, Proc. Natl. Acad. Sci. USA 89:7257-7261; Wei et al., 1994, Gene Therapy, 1:261-268).

In certain other embodiments, the gene of interest (e.g., osteocalcin) can be transferred into a target cell using a retroviral vector. Retroviruses refer to viruses that belong to the Retroviridae family, and include oncoviruses, foamy viruses (Russell & Miller, 1996, J. Virol. 70:217-222; Wu et al., 1999, J. Virol. 73:4498-4501, and lentiviruses (for example, HIV-1 (Naldini et al., 1996, Science 272:263-267; Poeschla et al., 1996, Proc. Natl. Acad. Sci. USA 93:11395-11399; Srinivasakumar et al., 1997, J. Virol. 71:5841-5848; Zufferey et al., 1997, Nat. Biotechnol. 15:871-875; Kim et al., 1998, J. Virol. 72:811-816) and feline immunodeficiency virus (Johnston et al., 1999, J. Virol. 73:4991-5000; Johnston & Power, 1999, Virol. 73:2491-2498; Poeschla et al., 1998, Nat. Med. 4:354-357). The disclosures of these publications may be adapted for use in the methods of the present invention. Numerous gene therapy methods that take advantage of retroviral vectors for treating a wide variety of diseases are well-known in the art and can be adapted for use in the methods of the present invention (see, e.g., U.S. Pat. Nos. 4,405,712 and 4,650,764; Friedmann, 1989, Science, 244:1275-1281; Mulligan, 1993, Science, 260:926-932; Crystal, 1995, Science 270:404-410, and U.S. Pat. No. 6,899,871, each of which are incorporated herein by reference in their entirety). An increasing number of these methods are currently being applied in human clinical trials (Morgan, 1993, BioPharm, 6:32-35; see also The Development of Human Gene Therapy, Theodore Friedmann, Ed., Cold Spring Harbor Laboratory Press, Cold Spring Harbor, N.Y., 1999. ISBN 0-87969-528-5, which is incorporated herein by reference in its entirety).

Efficacy of the methods of treatment described herein can be monitored by determining whether the methods ameliorate any of the symptoms of the disease or disorder being treated. Alternatively, one can monitor the level of serum undercarboxylated/uncarboxylated osteocalcin (either in absolute terms or as a ratio of undercarboxylated/uncarboxylated osteocalcin/total osteocalcin), which levels should increase in response to therapy.

Diagnostics

The present invention provides methods and compositions for diagnosing cognitive disorders in mammals based on decreased levels of undercarboxylated/uncarboxylated osteocalcin. Such cognitive disorders include, but are not limited to, cognitive loss due to neurodegeneration associated with aging, lessening of anxiety, lessening of depression, lessening of memory loss, learning difficulties, and lessening of cognitive disorders associated with food deprivation during pregnancy.

In a specific embodiment of the invention, a method is provided for diagnosing a patient having or at risk of developing a cognitive disorder selected from the group consisting of cognitive loss due to neurodegeneration associated with aging, lessening of anxiety, lessening of depression, lessening of memory loss, learning difficulties, and lessening of cognitive disorders associated with food deprivation during pregnancy, comprising: (i) determining a patient level of undercarboxylated/uncarboxylated osteocalcin in a biological sample taken from the patient and a control level of undercarboxylated/uncarboxylated osteocalcin in a biological sample taken from a subject that does not have the disorder, (ii) comparing the patient and control levels, and (iii) diagnosing the patient as having or as being at risk of developing the disorder if the patient level is lower than the control level.

"Biological samples" include solid and fluid body samples. The biological samples of the present invention may include tissue, organs, cells, protein or membrane extracts of cells, blood or biological fluids such as blood, serum, ascites fluid or brain fluid (e.g., cerebrospinal fluid). Preferably, the biological sample is blood or cerebrospinal fluid.

In another embodiment of the invention, a method is provided for diagnosing a patient having or at risk of developing a cognitive disorder selected from the group consisting of cognitive loss due to neurodegeneration associated with aging, anxiety, depression, memory loss, learning difficulties, and cognitive disorders associated with food deprivation during pregnancy, comprising: (i) determining a patient level of undercarboxylated/uncarboxylated osteocalcin in a biological sample taken from the patient; and (ii) comparing the patient level to a standard level; where, if the patient level is lower than the standard level, diagnosing the patient as having or at risk of developing the disorder. In instances where the method is practiced on humans, the standard level can be a level of undercarboxylated/uncarboxylated osteocalcin that has been previously determined to be the normal range for humans who are not at risk of developing the disorder. In preferred embodiments, the biological sample is blood, serum, plasma, cerebrospinal fluid, urine, a cell sample, or a tissue sample.

A "standard level" of undercarboxylated/uncarboxylated osteocalcin in humans can include values of 0.1 ng/ml to 10 ng/ml, preferably 0.2 ng/ml to 7.5 ng/ml, more preferably 0.5 ng/ml to 5 ng/ml, and even more preferably 1 ng/ml to 5 ng/ml of undercarboxylated/uncarboxylated osteocalcin. A standard level of undercarboxylated/uncarboxylated osteocalcin in humans can also include about 0.1 ng/ml, about 0.5 ng/ml, about 1 ng/ml, about 2 ng/ml, about 3 ng/ml, about 4 ng/ml, about 5 ng/ml, about 6 ng/ml, about 7 ng/ml, or about 10 ng/ml of undercarboxylated/uncarboxylated osteocalcin.

In another embodiment of the invention, a method is provided for diagnosing a patient having or at risk of developing a disorder selected from the group consisting of cognitive loss due to neurodegeneration associated with aging, lessening of anxiety, lessening of depression, lessening of memory loss, learning difficulties, and lessening of cognitive disorders associated with food deprivation during pregnancy, comprising: (i) determining the ratio of undercarboxylated/uncarboxylated osteocalcin to total osteocalcin in a biological sample taken from the patient; and (ii) comparing the ratio to a standard ratio; where, if the patient ratio is lower than the standard ratio, diagnosing the patient as having or being at risk of developing the cognitive disorder. In certain embodiments, the standard ratio is 5%-10%, 10%-15%, 15%-20%, 20%-25%, 25%-30%, or 30%-35%. In certain embodiments, the standard ratio is about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, or 35%. Preferably, the patient is a human. In preferred embodiments, the biological sample is blood, serum, plasma, cerebrospinal fluid, urine, a cell sample, or a tissue sample.

Assays for detecting the levels of protein expression, e.g., osteocalcin expression, are well known to those of skill in the art. Such assays include, for example, antibody-based immunoassays. Methods for using antibodies as disclosed herein are particularly applicable to the cells, tissues and other biological samples from patient with cognitive disorders in mammals that differentially express osteocalcin, OST-PTP, PTP-1B, or gamma-carboxylase. The methods use antibodies that selectively bind to the protein of interest and its fragments or variants.

The amount of osteocalcin in a biological sample may be determined by an assay such as a radioimmunoassay, an immunoradiometric assay, and/or an enzyme immunoassay. A "radioimmunoassay" is a technique for detecting and measuring the concentration of an antigen using a labeled (e.g., radioactively labeled) form of the antigen. Examples of radioactive labels for antigens include $^{3}H$, $^{14}C$, and $^{125}I$. The concentration of antigen (e.g., osteocalcin) in a biological sample may be measured by having the antigen in the sample compete with a labeled (e.g., radioactively, fluorescently) antigen for binding to an antibody to the antigen. To ensure competitive binding between the labeled antigen and the unlabeled antigen, the labeled antigen is present in a concentration sufficient to saturate the binding sites of the antibody. The higher the concentration of antigen in the sample, the lower the concentration of labeled antigen that will bind to the antibody.

In a radioimmunoassay, to determine the concentration of labeled antigen bound to antibody, the antigen-antibody complex must be separated from the free antigen. One method for separating the antigen-antibody complex from the free antigen is by precipitating the antigen-antibody complex with an anti-isotype antiserum. Another method for separating the antigen-antibody complex from the free antigen is by precipitating the antigen-antibody complex with formalin-killed *S. aureus*. Yet another method for separating the antigen-antibody complex from the free antigen is by performing a "solid-phase radioimmunoassay" where the antibody is linked (e.g., covalently) to Sepharose® beads, polystyrene wells, polyvinylchloride wells, or microtiter wells. By comparing the concentration of labeled antigen bound to antibody to a standard curve based on samples having a known concentration of antigen, the concentration of antigen in the biological sample can be determined.

An "Immunoradiometric Assay" (IRMA) is an immunoassay in which the antibody reagent is radioactively labeled. An IRMA requires the production of a multivalent antigen conjugate, by techniques such as conjugation to a protein, e.g., rabbit serum albumin (RSA). The multivalent antigen conjugate must have at least 2 antigen residues per molecule and the antigen residues must be of sufficient distance apart to allow binding by at least two antibodies to the antigen. For example, in an IRMA the multivalent antigen conjugate can be attached to a solid surface such as a plastic sphere. Unlabeled "sample" antigen and antibody to antigen which is radioactively labeled are added to a test tube containing the multivalent antigen conjugate coated sphere. The antigen in the sample competes with the multivalent antigen conjugate for antigen antibody binding sites. After an appropriate incubation period, the unbound reactants are removed by washing and the amount of radioactivity on the solid phase is determined. The amount of bound radioactive antibody is inversely proportional to the concentration of antigen in the sample.

The most common enzyme immunoassay is the "Enzyme-Linked Immunosorbent Assay (ELISA)." The "Enzyme-Linked Immunosorbent Assay (ELISA)" is a technique for detecting and measuring the concentration of an antigen using a labeled (e.g., enzyme linked) form of the antibody. In a "sandwich ELISA," an antibody (e.g., to osteocalcin) is linked to a solid phase (e.g., a microtiter plate) and exposed to a biological sample containing antigen (e.g., osteocalcin). The solid phase is then washed to remove unbound antigen. A labeled (e.g., enzyme linked) antibody is then bound to the bound-antigen (if present) forming an antibody-antigen-antibody sandwich. Examples of enzymes that can be linked to the antibody include alkaline phosphatase, horseradish peroxidase, luciferase, urease, and β-galactosidase. The enzyme linked antibody reacts with a substrate to generate a colored reaction product that can be assayed.

In a "competitive ELISA," antibody is incubated with a sample containing antigen (e.g., osteocalcin). The antigen-antibody mixture is then contacted with an antigen-coated solid phase (e.g., a microtiter plate). The more antigen present in the sample, the less free antibody that will be available to bind to the solid phase. A labeled (e.g., enzyme linked) secondary antibody is then added to the solid phase to determine the amount of primary antibody bound to the solid phase.

In an "immunohistochemistry assay," a section of tissue is tested for specific proteins by exposing the tissue to antibodies that are specific for the protein that is being assayed. The antibodies are then visualized by any of a number of methods to determine the presence and amount of the protein present. Examples of methods used to visualize antibodies are, for example, through enzymes linked to the antibodies (e.g., luciferase, alkaline phosphatase, horseradish peroxidase, or β-galactosidase), or chemical methods (e.g., DAB/Substrate chromagen).

In addition to detecting levels of protein expression, the diagnostic assays of the invention may employ methods designed to detect the level of RNA expression. Levels of RNA expression may be determined using methods well known to those of skill in the art, including, for example, the use of northern blots, RT-PCR or in situ hybridizations.

Carboxylation of osteocalcin confers a greater affinity for hydroxyapatite. Total osteocalcin may be measured by immunoassay followed by incubation with hydroxyapatite and centrifugation. The supernatant, which contains osteocalcin that has not adsorbed to hydroxyapatite is then measured using the same immunoassay. The results of this procedure can be expressed either as absolute concentrations or as a ratio of undercarboxylated to carboxylated osteocalcin.

Another procedure uses monoclonal antibodies that distinguish the carboxylation state of all or some of the Glu/Gla residues of osteocalcin. For example, GluOC4-5 (TaKaRa catalog no. M171) reacts with human osteocalcin with glutamic acid residues (decarboxylated) at positions 21 and 24, and does not react with react with Gla-type osteocalcin.

For a review of osteocalcin measurement methods, see Lee et al., 2000, Ann. Clin. Biochem. 37:432-446.

Drug Screening and Assays

Cell-based and non-cell based methods of drug screening are provided to identify candidate agents that reduce OST-PTP, PTP-1B, or gamma-carboxylase activity or expression, and/or increase the level of undercarboxylated/uncarboxylated osteocalcin activity or expression. Such agents find use in treating or preventing cognitive disorders in mammals.

Non-cell based screening methods are provided to identify compounds that bind to OST-PTP, PTP-1B, gamma-carboxylase or osteocalcin and thereby modulate the activity of these proteins.

Such non-cell based methods include a method to identify, or assay for, an agent that binds to OST-PTP, the method comprising the steps of: (i) providing a mixture comprising OST-PTP or a fragment or variant thereof, (ii) contacting the mixture with a candidate agent, (iii) determining whether the candidate agent binds to the OST-PTP, wherein if the agent binds to the OST-PTP or a fragment or variant thereof (iv) determining whether the agent reduces the ability of OST-PTP to dephosphorylate gamma-carboxylase and (v) administering the agent to a patient in need of treatment for a cognitive disorder in mammals. In certain embodiments, the mixture comprises membrane fragments comprising OST-PTP or a fragment or variant thereof.

A screening method is provided to identify or assay for an agent that binds to the phosphatase 1 domain of OST-PTP, the method comprising the steps of: (i) providing a mixture comprising the phosphatase 1 domain of OST-PTP or a fragment or variant thereof, (ii) contacting the mixture with an agent, (iii) determining whether the agent binds to the phosphatase 1 domain of OST-PTP, wherein if the agent binds to the phosphatase 1 domain of OST-PTP or a fragment or variant thereof (iv) determining whether the agent inhibits the phosphatase 1 domain of OST-PTP and, if the agent inhibits the phosphatase 1 domain of OST-PTP (v) administering the agent to a patient in need of treatment for a cognitive disorder in mammals.

A screening method is provided to identify or assay for an agent that binds to PTP-1B, the method comprising the steps of: (i) providing a mixture comprising PTP-1B or a fragment or variant thereof, (ii) contacting the mixture with a candidate agent, (iii) determining whether the candidate agent binds to the PTP-1B, wherein if the agent binds to the PTP-1B or a fragment or variant thereof (iv) determining whether the agent reduces the ability of PTP-1B to dephosphorylate gamma-carboxylase and (v) administering the agent to a patient in need of treatment for a cognitive disorder in mammals. In certain embodiments, the mixture comprises membrane fragments comprising PTP-1B or a fragment or variant thereof.

A screening method is provided to identify, or assay for, an agent that binds to gamma-carboxylase, the method comprising the steps of: (i) providing a mixture comprising the gamma-carboxylase or a fragment or variant thereof, (ii) contacting the mixture with an agent, (iii) determining whether the agent binds to the gamma-carboxylase, wherein if the agent binds to the gamma-carboxylase or a fragment or variant thereof (iv) administering the agent to a patient in need of treatment for a cognitive disorder in mammals. The method may further comprise the step of determining whether the agent reduces gamma-carboxylase activity.

The binding of the agent to the target molecule in the above-described assays may be determined through the use of competitive binding assays. The competitor is a binding moiety known to bind to the target molecule. Under certain circumstances, there may be competitive binding as between the agent and the binding moiety, with the binding moiety displacing the agent or the agent displacing the binding moiety.

Either the agent or the competitor may be labeled. Either the agent, or the competitor is added first to the protein for a time sufficient to allow binding. Incubations may be performed at any temperature which facilitates optimal binding, typically between 4° C. and 40° C. Incubation periods may also be chosen for optimum binding, but may also optimized to facilitate rapid high throughput screening. Typically, between 0.1 and 1 hour will be sufficient. Excess agent and competitor are generally removed or washed away.

Using such assays, the competitor may be added first, followed by the agent. Displacement of the competitor is an indication that the agent is binding to the target molecule and thus is capable of binding to, and potentially modulating, the activity of the target molecule. In this embodiment, either component can be labeled. Thus, for example, if the competitor is labeled, the presence of label in the wash solution indicates displacement by the agent.

In another example, the agent is added first, with incubation and washing, followed by the competitor. The absence of binding by the competitor may indicate that the agent is bound to the target molecule with a higher affinity than the competitor. Thus, if the agent is labeled, the presence of the label on the target molecule, coupled with a lack of competitor binding, may indicate that the agent is capable of binding to the target molecule.

The method may comprise differential screening to identify agents that are capable of modulating the activity of the target molecule. In such an instance, the methods comprise combining the target molecule and a competitor in a first sample. A second sample comprises an agent, the target molecule, and a competitor. Addition of the agent is performed under conditions which allow the modulation of the activity of the target molecule. The binding of the competitor is determined for both samples, and a change, or difference in binding between the two samples indicates the presence of an agent capable of binding to the target molecule and potentially modulating its activity. That is, if the binding of the competitor is different in the second sample relative to the first sample, the agent is capable of binding to the target molecule.

Positive controls and negative controls may be used in the assays. Preferably, all control and test samples are performed in at least triplicate to obtain statistically significant results. Incubation of all samples is for a time sufficient for the binding of the agent to the target molecule. Following incubation, all samples are washed free of non-specifically bound material and the amount of bound, generally labeled agent determined. For example, where a radiolabel is employed, the samples may be counted in a scintillation counter to determine the amount of bound agent.

A variety of other reagents may be included in the screening assays. These include reagents like salts, neutral proteins, e.g. albumin, detergents, etc. which may be used to facilitate optimal protein-protein binding and/or reduce non-specific or background interactions. Also, reagents that otherwise improve the efficiency of the assay, such as protease inhibitors, nuclease inhibitors, anti-microbial agents, etc., may be used. The mixture of components may be added in any order that provides for the requisite binding.

Thus, in one example, the methods comprise combining a sample comprising OST-PTP, PTP-1B, or gamma-carboxylase and an agent, and evaluating the effect on OST-PTP, PTP-1B, or gamma-carboxylase enzyme activity. By enzyme activity, specifically OST-PTP, PTP-1B, or gamma-carboxylase enzyme activity, is meant one or more of the biological activities associated with the enzyme. For OST-PTP and PTP-1B, this activity is preferably the dephosphorylation of gamma-carboxylase; for gamma-carboxylase, it is the carboxylation of osteocalcin. The screening assays are designed to find agents that reduce OST-PTP, PTP-1B, or gamma-carboxylase activity, and/or increase levels of undercarboxylated/uncarboxylated osteocalcin.

Specifically, a screening method is provided to identify an agent that reduces OST-PTP activity, the method comprising the steps of: (a) providing a control mixture comprising OST-PTP or a fragment or variant thereof and a test mixture comprising OST-PTP or a fragment or variant thereof, (b) contacting the test mixture with an agent, (c) determining the level of activity of OST-PTP in the test mixture and in the control mixture, (d) identifying the agent as an agent that reduces OST-PTP activity if the level of OST-PTP activity in the test mixture is lower than the level of OST-PTP activity in the control mixture, and (e) administering the identified agent to a patient in need of treatment for a cognitive disorder in mammals.

A screening method is provided to identify an agent that reduces PTP-1B activity, the method comprising the steps of: (a) providing a control mixture comprising PTP-1B or a fragment or variant thereof and a test mixture comprising PTP-1B or a fragment or variant thereof, (b) contacting the test mixture with an agent, (c) determining the level of activity of PTP-1B in the test mixture and in the control mixture, (d) identifying the agent as an agent that reduces PTP-1B activity if the level of PTP-1B activity in the test mixture is lower than the level of PTP-1B activity in the control mixture, and (e) administering the identified agent to a patient in need of treatment for a cognitive disorder in mammals.

A screening method is provided to identify an agent that reduces gamma-carboxylase activity, the method comprising the steps of: (a) providing a control mixture comprising gamma-carboxylase or a fragment or variant thereof and a test mixture comprising gamma-carboxylase or a fragment or variant thereof, (b) contacting the test mixture with an agent, (c) determining the level of activity of gamma-carboxylase in the test mixture and in the control mixture, (d) identifying the agent as an agent that reduces gamma-carboxylase activity if the level of gamma-carboxylase activity in the test mixture is lower than the level of gamma-carboxylase activity in the control mixture, and (e) administering the identified agent to a patient in need of treatment for a cognitive disorder in mammals.

The present invention also provides a screening method to identify an agent that decarboxylates osteocalcin, the method comprising the steps of: (a) providing a control mixture comprising carboxylated osteocalcin and a test mixture comprising carboxylated osteocalcin, (b) adding to the test mixture an agent, (c) determining the level of carboxylated osteocalcin in the test mixture and in the control mixture, (d) identifying the agent as an agent that decarboxylates osteocalcin if the level of carboxylated osteocalcin in the test mixture is lower than the level of carboxylated osteocalcin in the control mixture, and (e) administering the identified agent to a patient in need of treatment for a cognitive disorder in mammals.

A cell-based method is provided for identifying an agent that increases osteocalcin gene expression, the method comprising steps: (a) determining a first expression level of osteocalcin in a cell, (b) determining a second expression level of osteocalcin after contact with a test agent; and (c) comparing the first expression level with the second expression level, wherein if the first expression level is lower than the second expression level the agent is identified as an agent that increases osteocalcin gene expression, and (e) administering the identified agent to a patient in need of treatment for a cognitive disorder in mammals. The level of osteocalcin gene expression may be determined by measuring the amount of osteocalcin mRNA made or the amount of osteocalcin protein made. In certain embodiments, the cell is an osteoblast.

The present invention also provides screening methods to identify agents that do not activate GPRC6A and are suitable for use in the prevention and treatment of a cognitive disorder in mammals. In certain embodiments, the method comprises:

(a) providing a cell that expresses GPRC6A;

(b) exposing the cell to a candidate substance; and (c) determining that the candidate substance does not bind to and/or activate the GPRC6A expressed by the cell.

Optionally, the method also comprises: (d) determining if the candidate substance is suitable for use in the prevention and treatment of a cognitive disorder in mammals.

In certain embodiments, step (a) comprises providing cells that recombinantly express GPRC6A. In certain embodiments, the cells that recombinantly express GPRC6A are NIH 3T3 cells, HEK 293 cells, BHK cells, COS cells, CHO cells, *Xenopus* oocytes, or insect cells. In certain embodiments, the GPRC6A is human GPRC6A. In certain embodiments, the GPRC6A is encoded by the nucleotide sequence shown in SEQ ID NO: 30. In certain embodiments, the GPRC6A comprises the amino acid sequence shown in SEQ ID NO: 31.

In certain embodiments, the candidate substance is from a library of candidate substances. In certain embodiments, the entire library of substances is exposed to the cell. In certain embodiments, a portion of the library is exposed to the cell.

In certain embodiments, step (b) is carried out by growing the cell in tissue culture and adding the candidate substance to the medium in which the cell is growing or has been grown. Alternatively, the medium in which the cell is growing or has been grown may be removed and fresh medium containing the candidate substance may be added the tissue culture plate or well in which the cell is growing or has been grown.

In certain embodiments, step (c) comprises determining if the candidate substance competes with labeled uncarboxlated osteocalcin for binding to the GPRC6A. In certain embodiments, step (c) comprises labeling the candidate substance and determining if the labeled candidate substance binds to the GPRC6A expressed by the cell.

In certain embodiments, step (c) comprises determining if the candidate substance produces a physiological response in the cell selected from the group consisting of: an increase in the concentration of cAMP in the cell. an increase in testosterone synthesis in the cell, an increase in the expression of StAR in the cell, an increase in the expression of Cyp11a in the cell, an increase in the expression of Cyp17 in the cell, an increase in the expression of 3β-HSD in the cell, an increase in the expression of Grth in the cell, an increase in the expression of tACE in the cell, an increase in CREB phosphorylation in the cell, and a decrease in the amount cleaved Caspase 3 in the cell. The physiological response may also be a combination of any of the foregoing physiological responses. In certain embodiments, the physiological response is an increase in the concentration of cAMP in the cell together with a lack of an increase in tyrosine phosphorylation, ERK activation, and intracellular calcium accumulation. In embodiments where a physiological response is determined, it may be advantageous to use a cell that does not naturally express GPRC6A but that has been engineered to recombinantly expresses GPRC6A. In such cases, the cell prior to transformation to a state that recombinantly expresses GPRC6A can serve as a negative control.

In certain embodiments, step (c) comprises determining if the candidate substance affects the binding of a G protein to the GPRC6A. Here, too, it may be advantageous to use cells that recombinantly express GPRC6A and to use those same cells before transformation as negative controls. In certain embodiments, the cell is co-transfected with a construct encoding GPRC6A and a construct encoding a $G_{\alpha}$ protein. See, e.g., Christiansen et al., 2007, Br. J. Pharmacol. 150: 798-807 and Pi et al., 2005, J. Biol. Chem. 280:40201-40209.

The present invention also provides screening methods to identify agents that do not activate GPRC6A and are suitable for use in the prevention and treatment of a cognitive disorder in mammals where the methods comprise:

(a) providing cell membranes containing GPRC6A protein;

(b) exposing the cell membranes to a candidate substance;

(c) determining that the candidate substance does not bind to the GPRC6A in the cell membranes; and (d) determining if the candidate substance is suitable for use in the prevention and treatment of a cognitive disorder in mammals.

In certain embodiments, step (a) comprises providing cell membranes from cells that recombinantly express GPRC6A. In certain embodiments, the cells that recombinantly express GPRC6A are NIH 3T3 cells, HEK 293 cells, BHK cells, COS cells, CHO cells, *Xenopus* oocytes, or insect cells. In certain embodiments, the GPRC6A is human GPRC6A. In certain embodiments, the GPRC6A is encoded by the nucleotide sequence shown in SEQ ID NO: 30. In certain embodiments, the GPRC6A comprises the amino acid sequence shown in SEQ ID NO:

In certain embodiments, the candidate substance is from a library of candidate substances. In certain embodiments, the entire library of substances is exposed to the cell membranes. In certain embodiments, a portion of the library is exposed to the cell membranes.

In certain embodiments, step (c) comprises determining if the candidate substance competes with labeled uncarboxlated osteocalcin for binding to the GPRC6A. In certain embodiments, step (c) comprises labeling the candidate substance and determining if the labeled candidate substance binds to the GPRC6A in the cell membranes.

In certain embodiments, step (d) comprises administering the candidate substance to a mammal and determining that the candidate substance produces an effect in the mammal selected from the group consisting of lessening of cognitive loss due to neurodegeneration associated with aging, lessening of anxiety, lessening of depression, lessening of memory loss, improving learning, and lessening of cognitive disorders associated with food deprivation during pregnancy.

In certain embodiments of the methods disclosed above, GPRC6A is the protein disclosed at GenBank accession no. AF502962. The nucleotide and amino acid sequences disclosed at GenBank accession no. AF502962 are shown in FIGS. 23 and 24 herein, respectively.

In certain embodiments of the methods disclosed above, GPRC6A is a protein homologous to the protein disclosed at GenBank accession no. AF502962. In certain embodiments of the methods disclosed above, GPRC6A is a protein having about 80-99%, about 85-97%, or about 90-95% amino acid sequence identity to the protein disclosed at GenBank accession no. AF502962.

In certain embodiments of the methods disclosed above, GPRC6A is the protein disclosed Wellendorph & Bräuner-Osborne, 2004, Gene 335:37-46.

In certain embodiments of the present invention, the agents identified by the methods of screening against GPRC6A are administered to a mammal in need of treatment for a cognitive disorder. Accordingly, the present invention includes a method of treating cognitive disorders in mammals comprising administering to a mammal in need of treatment for a cognitive disorder a pharmaceutical composition comprising a therapeutically effective amount of an agent that increases undercarboxylated/uncarboxylated osteocalcin levels but does not activate GPRC6A and a pharmaceutically acceptable carrier or excipient.

In certain embodiments, the an agent that does not activate GPRC6A is identified by a method comprising:

(a) providing a cell that expresses GPRC6A;

(b) exposing the cell to a candidate substance; and (c) determining that the candidate substance does not bind to and/or activate the GPRC6A expressed by the cell.

Agents that activate GPCR6A include ornithine, lysine, and arginine and may be used as control in the above-described assays (Christiansen et al., 2007, Br. J. Pharmacol. 150:798-807).

Gamma carboxylase catalyzes the posttranslational modification of specific glutamic acid residues within osteocalcin to form γ-carboxyglutamic acid residues. In an embodiment of the assays described herein, the level of gamma carboxylase activity or decarboxylase activity is determined by measuring the level of osteocalcin carboxylation.

Cells to be used in the screening or assaying methods described herein include cells that naturally express OST-PTP, the phosphatase 1 domain of OST-PTP, PTP-1B, gamma-carboxylase, or osteocalcin as well as cells that have been genetically engineered to express (or overexpress) OST-PTP, the phosphatase 1 domain of OST-PTP, PTP-1B gamma-carboxylase, or osteocalcin. Such cells include transformed osteoblasts that overexpress OST-PTP, the phosphatase 1 domain of OST-PTP, PTP-1B, or gamma-carboxylase.

A method is provided for identifying an agent useful for treating or preventing a cognitive disorder in mammals comprising: (a) providing an animal that has a cognitive disorder, (b) determining the amount of undercarboxylated/uncarboxylated osteocalcin in a pre-administration biological sample taken from the animal, (c) administering an agent to the animal, (d) determining the amount of undercarboxylated/uncarboxylated osteocalcin in a post-administration biological sample taken from the animal, and (e) identifying the agent as useful for treating or preventing the cognitive disorder in mammals if the amount of undercarboxylated/uncarboxylated osteocalcin in the post-administration biological sample is higher than the amount of undercarboxylated/uncarboxylated osteocalcin in the pre-administration biological sample.

The term "agent" as used herein includes any molecule, e.g., protein, oligopeptide, small organic molecule, polysaccharide, polynucleotide, lipid, etc., or mixtures thereof. Some of the agents can be used therapeutically. An agent may be OST-PTP, PTP-1B, gamma-carboxylase, osteocalcin, or fragments thereof.

Generally, in the assays described herein, a plurality of assay mixtures is run in parallel with different agent concentrations to obtain a differential response to the various concentrations. Typically, one of these concentrations serves as a negative control, i.e., is at zero concentration or below the level of detection.

Agents for use in screening encompass numerous chemical classes, though typically they are organic molecules, preferably small organic compounds having a molecular weight of more than 100 and less than about 2,500 daltons, preferably less than about 500 daltons. Agents comprise functional groups necessary for structural interaction with proteins, particularly hydrogen bonding, and typically include at least an amine, carbonyl, hydroxyl or carboxyl group, preferably at least two of these functional chemical groups. The agents often comprise cyclical carbon or heterocyclic structures and/or aromatic or polyaromatic structures substituted with one or more of the above functional groups. Agents are also found among biomolecules including peptides, saccharides, fatty acids, steroids, purines, pyrimidines, derivatives, structural analogs or combinations thereof. Particularly preferred biomolecules are peptides.

Libraries of high-purity small organic ligands and peptides that have well-documented pharmacological activities are available from numerous sources for use in the assays herein. One example is an NCI diversity set which contains 1,866 drug-like compounds (small, intermediate hydrophobicity). Another is an Institute of Chemistry and Cell Biology (ICCB; maintained by Harvard Medical School) set of known bioactives (467 compounds) which includes many extended, flexible compounds. Some other examples of the ICCB libraries are: Chem Bridge DiverSet E (16,320 compounds); Bionet 1 (4,800 compounds); CEREP (4,800 compounds); Maybridge 1 (8,800 compounds); Maybridge 2 (704 compounds); Maybridge HitFinder (14,379 compounds); Peakdale 1 (2,816 compounds); Peakdale 2 (352 compounds); ChemDiv Combilab and International (28,864 compounds); Mixed Commercial Plate 1 (352 compounds); Mixed Commercial Plate 2 (320 compounds); Mixed Commercial Plate 3 (251 compounds); Mixed Commercial Plate 4 (331 compounds); ChemBridge Microformat (50,000 compounds); Commercial Diversity Set1 (5,056 compounds). Other NCI Collections are: Structural Diversity Set, version 2 (1,900 compounds); Mechanistic Diversity Set (879 compounds); Open Collection 1 (90,000 compounds); Open Collection 2 (10,240 compounds); Known Bioactives Collections: NINDS Custom Collection (1,040 compounds); ICCB Bioactives 1 (489 compounds); SpecPlus Collection (960 compounds); ICCB Discretes Collections. The following ICCB compounds were collected individually from chemists at the ICCB, Harvard, and other collaborating institutions: ICCB1 (190 compounds); ICCB2 (352 compounds); ICCB3 (352 compounds); ICCB4 (352 compounds). Natural Product Extracts: NCI Marine Extracts (352 wells); Organic fractions—NCI Plant and Fungal Extracts (1,408 wells); Philippines Plant Extracts 1 (200 wells); ICCB-ICG Diversity Oriented Synthesis (DOS) Collections; DDS1 (DOS Diversity Set) (9600 wells). Compound libraries are also available from commercial suppliers, such as ActiMol, Albany Molecular, Bachem, Sigma-Aldrich, TimTec, and others.

Known and novel pharmacological agents identified in screens may be further subjected to directed or random chemical modifications, such as acylation, alkylation, esterification, or amidification to produce structural analogs.

When screening, designing, or modifying compounds, other factors to consider include the Lipinski rule-of-five (not more than 5 hydrogen bond donors (OH and NH groups); not more than 10 hydrogen bond acceptors (notably N and O); molecular weight under 500 g/mol; partition coefficient log P less than 5), and Veber criteria, which are recognized in the pharmaceutical art and relate to properties and structural features that make molecules more or less drug-like.

The agent may be a protein. By "protein" in this context is meant at least two covalently attached amino acids, and includes proteins, polypeptides, oligopeptides and peptides. The protein may be made up of naturally occurring amino acids and peptide bonds, or synthetic peptidomimetic structures. Thus "amino acid," or "peptide residue," as used herein means both naturally occurring and synthetic amino acids. For example, homo-phenylalanine, citrulline and norleucine are considered amino acids for the purposes of the invention. "Amino acids" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations.

The agent may be a naturally occurring protein or fragment or variant of a naturally occurring protein. Thus, for example, cellular extracts containing proteins, or random or directed digests of proteinaceous cellular extracts, may be used. In this way, libraries of prokaryotic and eukaryotic proteins may be made for screening against one of the various proteins. Libraries of bacterial, fungal, viral, and mammalian proteins, with the latter being preferred, and human proteins being especially preferred, may be used.

Agents may be peptides of from about 5 to about 30 amino acids, with from about 5 to about 20 amino acids being preferred, and from about 7 to about 15 being particularly preferred. The peptides may be digests of naturally occurring proteins as is outlined above, random peptides, or "biased" random peptides. By "random" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized agent bioactive proteinaceous agents.

The library may be fully randomized, with no sequence preferences or constants at any position. Alternatively, the library may be biased. That is, some positions within the sequence are either held constant, or are selected from a limited number of possibilities. For example, the nucleotides or amino acid residues are randomized within a defined class, for example, of hydrophobic amino acids, hydrophilic residues, sterically biased (either small or large) residues, towards the creation of cysteines, for cross-linking, prolines for SH3 domains, serines, threonines, tyrosines or histidines for phosphorylation sites, etc., or to purines, etc.

The agent may be an isolated nucleic acid, preferably antisense, siRNA, or cDNA that binds to either the gene encoding the protein of interest, or its mRNA, to block gene expression or mRNA translation, respectively. By "nucleic acid" or "oligonucleotide" or grammatical equivalents herein means at least two nucleotides covalently linked together. Such nucleic acids will generally contain phosphodiester bonds, although in some cases, as outlined below, nucleic acid analogs are included that may have alternate backbones, comprising, for example, phosphoramide (Beaucage et al., 1993, Tetrahedron 49:1925 and references therein; Letsinger, 1970, J. Org. Chem. 35:3800; Sprinzl et al., 1977, Eur. J. Biochem. 81:579; Letsinger et al., 1986, Nucl. Acids Res. 14:3487; Sawai et al, 1984, Chem. Lett. 805; Letsinger et al., 1988, J. Am. Chem. Soc. 110:4470; and Pauwels et al., 1986, Chemica Scripta 26:141); phosphorothioate (Mag et al., 1991, Nucleic Acids Res. 19:1437; and U.S. Pat. No. 5,644,048), phosphorodithioate (Briu et al., 1989, J. Am. Chem. Soc. 111:2321); O-methylphophoroamidite linkages (see Eckstein, Oligonucleotides and Analogues: A Practical Approach, Oxford University Press), and peptide nucleic acid backbones and linkages (see Egholm, 1992, J. Am. Chem. Soc. 114:1895; Meier et al., 1992, Chem. Int. Ed. Engl. 31:1008; Nielsen, 1993, Nature, 365: 566; Carlsson et al., 1996, Nature 380:207); all of which publications are incorporated by reference and may be consulted by those skilled in the art for guidance in designing nucleic acid agents for use in the methods described herein.

Other analog nucleic acids include those with positive backbones (Denpcy et al., 1995, Proc. Natl. Acad. Sci. USA 92:6097); non-ionic backbones (U.S. Pat. Nos. 5,386,023; 5,637,684; 5,602,240; 5,216,141; and 4,469,863; Kiedrowshi et al., 1991, Angew. Chem. Intl. Ed. English 30:423; Letsinger et al., 1988, J. Am. Chem. Soc. 110:4470; Letsinger et al., 1994, Nucleoside & Nucleoside 13:1597; Chapters 2 and 3, ASC Symposium Series 580, "Carbohydrate Modifications in Antisense Research," Ed. Y. S. Sanghui and P. Dan Cook; Mesmaeker et al., 1994, Bioorganic & Medicinal Chem. Lett. 4:395; Jeffs et al., 1994, J. Biomolecular NMR 34:17); and non-ribose backbones, including those described in U.S. Pat. Nos. 5,235,033 and 5,034,506, and Chapters 6 and 7, ASC Symposium Series 580, "Carbohydrate Modifications in antisense Research," Ed. Y. S. Sanghui and P. Dan Cook. Nucleic acids containing one or more carbocyclic sugars are also included within the definition of nucleic acids that may be used as agents as described herein. Several nucleic acid analogs are described in Rawls, C & E News Jun. 2, 1997 page 35. All of these references are hereby expressly incorporated by reference. These modifications of the ribose-phosphate backbone may be done to facilitate the addition of additional moieties such as labels, or to increase the stability and half-life of such molecules in physiological environments. In addition, mixtures of naturally occurring acids and analogs can be made. Alternatively, mixtures of different nucleic acid analogs, and mixtures of naturally occurring nucleic acids and analogs may be made. The nucleic acids may be single stranded or double stranded, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xanthine hypoxanthine, isocytosine, isoguanine, etc.

As described above generally for proteins, nucleic acid agents may be naturally occurring nucleic acids, random nucleic acids, or "biased" random nucleic acids. For example, digests of prokaryotic or eukaryotic genomes may be used as outlined above for proteins.

The agents may be obtained from combinatorial chemical libraries, a wide variety of which are available in the literature. By "combinatorial chemical library" herein is meant a collection of diverse chemical compounds generated in a defined or random manner, generally by chemical synthesis. Millions of chemical compounds can be synthesized through combinatorial mixing.

The determination of the binding of the agent to one of the various proteins such as OST-PTP, PTP-1B, or gamma-carboxylase may be done in a number of ways. In a preferred embodiment, the agent is labeled, and binding determined directly. For example, this may be done by attaching all or a portion of one of the various proteins to a solid support, adding a labeled agent (for example an agent comprising a radioactive or fluorescent label), washing off excess reagent, and determining whether the label is present on the solid support. Various blocking and washing steps may be utilized as is known in the art.

By "labeled" herein is meant that the agent is either directly or indirectly labeled with a label which provides a detectable signal, e.g. a radioisotope (such as $^{3}H$, $^{14}C$, $^{32}P$, $^{33}P$, $^{35}S$, or $^{125}I$), a fluorescent or chemiluminescent compound (such as fluorescein isothiocyanate, rhodamine, or luciferin), an enzyme (such as alkaline phosphatase, beta-galactosidase or horseradish peroxidase), antibodies, particles such as magnetic particles, or specific binding molecules, etc. Specific binding molecules include pairs, such as biotin and streptavidin, digoxin and antidigoxin, etc. For the specific binding members, the complementary member would normally be labeled with a molecule which provides for detection, in accordance with known procedures, as outlined above. The label can directly or indirectly provide a detectable signal. Only one of the components may be labeled. Alternatively, more than one component may be labeled with different labels.

Transgenic mice, including knock in and knock out mice, and isolated cells from them (especially osteoblasts) that over or under express the nucleic acids disclosed herein (e.g., cDNA for Esp, PTP-1B, osteocalcin, gamma-carboxylase) can be made using routine methods known in the art. In certain instances, nucleic acids are inserted into the genome of the host organism operably connected to and under the control of a promoter and regulatory elements (endogenous or heterogeneous) that will cause the organism to over express the nucleic acid gene or mRNA. One example of an exogenous/heterogeneous promoter included in the transfecting vector carrying the gene to be amplified is alpha 1(I) collagen. Many such promoters are known in the art.

Human osteoblasts can be transfected with vectors carrying the cDNA for human Esp, human PTP-1B, or human osteocalcin (or fragments or variants thereof) operably linked to known promoters and regulatory elements that cause the transfected human osteoblast to overexpress osteocalcin (or fragments or variants thereof).

Disclosed herein are transgenic mice and mouse cells, and transfected human cells overexpressing osteocalcin (or fragments or variants thereof), OST-PTP, PTP-1B, or gamma-carboxylase. Also disclosed herein are double mutant mice that have deletions of one or both alleles for osteocalcin, Esp, and gamma-carboxylase, and various combinations of double mutants.

Also disclosed herein are vectors carrying the cDNA or mRNA encoding the proteins for insertion into the genome of a target animal or cell. Such vectors can optionally include promoters and regulatory elements operably linked to the cDNA or mRNA. By "operably linked" is meant that promoters and regulatory elements are connected to the cDNA or mRNA in such a way as to permit expression of the cDNA or mRNA under the control of the promoters and regulatory elements.

Antisense and small interfering RNAs for use in reducing expression of OST-PTP, PTP-1B, and/or gamma-carboxylase, thereby treating or preventing a cognitive disorder in a mammal can be made that specifically hybridize to the gene and/or mRNA encoding OST-PTP, PTP-1B, or gamma-carboxylase, respectively. The sequence for mouse (OST-PTP, Ptprv) cDNA is set forth in SEQ ID NO:10. The amino acid sequence for OST-PTP, Ptprv) protein is set forth in SEQ ID NO:11. This cDNA, or antisense and small interfering RNAs based on this cDNA, will hybridize with mRNA for OST-PTP and thereby interfere with its translation. Reducing OST-PTP expression will increase the level of undercarboxylated/uncarboxylated osteocalcin, thereby providing a therapeutic benefit with respect to disorders related to cognition in mammals. The sequence for human PTP-1B cDNA is set forth in SEQ ID NO:16. The amino acid sequence for human PTP-1B protein is set forth in SEQ ID NO:17. This cDNA, or antisense and small interfering RNAs based on this cDNA, will hybridize with mRNA for human PTP-1B and thereby interfere with its translation. Reducing human PTP-1B expression will increase the level of undercarboxylated/uncarboxylated osteocalcin, thereby providing a therapeutic benefit with respect to cognitive disorders in mammals. The cDNA for mouse gamma-carboxylase is identified by SEQ ID NO:8, and its amino acid sequence is SEQ ID NO:9. This cDNA, or antisense and small interfering RNAs based on this cDNA, will hybridize with mRNA for gamma-carboxylase and thereby interfere with its translation and is a preferred embodiment. The cDNA for human gamma-carboxylase is identified by SEQ ID NO:6, and the amino acid sequence is SEQ ID NO:7. Human gamma-carboxylase cDNA can be used therapeutically to reduce gamma-carboxylase expression to treat or prevent a cognitive disorder in humans.

The invention is illustrated herein by the following examples, which should not be construed as limiting. The contents of all references, pending patent applications and published patents, cited throughout this application are hereby expressly incorporated by reference. Those skilled in the art will understand that this invention may be embodied in many different forms and should not be construed as limited to the embodiments set forth herein. Rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

EXAMPLES

Example 1—Materials and Methods

In Vivo Experiments

Osteocalcin$^{-/-}$, Gprc6a$^{-/-}$, Osteocalcin-mCherry, and Osteocalcin floxed mice have been previously described (Ducy et al., 1996, Nature 382:448-452; Oury et al., 2011, Cell 144:796-809). Mouse genotypes were determined by PCR. For all experiments, controls were littermate female WT, Cre-expressing, or flox/flox. All mice were maintained on a pure 129-Sv genetic background except for the inducible deletion Osteocalcin model (mix background: 25% C57/BL6 and 75% 129sv). For inducible gene deletion mice, tamoxifen was prepared in corn oil and injected intraperitoneally (IP) (1 mg/20 g of body weight) over one week. For osteocalcin delivery to pregnant mice, IP injections (240 ng/day) were performed as soon as a plug was present daily until delivery (E0.5-E18.5). For osteocalcin or leptin infusion in adult Osteocalcin$^{-/-}$ or ob/ob mice, pumps (Alzet micro-osmotic pump, Model 1002) delivering osteocalcin (300 ng/hr), leptin (50 ng/hr), or vehicle were surgically installed subcutaneously in the backs of 3-month old mice. For the postnatal rescue of cognitive functions in Osteocalcin$^{-/-}$ mice, osteocalcin (10 ng/hour) or vehicle were delivered intrasubventricularly (icy) as previously described (Ducy et al., 2000, Cell 100:197-207). Leptin and osteocalcin content in sera and tissues were determined by ELISA.

Maternal-fetal transport of osteocalcin was monitored using ex vivo dual perfusion of the mouse placenta (Goeden & Bonnin, 2013, Nature Protocols 8:66-74). Osteocalcin (300 ng/ml) was injected on the maternal side through the uterine artery in placentas obtained from WT mice at E14.5, E15.5, and E18.5 of pregnancy (n=3 independent perfusions per age). Osteocalcin transport through the placenta was analyzed by measuring the concentration of osteocalcin present in fetal eluates obtained through the umbilical vein, each time point (1-9) corresponding to a 10 minute collection period (at 5 μl/min). Collection time points (from 10 to 30 min of perfusion) were obtained during materal fluid infusion; time points 4-6 (from 30 to 60 min of perfusion) were obtained during osteocalcin infusion into the maternal uterine artery, whereas for time points 7-9 (from 60 to 90 min of perfusion, respectively) the maternal uterine artery was infused with maternal fluid alone.

Histology

All dissections were performed in ice-cold PBS 1× under a Leica MZ8 dissecting light microscope. Brainstems were isolated from the cerebellum and the hypothalamus was removed from the midbrain during collection. All parts of the brain isolated were flash frozen in liquid nitrogen and kept at −80° C. until use.

Immunofluorescence of whole adult and embryonic brains was performed on 20 μm coronal cryostat slices of tissue fixed with 4% PFA, embedded in cryomatrix (Tissue-Tek) and stored at −80° C. Sections were allowed to dry at room temperature, post-fixed in 4% PFA followed by permeabilization with 0.1% Triton detergent. After room temperature blocking with donkey serum, sections were incubated with anti 5-HT (Sigma) or anti-Neun antibody (Millipore) overnight at 4° C. Anti-5-HT slides were further incubated with donkey anti-rabbit cy-3 conjugated antibody (Jackson Laboratories). Slides were mounted with Fluorogel (Electron Microscopy Sciences).

For in situ mRNA hybridization, 20 μM coronal and sagittal sections of adult mouse brain were cryostat sectioned and collected on positively charged microscope slides. Cryosections were incubated with a DIG-labeled probe at 69° C. followed by incubation with alkaline phosphatase-conjugated anti-DIG antibody, and developed by incubation with NBT/BLIP.

Cresyl violet staining to visualize brain morphology was carried out by incubating 20 μm cryosections defatted with 1:1 chloroform:ethanol in cresyl violet acetate (1 g/L) overnight. The stain was differentiated using ethanol and xylene and mounted using DPX mounting medium for histology (Sigma).

To assess apoptosis in WT and Osteocalcin$^{-/-}$ brains, 20 μm cryostat sections were processed using the APOPTAG® Fluorescein Direct In Situ Apoptosis Detection Kit (Millipore) according to manufacturer's protocol. Images were obtained using Leica DM 4000B, and Image J was used to quantify cell number and intensity of staining.

Binding Assays

Brains from 8-week-old mice were snap-frozen in isopentane, and 20 mm thick sections were prepared and desiccated overnight at 4° C. under vacuum. On the following day, sections were rehydrated in ice-cold binding buffer (50 mM TrisHCl [pH 7.4], 10 mM $MgCl_2$, 0.1 mM EDTA and 0.1% BSA) for 15 min and incubated for 1 hr in the presence of biotinylated osteocalcin (3, 30, 300, 3000 ng/ml) or biotynylated recombinant GST as a control (10 μg/ml). After washing in harvesting buffer (50 mM Tris-HCl, pH 7.4), samples were fixed in 4% paraformaldehyde for 15 min, washed in PBS and incubated with goat anti-biotin antibody (1:1000, Vector laboratories) over night at 4° C. Signal was visualized by incubating with anti-goat IgG Cy-3 using Leica DM 5000B microscope (Leica). The binding assays were perform on adjacent sections for each conditions tested.

Biochemistry and Molecular Biology

For western blotting, frozen hippocampi from E18.5 embryos were lysed and homogenized in 250 μl tissue lysis buffer (25 mM Tris HCl 7.5; 100 mM NaF; 10 mM $Na_4P_2O_7$; 10 mmM EDTA; 1% NP 40). Samples were pooled together in threes by genotype to reduce variability. Proteins were transferred to nitrocellulose membranes and blocked with TBST-5% milk prior to overnight incubation with primary antibody in TBST-5% BSA. HRP-coupled secondary antibodies and ECL were used to visualize the signal.

For gene expression studies, RNA was isolated from primary neurons or tissue using TRIZOL® (Invitrogen). cDNA synthesis was performed following a standard protocol from Invitrogen and qPCR analyses were done using specific quantitative PCR primers from SABiosciences (www.sabiosciences.com/RT2PCR.php).

Serotonin, dopamine, norepinephrine, and GABA contents were measured by HPLC as previously described (Bach et al., 2011, J. Neurochem. 118:1067-1074). Neurotransmitter contents in 7 to 15 mice of each genotype were measured in cerebral cortex, striatum, hippocampus, hypothalamus, midbrain, brainstem, and cerebellum.

Cell Biology

For primary culture of hindbrain neurons, E14.5 embryos were obtained from matings of 129-Sv WT mice. Hindbrains were dissected out and collected in ice-cold filter sterilized HBSS buffered with 10 mM HEPES until dissection was complete, at which point they were finely chopped into 2 mm cubes, dissociated by trituration with a fire-polished Pasteur pipette and spun down at 4° C. Cells were then plated onto poly-D-lysine coated coverslips or dishes in Neurobasal medium supplemented with 2% B27, 0.25 mM Glutamax, 0.25 mM L-glutamine, penicillin G (50 U/ml), and streptomycin sulphate (50 mg/ml). Cultures were fed every 3-6 days with one half replacement medium without L-glutamine.

For calcium imaging, primary hindbrain neurons seeded on 12 mm coverslips were allowed the appropriate time to form structural networks. These cultures were washed with HBSS and loaded with 2.5 μM FURA-2, AM calcium indicator for 45 minutes at room temperature, according to the manufacturer's protocol. Cells were then washed to remove excess indicator and incubated for 30 minutes to allow internalized esters to become de-esterified. 30 ng/ml of osteocalcin was prepared with the control buffer of 1×HBBS supplemented with 10 mM HEPES buffer and 2 mM $CaCl_2$. Using a Zeiss microscope with a perfusion system, coverslips were first perfused with control and osteocalcin. After each stimulation, cells were depolarized with 50 mM KCl to determine the percentage of live cells being imaged. All treatments were recorded using two-photon laser scanning microscopy by Prairie Technologies and analyzed by Z axis profile plotting using ImageJ.

Brain Explants

Brains were dissected and incubated for 30 minutes in ice cold oxygenated artificial cerebrospinal fluid (ACSF). Brains were then sliced at 500 μm at the midbrain, −1.55 to −2.35 mm from the bregma, and at the level of the brainstem, from −4.04 to −4.48 mm and from −4.60 to −5.20 mm from the bregma, to include the median and dorsal raphe, respectively. These slices were incubated in ACSF for 1 h, constantly oxygenated (95% 02 and 5% $CO_2$) for 4 h, after which they were treated with either osteocalcin (10 ng/ml) or PBS for four hours. Expression of Tph2, TH, GAD1, GAD2, and Ddc was measured by qPCR.

Electrophysiology

Brain slice preparations and electrophysiological recordings were performed according to methods known in the art. Briefly, WT mice were anesthetized with ether and then decapitated. The brains were rapidly removed and immersed in an oxygenated bath solution at 40° C. containing (in mM): sucrose 220, KCl 2.5, $CaCl_2$ 1, $MgCl_2$ 6, $NaH_2PO_4$ 1.25, $NaHCO_3$ 26, and glucose 10 pH 7.3 with NaOH. Coronal slices (350 μm thick) containing dorsal raphe (DR) were cut on a vibratome and maintained in a holding chamber with artificial cerebrospinal fluid (ACSF) (bubbled with 5% $CO_2$ and 95% $O_2$) containing (in mM): NaCl 124, KCl 3, $CaCl_2$ 2, $MgCl_2$ 2, $NaH_2PO_4$ 1.23, $NaHCO_3$ 26, glucose 10, pH 7.4 with NaOH, and were transferred to a recording chamber constantly perfused with bath solution (330 C) at 2 ml/min after at least a 1 hr recovery. Whole-cell current clamp was performed to observe action potentials in DR serotoninergic (5-HT) neurons with a Multiclamp 700A amplifier (Axon instrument, CA). Patch pipettes with a tip resistance of 4-6 MS2 were made of borosilicate glass (World Precision Instruments) with a Sutter pipette puller (P-97) and filled with a pipette solution containing (in mM): K-gluconate (or Cs-gluconate) 135, $MgCl_2$ 2, HEPES 10, EGTA 1.1, Mg-ATP 2, $Na_2$-phosphocreatine 10, and $Na_2$-GTP 0.3, pH 7.3 with KOH. After a giga-Ohm (GΩ) seal and whole-cell access were achieved, the series resistance (between 20 and 40 MΩ) was partially compensated by the amplifier. 5-HT neurons were identified according to their unique properties (long duration action potential, activation by norepinephrine, and inhibition by serotonin itself. Under current clamp, 5-HT neurons were usually quiescent in slices because of the loss of noradrenergic inputs. The application of α1-adrenergic agonist phenylephrine (PE, 3 μM) elicited action potentials and the application of serotonin creatinine sulfate complex (3 μM) inhibited action potentials in these neurons. The effect of leptin on 5-HT neurons was examined in DR neurons responding to both PE and serotonin. Before the application of osteocalcin, action potentials in brainstem neurons were restored by application of PE in the bath. All data were sampled at 3-10 kHz and filtered at 1-3 kHz with an Apple Macintosh computer using Axograph 4.9 (Axon Instruments). Electrophysiological data were analyzed with Axograph 4.9 and plotted with Igor Pro software (WaveMetrics, Lake Oswego, Oreg.).

Physiological Measurements

Physical activity, including ambulatory activity (xamb) and total activity (xtot) was measured using infrared beams connected to the Oxymax system as previously described (Ferron et al, 2012, Bone 50:568-575). Energy expenditure measurements were obtained using a six-chamber oxymax system (Columbus Instruments, Ohio). After 30 hr acclimation to the apparatus, data for 24 hr measurement were collected and analyzed as recommended by the manufacturer. Oxygen consumption was calculated by taking the difference between input oxygen flow and output oxygen flow. Carbon dioxide production was calculated by taking the difference between output and input carbon dioxide flows. The respiratory exchange ratio (RER) corresponded to the ratio between carbon dioxide production and oxygen consumption ($RER=VCO_2/VO_2$). Heat production was calculated by indirect calorimetry using the flowing formulas:

$$Heat=CV\times VO_2/BW$$

$$CV=3.815+1.232\times RER$$

Behavioral Studies

Tail Suspension Test (TST)

Tail suspension testing was performed as previously described (Mayorga et al., 2001, J. Pharmacology Exper. Therapeutics 298:1101-1107; Stem et al., 1985, Psychopharmacology 85:367-370). Mice were transported a short distance from the holding facility to the testing room and left there undisturbed for at least 1 hour. Mice were individually suspended by the tail (distance from floor was 35 cm) using adhesive tape (distance from tip of tail was 2 cm). Typically, mice demonstrated several escape-oriented behaviors interspersed with temporally increasing bouts of immobility. The parameter recorded was the number of seconds spent immobile. Mice were scored by a highly trained observer, over a 5 min period, blind to the genotype of the mice.

Open Field Paradigm Test (OFT)

Anxiety and locomotor activity of mice were measured using the open field test (David et al., 2009, Neuron 62:479-493). Each animal was placed in a 43×43 cm open field chamber, and tested for 30 min. Mice were monitored throughout each test session by video tracking and analyzed using Matlab software. Mice were placed individually into the center of the open-field arena and allowed to explore freely. The overall motor activity was quantified as the total distance travelled. The anxiety was quantified measuring the number of rearings and the time and distance spent in the center versus periphery of the open field chamber (in %).

Elevated Plus Maze Test (EPMT)

Each mouse was allowed to explore the apparatus for 5 min. Global activity was assessed by measuring the number of entries into the open arms (David et al, 2009, Neuron 62:479-493). Anxiety was assessed by comparing the time spent in the open arms.

Mouse Forced Swim Test (FST)

The forced swimming test was carried out according to the method described by David et al., 2009, Neuron 62:479-493. Briefly, mice were dropped individually into glass cylinders (height: 25 cm, diameter: 10 cm) containing 10 cm water height, maintained at 23-25° C. Animals were tested for a total of 6 min. The total duration of immobility time was recorded. Mice were considered immobile when they made no attempts to escape with the exception of the movements necessary to keep their heads above the water. Mice were scored by an observer blind to their genotypes.

Light and Dark Test

The test was performed in a quiet, darkened room. Mice were individually housed in cages containing a handful of bedding from their home cage and acclimated to the room at least 1 h before the test. Naïve mice were placed individually in the testing chamber in the dark compartment. The test was 5 min in duration, and time spent and number of entries in light compartments were recorded a highly trained observer, blind to the genotype of the mice.

Morris Water Maze Test

Spatial memory was assessed with Morris water maze (MWM) setup (Morris, 1981, Nature 297:681-683) using a training protocol adapted for mice (D'Hooge et al., 2005, J. Soc. Neurosci. 25:6539-6549). The maze had a diameter of 150 cm and contained water (23° C.) that was made opaque with non-toxic white paint. The pool was located in a brightly lit room with distal visual cues, including computer, tables and posters with geometric figures attached to the walls. Spatial learning is assessed across repeated trials (4 trials/day for 10 days).

During trials, a small platform (diameter 10 cm) was hidden beneath the surface at a fixed position. Mice were placed in the water at the border of the maze and had to reach the platform after which they were transported back to their home cage. Mice that did not reach the platform within 2 min were gently guided towards the platform and were left on it for 10 s before being placed back in their cages. Four of such daily training trials (inter trial interval: 5 min) were given on 10 subsequent days. Starting positions in the pool varied between four fixed positions (0°, 90°, 180° and 270°) so that each position was used. Since a decrease in latency to find the platform was already present on the second acquisition day, the first acquisition day is also reported.

Figure 1B:
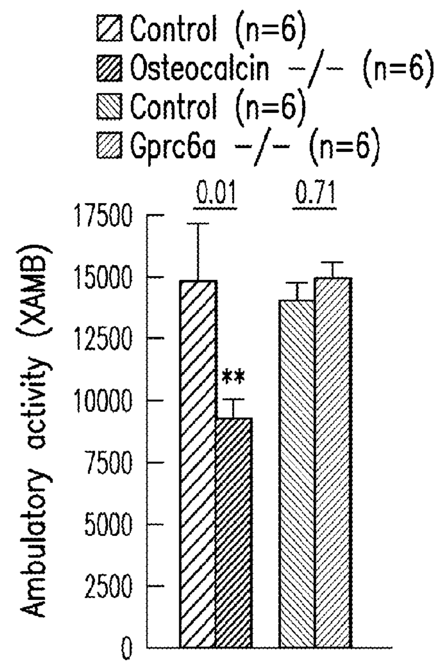
Figure 1C:
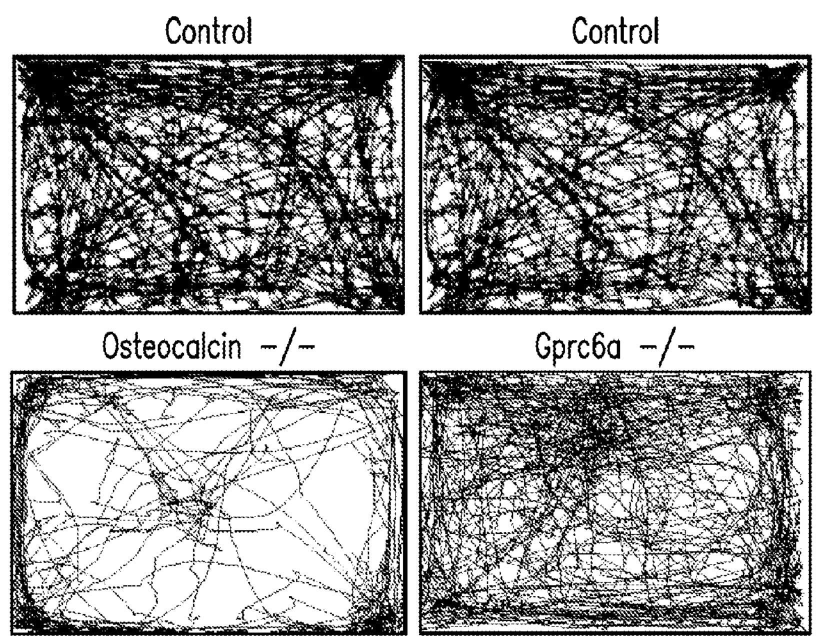

Example 2—Osteocalcin Crosses the Blood Brain Barrier and Binds to Specific Neurons in the Brain The passivity of Osteocalcin$^{-/-}$ mice is an obvious feature noticed by all investigators handling them. This phenotype was quantified in three-month old Osteocalcin$^{-/-}$ female mice, which demonstrated a significant decrease in locomotor and ambulatory activity during light and dark phases as compared to wild-type (WT) littermates (FIG. 1A-C). Since this observation was made in female mutant mice, it rules out the possibility that this phenotype was secondary to a lack of sex steroid hormones because osteocalcin does not regulate their synthesis in female mice (Oury). Likewise, it was not secondary to a measurable deficit in muscle functions since Osteocalcin$^{-/-}$ and WT mice ran similarly on a treadmill apparatus. This decrease in locomotion was not seen in mice lacking gprc6a, the only known osteocalcin receptor (FIGS. 1A-C) and the receptor that is believed to mediate osteocalcin's metabolic functions. This latter result implied that the passivity of the Osteocalcin$^{-/-}$ mice cannot be a consequence of their metabolic abnormalities, since those are equally severe in Osteocalcin$^{-/-}$ and Gprc6a$^{-/-}$ mice.

Figure 3A:
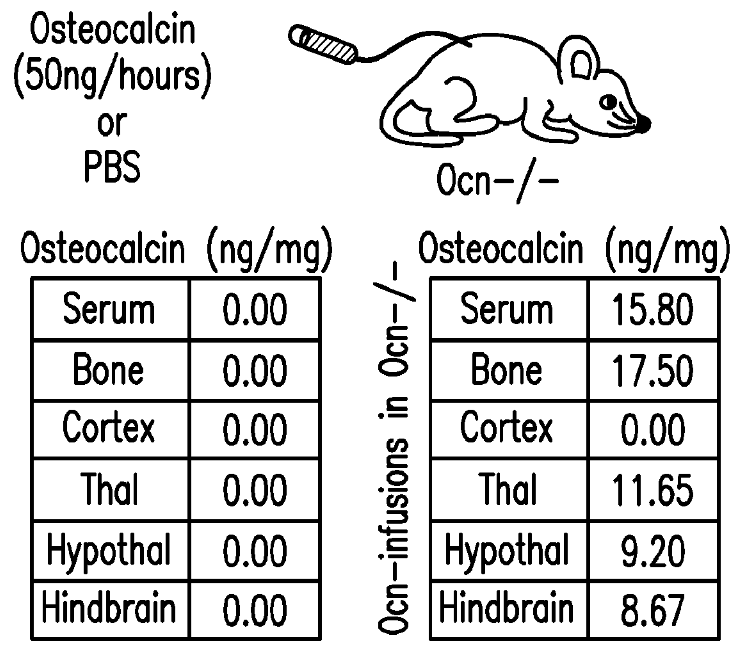
FIG. 3. Osteocalcin binds to neurons in the brain. (A) Measurement of the total osteocalcin in 3 month-old Osteocalcin$^{-/-}$ mice infused subcutaneously for 7 days with either uncarboxylated osteocalcin (300 ng/hour, right panel) or PBS (left panel). Osteocalcin levels were measured in bone, serum, and different parts of the brain (cortex, midbrain, hypothalamus, brainstem, and cerebellum). (B) Subcutaneous infusion of leptin (50 ng/ml, right panel) or PBS (left panel) for 7 days in ob/ob mice. Leptin levels were measured in serum, cortex, midbrain, hypothalamus, brainstem, and cerebellum. (C) Binding of GST-biotin (30 μg/ml) (panel 1) and biotinylated osteocalcin (300 ng/ml) (panels 2-4) to the dorsal (DR) and median (MR) raphe nuclei of the brainstem (identified by anti-5-HT immunofluorescence), to the ventral tegmental area (VTA) of the midbrain (identified by anti-TH immunofluorescence), and to the CA3 and CA4 of the hippocampus (identified anatomically). Panel 5 shows competition with unlabeled osteocalcin (1,000-fold excess). Binding with GST-biotin, osteocalcin-biotinylated, and competition assays were performed on adjacent sections. (D) Expression of Tph2 and GAD 1 in brainstem, and Th in midbrain explants from WT and Gprc6a$^{-/-}$ mice, treated with 10 ng/ml osteocalcin or vehicle. (E) Gene expression in WT primary hindbrain neuron cultures treated with 10 ng/ml osteocalcin or vehicle. (F) Calcium flux response of primary hindbrain cultured neurons to osteocalcin treatment. (G-H) Extracellular current recordings of (G) neurons of the dorsal raphe nucleus and (H) GABAergic interneurons of the brainstem treated with osteocalcin (10 ng/ml).
Figure 3B:
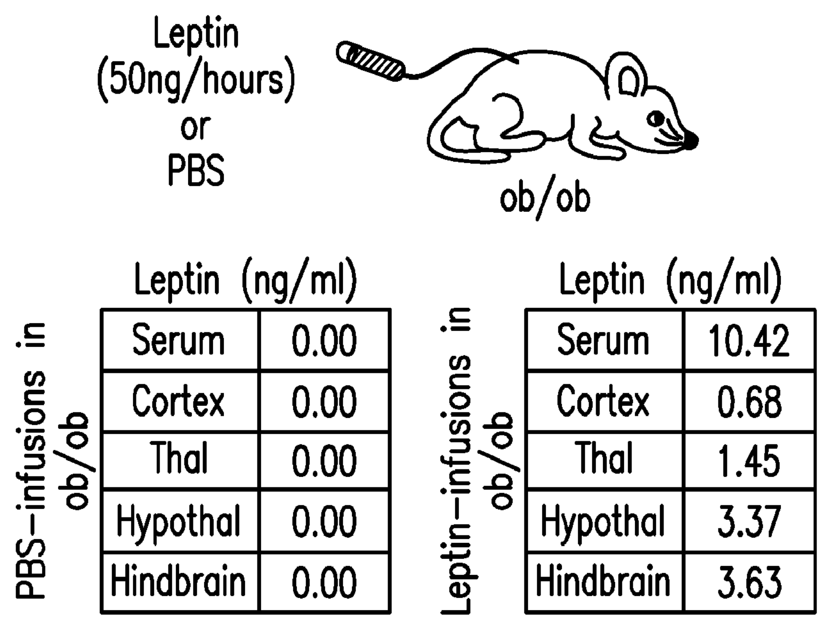

To understand how this behavioral phenotype develops, whether osteocalcin crosses the blood brain barrier (BBB) was tested by installing pumps that subcutaneously delivered vehicle or uncarboxylated osteocalcin (50 ng/hour) in three-month-old Osteocalcin$^{-/-}$ mice. The positive control for this experiment was subcutaneous infusion of leptin (50 ng/hour) in 3 month-old ob/ob mice, since leptin is known to cross the BBB (Banks et al., 1996, Peptides 17:305-311). Seven days later, osteocalcin and leptin content were measured in blood, bone, and in various parts of the brain in Osteocalcin−/− and ob/ob mice, respectively. In ob/ob mice, leptin could be detected in the brainstem and hypothalamus, two structures where it binds (FIG. 3B) (Yadav et al., 2009, Cell 138:976-989, Friedman et al., 2000, Nature 395:763-770). Osteocalcin accumulated in Osteocalcin−/− mice in the brainstem, thalamus, and ypothalamus, where its concentration approached 50% of that observed in serum (FIG. 3A).

Figure 3C:
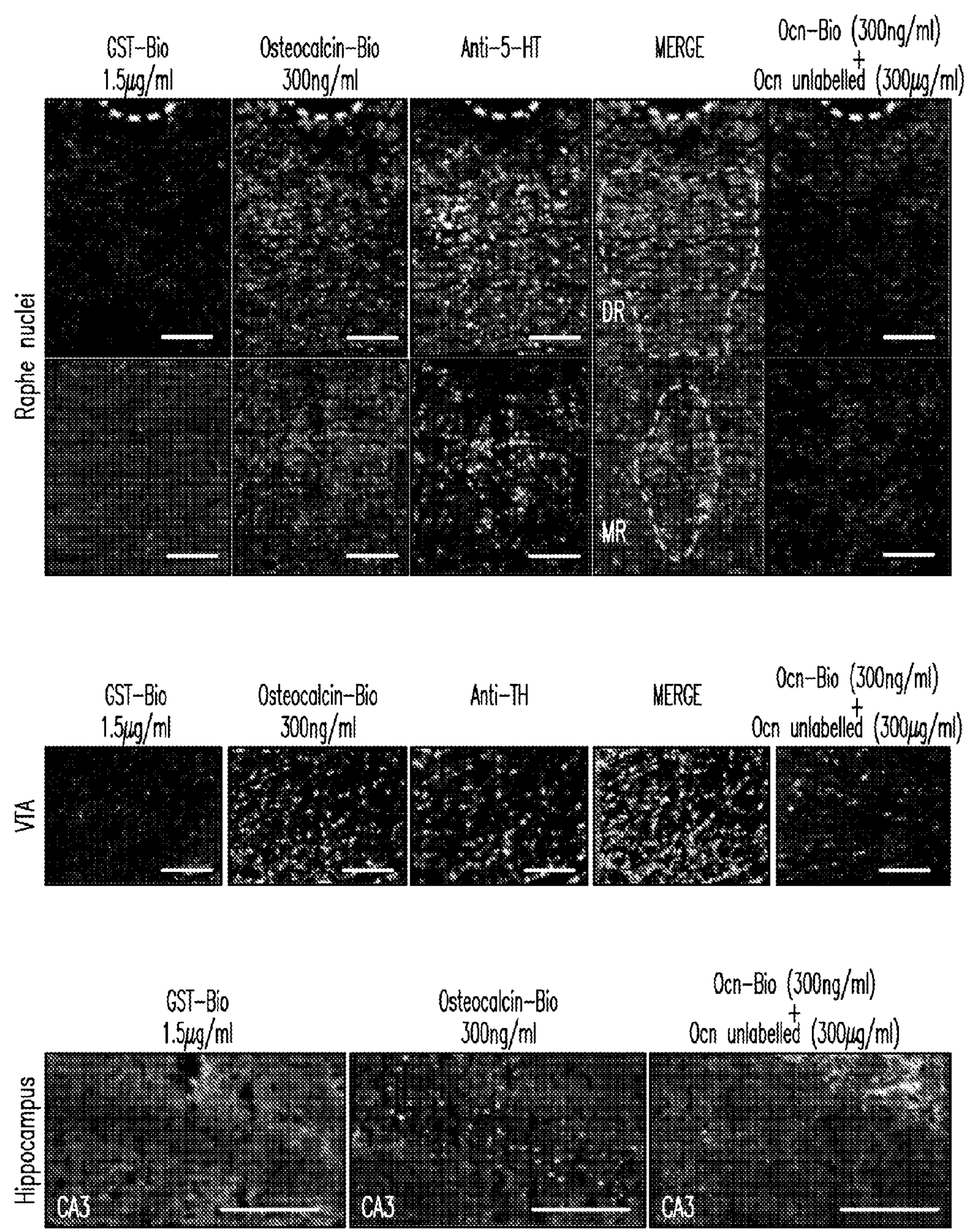

This accumulation in discrete regions of the brain raised the question of whether osteocalcin binds to specific neurons in the brain. This was tested by incubating sections of adult or embryonic (E18.5) WT brains with biotinylated undercarboxylated osteocalcin or GST-biotin alone (30 μg/ml), followed by immunofluorescence analysis using an anti-biotin antibody. In the conditions of this assay, osteocalcin bound to several neuronal populations in the forebrain, midbrain, and brainstem (FIG. 3C). In the midbrain, osteocalcin bound to the ventral tegmental area and the substantia nigrae, two nuclei located close to the midline on the floor of the midbrain (FIG. 3C). In the brainstem, osteocalcin bound to neurons of the raphe nuclei (FIG. 3C). Osteocalcin binding in the midbrain and brainstem was specific since it was chased away by an excess of unlabeled osteocalcin but not by an excess of GST (FIG. 3C).

Figure 1D:
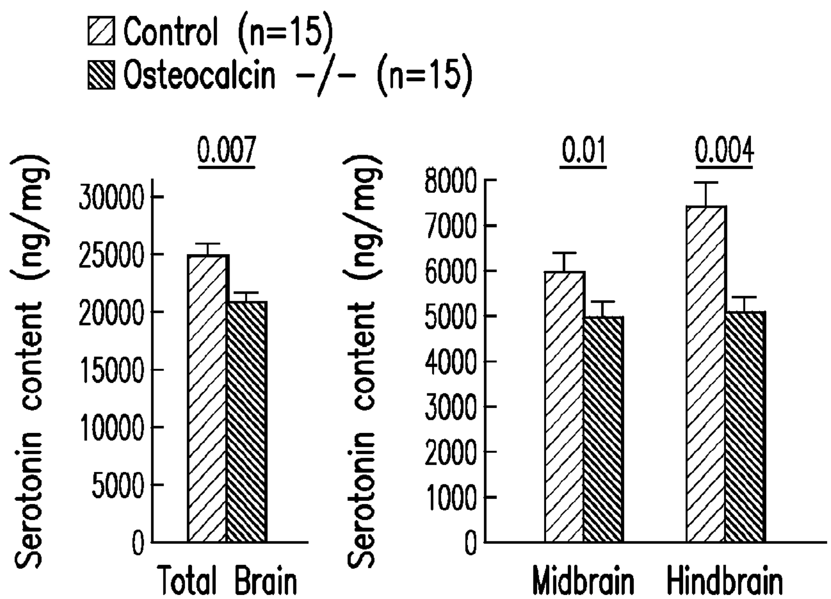
Figure 1E:
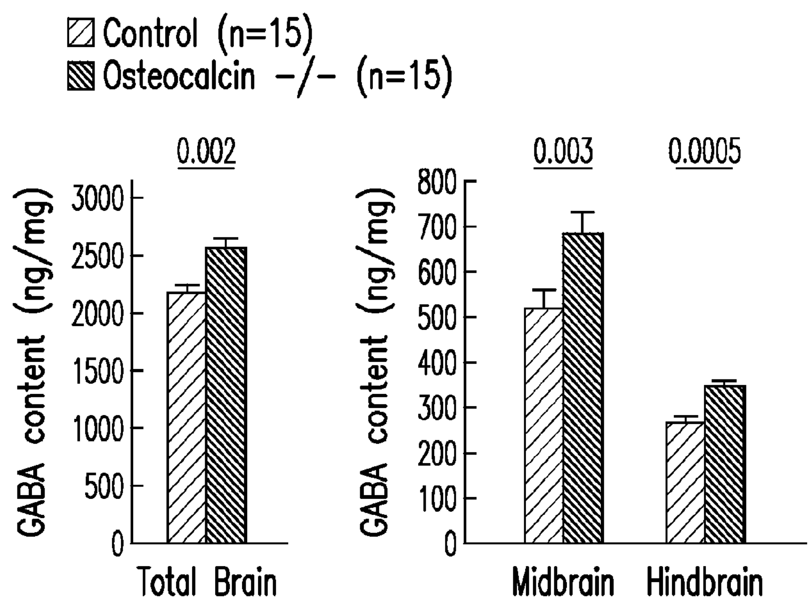
Figure 1F:
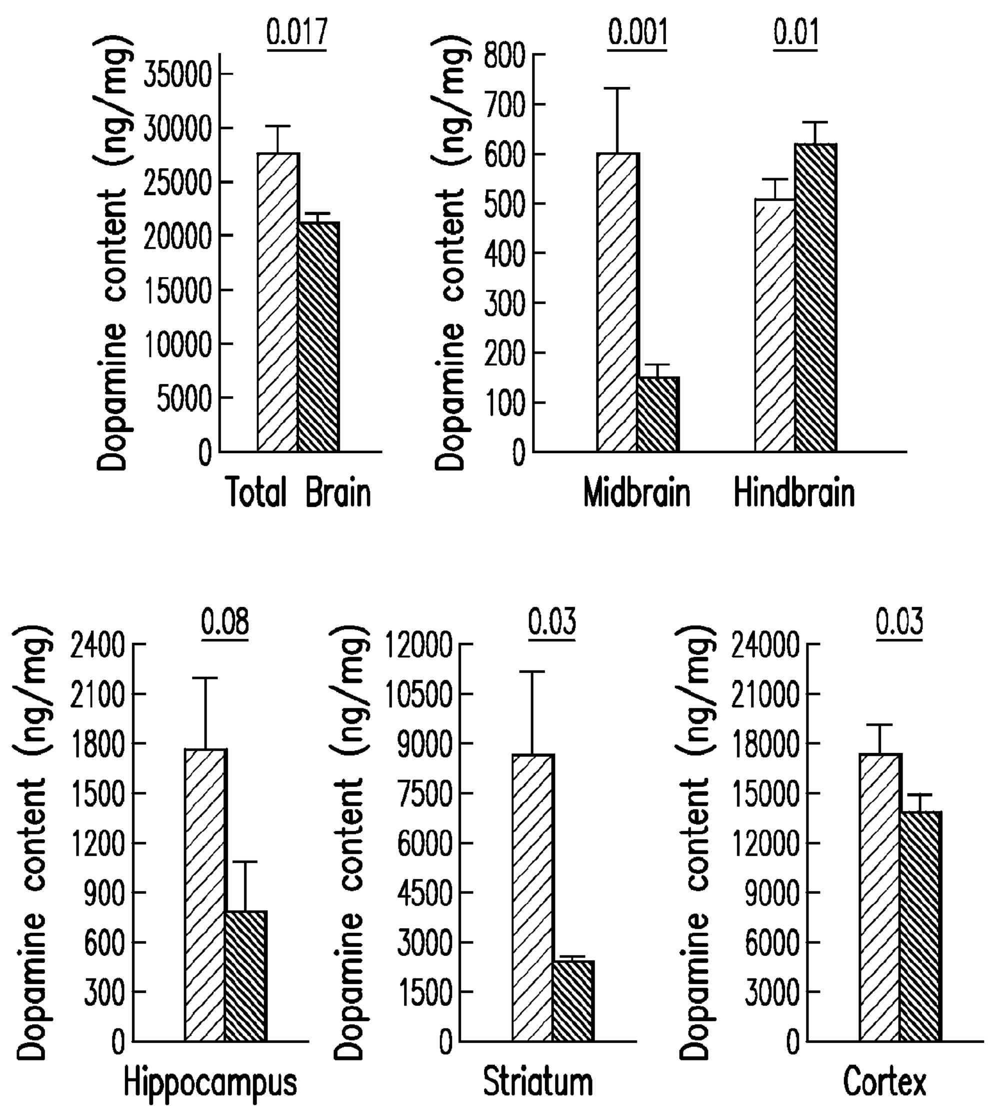
Figure 1G:
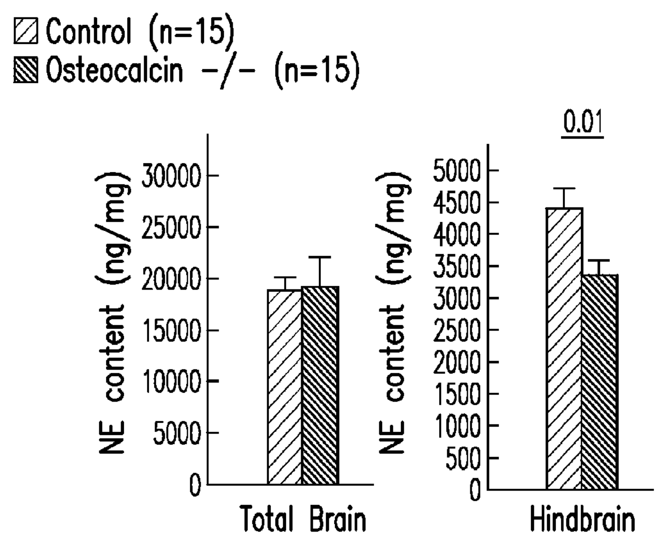

Example 3—Osteocalcin Affects the Biosynthesis of Various Neurotransmitters in the Brain That osteocalcin binds specifically to neurons of the raphe, where brain-derived serotonin is synthesized, together with the influence that brain serotonin exerts on bone mass accrual (Yadav et al., 2009, Cell 138:976-989; Oury et al., 2010, Genes & Development 24:2330-2342), raised the possibility that osteocalcin may influence the synthesis of various neurotransmitters, and that the absence of this regulation may explain the passivity of Osteocalcin$^{-/-}$ mice. The content of serotonin, dopamine, norepinephrine, γ-aminobutyric acid (GABA) and their metabolites in various areas of the brain of three-month old WT and Osteocalcin$^{-/-}$ mice was measured through high pressure liquid chromatography (HPLC). Serotonin and norepinephrine contents were significantly decreased in the brainstem while dopamine content was markedly decreased in the midbrain, cortex, and striatum of Osteocalcin$^{-/-}$ mice compared to WT mice (FIGS. 1D, 1F-G). Of note, this pattern of neurotransmitter accumulation in Osteocalcin$^{-/-}$ mice was similar to what is observed in Tph2$^{+/-}$ mice. Conversely, GABA content was increased in all areas tested in the brains of Osteocalcin$^{-/-}$ mice (Figure E), This is different from what was observed in Tph2$^{+/-}$ mice in which GABA content was increased only in the hindbrain. The content of neurotransmitters was indistinguishable between WT and Gprc6a$^{-/-}$ brains.

Figure 1H:
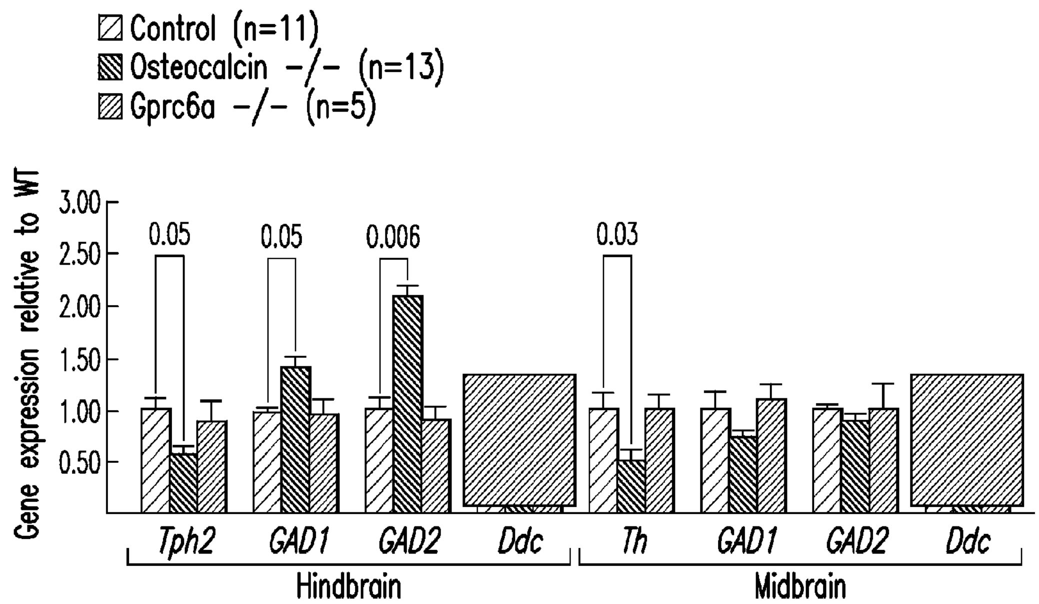

The expression of genes encoding rate limiting enzymes implicated in the biosynthesis of these neurotransmitters was studied. Expression of Tph2, the initial and rate limiting enzyme in brain serotonin synthesis, was decreased in the brainstem of Osteocalcin$^{-/-}$ mice and the expression of Th, the rate limiting enzyme in dopamine synthesis, was decreased in the midbrain (FIG. 1H). The same was true for aromatic L-amino decarboxylase (Ddc). Conversely, expression of GAD1 and 2, two enzymes required for GABA biosynthesis, was increased in brainstem of Osteocalcin$^{-/-}$ mice. Expression of all these genes was similar in Gprc6a$^{-/-}$ and WT mice (FIG. 1H), further indicating that osteocalcin signals in the brain in a Gprc6a-independent manner.

A consequence of the positive regulation of Th expression by osteocalcin is that the sympathetic tone as determined by norepinephrine content in the brainstem and Ucp1 expression in brown fat is significantly decreased in Osteocalcin$^{-/-}$ mice. This provides an explanation for the high bone mass originally noted in these mutant mice (Ducy et al., 1996 Nature 382:448-452).

Figure 3D:
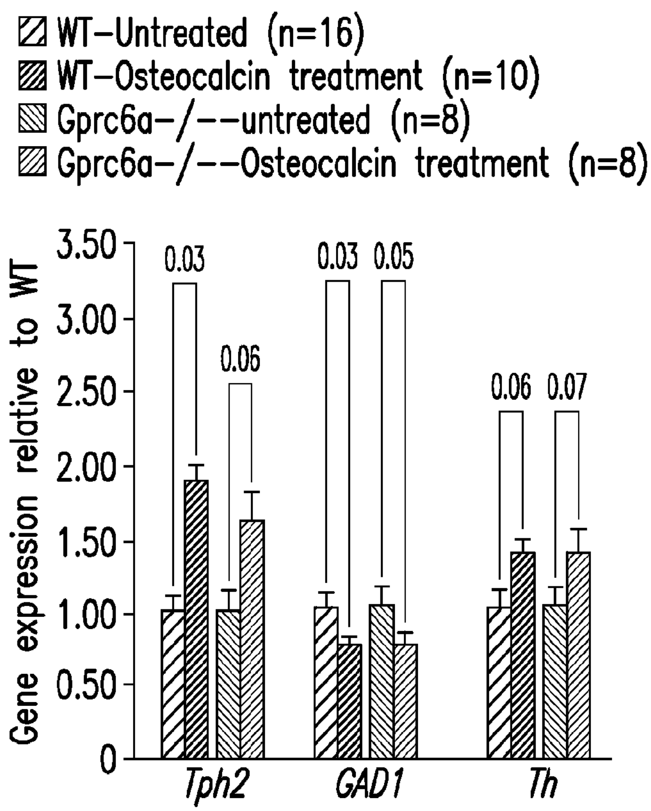
Figure 3E:
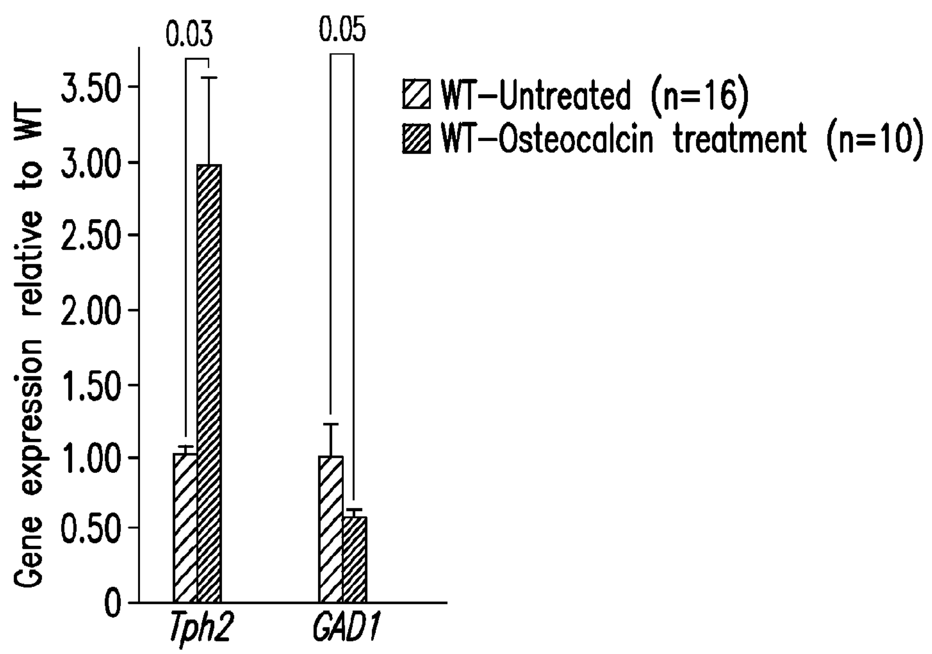
Figure 3F:
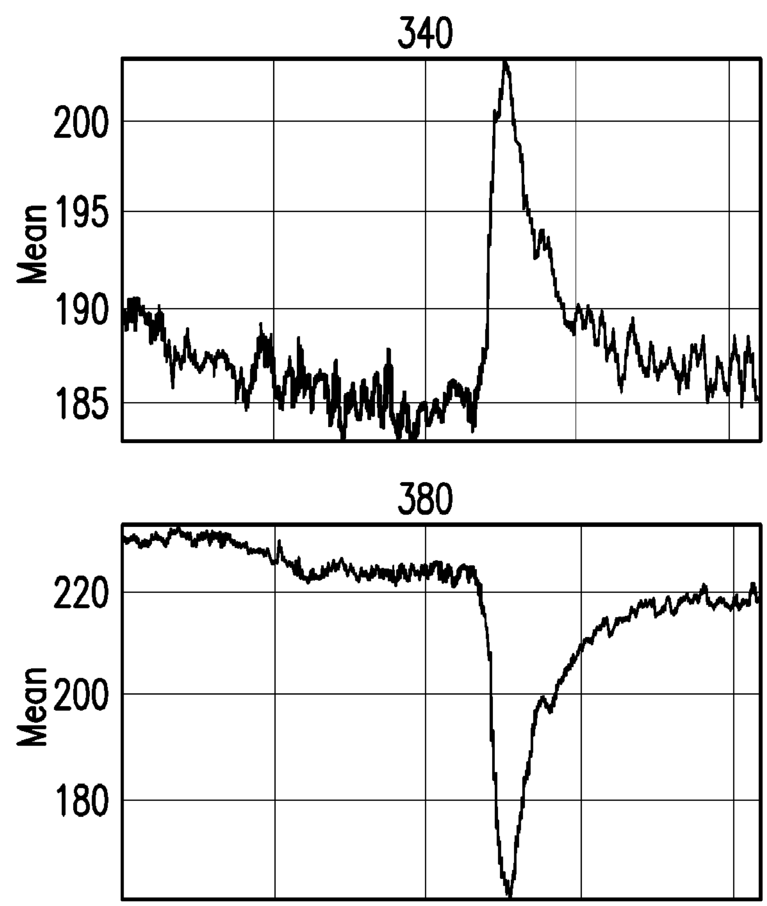
Figure 3G:
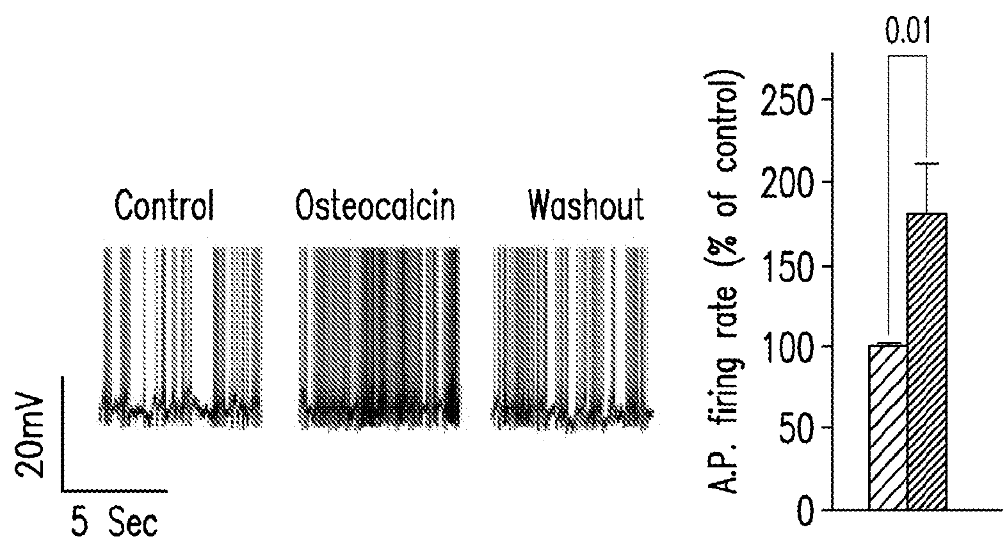
Figure 3H:
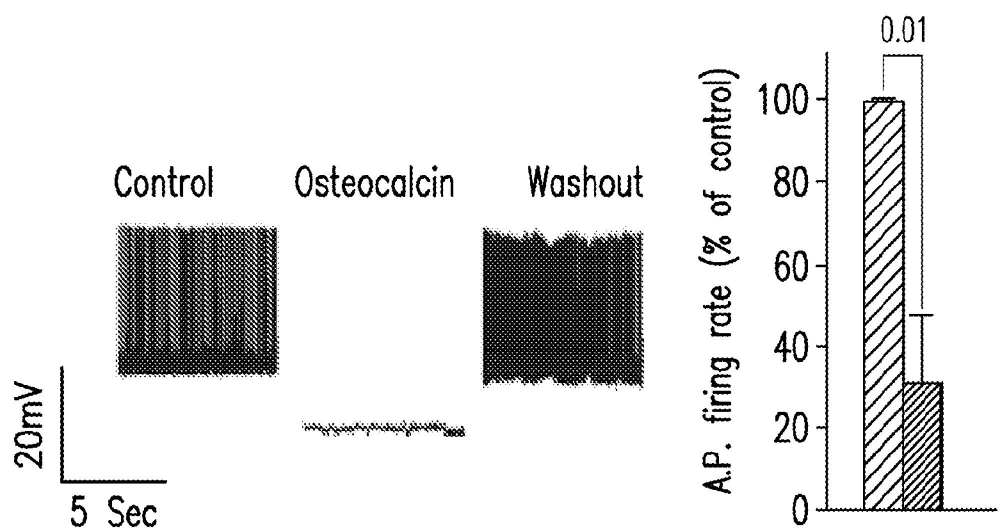
Figure 4A:
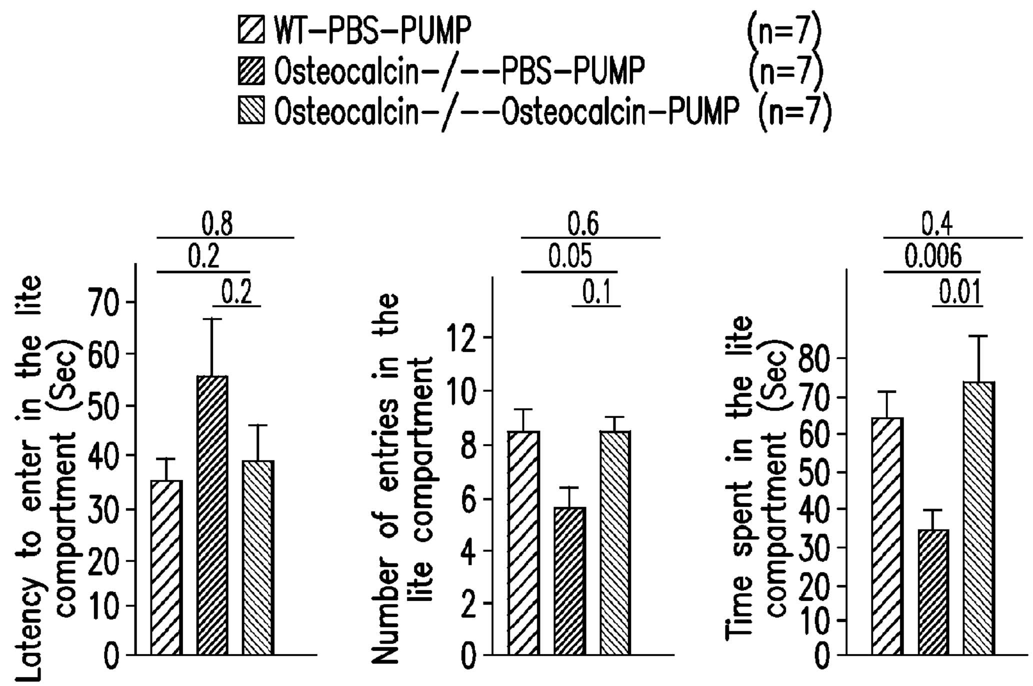
FIG. 4. Administration of osteocalcin prevents anxiety and depression. (A-E) Behavioral analyses of adult Osteocalcin$^{-/-}$ mice receiving osteocalcin through intracerebroventricular (ICV) infusions. (A) Light and Dark test, (B) Elevated plus maze test, (C) Open field test, (D) Forced swim test, and (E) Tail suspension test performed in a cohort of WT (n=7) and Osteocalcin$^{-/-}$ infused with vehicle or osteocalcin (10 ng/hour). In each set of three bars, the rightmost bar represents the results following administration of osteocalcin.
Figure 4B:
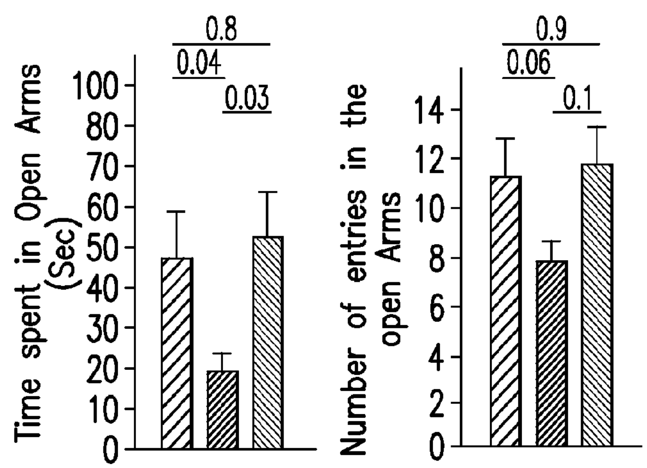
Figure 4C:
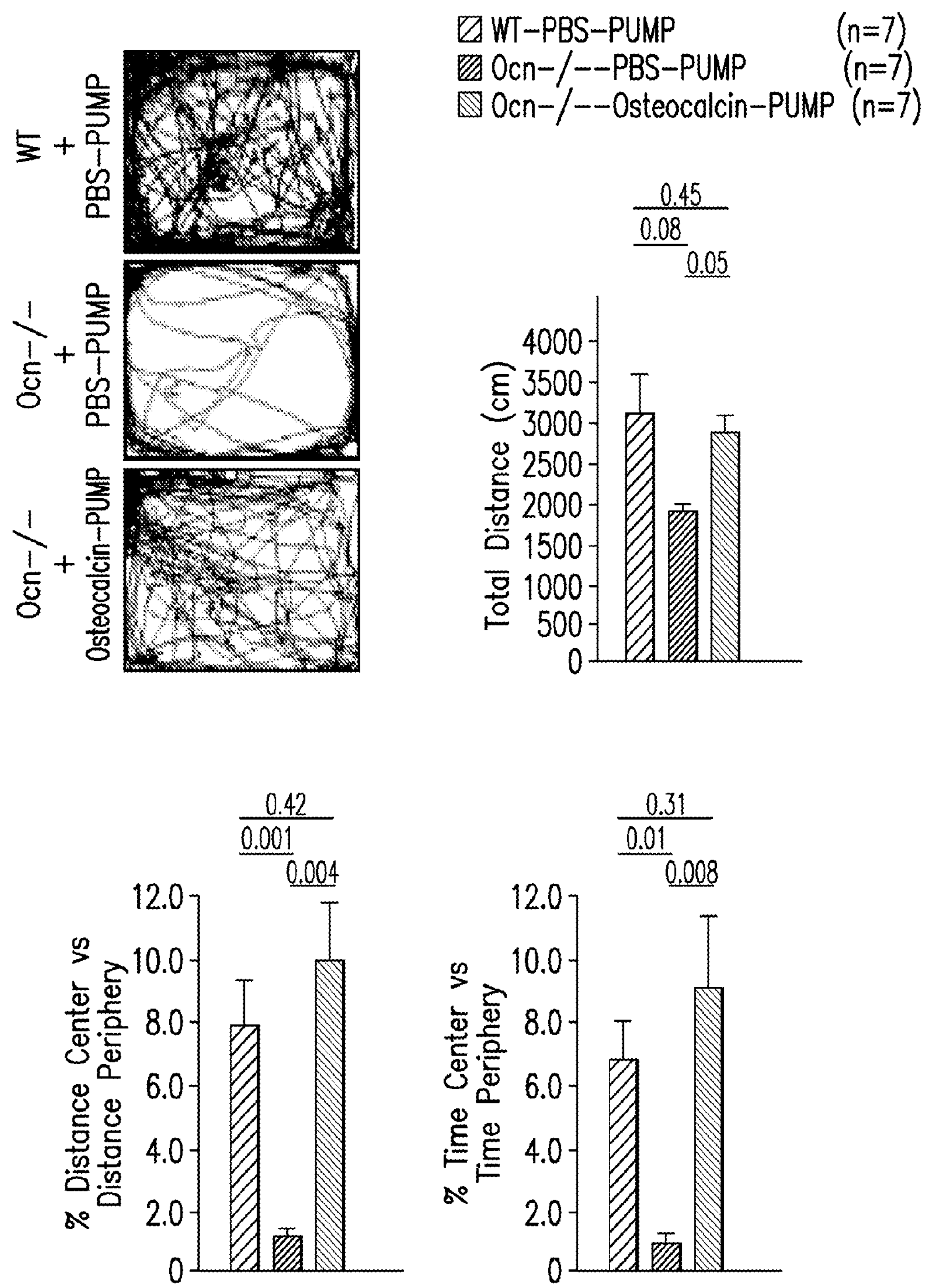
Figure 4D:
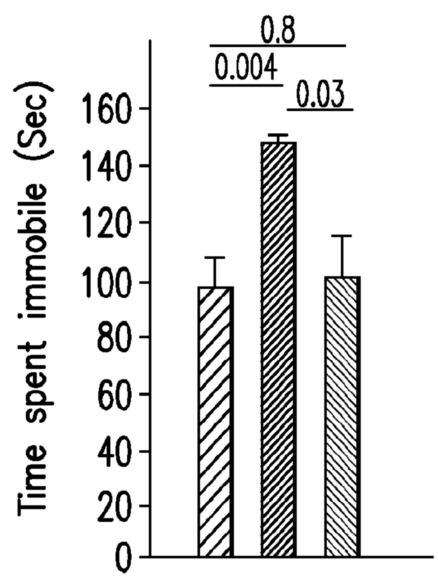
Figure 4E:
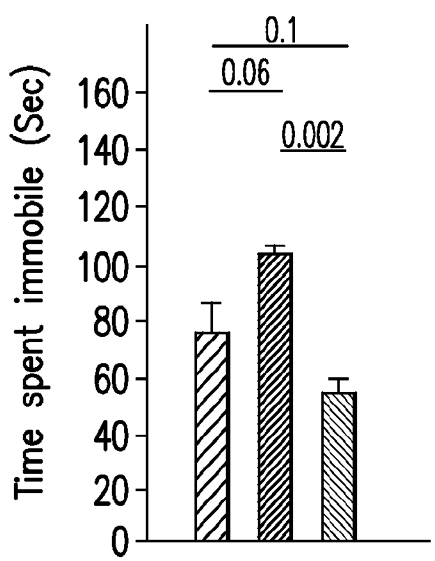

To determine if osteocalcin acts directly on neurons to modulate neurotransmitter synthesis, several types of assays were performed. First, brainstem and midbrain explants from WT and Gprc6a$^{-/-}$ mice were generated. Brains were sliced (500 μm) at the level of the median and dorsal raphe of the brainstem (from −4.04 to −4.48 mm and from −4.60 to −5.20 mm, respectively), so that they would be enriched in serotonin-producing neurons, as well as at the level of substantia nigrae and ventral tegmental areas (VTA) of the midbrain (from −1.55 to −2.35 mm and from −2.55 to −3.25 mm, respectively). Enrichment in serotoninergic and catecholaminergic neurons in these explants was verified by their high Tph2 and Th expression. While leptin, used here as a positive control, reduced, as it should, Tph2 expression in WT or Gprc6a$^{-/-}$ brainstem explants, osteocalcin (3 ng/ml) increased expression of this gene 2.5 fold in both WT and Gprc6a$^{-/-}$ explants. (FIG. 3D). Additionally, osteocalcin increased Th expression in midbrain explants and decreased Gad1 expression in both WT and in Gprc6a$^{-/-}$ hindbrain explants (FIG. 3D). Second, the cultured WT and Gprc6a$^{-/-}$ mouse primary hindbrain neurons (MPHN) were treated with osteocalcin (3 ng/ml). Tph2 expression increased more than three-fold and GA' expression decreased by 65% in both WT and Gprc6a–/– primary brainstem neuronal culture following a 2 or 4 hours treatment with osteocalcin (FIG. 3E). Third, to further confirm that osteocalcin signals in neurons of the hindbrain, calcium flux in MPHN treated with undercarboxylated or carboxylated osteocalcin (FIG. 3F) was measured. Undercarboxylated but not carboxylated osteocalcin induced changes in calcium fluxes in those neurons. Finally, an electrophysiological analysis showed, through whole cell current clamp recording, that osteocalcin activates the action potential frequency of brainstem neurons but decreases it in neurons of the locus coeruleus (FIG. 3G). Moreover, osteocalcin inhibits the action potential frequency of the GABAergic interneurons of the hindbrain (FIG. 3H).

Taken together, results of these four different assays support the notion that osteocalcin not only binds to but acts directly, in a Gprc6a-independent manner, on neurons in the raphe to increase Tph2 expression, serotonin accumulation, Th expression, and norepinephrine content, as well as to inhibit GABA synthesis. Osteocalcin also signals in neurons of the midbrain to promote Th expression and dopamine accumulation in that region. Hence, in a feedback manner, bone signals via osteocalcin to serotonergic neurons that are a regulator of bone mass. A consequence of the regulation of Th expression by osteocalcin is that the sympathetic tone is low in Osteocalcin$^{-/-}$ mice, a feature that explains the high bone mass originally noted in these mutant mice (Ducy et al., 1996, Nature 382:448-452).

Example 4—Osteocalcin Affects Several Types of Behavior

An implication of the regulation of serotonin and dopamine by osteocalcin is that Osteocalcin$^{-/-}$ mice should demonstrate broad cognitive impairments that, along with their low sympathetic tone, may explain their passivity. To test if this is the case, Osteocalcin$^{-/-}$, Osteocalcin$^{+/-}$, Esp$^{-/-}$, and Gprc6a$^{-/-}$ mice were subjected to a battery of behavioral tests. As controls in these experiments, WT littermates and Tph2$^{+/-}$ mice that demonstrated a decrease in serotonin and dopamine content similar to that one observed in Osteocalcin$^{-/-}$ mice were used.

Figure 2A:
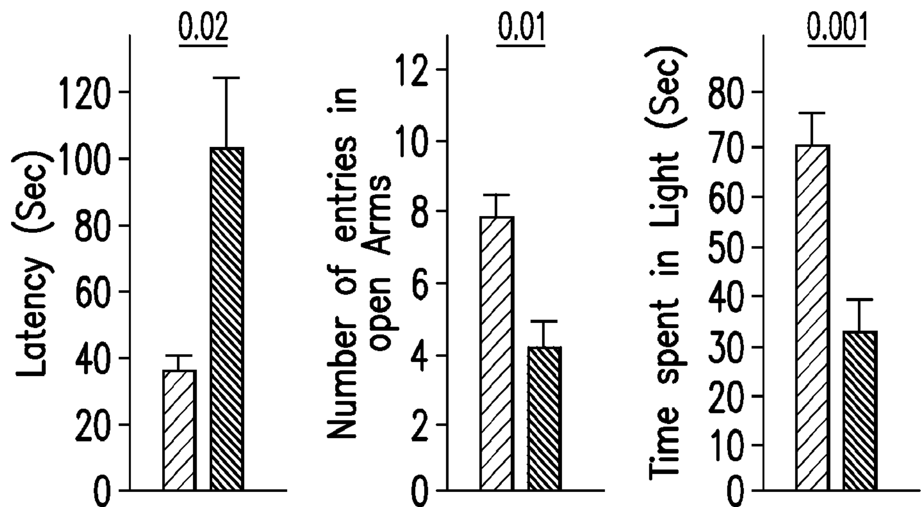
FIG. 2. Osteocalcin affects anxiety, depression, memory, and learning. (A-L) Behavioral analysis of (A, C, E, G, I and K) Osteocalcin$^{-/-}$ (n=21), (B, D, F, H, J and L) Gprc6a$^{-/-}$ (n=16) and WT (n=21 and n=15) littermate mice. (A-B) Light and Dark test (L/DT): The latency (Sec=seconds) to enter in the lit compartment, number of transitions between compartments, and amount of time spent in the lit compartment were measured. (C-D) Elevated Plus Maze test (EPMT): Number of entries and amount of time spent (Sec=seconds) in the open arms were scored. (E-F) Open field test (OFT): Total distance (cm), % of the distance traveled, and time spent in the center versus periphery as well as number of rearing events were measured. The video tracking of each group of mice are represented on the right panel. (G-J) Representation of the time spent (seconds) immobile during the (G-H) forced swim test and the (I-J) Tail suspension test. Both tests assess depression-like behavior. (K-L) Morris Water Maze test performed over 10 days. The graphic shows the time (seconds) needed for each group of mice to locate a submerged platform in the swimming area. The video trackings on the left panel are the representations of the standards obtained for each group analyzed. Error bars represent SEM. Student's T-test is represented on the top of the bars.
Figure 2B:
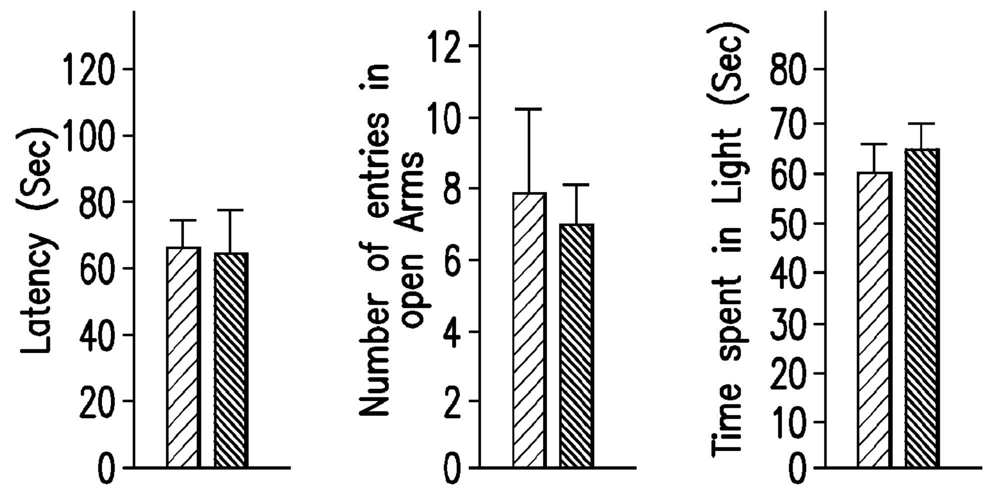
Figure 2C:
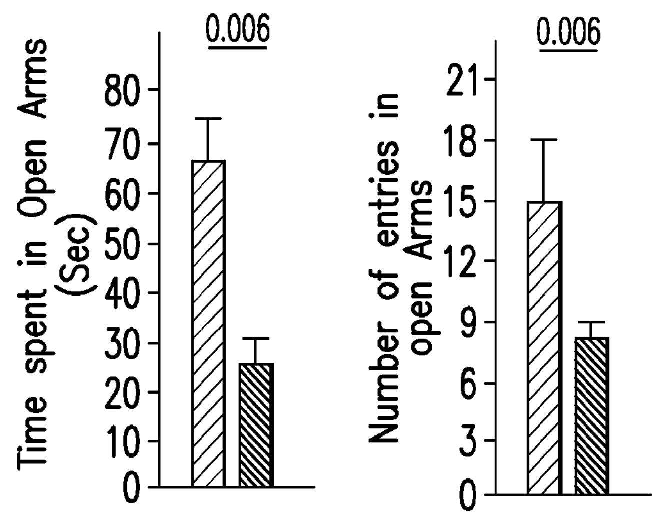
Figure 2D:
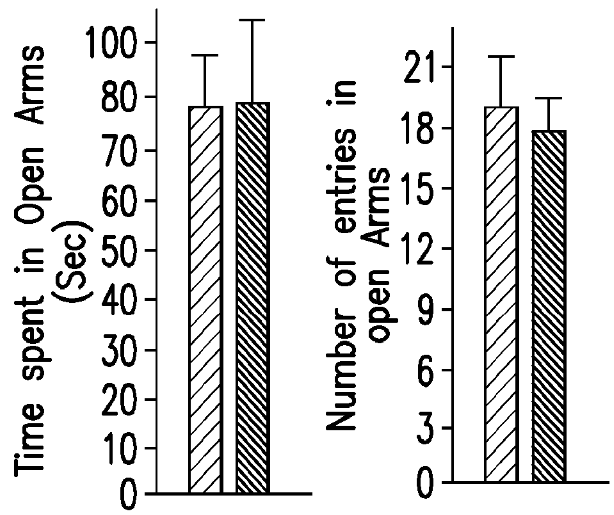
Figure 2E:
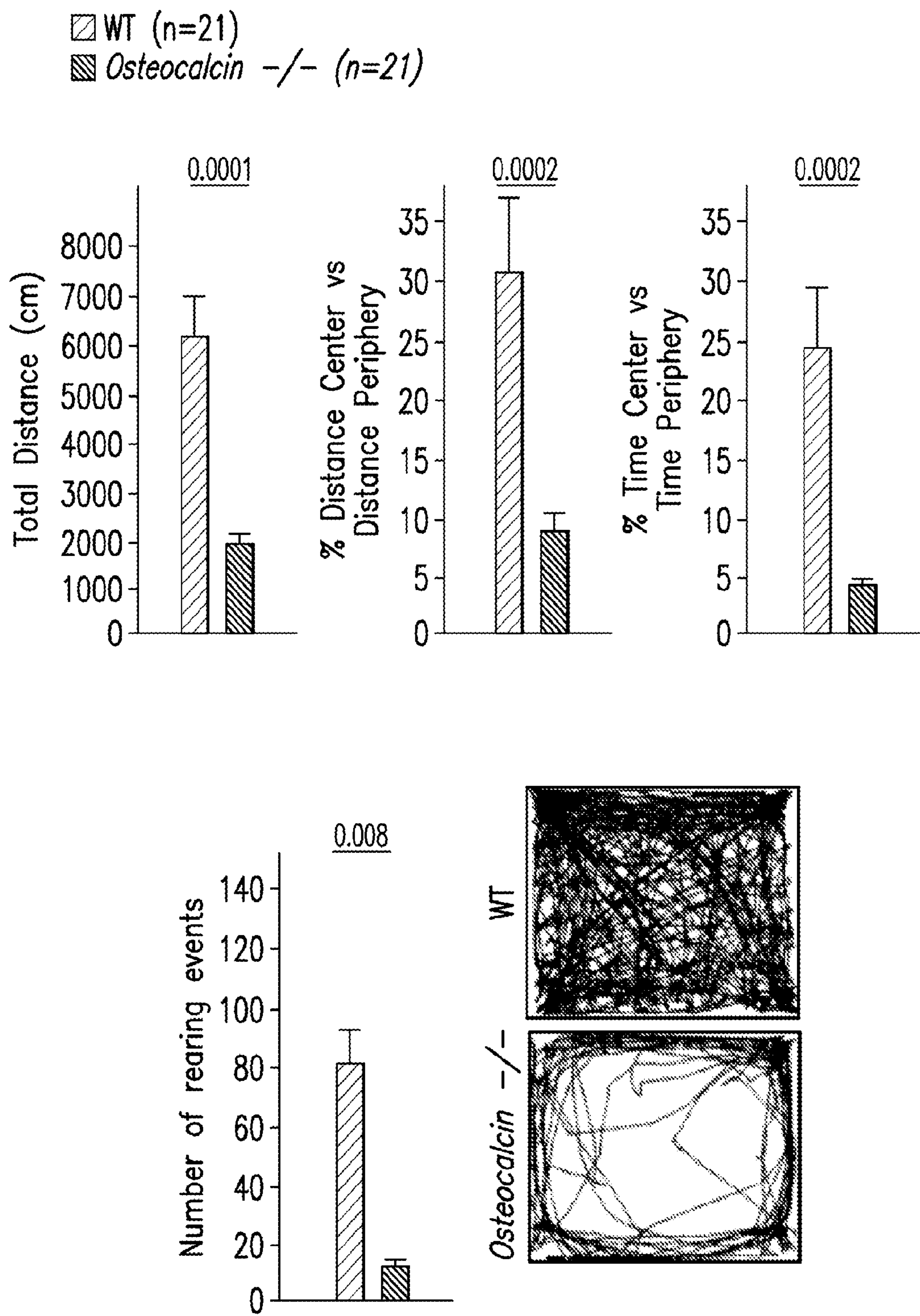
Figure 2F:
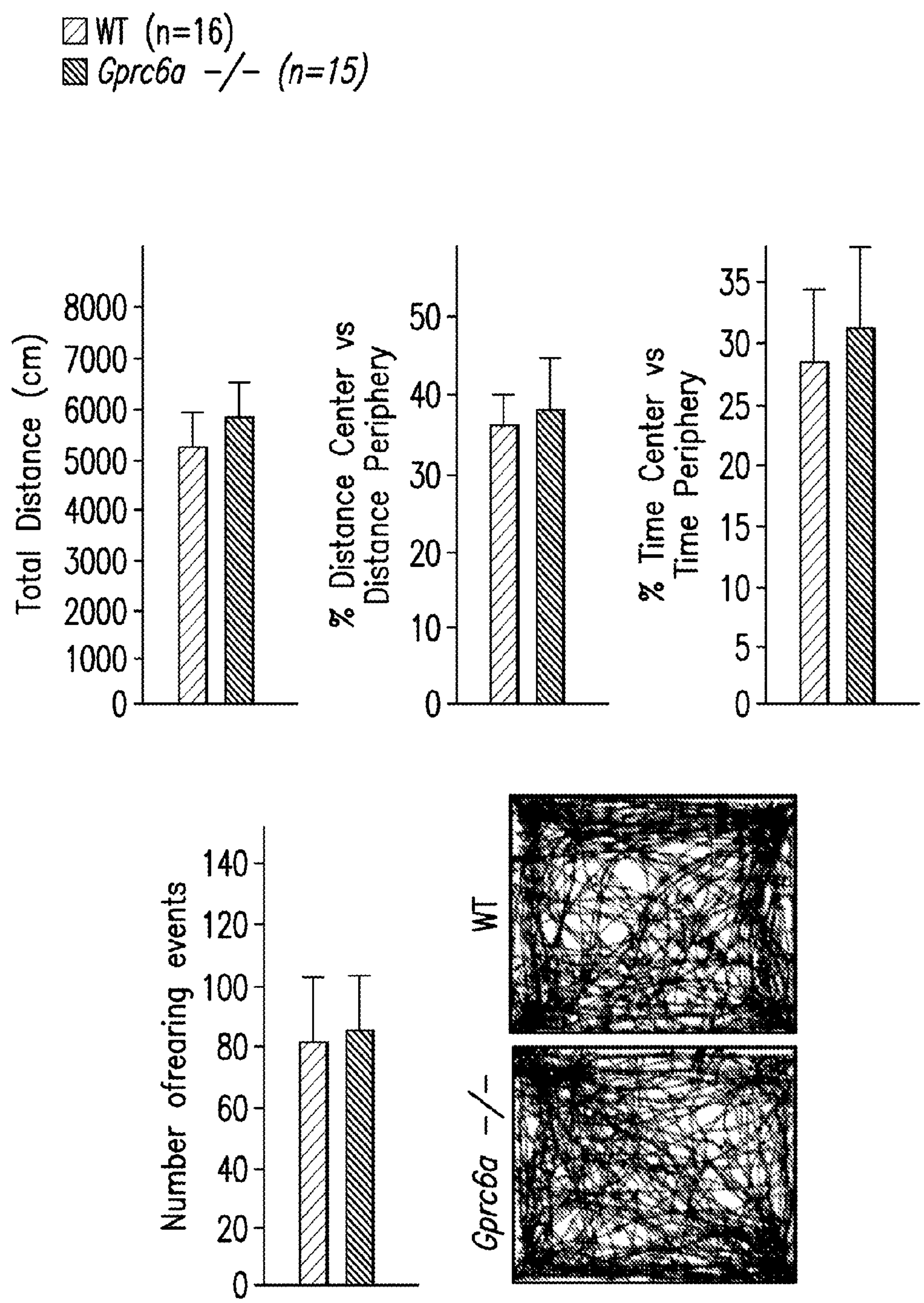

Anxiety-like behavior was analyzed through three conflict-based tests. The first, the dark/light transition test (DLT), is based on the innate aversion of rodents to brightly illuminated areas and on their spontaneous exploratory behavior to avoid the light (Crawley et al., 1985, Neuroscience and Biobehavorial Reviews 9:37-44; David et al., 2009, Neuron 62:479-493). The test apparatus consists of a dark, safe compartment and an illuminated, aversive one. Mice are tested for 6 min each and three parameters recorded: (i) latency to enter the lit compartment, (ii) time spent in the lit compartment, and (iii) number of transitions between compartments. In Osteocalcin$^{-/-}$ mice, there was an increase in the latency to enter in the lit compartment and a decrease of time spent in the lit compartment, two indications of anxiety-related behavior. There was also a decrease in the number of transitions between compartments, another indication of anxiety-related behavior and of motor-exploratory activity (FIG. 2A-B). Conversely, the opposite was true in Esp$^{-/-}$ mice. The elevated plus maze (EPM) test (Lira et al., 2003, Biological Psychiatry 54:960-971; Holmes et al., 2000, Physiology and Behavior 71:509-516) that exploits the aversion of rodents to open spaces was also used. The EPM is comprised of two open and two enclosed arms, each with an open roof elevated 60 cm from the floor. Testing takes place in bright ambient light conditions. Animals are placed onto the central area facing one closed arm and allowed to explore the EPM for 5 min. The total number of arm entries and time spent in open arms measure general activity. A decrease in the proportion of time spent and in the number of entries into the open arms indicates an increase in anxiety. This is exactly what was seen in Osteocalcin$^{-/-}$ mice, while Esp$^{-/-}$ mice demonstrated less anxiety-like behaviors and more exploratory drive than WT littermates (FIG. 2C-D). Lastly, we used the open field paradigm test (OFT) in which a novel environment evokes anxiety and exploration (David et al., 2009, Neuron 62:479-493; Sahay et al., 2011, Nature 472:466-470). Animals are placed in the center of an open field box and video-tracked under normal light conditions over 30 min. Osteocalcin$^{-/-}$ mice demonstrated a drastic decrease in the distance moved, in time spent in the center, and in vertical activity compared to WT littermates, all features indicative of increased anxiety (FIG. 2E-F).

Figure 2G:
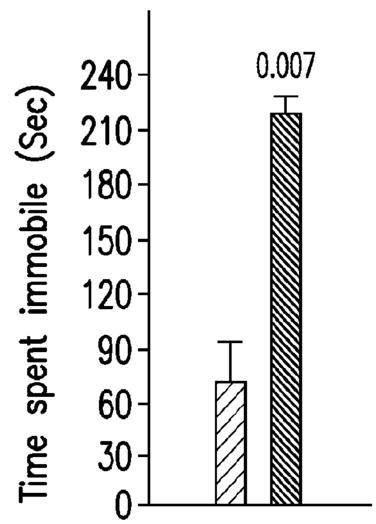
Figure 2H:
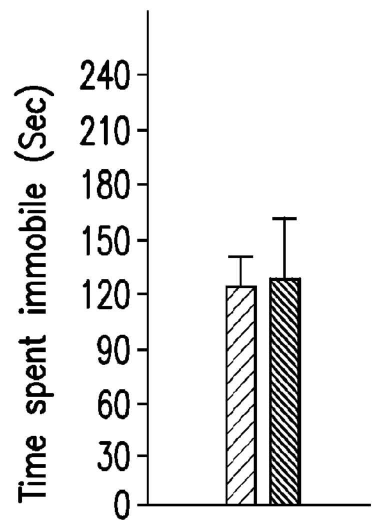
Figure 2I:
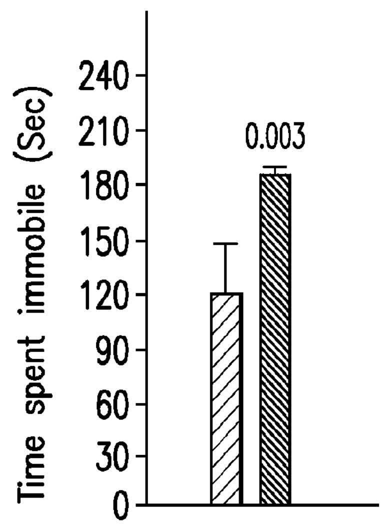
Figure 2J:
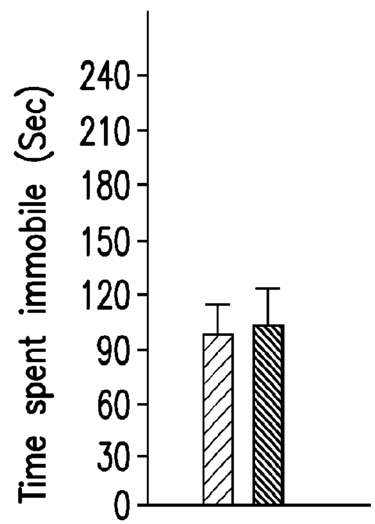

Anxiety is often accompanied by depression. This was assessed by the tail suspension test (TST), in which animals are subjected to the short-term, inescapable stress of being suspended by their tails, to which they respond by developing an immobile posture (Cryan et al., 2005, Neurosci. Behavorial Rev. 20:571-625; Crowley et al., 2006; Neuropsychopharmacology 29:571-576; David et al., 2009, Neuron 62:479-493). In this test, the more time mice remain immobile, the more depressed they are. This is what was observed in Osteocalcin$^{-/-}$ mice (FIG. 2G-H). In the forced swim test (FST), mice are subjected to two trials during which they are forced to swim in a glass cylinder filled with water from which they cannot escape. The first trial lasts 15 minutes. Twenty-four hours later, a second trial is performed that lasts 6 minutes. Over time, mice cease their attempts to escape and float passively, indicative of a depression-like state. Consistent with the other behavioral tests, Osteocalcin$^{-/-}$ mice spent 45% more time floating than WT mice (FIG. 2I-J).

Figure 2K:
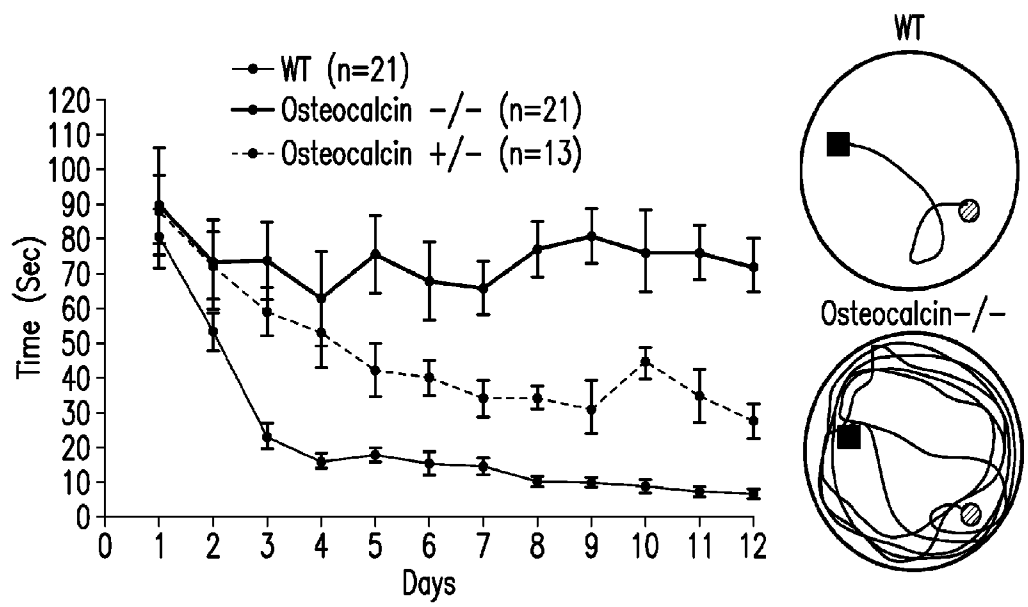
Figure 2L:
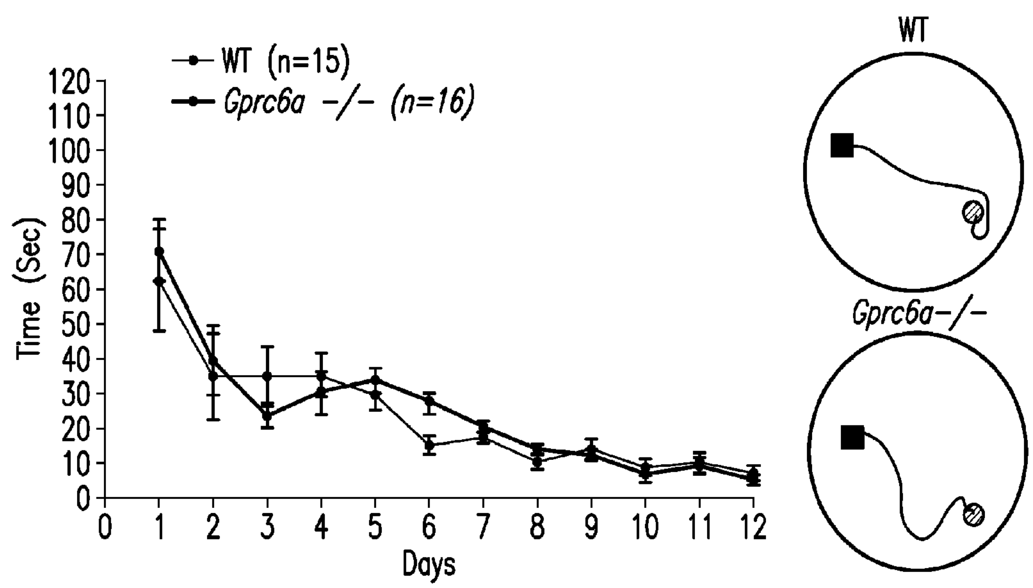

To assess memory and spatial learning behavior, Osteocalcin$^{-/-}$ and Osteocalcin$^{+/-}$ mice were subjected to the Morris water maze (MWMT) task. This test relies on the ability of mice to learn distance cues and to navigate around the perimeter of an open swimming arena to locate a submerged platform to escape the water. Spatial learning is assessed across repeated trials (4 trials/day for 12 days). Osteocalcin$^{+/-}$ and Osteocalcin$^{-/-}$ mice showed a delayed and a complete inability to learn, respectively (FIG. 2K-L).

As noted for neurotransmitter content and for gene expression in the brain, Gprc6a$^{-/-}$ mice were indistinguishable from WT littermates in all these tests. Collectively, these tests indicate that osteocalcin prevents anxiety and depression, and enhances exploratory behavior, memory, and learning.

Example 5—Administration of Osteocalcin Corrects Cognitive Defects

The pharmacological relevance of this ability of osteocalcin to signal in neurons was established by delivering uncarboxylated osteocalcin through intracerebro-ventricular (ICV) infusions (10 ng/hour) in WT and Osteocalcin$^{-/-}$ mice. The localization of the cannula was verified by administering methylene blue through these pumps. The dye labeled all ventricles, indicating that osteocalcin was probably diffusing throughout the brain. Moreover, measurements of osteocalcin in the blood of infused Osteocalcin$^{-/-}$ mice showed that there was no leakage of the centrally delivered hormone into the general circulation. This week-long treatment with uncarboxylated osteocalcin corrected the anxiety and depression features noted in Osteocalcin$^{-/-}$ mice (FIG. 4A-E). Collectively, the results described herein indicate that osteocalcin prevents anxiety and depression in the mouse by acting directly in the brain.

Example 6—Osteocalcin Regulates Cognitive Functions Post-Natally

The results presented above raised the following two questions: Is there a cryptic expression of osteocalcin in the brain that could explain these functions? And, if not, does the influence of osteocalcin on cognitive functions occur post-natally?

Figure 5A:
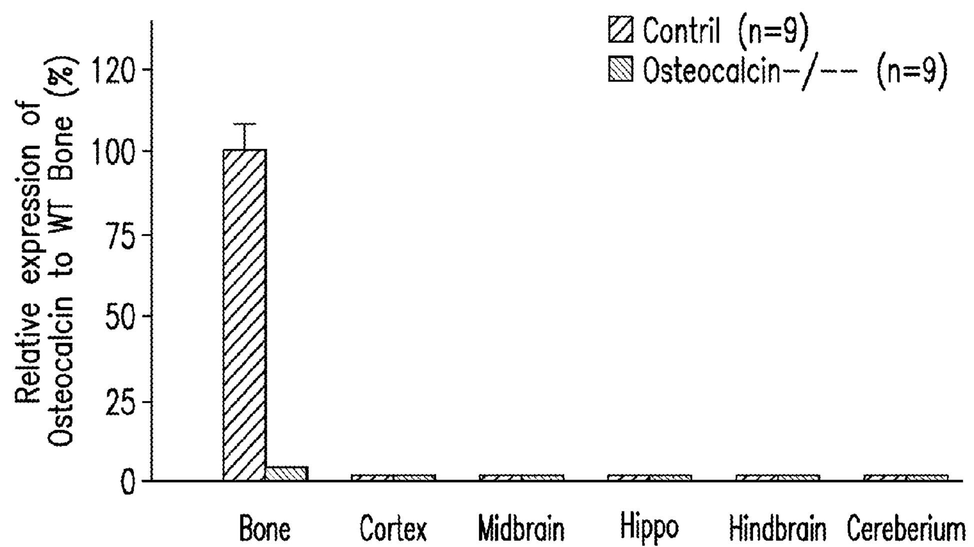
FIG. 5. (A) Expression of osteocalcin in the brains of WT mice is not detected above that in the brains of Osteocalcin$^{-/-}$ mice as judged by quantitative PCR. (B) Expression of osteocalcin in the brains of WT mice is not detected above that in the brains of Osteocalcin$^{-/-}$ mice as judged by in situ hybridization. (C) m-Cherry expression is seen in bone but not in the brain of a mouse model in which the m-Cherry gene was knocked into the Osteocalcin locus. (D) Tamoxifen-treated Osteocalcin$_{osb}^{ert2-/-}$ mice showed a significant increase in anxiety-like and depression-like behavior when compared to α1(I)Collagen-Cre$^{ert2}$ or Osteocalcin$^{flox/flox}$ mice as judged by the DLT test. (E) Tamoxifen-treated Osteocalcin$_{osb}^{ert2-/-}$ mice showed a significant increase in anxiety-like and depression-like behavior when compared to α1(I)Collagen-Cre$^{ert2}$ or Osteocalcin$^{flox/flox}$ mice as judged by the EPM test. (F) Tamoxifen-treated Osteocalcin$_{osb}^{ert2-/-}$ mice showed a significant increase in anxiety-like and depression-like behavior when compared to α1(I)Collagen-Cre$^{ert2}$ or Osteocalcin$^{flox/flox}$ mice as judged by the tail suspension test. (G) Tamoxifen-treated Osteocalcin$_{osb}^{ert2-/-}$ mice showed a significant increase in anxiety-like and depression-like behavior when compared to α1(I)Collagen-Cre$^{ert2}$ or Osteocalcin$^{flox/flox}$ mice as judged by the tail suspension test. (H) Tamoxifen-treated Osteocalcin$_{osb}^{ert2-/-}$ mice showed a significant increase in anxiety-like and depression-like behaviors when compared to α1(I)Collagen-Cre$^{ert2}$ or Osteocalcin$^{flox/flox}$ mice as judged by the EPM test. (I) Spatial learning and memory are affected in tamoxifen-treated Osteocalcin$_{osb}^{ert2-/-}$ mice.
Figure 5B:
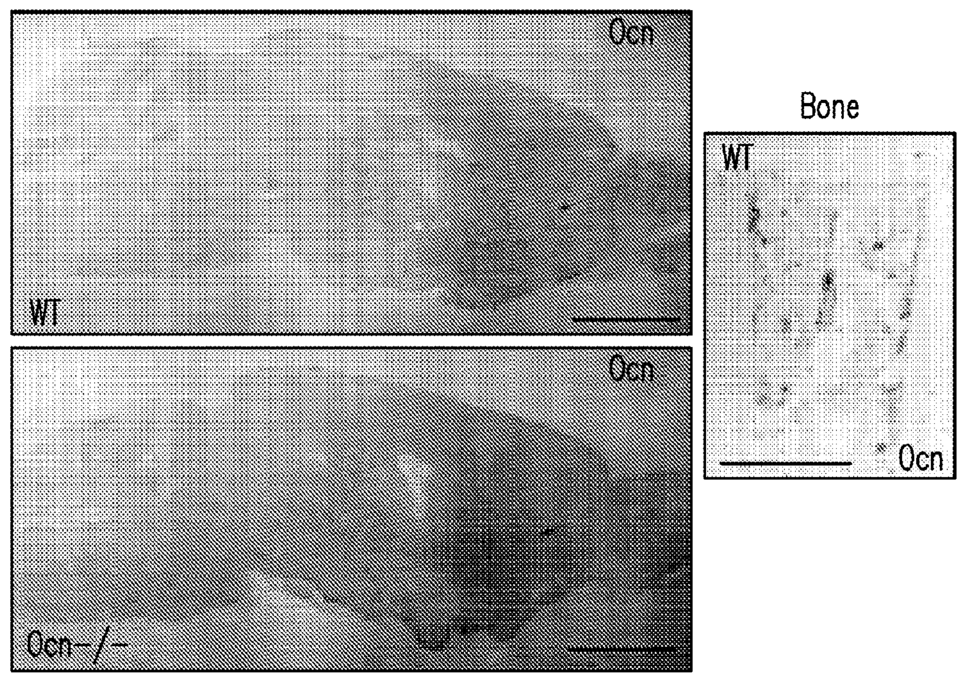
Figure 5C:
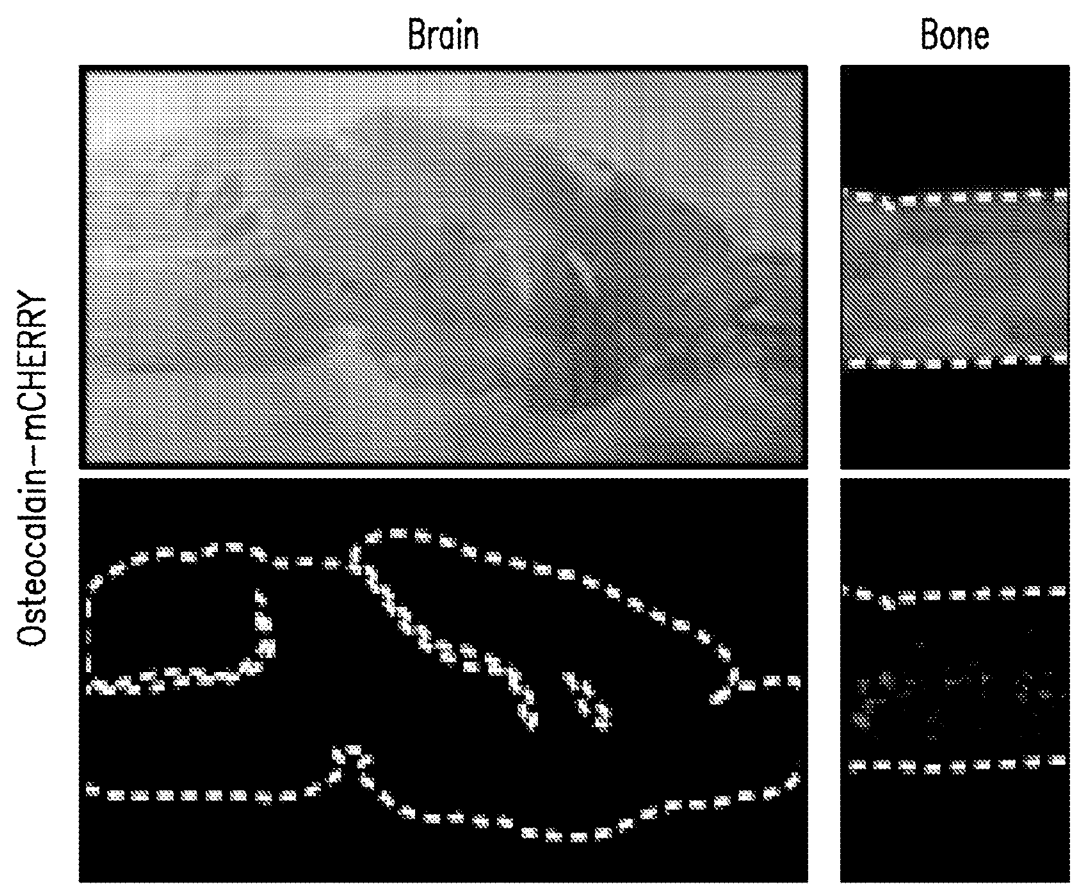
Figure 5D:
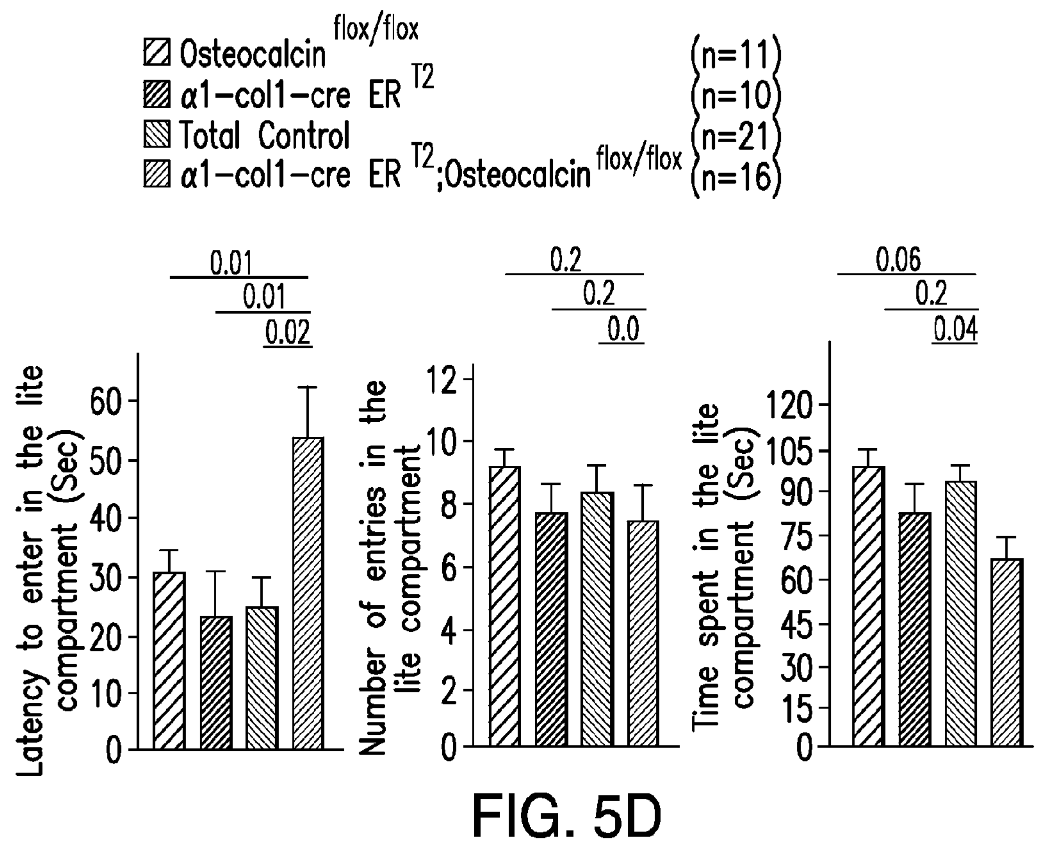
Figure 5E:
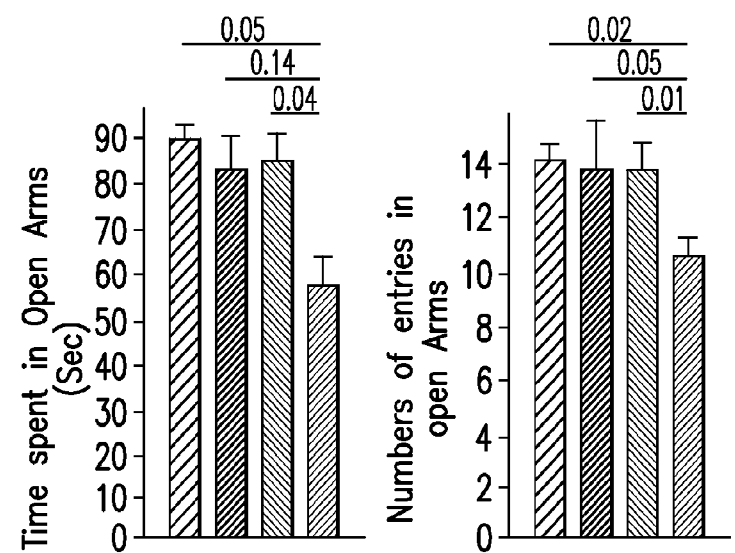
Figures 5F, 5G:
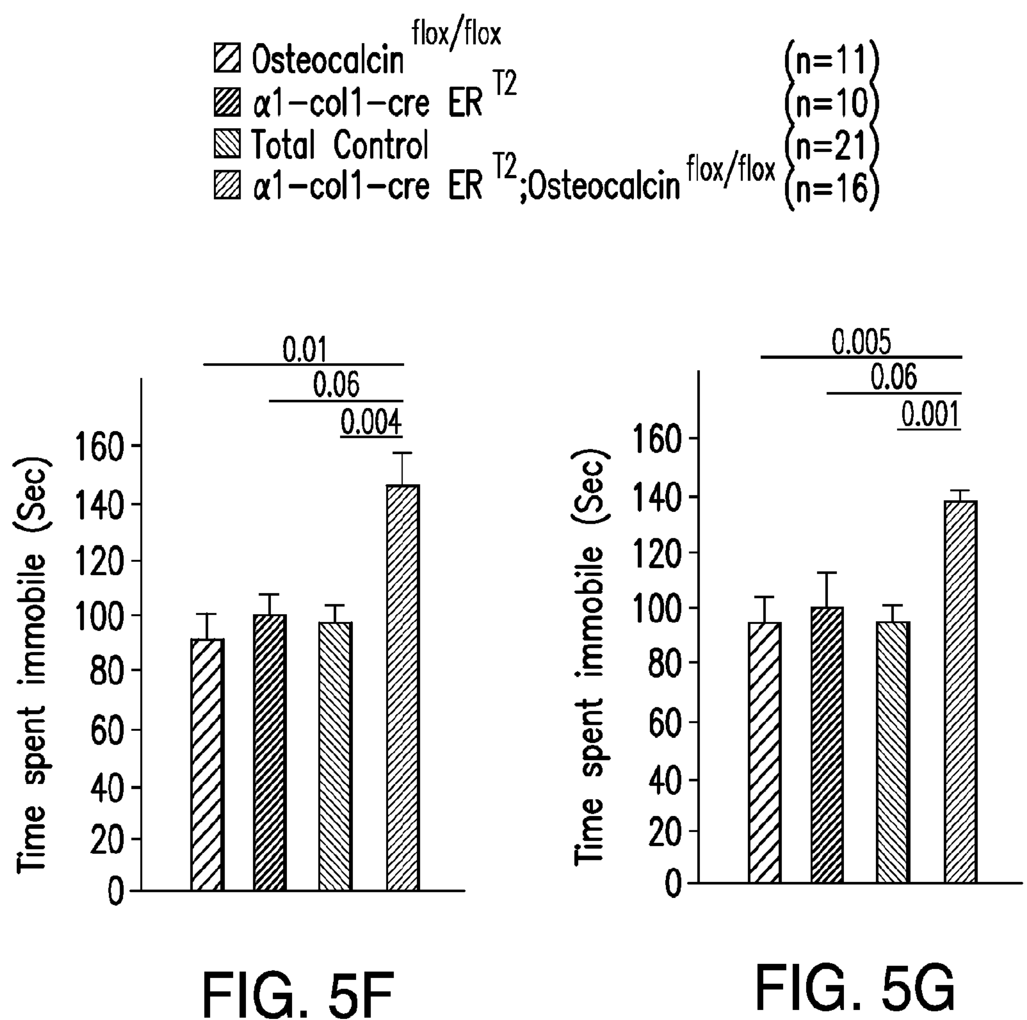
Figure 5H:
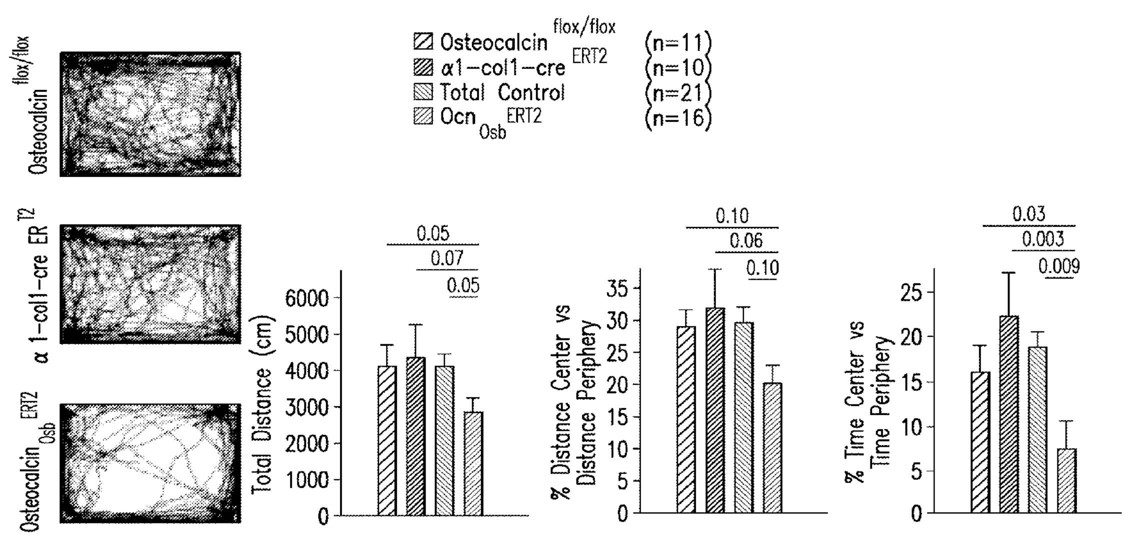
Figure 5I:
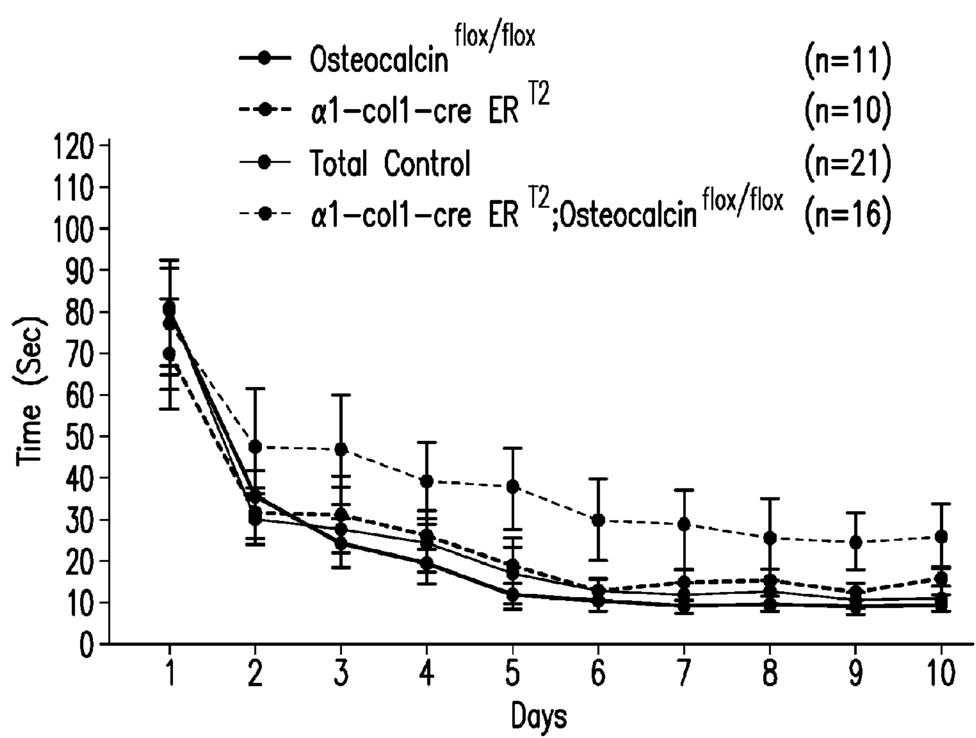

Whether tested by quantitative PCR or in situ hybridization, expression of osteocalcin in the brain of WT adult mice above what was seen in Osteocalcin$^{-/-}$ brain (FIG. 5A-B) was not detected. Moreover, when using a mouse model in which the m-Cherry gene was knocked into the Osteocalcin locus, m-Cherry expression was seen in bone but not in the brain (FIG. 5C). In view of these results, an osteoblast-specific and inducible deletion of osteocalcin was performed by crossing mice harboring a floxed allele of osteocalcin with mice expressing Cre$^{ert2}$ under the control of osteoblast-specific regulatory elements of the mouse Colla1 gene to delete osteocalcin only in osteoblasts (Osteocalcin$_{osb}^{ert2-/-}$ mice).) That Osteocalcin$_{osb}^{ert2-/-}$ mice showed a marked reduction in osteocalcin circulating levels following treatment with tamoxifen (1 mg/g BW daily for 5 days) verified that the osteocalcin gene had been efficiently inactivated.

Osteocalcin$_{osb}^{ert2-/-}$ mice were treated at 6 weeks with daily injections of tamoxifen (1 mg/20 g of body weight) for 1 week. To ensure that a stable deletion of osteocalcin was achieved, mice were re-injected with another round of tamoxifen every 3 weeks. Six weeks later, α1(I)Collagen-Cre$^{ert2}$, Osteocalcin$^{flox/flox}$, and Osteocalcin$_{osb}^{ert2-/-}$ mice were then subjected to behavioral analysis. Tamoxifen-treated Osteocalcin$_{osb}^{ert2-/-}$ mice showed a significant increase in anxiety-like and depression-like behaviors when compared to α1(I)Collagen-Cre$^{ert2}$ or Osteocalcin$^{flox/flox}$ mice (FIG. 5D-I). Spatial learning and memory were also affected in tamoxifen-treated Osteocalcin$_{osb}^{ert2-/-}$ mice but more mildly than in mice harboring a constitutive deletion of Osteocalcin (FIG. 5J). At the molecular level, there was a decrease in Tph2 and Th expression in the brainstem and midbrain respectively of Osteocalcin$_{osb}^{ert2-/-}$ mice treated with tamoxifen and an increase in Gad1 and Gad2 expression in their brainstem (FIG. 5K). These experiments indicate that osteocalcin regulation of anxiety and depression-like behaviors occurs post-natally, while spatial learning and memory seemed to be only partially affected by osteocalcin post-natally.

Example 7—Maternal Osteocalcin Crosses the Placenta

Figure 6A:
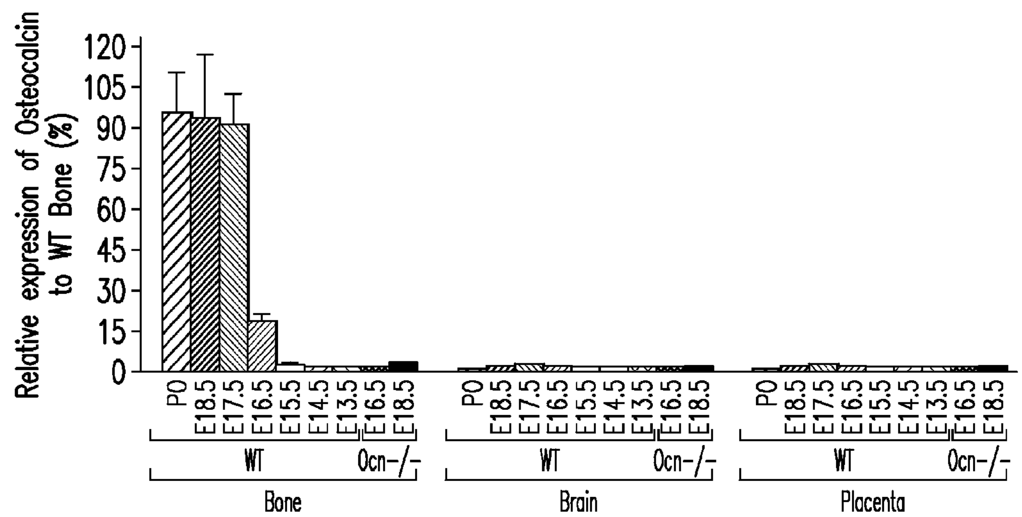
FIG. 6. Maternal osteocalcin favors fetal neurogenesis. (A) Expression of osteocalcin (qPCR) in bone, brain, and placenta of WT and Ocn$^{-/-}$ newborns (postnatal day [P] 0) and embryos (E13.5-E18.5). (B) Osteocalcin circulating levels in WT or Ocn$^{-/-}$ newborns (P0) and embryos (E13.5-E18.5). (C) Ex vivo dual-perfusion system that monitors the transport of osteocalcin across the placenta. Uncarboxylated mouse osteocalcin (300 ng/ml) was injected through the uterine artery in placentas obtained from WT mice at E14.5, E15.5, and E18.5 of pregnancy. Osteocalcin in fetal eluates is represented as % of maternal input. (D) Circulating levels of osteocalcin in WT embryos originating from WT or Ocn$^{+/-}$ mothers, of Ocn$^{+/-}$ embryos originating from Ocn$^{+/-}$ Ocn$^{-/-}$ mothers, and of Ocn$^{-/-}$ embryos originating from Ocn$^{+/-}$ or Ocn$^{-/-}$ mothers. Measurements were performed at E16.5 and E18.5. (E) Cresyl violet stain of lateral ventricles of hippocampi of E18.5 WT embryos originating from WT mothers and Ocn$^{-/-}$ embryos originating from Ocn$^{+/-}$ or Ocn$^{-/-}$ mothers. The measurements of the lateral ventricle area over brain area are represented below the images (in %) (scale bars=0.5 mm). (F) Number of apoptotic cells (stained by TUNEL assay) in hippocampi of E18.5 WT embryos carried by WT mothers and Ocn$^{-/-}$ embryos carried by Ocn$^{+/-}$ or Ocn$^{-/-}$ mothers. (G and H) CFC (G) and NOR (H) performed in WT and Ocn$^{-/-}$ mice born from Ocn$^{-/-}$ or Ocn$^{+/-}$ mothers (n=7-18 per group). In the CFC, Ocn$^{-/-}$ mice born from Ocn$^{-/-}$ mother mice exhibited significantly less context-elicited freezing than WT mice in context A and A'. In the NOR, there was a significant increase in the exploratory period in Ocn$^{-/-}$ mice born from Ocn$^{-/-}$ mothers compared to Ocn$^{-/-}$ mice born from Ocn$^{+/-}$ mothers or WT mice when a novel object was introduced. (I and J) BrdU and DCX Immunohistochemistry showing a significantly lower number of BrdU$^{+}$ (I) and DCX$^{+}$ (J) cells in the dentate gyms (DG) of WT and Ocn$^{-/-}$ mice born from Ocn$^{-/-}$ or Ocn$^{+/-}$ mothers. This decrease was even more pronounced in the ventral region of the DG. (Scale bars=0.2 mm.) For (A)-(F), (I), and (J), the statistical test on the top of each graph represents the Student's t test; p<0.05 is significant. For (G) and (H), the statistical test on the top of each graph represents an ANOVA. Significant ANOVAs were followed up with Fisher's PLSD tests where appropriate. *p value<0.05, p value<0.01, *p value<0.001.
Figure 6B:
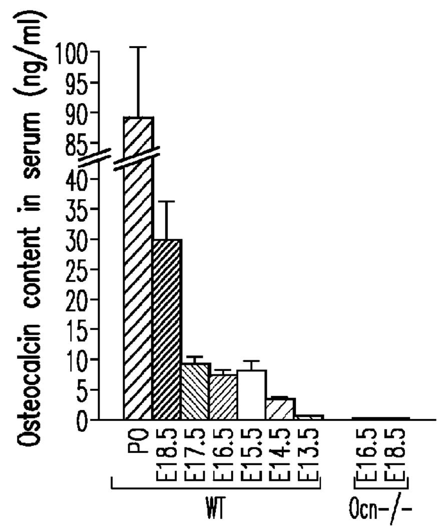

Osteocalcin can be measured in the serum of WT embryos as early as E14.5 (FIG. 6A). Studying Osteocalcin expression during development between E13.5 and E18.5 by qPCR or through in situ hybridization failed to detect expression of Osteocalcin anywhere in the embryo except in the developing skeleton (FIG. 6B). Likewise, in the mouse model in which the m-Cherry reporter gene had been knocked into the Osteocalcin locus m-Cherry was expressed in the developing skeleton but not in the developing brain between E13.5 and E18.5. Osteocalcin expression was not detected in the placenta at any of these developmental stages. Hence, during development as is the case after birth, Osteocalcin is a bone-specific gene. The most important result of this survey though was that Osteocalcin expression could not be detected in the developing skeleton until E16.5, two days after the protein is detectable in the blood of the embryos (FIG. 6A-B). This observation suggested that maternal-derived osteocalcin might reach the fetal blood stream.

Figure 6C:
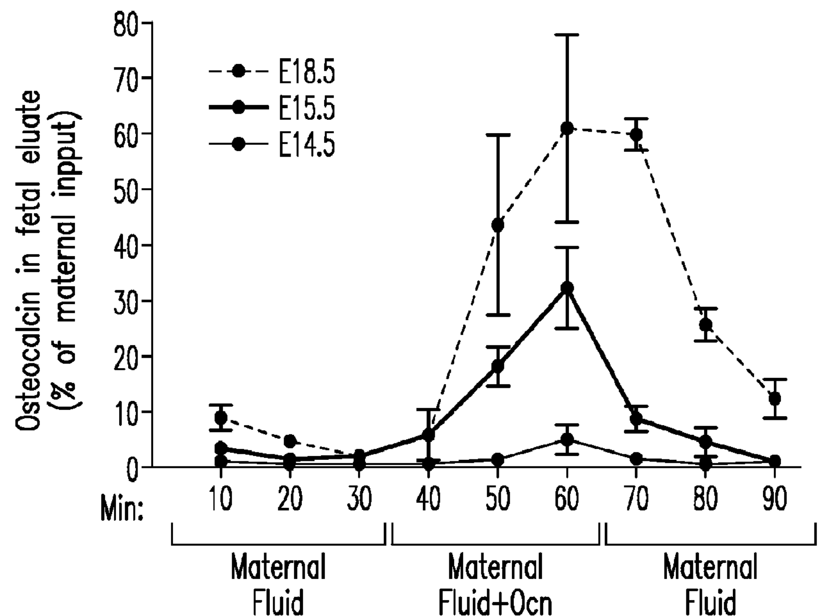

Any influence of maternal osteocalcin on fetal brain development requires that this hormone cross the placenta. This was investigated through an ex vivo dual perfusion system that monitors the transport of substances across the mouse placenta (Bonnin et al., 2011, Nature 472:347-350; Goeden and Bonnin, 2012, Nature Protocols 8:66-74). This analysis revealed that osteocalcin begins to cross the placenta at day 14.5 of gestation, a developmental stage when Osteocalcin expression cannot be detected in the embryos. A larger transplacental transfer of maternal osteocalcin to the fetal circulation was observed at day 15.5 or 18.5 of gestation (FIG. 6C).

Figure 6D:
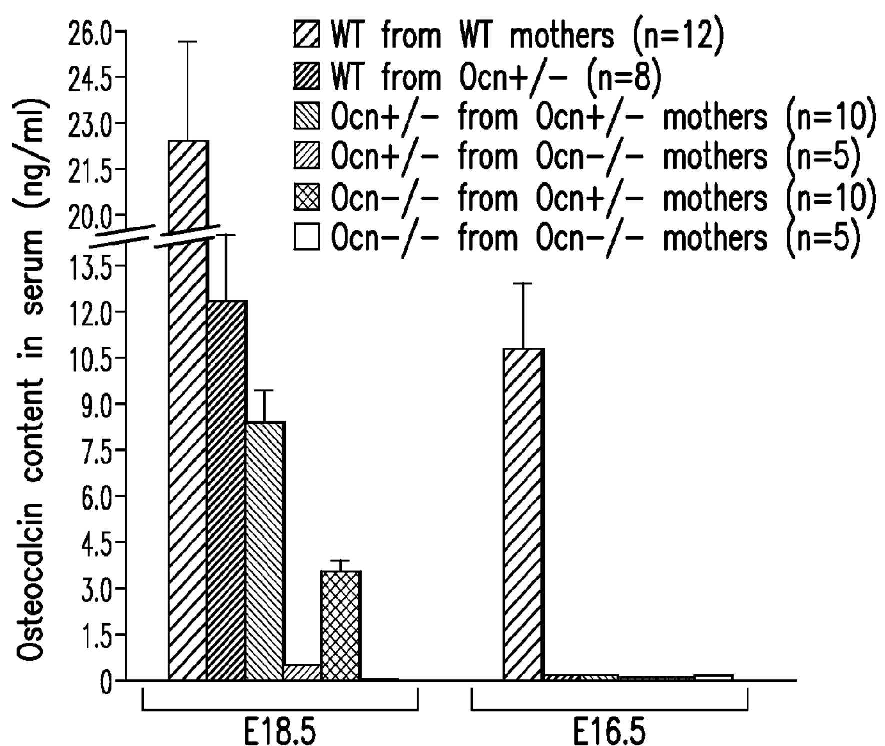

Given the ability of osteocalcin to cross the placenta its circulating levels in embryos of various genotypes and origins were measured. That osteocalcin was detectable (3.6 ng/ml) in the serum of E18.5 Osteocalcin$^{-/-}$ embryos carried by Osteocalcin$^{+/-}$ mothers (FIG. 6D) verified that in vivo maternal osteocalcin crosses the placenta. Still at E18.5, osteocalcin circulating levels in WT embryos were 27.9 ng/ml when carried by WT mothers but only 7.4 ng/ml when their mothers were Osteocalcin$^{+/-}$. In E16.5 embryos, there were 6.9 ng/ml of osteocalcin in the serum of WT embryos carried by WT mothers while the hormone could not be detected in the serum of WT or Osteocalcin embryos carried by Osteocalcin mothers (FIG. 6D). Osteocalcin also could not be detected at that embryonic stage in Osteocalcin$^{-/-}$ embryos carried by Osteocalcin$^{+/-}$ mothers (FIG. 6D). These results indicate that maternally-derived osteocalcin contributes significantly to the pool of this hormone found in the serum of E16.5 and E18.5 embryos.

Example 8—Maternal Osteocalcin Affects Brain Development

To assess the influence of maternal osteocalcin on fetal brain development, an histological analysis of WT, Osteocalcin$^{+/-}$ and Osteocalcin$^{-/-}$ embryos originating from either WT, Osteocalcin$^{+/-}$ or Osteocalcin$^{-/-}$ mothers was performed.

Figure 6E:
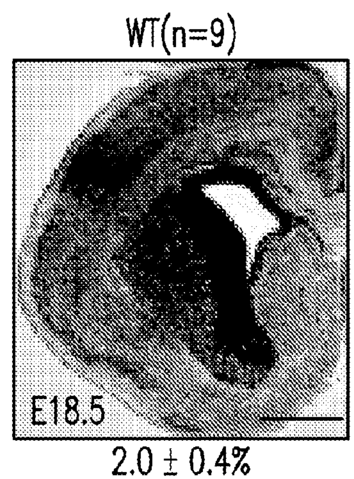
Figure 6E:
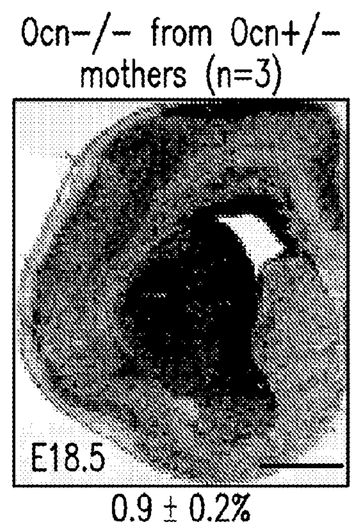
Figure 6E:
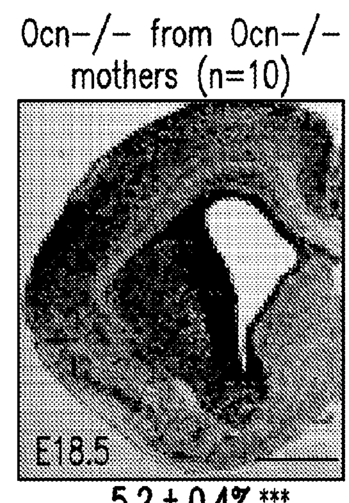
Figure 6F:
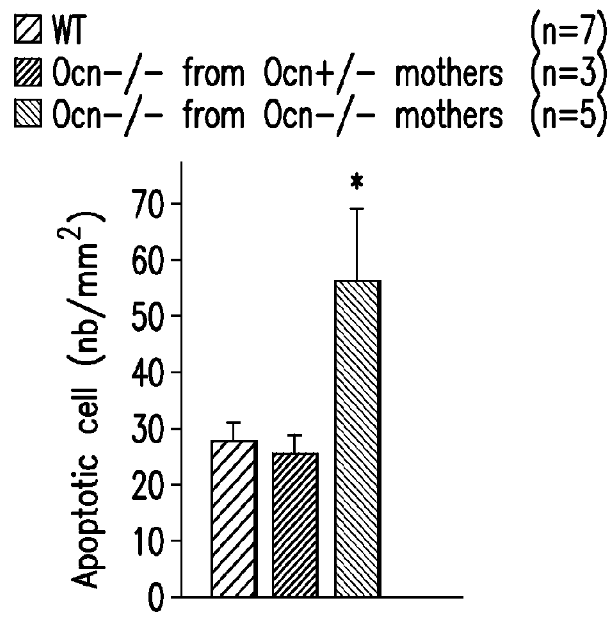
Figure 6G:
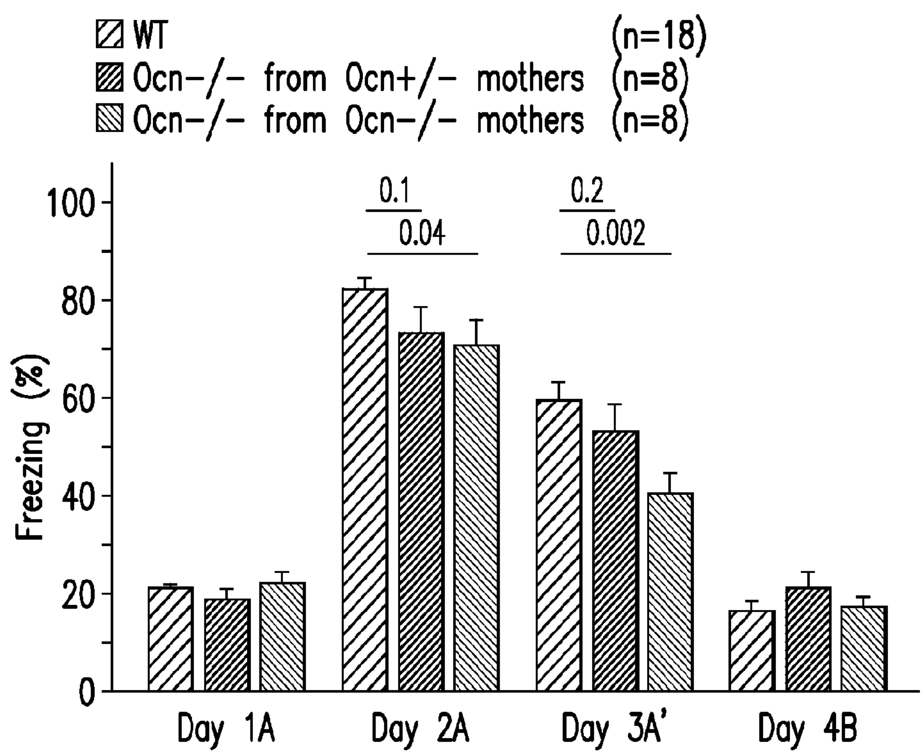
Figure 6H:
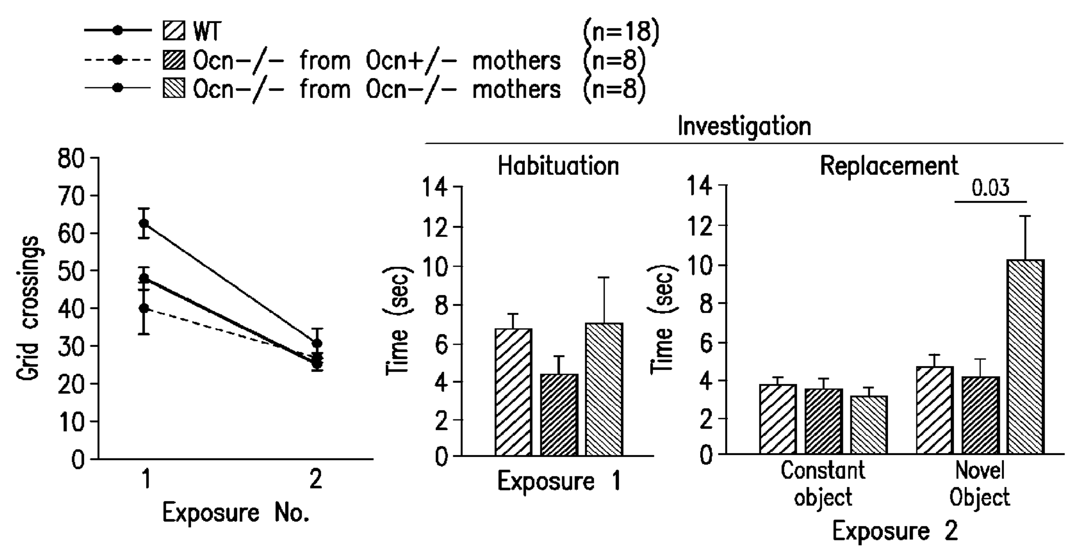
Figure 6I:
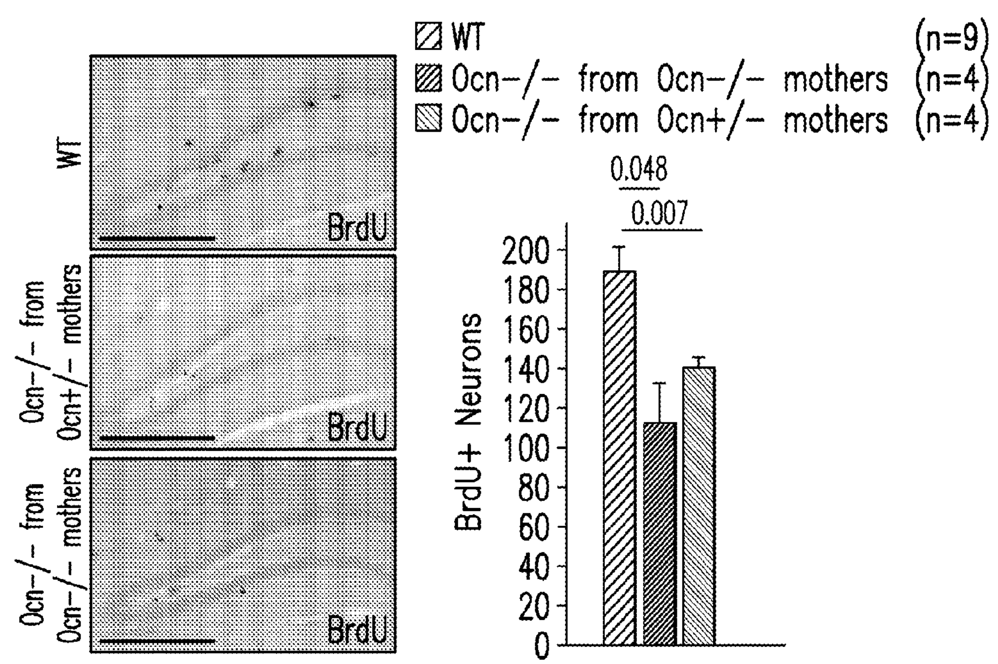
Figure 6J:
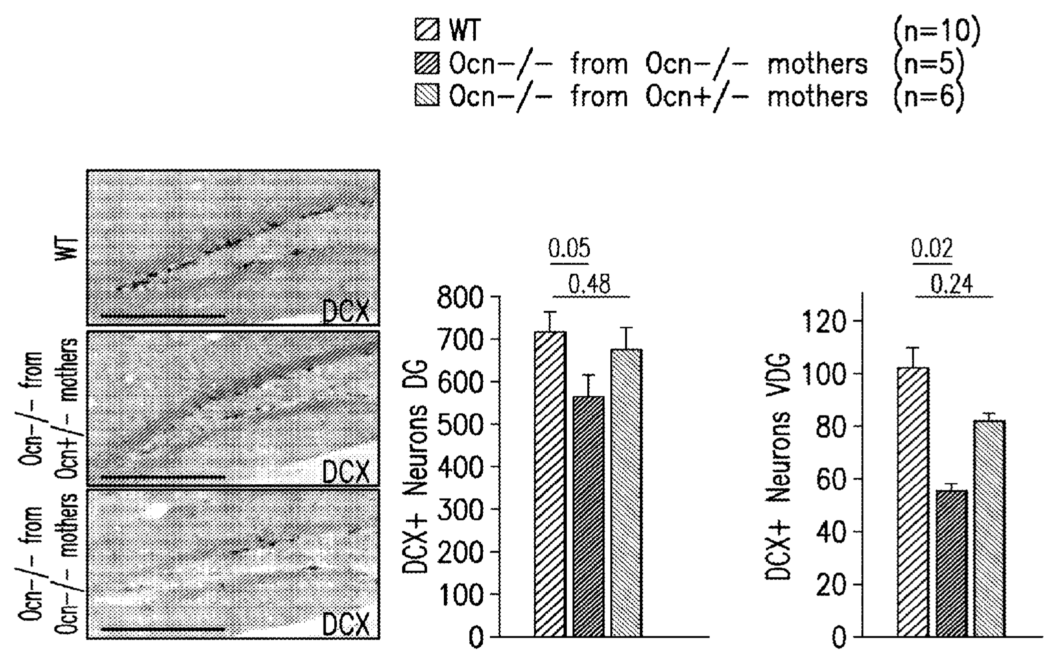

Regardless of the genotype of the mothers, there was no difference in the ratio of brain weight over body weight between WT and Osteocalcin$^{-/-}$ embryos at E16.5 (FIG. 6E). In contrast, this ratio was significantly decreased in E18.5 Osteocalcin$^{-/-}$ embryos originating from Osteocalcin$^{-/-}$ mothers compared to Osteocalcin$^{-/-}$ embryos carried by Osteocalcin$^{+/-}$ mothers or WT embryos carried by WT mothers (FIG. 6E). Consistent with these observations, cresyl violet staining of histological sections showed an enlargement of the cerebral ventricles in the brains of E18.5 Osteocalcin$^{-/-}$ embryos originating from Osteocalcin$^{-/-}$ mothers compared to the ones originating from Osteocalcin$^{+/-}$ mothers (FIG. 6F). When measured by a Tunnel assay, there were significantly more apoptotic cells in the hippocampus of E18.5 Osteocalcin$^{-/-}$ embryos originating from Osteocalcin$^{-/-}$ mothers than in Osteocalcin$^{+/-}$ embryos originating from Osteocalcin$^{+/-}$ mothers or in WT embryos originating from WT mothers (FIG. 6G). A NeuN immunofluorescence study verified that there were fewer neurons in the hippocampus of E18.5 embryos, regardless of their genotype, if they were carried by Osteocalcin$^{-/-}$ mothers than in embryos carried by Osteocalcin$^{+/-}$ mothers (FIG. 6H). There was also a thinning of the molecular layer of the gyrus dentate in the hippocampus of adult Osteocalcin$^{-/-}$ mice born from Osteocalcin$^{-/-}$ mothers compared to those born from Osteocalcin$^{+/-}$ mothers. Taken together, these observations indicate that maternal osteocalcin is necessary for proper development of the embryonic mouse brain.

Example 9—Maternal Osteocalcin Favors Spatial Memory and Learning in Adult Offspring The influence of maternally-derived osteocalcin on fetal brain development raised the question of whether osteocalcin has any influence on cognitive functions in the offspring later in life. To address this question, three month-old Osteocalcin$^{-/-}$ mice born from either Osteocalcin$^{-/-}$ or Osteocalcin$^{+/-}$ mothers were subjected to behavioral tests. While the anxiety and depression-like phenotypes were equally severe in Osteocalcin$^{-/-}$ mice regardless of the genotype of their mothers, the deficit in learning and memory was significantly more severe in Osteocalcin$^{-/-}$ mice born from Osteocalcin$^{-/-}$ mothers than in those born from Osteocalcin$^{+/-}$ mothers (FIG. 7A-F). This result indicated that maternal osteocalcin is needed for the acquisition of spatial learning and memory in adult offspring.

Figure 7A:
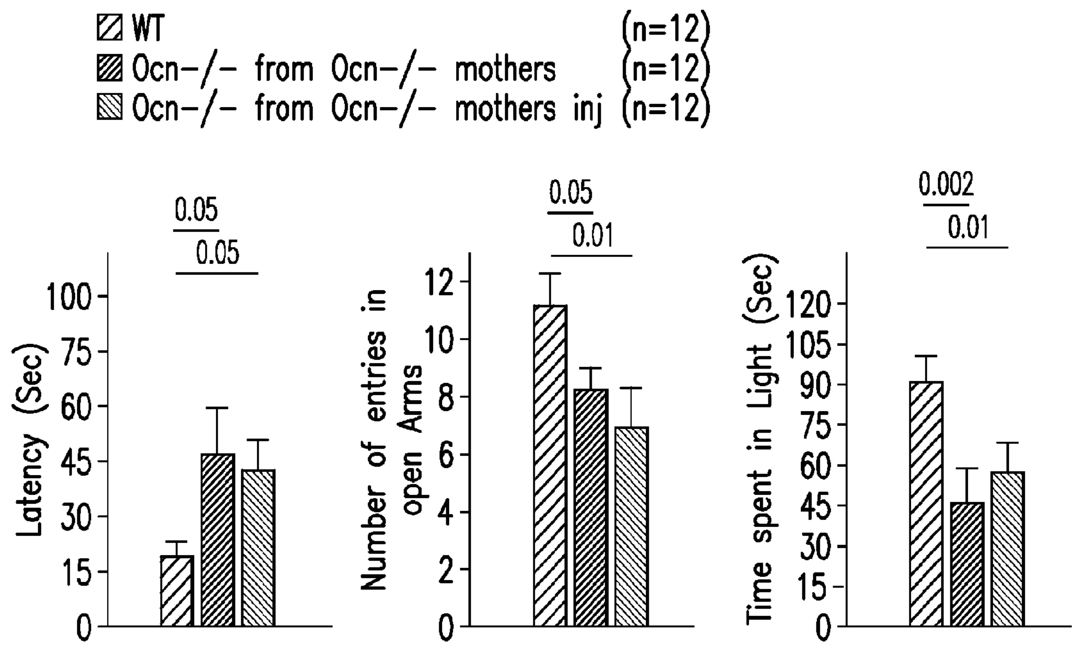
FIG. 7. Maternal osteocalcin determines spatial learning and memory in adult offspring. (A-F) DLT (A), EPMT (B), OFT (C), FST (D), TST (E), and MWMT (F) performed in 3-month-old Ocn$^{-/-}$ mice born from Ocn$^{-/-}$ mothers injected once a day with vehicle or osteocalcin (240 ng/day) during pregnancy compared to WT mice. (G) Surface of the lateral ventricle over brain area (%) of E18.5 hippocampi coronal sections of WT embryos originating from WT mothers and Ocn$^{-/-}$ embryos originating from osteocalcin-injected Ocn$^{-/-}$ mothers. (H) Number of apoptotic cells (stained by TUNEL assay) of E18.5 hippocampi coronal sections of WT embryos originating from WT mothers and Ocn$^{-/-}$ embryos originating from Ocn$^{-/-}$ mothers injected with osteocalcin (240 ng/day). (I) Cresyl violet, NeuN immunofluorescence, and dentate gyms area (% versus WT) of WT and Ocn$^{-/-}$ embryos originating from osteocalcin-injected Ocn$^{-/-}$ mothers. Scale bars=0.5 mm.
Figure 7B:
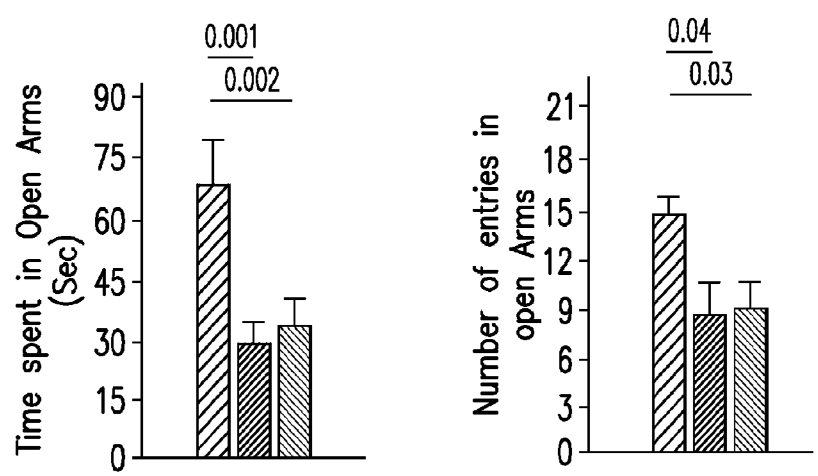
Figure 7C:
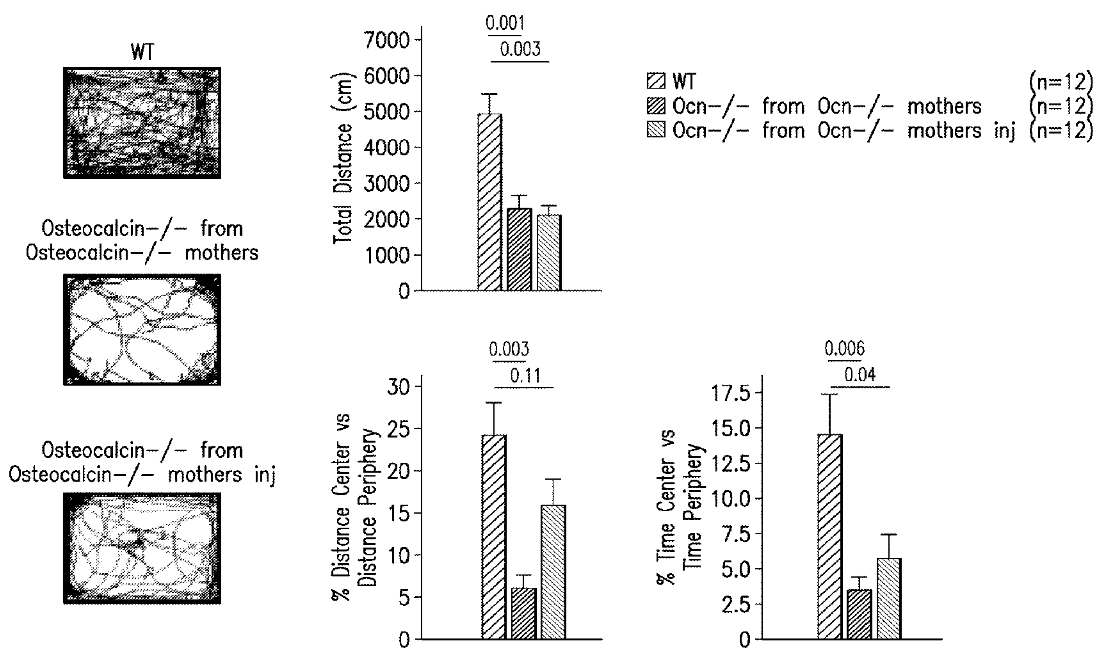
Figure 7D:
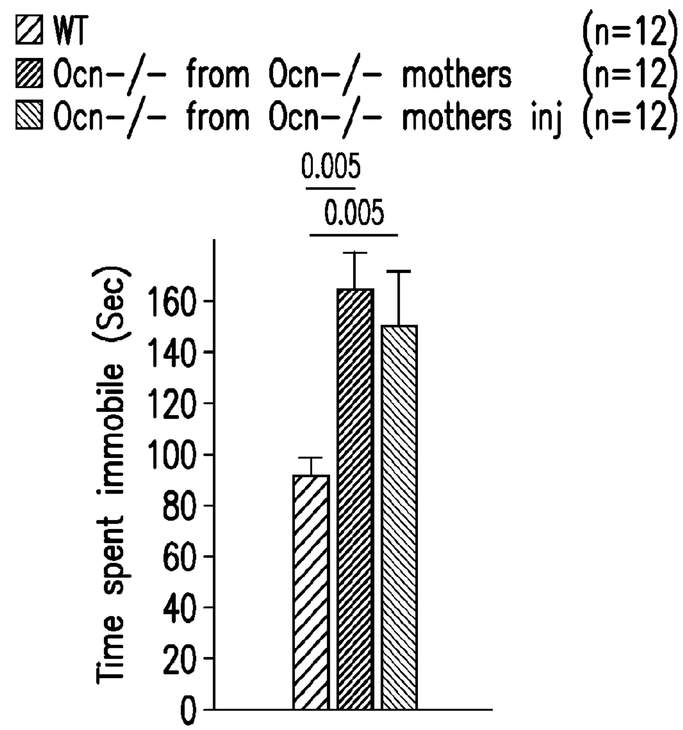
Figure 7E:
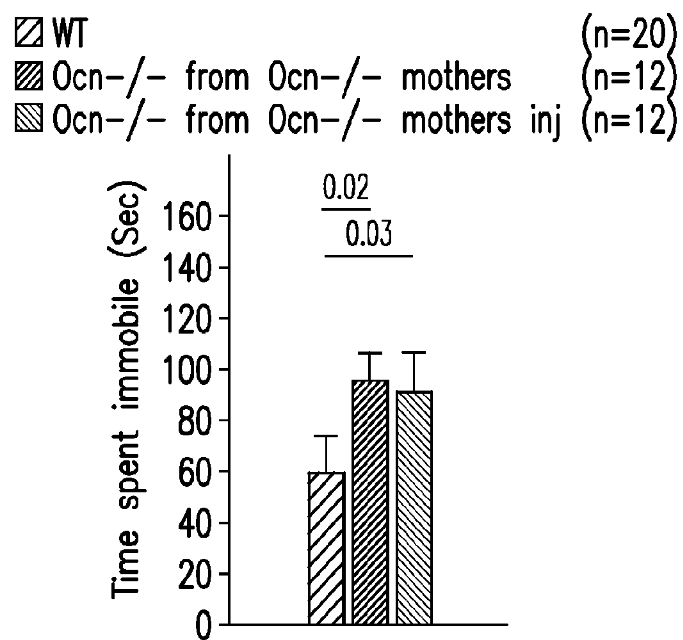
Figure 7F:
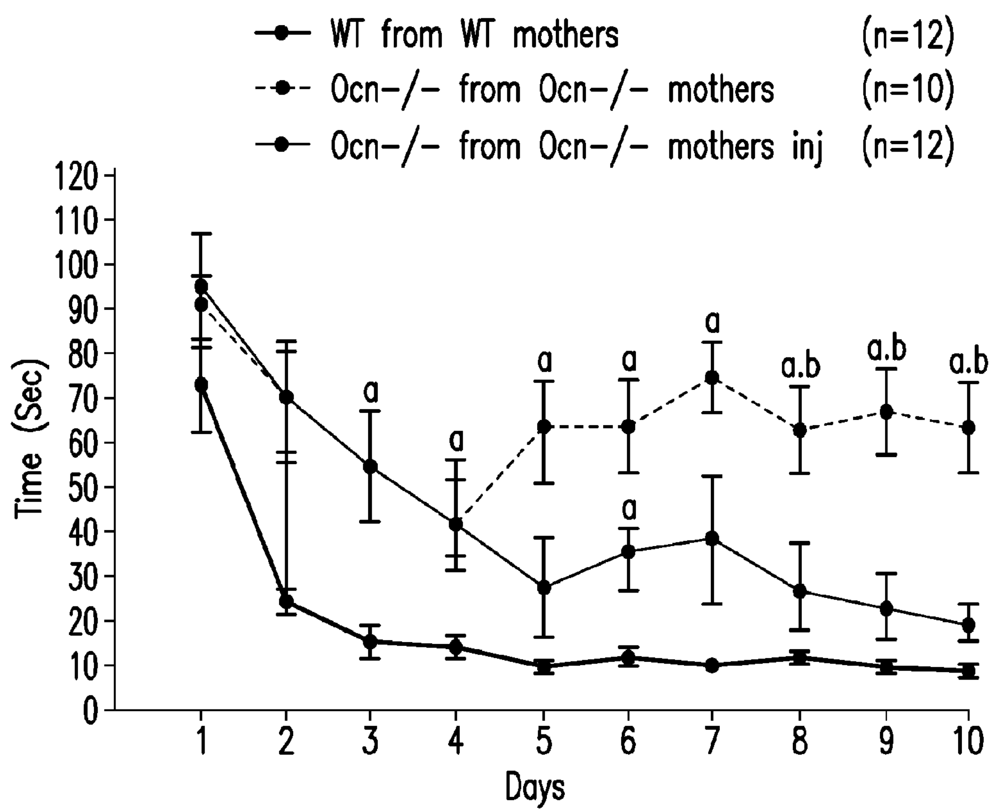
Figure 7G:
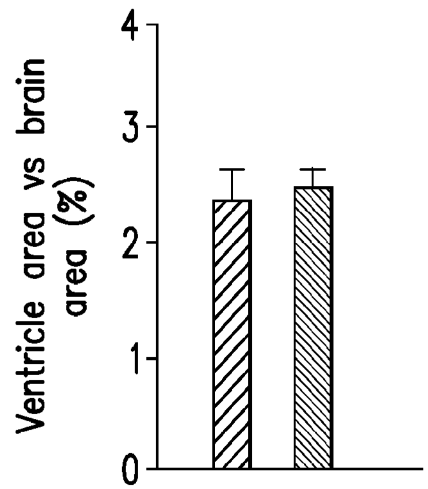
Figure 7H:
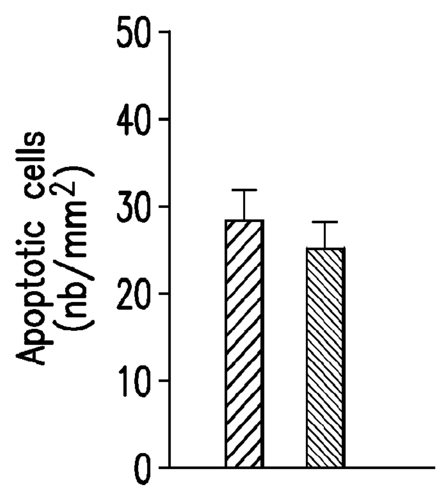
Figure 7I:
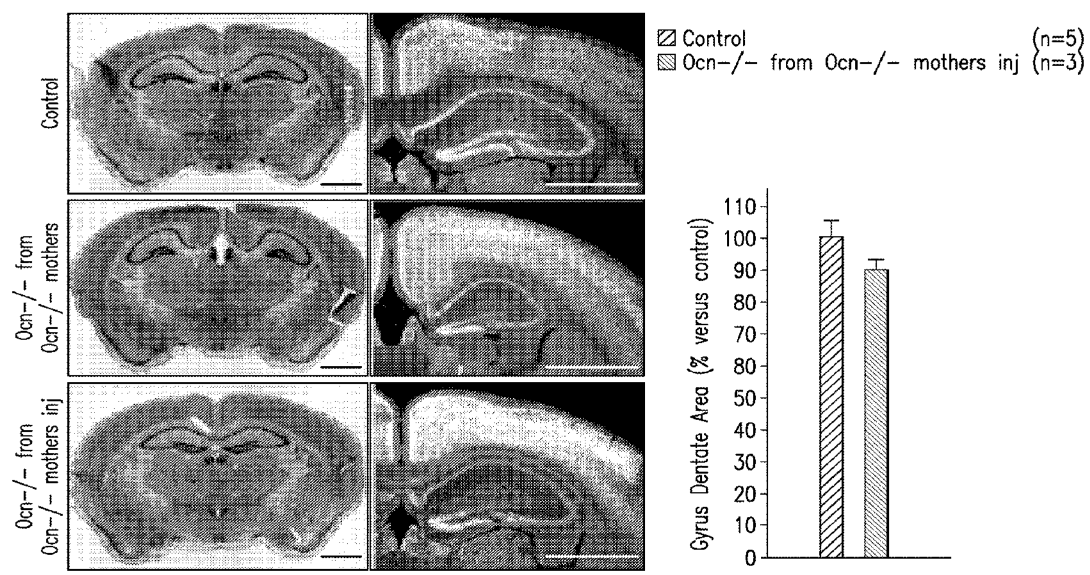
Figure 7J:
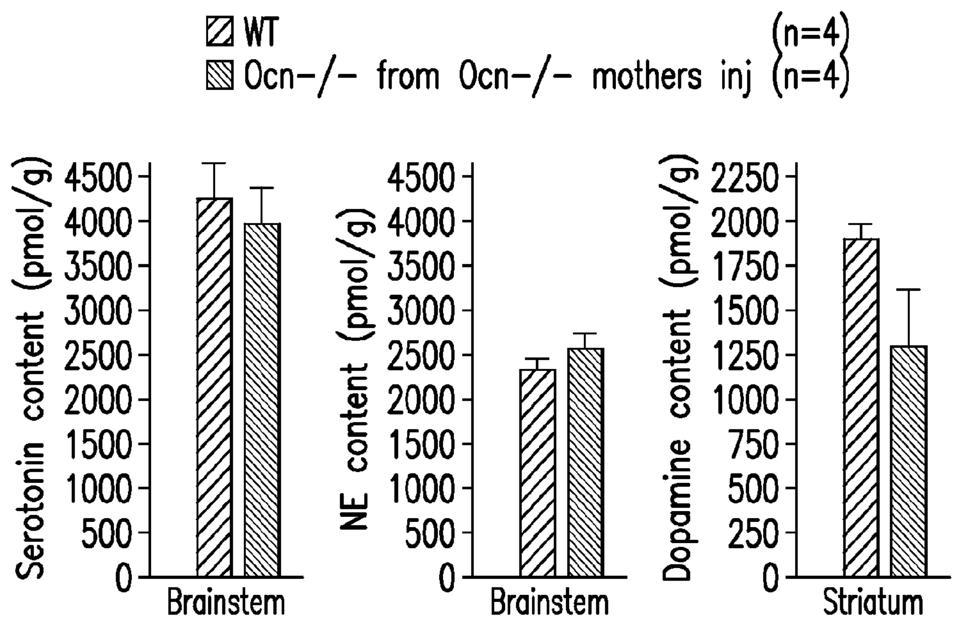
Figure 7K:
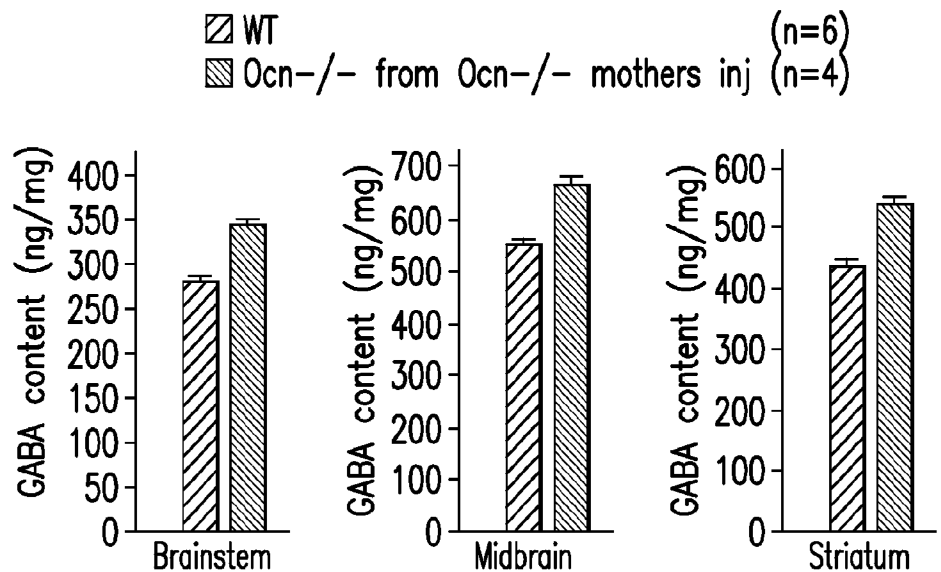

To further evaluate the importance of maternal osteocalcin for the acquisition of spatial learning and memory in adult offspring, pregnant Osteocalcin$^{-/-}$ mothers from E0.5 to E18.5 were treated with injections, once a day, of osteocalcin (240 ng/day). Osteocalcin was never injected in these females or their pups after delivery. This pregnancy-only treatment did not have any beneficial effect on the anxiety or depression phenotypes of the Osteocalcin$^{-/-}$ mice but rescued over two third of their deficit in learning and memory, indicating that this phenotype is, to a large extent, of developmental origin (FIG. 7A-G). Consistent with this observation, cresyl violet staining of histological sections showed a rescue of the cerebral ventricle enlargement in the brains of E18.5 Osteocalcin$^{-/-}$ embryos after injection of the pregnant Osteocalcin$^{-/-}$ mothers (FIG. 7H). Likewise, the number of apoptotic cells was reduced and the number of NeuN positive cells was increased compared to Osteocalcin$^{-/-}$ embryos originating from Osteocalcin$^{-/-}$ mothers that were not injected (FIG. 7I-J). This staining also showed a rescue of the thickness defect in the CA3 and CA4 regions of the hippocampus in adult Osteocalcin$^{-/-}$ originating from Osteocalcin$^{-/-}$ mothers (FIG. 7H). Lastly, a Western blot analysis showed a decrease in Caspase-3 cleaved protein level in the hippocampus of Osteocalcin$^{-/-}$ E18.5 embryos originating from Osteocalcin$^{-/-}$ mothers injected compare to the ones originating from Osteocalcin$^{-/-}$ mothers that were not injected (FIG. 7K).

Example 10—Recombinant Osteocalcin

Recombinant osteocalcin was bacterially produced and purified on glutathione beads according to standard procedures. Osteocalcin was then cleaved from the GST subunit using thrombin digestion. Thrombin contamination was removed using an affinity column. The purity of the product was qualitatively assessed by SDS-PAGE. Bacteria do not have a gamma-carboxylase gene. Therefore, recombinant osteocalcin produced in bacteria is always completely undercarboxylated at all three sites.

Figure 8A:
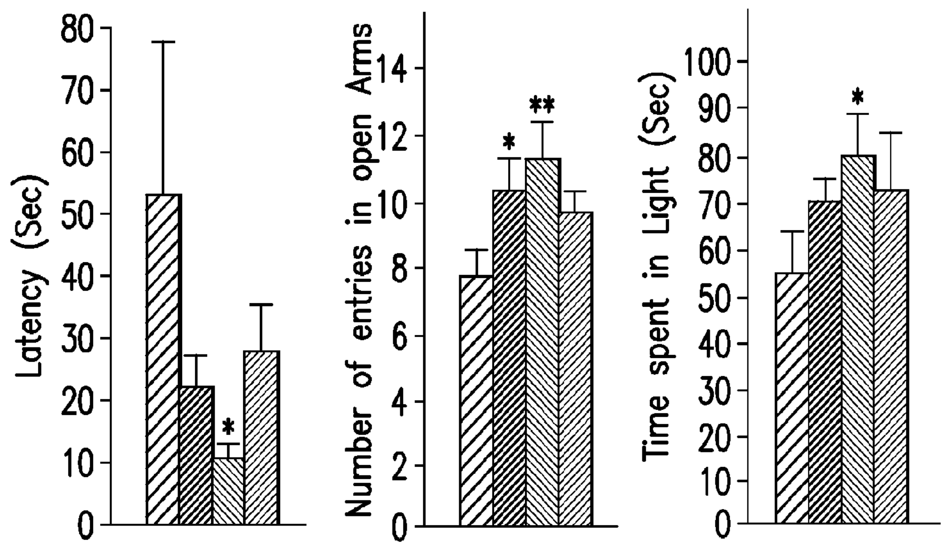
FIG. 8. Osteocalcin improves cognitive function in adult wild-type (WT) mice. Results from dark and light (DLT) and elevated plus maze tests (EPMT) performed in 3-month old WT mice infused ICV with vehicle (PBS) or Ocn (3, 10, 30 ng/hour) are shown. (A) DLT measuring the latency to enter, the number of entries, and the time spend in lit compartment. (B) EPMT measuring the number of entries into open arms and the time spend in lit compartments.
Figure 8B:
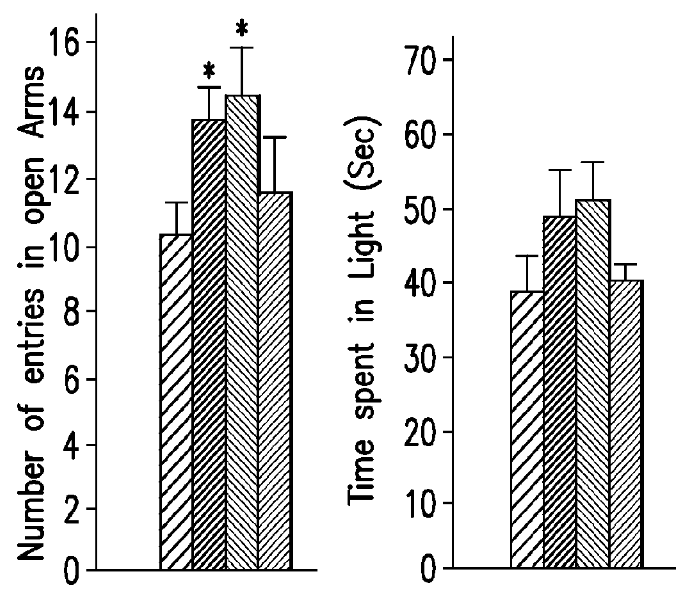

Example 11—Direct Delivery of Osteocalcin to the Brain Improves Cognitive Function in Wild-Type (WT) Adult Mice in a Dose Dependent Manner To determine if osteocalcin is sufficient to improve cognitive function in adult mice, WT 2-month old mice were implanted with ICV pumps delivering vehicle (PBS), or 3, 10, or 30 ng/hr recombinant uncarboxylated full-length mouse osteocalcin for a period of one month. After one month of infusion, animals were subjected to behavioral testing. Based on their performance in the dark to light transition (D/LT) test and the elevated plus maze (EPMT) test, animals receiving 3 or 10 ng/hour of recombinant uncarboxylated full-length mouse osteocalcin showed a decrease in anxiety-like behavior. This improvement is evidenced by an increase in the exploration of the lit compartment and open arms in the D/LT and EMP tests, respectively (FIG. 8A-B).

Figure 9:
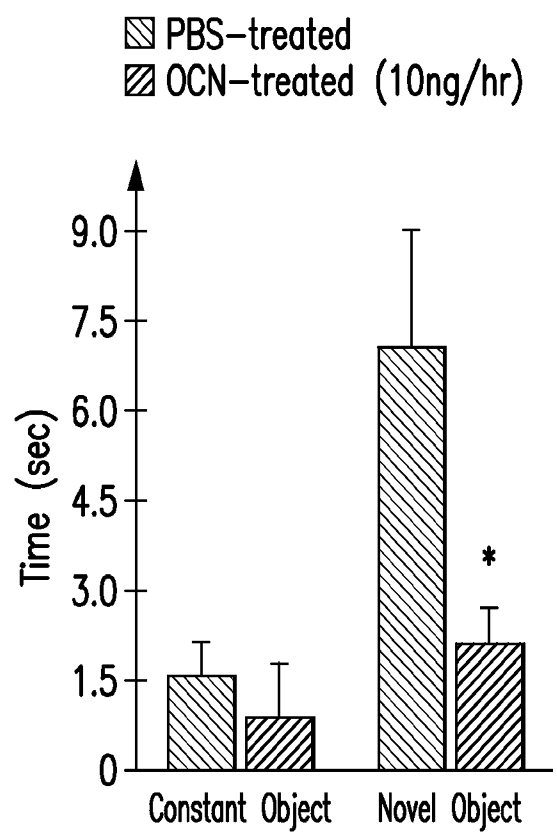
FIG. 9. Osteocalcin improves hippocampal function in aged wild-type (WT) mice. Constant and novel object investigation in the Novel Object Recognition test in 17 month old mice treated for 1 month with vehicle or 10 ng/hr recombinant uncarboxylated osteocalcin.

Example 12—Direct Delivery of Osteocalcin to the Brain of Aged Wild Type (WT) Mice Improves Hippocampal Functions ICV pumps delivering (10 ng/hr) recombinant uncarboxylated full-length mouse osteocalcin were implanted in 16 month old WT mice. After an infusion period of one month, the mice were subjected to a modified version of the Novel Object Recognition test, to assay memory and hippocampal function. Briefly, mice were given five 5 minute exposures, with 3 minute resting intervals between exposures, to a novel arena containing two objects. During exposures 1-4, mice were habituated to these two objects, which elicited equal amounts of exploration. In the fifth exposure, one of the objects was replaced with a novel object. Aged mice receiving either PBS or recombinant uncarboxylated full-length mouse osteocalcin were both able to discriminate between the novel and constant objects. However, FIG. 9 shows that mice which had received osteocalcin treatment spent less time exploring the novel object than mice treated with vehicle alone, indicating improved efficiency in hippocampal context encoding and/or acquisition efficiency (Denny et al., 2012, Hippocampus 22:1188-1201).

Figure 10A:
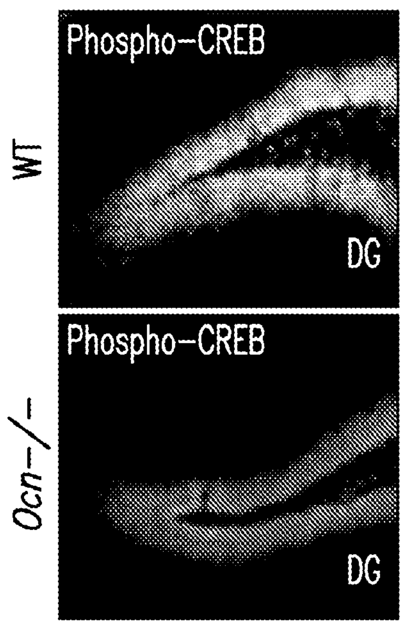
FIG. 10. Osteocalcin administration results in CREB phosphorylation. (A) p-CREB immunofluorescence (IF) in the dentate gyms (DG) of WT and Ocn−/− hippocampal region. (B) p-CREB IF in WT brain sections following a dual stereotactic injection of vehicle (PBS) (on the left) or Ocn (10 ng) (on the right) in the hippocampus. The arrows point toward the DG. (C) PKA IF in WT brain sections following a dual stereotactic injection of vehicle (PBS) (on the right) or Ocn (10 ng) (on the left) in the hippocampus.
Figure 10B:
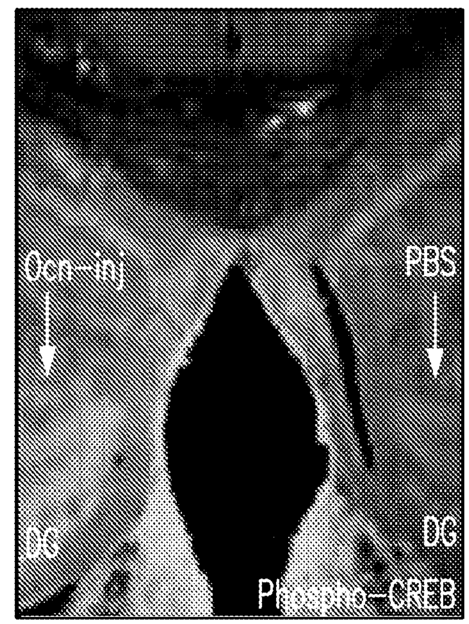
Figure 10C:
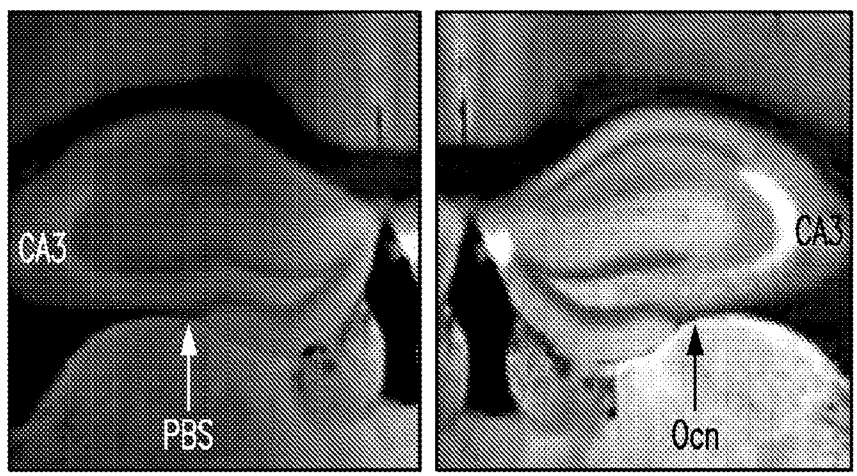

Example 13—Osteocalcin is Necessary and Sufficient for CREB Phosphorylation in the Hippocampal The resulting effects on animal behavior of direct recombinant uncarboxylated osteocalcin delivery raise the question of the molecular mechanism of action of osteocalcin in the brain. Given that osteocalcin acts through a G-protein coupled receptor pathway in other tissues, e.g., pancreas and testis, the phosphorylated CREB levels in the hippocampi of Ocn−/− and WT animals was checked. It was observed that pCREB staining is dramatically decreased in the dentate gyrus (DG) of the hippocampus in Ocn−/− animals (FIG. 10A). The hippocampus is essential for optimal spatial learning and memory in rodents. It was then asked whether the acute stereotactic injection of 10 ng of recombinant uncarboxylated osteocalcin directly into the hippocampus of WT animals would affect pCREB levels. At 16 h post injection, pCREB staining was increased in the hemisphere injected with osteocalcin versus the one injected with PBS in the same animal (FIG. 10B). Moreover, a widespread and dramatic increase in PKA staining, known to lead to CREB activation, was observed in the injected hemisphere at the 16 h post injection timepoint (FIG. 10C).

Figure 11:
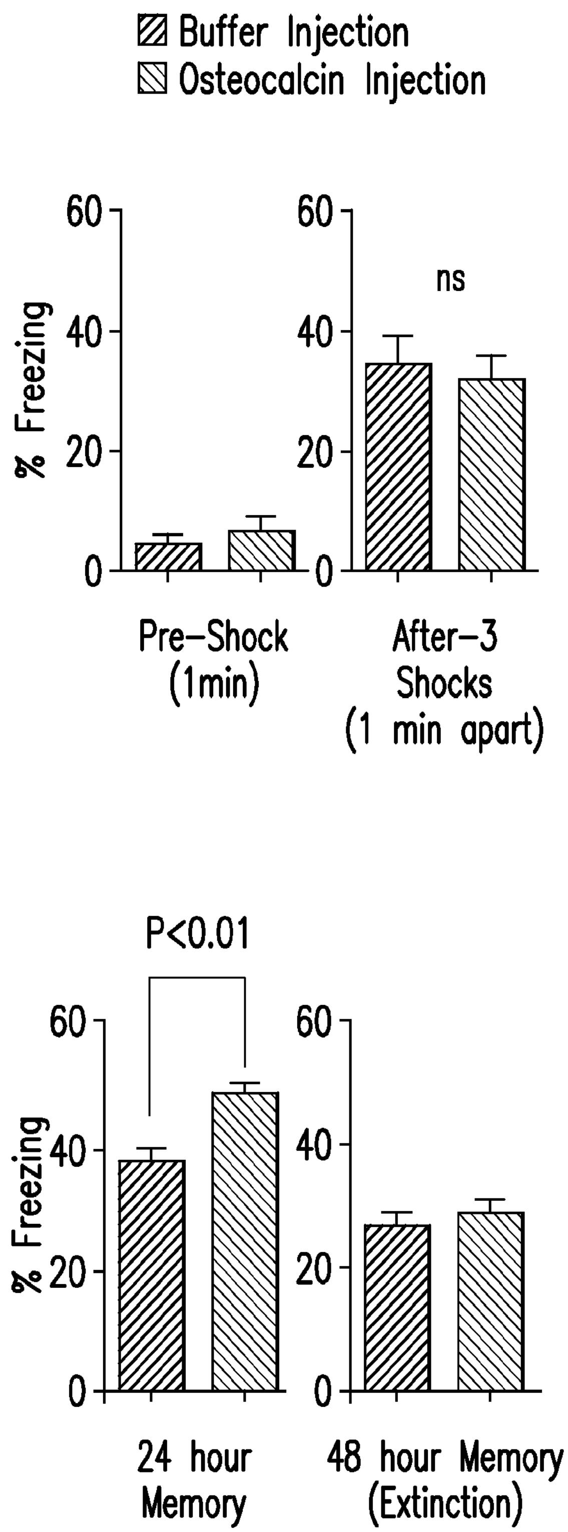
FIG. 11. CREB activation by osteocalcin is functionally relevant. Contextual fear conditioning in 3.5 month old mice injected acutely with 10 ng recombinant uncarboxylated osteocalcin 24 hours prior to context exposure. 3 shocks of 0.55 mA were delivered to mice 1 min apart. On Day 1, % freezing was the same for both groups. % freezing was measured again 24 hours after the initial shocks. Osteocalcin injected mice showed increased freezing along with hyperexcitability.

To determine whether these acute injections and corresponding activation of the CREB pathway are functionally relevant, Contextual Fear Conditioning (CFC), a hippocampus dependent task that assesses long term memory, was performed. Mice were injected acutely in both hemispheres with either PBS or 10 ng recombinant uncarboxylated osteocalcin. Mice injected with osteocalcin (n=4 per group) displayed increased freezing behavior as compared to controls (FIG. 11), indicating that just one dose of osteocalcin improved long term memory recall.

Nucleotide and Amino Acid Sequences

```
Human Osteocalcin cDNA
                                                                SEQUENCE ID NO: 1
cgcagccacc gagacaccat gagagccctc acactcctcg ccctattggc cctggccgca ctttgcatcg ctggccaggc

aggtgcgaag cccagcggtg cagagtccag caaaggtgca gcctttgtgt ccaagcagga gggcagcgag gtagtgaaga

gacccaggcg ctacctgtat caatggctgg gagccccagt ccccctaccc gatcccctgg agcccaggag ggaggtgtgt

gagctcaatc cggactgtga cgagttggct gaccacatcg gctttcagga ggcctatcgg cgcttctacg gcccggtcta

gggtgtcgct ctgctggcct ggccggcaac cccagttctg ctcctctcca ggcacccttc tttcctcttc cccttgccct

tgccctgacc tcccagccct atggatgtgg ggtccccatc atcccagctg ctcccaaata aactccagaa gaggaatctg

aaaaaaaaaa aaaaaaaa

Human Osteocalcin amino acid sequence
                                                                SEQUENCE ID NO: 2
MRALTLLALL ALAALCIAGQ AGAKPSGAES SKGAAFVSKQ EGSEVVKRPR RYLYQWLGAP VPYPDPLEPR REVCELNPDC

DELADHIGFQ EAYRRFYGPV

Mouse osteocalcin gene 1 cDNA
                                                                SEQUENCE ID NO: 3
agaacagaca agtcccacac agcagcttgg cccagaccta gcagacacca tgaggaccat ctttctgctc actctgctga

ccctggctgc gctctgtctc tctgacctca cagatgccaa gcccagcggc cctgagtctg acaaagcctt catgtccaag

caggagggca ataaggtagt gaacagactc cggcgctacc ttggagcctc agtccccagc ccagatcccc tggagcccac

ccgggagcag tgtgagctta accctgcttg tgacgagcta tcagaccagt atggcttgaa gaccgcctac aaacgcatct

atggtatcac tatttaggac ctgtgctgcc ctaaagccaa actctggcag ctcggctttg gctgctctcc gggacttgat

cctccctgtc ctctctctct gccctgcaag tatggatgtc acagcagctc caaaataaag ttcagatgag gaagtgcaaa

aaaaaaaaaa aaaa

Mouse osteocalcin gene 2 cDNA
                                                                SEQUENCE ID NO: 4
gaacagacaa gtcccacaca gcagcttggt gcacacctag cagacaccat gaggaccctc tctctgctca ctctgctggc

cctggctgcg ctctgtctct ctgacctcac agatcccaag cccagcggcc ctgagtctga caaagccttc atgtccaagc

aggagggcaa taaggtagtg aacagactcc ggcgctacct tggagcctca gtccccagcc cagatcccct ggagcccacc

cgggagcagt gtgagcttaa ccctgcttgt gacgagctat cagaccagta tggcttgaag accgcctaca aacgcatcta

cggtatcact atttaggacc tgtgctgccc taaagccaaa ctctggcagc tcggctttgg ctgctctccg ggacttgatc

ctccctgtcc tctctctctg ccctgcaagt atggatgtca cagcagctcc aaaataaagt tcagatgagg

Mouse osteocalcin gene 1 and 2 amino acid sequence
                                                                SEQUENCE ID NO: 5
MRTLSLLTLL ALAALCLSDL TDPKPSGPES DKAFMSKQEG NKVVNRLRRY LGASVPSPDP LEPTREQCEL NPACDELSDQ

YGLKTAYKRI YGITI

Human gamma-carboxylase cDNA
                                                                SEQUENCE ID NO: 6
gtgacccacc tgcctcctcc gcagagcaat ggcggtgtct gccgggtccg cgcggacctc gcccagctca gataaagtac

agaaagacaa ggctgaactg atctcagggc ccaggcagga cagccgaata gggaaactct tgggttttga gtggacagat

ttgtccagtt ggcggaggct ctgaatcgac caacggaccc tgcaagctta gctgtctttc gttttctttt tgggttcttg

atggtgctag acattcccca ggagcggggg ctcagctctc tggaccggaa gggctggatg tgtgccgctt ccccttgctg

gatgccctac gcccactgcc atgtatcttg tctacaccat catgtttctg gggcactggg gcatgatgct taccggataa
```

-continued gctgtgtgtt attcctgctg ccatactggt atgtgtttct cctggacaag acatcatgga acaaccactc ctatctgtat gggttgttgg cctttcagct gatgcaaacc actactggtc tgtggacggt ctgctgaatg cccataggag gtgccccttt ggaactatgc agtgctccgt ggccagatct tcattgtgta cttcattgcg ggtgtgaaaa agctggatgc agactgggtt gaaggctatt ccatggaata tttgtcccgg cactggctct tcagtccctt caaactgctg ttgtctgagg agctgactag cctgctggtc gtgcactggg gtgggctgct gcttgacctc tcagctggtt tcctgctctt ttttgatgtc tcaagatcca ttggcctgtt ctttgtgtcc tacttccact gcatgaattc ccagcttttc agcattggta tgttctccta cgtcatgctg gccagcagcc ctctcttctg ctcccctgag tggcctcgga agctggtgtc ctactgcccc cgaaggttgc aacaactgtt gcccctcaag gcagcccctc agcccagtgt ttcctgtgtg tataagagga gccggggcaa aagtggccag aagccagggc tgcgccatca gctgggagct gccttcaccc tgctctacct cctggagcag ctattcctgc cctattctca ttttctcacc cagggctata acaactggac aaatgggctg tatggctatt cctgggacat gatggtgcac tcccgctccc accagcacgt gaagatcacc taccgtgatg gccgcactgg cgaactgggc taccttaacc ctggggtatt tacacagagt cggcgatgga aggatcatgc agacatgctg aagcaatatg ccacttgcct gagccgcctg cttcccaagt ataatgtcac tgagccccag atctactttg atatttgggt ctccatcaat gaccgcttcc agcagaggat tttgaccct cgtgtggaca tcgtgcaggc cgcttggtca ccctttcagc gcacatcctg ggtgcaacca ctcttgatgg acctgtctcc ctggagggcc aagttacagg aaatcaagag cagcctagac aaccacactg aggtggtctt cattgcagat ttccctggac tgcacttgga gaattttgtg agtgaagacc tgggcaacac tagcatccag ctgctgcagg gggaagtgac tgtggagctt gtggcagaac agaagaacca gactcttcga gagggagaaa aaatgcagtt gcctgctggt gagtaccata aggtgtatac gacatcacct agcccttctt gctacatgta cgtctatgtc aacactacag agcttgcact ggagcaagac ctggcatatc tgcaagaatt aaaggaaaag gtggagaatg gaagtgaaac agggcctcta cccccagagc tgcagcctct gttggaaggg gaagtaaaag gggccctga gccaacacct ctggttcaga cctttcttag acgccaacaa aggctccagg agattgaacg ccggcgaaat actcctttcc atgagcgatt cttccgcttc ttgttgcgaa agctctatgt ctttcgccgc agcttcctga tgacttgtat ctcacttcga aatctgatat taggccgtcc ttccctggag cagctggccc aggaggtgac ttatgcaaac ttgagaccct ttgaggcagt tggagaactg aatccctcaa acacggattc ttcacattct aatcctcctg agtcaaatcc tgatcctgtc cactcagagt tctgaagggg gccagatgtt gggtgcagat gtagaagcag ccagtcacag acccattcta tgcaatggac atttatttga aaaaaattct caaaagtttt tttttttttt ttgggggggc ggggttctaa agctgttttt aactccgaga ttacaactta gaggaaccaa ggaaataaag caaataagat ttaacaaccc aagattaaga ggccaggaag aggttagacg caatgtgaaa ctgtcctcct aggataaggt ttaaagtggc tttttggggg ctgggtgccg tggctcacgc ctgtaatccc agcattttgg gaggctgagg tgggcagatc acttgaggcc aggagttcga gaccagcctg gccaacatgg caaaacccct tctctactaa aaatacaaaa attagccaga cgtggtggtg ggtgcctgta atccaactac ccaggaggct gaggcatgag aatcgcttgg gcccaggagg tggaggttgc agtgagccga gatcgagcca ctgcactcct gggcaacaga gcaagacttc gtctcaaaat aaataaataa agtggctctt ggggaaaagc aatttaatgt accacgatga atagctaact gttcccaagt gtttgctatg tgcaacacac cgcgtgagca gtgttacctg cattattaca ttaggctgag aggtaaaata atttgcccga agacatacag ctagtgacga atggactgat ggtttgaact taacgtctat ttgacttaag gtcctgcacc ctgccacttg taattttcag aatcactgat aatctgaaat aatgcagctt aaaacatgtt ttcttaatta aaagtataaa aaaaaaaaaa aaaaaaaaaa aaaaaaaaaa aaaaaaaaaa aaaaaaaaaa aaaaaaaaaa aaaaaaaaaa aaaaaa Human gamma-carboxylase amino acid sequence

SEQUENCE ID NO.: 7

MAVSAGSART SPSSDKVQKD KAELISGPRQ DSRIGKLLGF EWTDLSSWRR LVTLLNRPTD PASLAVFRFL FGFLMVLDIP

QERGLSSLDR KYLDGLDVCR FPLLDALRPL PLDWMYLVYT IMFLGALGMM LGLCYRISCV LFLLPYWYVF LLDKTSWNNH

SYLYGLLAFQ LTFMDANHYW SVDGLLNAHR RNAHVPLWNY AVLRGQIFIV YFIAGVKKLD ADWVEGYSME YLSRHWLFSP

FKLLLSEELT SLLVVHWGGL LLDLSAGFLL FFDVSRSIGL FFVSYFHCMN SQLFSIGMFS YVMLASSPLF CSPEWPRKLV

-continued

SYCPRRLQQL LPLKAAPQPS VSCVYKRSRG KSGQKPGLRH QLGAAFTLLY LLEQLFLPYS HFLTQGYNNW TNGLYGYSWD

MMVHSRSHQH VKITYRDGRT GELGYLNPGV FTQSRRWKDH ADMLKQYATC LSRLLPKYNV TEPQIYFDIW VSINDRFQQR

IFDPRVDIVQ AAWSPFQRTS WVQPLLMDLS PWRAKLQEIK SSLDNHTEVV FIADFPGLHL ENFVSEDLGN TSIQLLQGEV

TVELVAEQKN QTLREGEKMQ LPAGEYHKVY TTSPSPSCYM YVYVNTTELA LEQDLAYLQE LKEKVENGSE TGPLPPELQP

LLEGEVKGGP EPTPLVQTFL RRQQRLQEIE RRRNTPFHER FFRFLLRKLY VFRRSFLMTC ISLRNLILGR PSLEQLAQEV

TYANLRPFEA VGELNPSNTD SSHSNPPESN PDPVHSEF

Mouse gamma-carboxylase cDNA

SEQUENCE ID NO: 8 agacagcaag tctaagtctg gaggttccac tgggtccgac ctggctgcag agaggctcac ctgtccctgc agtcatggct gtgcaccgcg gctccgcact ggttgctccc gcctcagata aagtacagaa aaacaagtct gcacagacat caggactgaa acagggcagc cgaatggaga aaattttagg gtttgaatgg acagatttat ctagctggca gagtgtcgtg accctgctta acaaaccaac ggaccctgca aacctggctg tctttcgttt tctctttgct ttcttgatgc tgctggacat tccccaggaa cgcggcctta gctccctgga ccgaaaatac ttggatgggc tggatgtgtg ccgtttcccc ttgctggatg ccttgcgccc actgccactg gactggatgt atcttgtcta caccatcatg tttctggggg cactgggcat gatgctgggg ctatgctacc ggctaagctg tgtgttattc ctgctaccgt actggtacgt gtttctcctg gacaagactt cgtggaacaa tcactcctat ctgtatggtt tgttggcctt tcagttgaca ttcatggatg caaaccacta ctggtctgtg gatggcttgc tgaatgcccg aaagaagaat gctcacgtgc ccctttggaa ctacacagtt ctgcgtggcc agatcttcat cgtgtacttc atcgcgggtg tgaagaagct cgatgctgac tgggttgggg gctactccat ggagcacctg tcccggcact ggctcttcag tcccttcaag ctggtgttgt cggaggagct gacaagcctg ctggtagtac actggtgtgg gcttctcctt gacctctcgg ctggcttcct gctcttcttt gatgcctcca gacccgtcgg cctgttcttc gtgtcctact ttcactgcat gaactcgcag ctcttcagca tcgggatgtt tccctatgtc atgctggcca gcagccctct cttctgctca gctgaatggc ctcggaagtt ggtagcccga tgcccgaaaa ggctgcaaga gctgctgccc accaaagccg ctcctcggcc tagtgcttcc tgtgtgtata agaggtcccg gggcaaagct ggcccgaagc ccgggctgcg ccaccagctg ggagccatct tcaccctgct ctacctccta gagcagctct tcctgcccta ttcccacttc ctgacccagg gttacaataa ctggacaaat gggctgtatg gctattcctg ggacatgatg gtgcactccc gctcccacca gcacgtaaag atcacctacc gcgacggcct cacgggcgag ctaggctacc ttaaccctgg ggtattcaca cagagccggc gatggaagga tcatgcagac atgctgaagc aatatgccac ttgcctgagc ctcctgcttc ccaagtacaa tgtcactgag ccccagatct actttgatat ttgggtctcc atcaatgacc gcttccagca gaggcttttt gaccctcgtg tggacatcgt gcaggctgtc tggtccccct tccagcgcac accttgggtg cagccactct tgatggattt atctccctgg aggaccaagt tacaggatat taagagcagt ctggacaacc acaccgaggt ggtcttcatt gcagatttcc ctgggcttca cttggagaat tttgtgagtg aagacctggg caacactagc atccagctgc tgcagggaga agtcaccgtg gaattggtgg cagaacagaa aaatcagact cttcaagaag gagagaaaat gcagttgcct gctggagagt accataaagt ctatactgta tcatctagtc cttcctgcta catgtacgtc tatgtcaaca ctacagaggt cgcactggag caagacctgg catatctgca agaattaaag gagaaggtgg agaacggaag tgaaacaggg cccctgcctc cagaacttca gcctcttttg gaaggggaag taaaaggggg ccctgagcca acacctctgg tccaaacttt tctcagacga cagaggaagc tccaagaaat tgaacgcagg cgaaatagcc ctttccatga gcgatttctc cgcttcgtgc tgcgaaagct ctacgtcttt cgacgcagct tcctgatgac tcgaatttca ctccgaaacc tgctattagg ccgcccttcc ctagagcaac tagcccaaga ggtgacatat gcaaacttgc gaccatttga accagttgat gagtcaagtg cttcaaacac agattcttca aatcacccgt cagagccaga ttctgagcat gttcactctg agttctgagg gatgtacaga tgctctgtgc agatgtgggg gcagcctgtt ataggcttat tgtctacgca aagaacatat ttttggagaa aaatgatatg ggacaggctt tcacagtaca gcccaggctg gcctcaaact catggttggt ccctctgctt cagcctgttt tgtaattaca tagtatcacc aaacctagtt gcttttccct ttacattttt tccccttata agttctttaa aattatagct tacatttttt ctttttcttt tttttttttt ttgtattttt tctttgtcaa gacaggtctc tctctgtgta gcactggctg tcctggaact cactctgtag tccaggctgg cctccaactc agaaattctc ctgcctctgc ctcccaagtg ctgggattaa aggtgtgtgc caccacgccc cactgggctt ttagttttta tagacaagat ttctccatgt agaccagacc agctctcctg agtgctgaaa ttaaaggcac gggacatcac tacctggctt tcttattaaa cttgttttag tggtctcaac aaaaa Mouse gamma-carboxylase amino acid sequence

SEQUENCE ID NO: 9

MAVHRGSALV APASDKVQKN KSAQTSGLKQ GSRMEKILGF EWTDLSSWQS VVTLLNKPTD PANLAVFRFL FAFLMLLDIP

QERGLSSLDR KYLDGLDVCR FPLLDALRPL PLDWMYLVYT IMFLGALGMM LGLCYRLSCV LFLLPYWYVF LLDKTSWNNH

SYLYGLLAFQ LTFMDANHYW SVDGLLNARK KNAHVPLWNY TVLRGQIFIV YFIAGVKKLD ADWVGGYSME HLSRHWLFSP

FKLVLSEELT SLLVVHWCGL LLDLSAGFLL FFDASRPVGL FFVSYFHCMN SQLFSIGMFP YVMLASSPLF CSAEWPRKLV

ARCPKRLQEL LPTKAAPRPS ASCVYKRSRG KAGPKPGLRH QLGAIFTLLY LLEQLFLPYS HFLTQGYNNW TNGLYGYSWD

MMVHSRSHQH VKITYRDGLT GELGYLNPGV FTQSRRWKDH ADMLKQYATC LSLLLPKYNV TEPQIYFDIW VSINDRFQQR

LFDPRVDIVQ AVWSPFQRTP WVQPLLMDLS PWRTKLQDIK SSLDNHTEVV FIADFPGLHL ENFVSEDLGN TSIQLLQGEV

TVELVAEQKN QTLQEGEKMQ LPAGEYHKVY TVSSSPSCYM YVYVNTTEVA LEQDLAYLQE LKEKVENGSE TGPLPPELQP

LLEGEVKGGP EPTPLVQTFL RRQRKLQEIE RRRNSPFHER FLRFVLRKLY VFRRSFLMTR ISLRNLLLGR PSLEQLAQEV

TYANLRPFEP VDESSASNTD SSNHPSEPDS EHVHSEF

Mouse Esp (OST-PTP, Ptprv) cDNA

SEQUENCE ID NO: 10 ggctgtggga gagcagaaga ggagctggaa gagcagccta caacagctgt cgggagggac cagggctagt tcacacttgg aagctgggat gccaggaccg gccctcctgc ctctctcggt ctccatcggc ctcctggtca gctcactcca cactgagacg attctgaagt aagatgctcc tggctcctca cagactctgc tacaagagac agagtgaagt gtccccaggg ctcagagcct ttgactctgc tccttccctt cccacggctg agttggcaca ggagcacctg ggtgagctgc accagactta agaagatgag gcccctgatt ctgttagctg ccctcctctg gctccaggac tctttggccc aggaagatgt atgctcatcc ttggatggga gcccagacag gcagggtgga ggtccacctc tgagtgtgaa cgtcagcagc cgcggaaagc ctaccagcct gtttctgagc tgggtagctg cagagccagg tggatttgac tatgccctct gcctcagggc tatgaacttg tcgggttttc cagaagggca acagctccaa gctcatacca acgagtccag ctttgagttc catggcctgg tgccagggag tcgctaccag ctggaactga ctgtcctaag accctgttgg cagaatgtca caattaccct cactgctcga actgccccta cagtggtccg tggactgcaa ctgcatagca ctgggagccc agccagcctg gaagcctcat ggagcgatgc ctctggggat caagacagct atcaacttct cctctaccac ccggaatccc acactctggc atgtaatgtc tctgtgtccc ctgacaccct gtcttacaat tttggtgacc tcttgccagg tagtcagtat gtcttggagg ttatcacctg ggctggcagt ctccatgcga agactagcat cctccaatgg acagagcctg tccctcctga tcacctaaca ctgcgtgcct tgggtaccag tagcctgcaa gccttctgga acagctctga aggggccacc tggtttcacc tgatacttac agacctccta gagggtacca acctgaccaa agtggtcaga caaggcatct caacccacac cttccttcgc ctgtctccgg gtacacctta ccagctgaag atctgtgctg ctgctgggcc ccaccagatt tggggaccca atgccactga gtggacctat ccctcttacc catctgacct ggtgctgacc ccccttatgga atgagctctg ggcaagctgg aaggcagggc agggagcccg ggatggctat gtactgaagt taagtgggcc agtggagaat acaactactc tgggtcctga ggagtgcaac gctgtcttcc cagggcccct gcctccagga cactacactt tggggctgag ggttctagct ggaccttatg atgcctgggt agagggcagt atctggctgg ctgaatctgc tgctcgtccc atggaggtcc ctggtgccag actgtggcta gaaggactgg aagctactaa gcaacctggg agacgggcgc tgctctattc tgttgatgcc ccaggcctcc tagggaacat ctctgtgtct tctggtgcca ctcatgtcac cttctgtggc ttggtacccg gagcgcacta cagggtggac attgcctcat ccatgggaga catcactcag agcctcacag gctacacaag tcccctgcca ccacagtctc tggagatcat cagccggaac agcccatctg acctgactat cggttgggct ccagcaccag ggcagatgga aggttataag gtcacctggc atcaggatgg cagccagagg tcacctggcg accttgttga cttgggccct gacatttcga gcctgactct gaaatctctg gtacctggtt cctgctacac cgtgtcagca tgggcctggt ctgggaacct cagctctgac tctcagaaga ttcacagttg -continued cacccgtccc gctcctccca ccaacctgag cctgggcttt gcccaccagc ctgcaacact gagggcttcc tggtgtcacc caccgggtgg cagggatgcc tttcagttac ggctttacag gctgaggccc ctgacactgg aaagtgagaa gatcctatcc caggaggccc agaacttctc ctgggcccag ctgcctgcag gctatgaatt ccaggtacag ctgtctacct tgtgggggtc ggaggagagc ggcagtgcca acaccacagg ctggacaccc ccctcagctc ctacattggt aaatgtgacc agtgaagccc ccacccagct ccacgtatcc tgggtccacg ctgctgggga ccggagcagc taccaagtga ccctatacca ggagagcact cggacagcca ccagcattgt ggggcccaag gcagacagca caagcttttg gggtttgact cctggcacta agtacaaggt ggaagccatc tcctgggctg ggcccctta cactgcagca gccaacgttt ctgcttggac ctacccactc acacccaatg agctgctcgc ctctatgcag gcaggcagtg ctgtggttaa cctggcctgg cccagtggtc ccttggggca agggacatgc catgcccaac tctcagatgc tggacacctt tcatgggagc aaccgctgtc gctaggccaa gacctcctca tgctaaggaa tcttatacca ggacatacgg tttcattgtc tgtgaagtgt cgggcaggac cactccaggc ctccactcac cccctggtgc tgtctgtaga gcctggccct gtggaagatg tgttctgtca acctgaggcc acctacctgt ccctgaactg gacgatgcct actggagatg tggctgtctg tctggtggag gtagagcagc tggtgccagg agggagcgct cattttgtct tccaggtcaa cacctcggag gatgcacttc tgctgcccaa cttgacgccc accacttctt accgccttag cctcactgtg ctgggtggga atcgccagtg gagccgggcg gttaccctgg tgtgcactac ttctgctgag gtttggcacc ccccagagct agctgaggcc ccccaggtgg agctggggac agggatgggt gtgacagtca cacgtggcat gtttggtaaa gatgacgggc agatccagtg gtatggcata attgccacca tcaacatgac actggcccag ccttcccagg aagccatcaa ccacacatgg tatgaccact actatagagg acatgactcc tacctggctc tcctgttccc aaacccttc tacccagagc cttgggctgt gccaagatcc tggacagtac ctgtgggtac agaggactgt gacaacaccc aggagatatg caatgggcat ctcaagccag gcttccagta taggttcagc attgcagcct ttagtaggct cagctctcca gagaccatcc tggccttctc cgccttctca gagcctcagg ctagcatctc tctggtggcc atgcccctga cagttatgat ggggactgtg gtgggctgca tcatcattgt gtgtgcagtg ctatgcttgt tgtgccggcg gcgcctgaag ggaccaaggt cagagaagaa tggcttttcc caggagttga tgccttacaa cctgtggcgg acccatcggc ccatccccag ccatagcttc cggcagagct atgaggccaa gagtgcacgt gcacaccagg ccttcttcca ggaatttgag gagctgaagg aggtgggcaa ggaccagccc agactagagg ctgagcatcc tgccaacatc accaagaacc ggtacccaca cgtgctacct tatgaccact ccagggtcag gctgacccag ctatcaggag agcctcattc tgactacatc aatgccaact tcatcccagg ctatagccac ccacaggaga tcattgccac ccaggggcct ctcaaaaaga cggtcgagga cttctggcgg ttggtgtggg agcagcaagt ccacgtgatc atcatgctaa ctgtgggcat ggagaatggg cgggtactgt gtgagcacta ctggccagtc aactccacgc ctgtcaccca cggtcacatc accacccacc tcctggcaga ggaatctgag gacgagtgga ccaggaggga attccagctg cagcacggtg cagagcaaaa acagaggcgc gtgaagcagc tgcagttcac gacctggcca gaccacagtg tccccgaggc tcccagctct ctgctcgctt ttgtggaact ggtgcaggag gaggtgaagg caactcaggg caaggggccc atcctggtgc attgcagtgc gggtgtgggc aggacaggca cctttgtggc tctcttaccg gctgttcgac aactagagga agaacaggtg gtcgatgtgt tcaacactgt gtacatactc cggctgcacc ggcccctcat gatccagacc ttgagtcaat acatcttcct gcacagctgc ctgctgaaca agattctgga agggccctct gacgcctcag actccggccc catccctgtg atgaattttg cacaagcttg tgccaagagg gcagccaatg ccaatgccgg tttcttgaag gagtacaggc tcctgaagca ggccatcaag gatgagactg gctctctgct gccctctcct gactataatc agaacagcat cgcctcctgt catcattctc aggagcagtt ggccctggtg gaggagagcc ctgctgataa catgctggca gcctcgctct tccctggtgg gccgtctggt cgcgaccatg tggtgctgac tggctcggcc ggaccaaagg aactctggga aatggtgtgg gaacatggcg cctatgtgct tgtctccctg ggtctgcctg ataccaagga gaagccacaa gacatctggc caatggagat gcagcctatt gtcacagaca tggtgacagt gcacagagtg gctgagagca acacagctgg ctggcccagt accctcatca gagttataca tggggacagt gggacggaaa ggcaggttca atgcctgcag tttccacact gcgagactgg gagtgagctc ccagctaaca ccctactgac cttccttgat gctgtgggcc agtgctgctc ccggggcaat agcaagaagc cagggaccct gctcagtcac tccagcaagg tcacaaacca gctgagcacc ttcttggcta tggaacagct gctacagcaa gcagggaccg agcgcacagt ggatgtcttc agtgtggccc tgaagcagac acaggcctgt ggccttaaga ccccaacgct ggagcagtat atctacctct acaactgtct gaacagcgca ttgaggaaca ggctgccccg agctaggaag tgaccttgcc ctgctaggca tcacgttcca gcaatccacc caggcctggc ttccccagga gaacagatct attcggcctc acgctgtcaa agggcagagt ctgggaataa agggtaaatc tcgag Mouse Esp (OST-PTP, Ptprv) amino acid sequence

SEQUENCE ID NO: 11

MRPLILLAAL LWLQDSLAQE DVCSSLDGSP DRQGGGPPLS VNVSSRGKPT SLFLSWVAAE PGGFDYALCL RAMNLSGFPE

GQQLQAHTNE SSFEFHGLVP GSRYQLELTV LRPCWQNVTI TLTARTAPTV VRGLQLHSTG SPASLEASWS DASGDQDSYQ

LLLYHPESHT LACNVSVSPD TLSYNFGDLL PGSQYVLEVI TWAGSLHAKT SILQWTEPVP PDHLTLRALG TSSLQAFWNS

SEGATWFHLI LTDLLEGTNL TKVVRQGIST HTFLRLSPGT PYQLKICAAA GPHQIWGPNA TEWTYPSYPS DLVLTPLWNE

LWASWKAGQG ARDGYVLKLS GPVENTTTLG PEECNAVFPG PLPPGHYTLG LRVLAGPYDA WVEGSIWLAE SAARPMEVPG

ARLWLEGLEA TKQPGRRALL YSVDAPGLLG NISVSSGATH VTFCGLVPGA HYRVDIASSM GDITQSLTGY TSPLPPQSLE

IISRNSPSDL TIGWAPAPGQ MEGYKVTWHQ DGSQRSPGDL VDLGPDISSL TLKSLVPGSC YTVSAWAWSG NLSSDSQKIH

SCTRPAPPTN LSLGFAHQPA TLRASWCHPP GGRDAFQLRL YRLRPLTLES EKILSQEAQN FSWAQLPAGY EFQVQLSTLW

GSEESGSANT TGWTPPSAPT LVNVTSEAPT QLHVSWVHAA GDRSSYQVTL YQESTRTATS IVGPKADSTS FWGLTPGTKY

KVEAISWAGP LYTAAANVSA WTYPLTPNEL LASMQAGSAV VNLAWPSGPL GQGTCHAQLS DAGHLSWEQP LSLGQDLLML

RNLIPGHTVS LSVKCRAGPL QASTHPLVLS VEPGPVEDVF CQPEATYLSL NWTMPTGDVA VCLVEVEQLV PGGSAHFVFQ

VNTSEDALLL PNLTPTTSYR LSLTVLGGNR QWSRAVTLVC TTSAEVWHPP ELAEAPQVEL GTGMGVTVTR GMFGKDDGQI

QWYGIIATIN MTLAQPSQEA INHTWYDHYY RGHDSYLALL FPNPFYPEPW AVPRSWTVPV GTEDCDNTQE ICNGHLKPGF

QYRFSIAAFS RLSSPETILA FSAFSEPQAS ISLVAMPLTV MMGTVVGCII IVCAVLCLLC RRRLKGPRSE KNGFSQELMP

YNLWRTHRPI PSHSFRQSYE AKSARAHQAF FQEFEELKEV GKDQPRLEAE HPANITKNRY PHVLPYDHSR VRLTQLSGEP

HSDYINANFI PGYSHPQEII ATQGPLKKTV EDFWRLVWEQ QVHVIIMLTV GMENGRVLCE HYWPVNSTPV THGHITTHLL

AEESEDEWTR REFQLQHGAE QKQRRVKQLQ FTTWPDHSVP EAPSSLLAFV ELVQEEVKAT QGKGPILVHC SAGVGRTGTF

VALLPAVRQL EEEQVVDVFN TVYILRLHRP LMIQTLSQYI FLHSCLLNKI LEGPSDASDS GPIPVMNFAQ ACAKRAANAN

AGFLKEYRLL KQAIKDETGS LLPSPDYNQN SIASCHHSQE QLALVEESPA DNMLAASLFP GGPSGRDHVV LTGSAGPKEL

WEMVWEHGAY VLVSLGLPDT KEKPQDIWPM EMQPIVTDMV TVHRVAESNT AGWPSTLIRV IHGDSGTERQ VQCLQFPHCE

TGSELPANTL LTFLDAVGQC CSRGNSKKPG TLLSHSSKVT NQLSTFLAME QLLQQAGTER TVDVFSVALK QTQACGLKTP

TLEQYIYLYN CLNSALRNRL PRARK

Mature human osteocalcin amino acid sequence

SEQUENCE ID NO: 12

YLYQWLGAPV PYPDPLEPRR EVCELNPDCD ELADHIGFQE AYRRFYGPV human osteocalcin variant amino acid sequence

SEQUENCE ID NO: 13

YLYQWLGAPV PYPDPLX$_1$PRR X$_2$VCX$_3$LNPDCD ELADHIGFQE AYRRFYGPV

Rat Esp (OST-PTP, Ptprv) cDNA

SEQUENCE ID NO: 14

```
  1 agaacagcct acaacagctg ccttccggga gggaccaggc tagttcacac ttggaagttg
 61 ggatgccagg agcagccttc tgtcttccga ggccttcctg ggtctcctgg tcagctcatt
121 ccacactgag atgattctaa agaaagatcc tcacacagac tctgctggaa gaaacaaagt
181 gaagtgtccc cagactttat caggatgagg cccctgattc tgttagctgc cctcctctgg
241 ctccagggct ttttggccga ggacgacgca tgctcatcct tggaagggag cccagacagg
301 cagggtggag gtccacttct gagtgtgaac gtcagtagcc atggaaagtc taccagcctg
361 tttctgagct gggtagctgc agagctgggc ggatttgact atgccctcag cctcaggagt
421 gtgaactcct caggttctcc agaagggcaa cagctccagg ctcacacaaa tgagtccggc
481 tttgagttcc atggcctggt gccagggagt cgctaccagc taaaactgac tgtcctaaga
541 ccctgttggc agaatgtcac aattaccctc actgcccgaa ctgccccgac agtggtccgt
601 ggactgcagc tgcatagcgc tgggagccca gccaggctgg aagcctcgtg gagtgatgcc
661 cctggagatc aagacagcta ccaacttctc ctctaccacc tggaatccca aactctggca
721 tgcaatgtct ctgtgtcccc tgacaccctg tcttacagtt ttggcgacct tttgccaggt
781 actcagtatg tcttggaggt tatcacctgg gctggcagtc tccatgcgaa gactagtatc
841 ctccagtgga cagagcctgt ccctcctgat cacctagcac tacgtgcctt gggtaccagt
901 agcctgcaag ccttctggaa cagctctgaa ggggccacct cgtttcacct gatgctcaca
```

-continued

```
 961 gacctcctcg gggcaccaa cacgactgcg gtgatcagac aaggggtctc gacccacacc
1021 tttcttcacc tatctccggg tacacctcat gagctgaaga tttgtgcttc tgctgggccc
1081 caccagatct ggggacccag tgccaccgag tggacctatc cctcttaccc atctgacctg
1141 gtgctgactc ccttacggaa tgagctctgg gccagctgga aggcagggct gggagcccgg
1201 gacggctatg tactgaagtt aagtgggcca atggagagta cgtctaccct gggcccggaa
1261 gagtgcaatg cagtcttccc agggcccctg cctccgggac actacacttt gcagctgaag
1321 gttctagctg gaccttatga tgcctgggtg gagggcagta cctggctggc tgaatctgct
1381 gcccttccca gggaggtccc tggtgccaga ctgtggctag atggactgga agcttccaag
1441 cagcctggga gacgggcgct actctattct gacgatgccc caggctccct agggaacatc
1501 tctgtgccct ctggtgccac tcacgtcatt ttctgtggcc tggtacctgg agcccactat
1561 agggtggaca ttgcctcatc cacgggggac atctctcaga gcatctcagg ctatacaagt
1621 cccctgccac cgcagtcact ggaggtcatc agcaggagca gcccatctga cctgactatt
1681 gcttggggtc cagcaccagg gcagctggaa ggttataagg ttacctggca tcaggatggc
1741 agccagaggt ctcctggcga ccttgttgac ttgggccctg acactttgag cctgactctg
1801 aaatctctgg tacccggctc ctgctacacc gtgtcagcat gggcctgggc cgggaacctc
1861 gactctgact ctcagaagat tcacagctgc acccgccccg ctcctcccac caacctgagt
1921 ctgggctttg cccaccagcc tgcggcactg aaggcttcct ggtatcaccc accgggtggc
1981 agggatgcct ttcacttacg gctttacagg ctgaggcctc tgacactgga aagtgagaag
2041 gtcctacctc gggaggccca gaacttctcc tgggcccagc tgactgcagg ctgtgagttc
2101 caggtacagc tgtctacctt gtgggggtct gagagaagca gcagtgccaa cgccacaggc
2161 tggacacccc cttcagctcc tacactggta aacgtgacca gcgatgctcc tacccagctc
2221 caagtatcct gggcccacgt tcctgggggc cggagccgct accaagtgac cctataccag
2281 gagagtaccc ggacagccac cagcatcatg gggcccaagg aagatggcac gagcttttg
2341 ggtttgactc ctggcactaa gtacaaggtg gaagtcatct cctgggctgg gcccctctac
2401 actgcagcag ccaacgtttc tgcctggacc tacccactca tacccaatga gctgctcgtg
2461 tcaatgcagg caggcagtgc tgtggttaac ctggcctggc ccagtggtcc cctggggcaa
2521 ggggcatgcc acgcccaact ctcagatgct ggacacctct catgggagca accccctgaaa
2581 ctaggccaag agctcttcat gctaagggat ctcacaccag gacataccat ctcgatgtca
2641 gtgaggtgtc gggcagggcc gctccaggcc tctacgcacc ttgtggtgct gtctgtggag
2701 cctggccctg tggaagatgt gctctgtcat ccagaggcca cctacctggc cctgaactgg
2761 acgatgcctg ctggagacgt ggatgtctgt ctggtggtgg tagagcggct ggtgccggga
2821 gggggcactc attttgtctt ccaggtcaac acctcagggg atgctcttct gttgcccaac
2881 ttgatgccca ccacttctta ccgccttagc ctcaccgttc tgggcaggaa tagtcggtgg
2941 agccgggcgg tttccctggt gtgcagtact tctgctgagg cttggcaccc cccagagcta
3001 gctgagcccc cccaggtgga gctggggaca gggatgggtg tgacagtcat gcgtggcatg
3061 tttggtaaag atgacgggca gatccagtgg tatggcataa ttgccaccat caacatgacg
3121 ctggcccagc cttcccggga agccatcaat tacacatggt atgaccacta ctatagagga
3181 tgtgagtcct tcctggctct cctgttccca aacccccttct acccagagcc ttgggctggg
3241 ccaagatcct ggacagtacc tgtgggtact gaggactgtg acaacaccca agagatatgc
3301 aatgggcgtc tcaagtcagg cttccagtat aggttcagcg ttgtggcctt tagtaggctc
3361 aacactccag agaccatcct cgccttctcg gccttctcag agccccgggc cagcatctct
3421 ctggcgatca ttcccctgac agttatgctg gggctgtgg tgggcagcat tgtcattgtg
3481 tgtgcagtgc tatgcttgct ccgctggcgg tgcctgaagg gaccaagatc agagaaggat
3541 ggcttttcca aggagctgat gccttacaac ctgtggcgga cccatcggcc tatccccatc
3601 catagcttcc ggcagagcta tgaggccaag agcgcacatg cacaccagac cttcttccag
3661 gaatttgagg agttgaagga ggtaggcaag gaccagcccc gactagaggc tgagcatccg
3721 gacaacatca tcaagaaccg gtacccacac gtgctgccct atgaccactc cagggtcagg
3781 ctgacccagc taccaggaga gcctcattct gactacatca atgccaactt catcccaggc
3841 tatagccaca cacaggagat cattgccacc caggggcctc tcaaaaagac gctagaggac
3901 ttctggcggt tggtatggga gcagcaagtc cacgtgatca tcatgctgac tgtgggcatg
3961 gagaacgggc gggtactgtg tgagcactac tggccagcca actccacgcc tgttactcac
4021 ggtcacatca ccatccacct cctggcagag gagcctgagg atgagtggac caggagggaa
4081 ttccagctgc agcacggtac cgagcaaaaa cagaggcgag tgaagcagct gcagttcact
4141 acctggccag accacagtgt cccggaggct cccagctctc tgctcgcttt tgtagaactg
4201 gtacaggagc aggtgcaggc cactcagggc aagggaccca tcctggtgca ttgcagtgct
4261 ggcgtgggga ggacaggcac ctttgtggct ctcttgcggc tactgcgaca actagaggaa
4321 gagaaggtgg ccgatgtgtt caacactgtg tacatactcc ggttgcaccg gcccctcatg
4381 atccagaccc tgagtcaata catcttcctg cacagttgcc tgctgaacaa gattctggaa
4441 gggcccctg acagctccga ctccggcccc atctctgtga tggattttgc acaggcttgt
4501 gccaagaggg cagccaacgc caatgctggt ttcttgaagg agtacaagct cctgaagcag
4561 gccatcaagg atgggactgg ctctctgctg ccccctcctg actacaatca gaacagcatt
4621 gtctcccgtc gtcattctca ggagcagttc gccctggtgg aggagtgccc tgaggatagc
4681 atgctggaag cctcactctt ccctggtggt ccgtctggtt gtgatcatgt ggtgctgact
4741 ggctcagccg gaccaaagga actctgggaa atggtgtggg agcatgatgc ccatgtgctc
4801 gtctccctgg gcctgcctga taccaaggag aagccaccag acatctggcc agtggagatg
4861 cagcctattg tcacagacat ggtgacagtg cacagagtgt ctgagagcaa cacaacaact
4921 ggctggccca gcaccctctt cagagtcata cacggggaga gtggaaagga aaggcaggtt
4981 caatgcctgc aatttccatg ctctgagtct gggtgtgagc tcccagctaa caccctactg
5041 accttccttg atgctgtggg ccagtgctgc ttccggggca agagcaagaa gccagggacc
5101 ctgctcagcc actccagcaa aaacacaaac cagctgggca ccttcttggc tatggaacag
5161 ctgttacagc aagcagggac agagcgcaca gtggacgtct tcaatgtggc cctgaagcag
5221 tcacaggcct gcggccttat gaccccaaca ctggagcagt atatctacct ctacaactgt
5281 ctgaacagcg cactgctgaa cgggctgccc agagctggga agtggcctgc gccctgctag
5341 gcgtcatgtt ccagcaaatc cacccaggcc tgacttccct aggagagtgg atccaccggg
5401 cctcacactg tccaagggca gagtccagga ataaagagac atggtc
```

Rat Esp (OST-PTP, Ptprv) amino acid sequence

SEQUENCE ID NO: 15

MRPLILLAALLWLQGFLAEDDACSSLEGSPDRQGGGPLLSVNVSSHGKSTSLFLSWVAAELGGFDYALSLRSVNSSGSPEGQQLQAH

TNESGFEFHGLVPGSRYQLKLTVLRPCWQNVTITLTARTAPTVVRGLQLHSAGSPARLEASWSDAPGDQDSYQLLLYHLESQTLACN

-continued

VSVSPDTLSYSFGDLLPGTQYVLEVITWAGSLHAKTSILQWTEPVPPDHLALRALGTSSLQAFWNSSEGATSFHLMLTDLLGGTNTT
AVIRQGVSTHTFLHLSPGTPHELKICASAGPHQIWGPSATEWTYPSYPSDLVLTPLRNELWASWKAGLGARDGYVLKLSGPMESTST
LGPEECNAVFPGPLPPGHYTLQLKVLAGPYDAWVEGSTWLAESAALPREVPGARLWLDGLEASKQPGRRALLYSDDAPGSLGNISVP
SGATHVIFCGLVPGAHYRVDIASSTGDISQSISGYTSPLPPQSLEVISRSSPSDLTIAWGPAPGQLEGYKVTWHQDGSQRSPGDLVD
LGPDTLSLTLKSLVPGSCYTVSAWAWAGNLDSDSQKIHSCTRPAPPTNLSLGFAHQPAALKASWYHPPGGRDAFHLRLYRLRPLTLE
SEKVLPREAQNFSWAQLTAGCEFQVQLSTLWGSERSSSANATGWTPPSAPTLVNVTSDAPTQLQVSWAHVPGGRSRYQVTLYQESTR
TATSIMGPKEDGTSFLGLTPGTKYKVEVISWAGPLYTAAANVSAWTYPLIPNELLVSMQAGSAVVNLAWPSGPLGQGACHAQLSDAG
HLSWEQPLKLGQELFMLRDLTPGHTISMSVRCRAGPLQASTHLVVLSVEPGPVEDVLCHPEATYLALNWTMPAGDVDVCLVVVERLV
PGGGTHFVFQVNTSGDALLLPNLMPTTSYRLSLTVLGRNSRWSRAVSLVCSTSAEAWHPPELAEPPQVELGTGMGVTVMRGMFGKDD
GQIQWYGIIATINMTLAQPSREAINYTWYDHYYRGCESFLALLFPNPFYPEPWAGPRSWTVPVGTEDCDNTQEICNGRLKSGFQYRF
SVVAFSRLNTPETILAFSAFSEPRASISLAIIPLTVMLGAVVGSIVIVCAVLCLLRWRCLKGPRSEKDGFSKELMPYNLWRTHRPIP
IHSFRQSYEAKSAHAHQTFFQEFEELKEVGKDQPRLEAEHPDNIIKNRYPHVLPYDHSRVRLTQLPGEPHSDYINANFIPGYSHTQE
IIATQGPLKKTLEDFWRLVWEQQVHVIIMLTVGMENGRVLCEHYWPANSTPVTHGHITIHLLAEEPEDEWTRREFQLQHGTEQKQRR
VKQLQFTTWPDHSVPEAPSSLLAFVELVQEQVQATQGKGPILVHCSAGVGRTGTFVALLRLLRQLEEEKVADVFNTVYILRLHRPLM
IQTLSQYIFLHSCLLNKILEGPPDSSDSGPISVMDFAQACAKRAANANAGFLKEYKLLKQAIKDGTGSLLPPPDYNQNSIVSRRHSQ
EQFALVEECPEDSMLEASLFPGGPSGCDHVVLTGSAGPKELWEMVWEHDAHVLVSLGLPDTKEKPPDIWPVEMQPIVTDMVTVHRVS
ESNTTTGWPSTLFRVIHGESGKERQVQCLQFPCSESGCELPANTLLTFLDAVGQCCFRGKSKKPGTLLSHSSKNTNQLGTFLAMEQL
LQQAGTERTVDVFNVALKQSQACGLMTPTLEQYIYLYNCLNSALLNGLPRAGKWPAPC

Human PTP-1B cDNA
GenBank HUMPTPBX Accession no. M31724

SEQUENCE ID NO: 16

```
   1 gggcgggcct cggggctaag agcgcgacgc ctagagcggc agacggcgca gtgggccgag
  61 aaggaggcgc agcagccgcc ctggcccgtc atggagatgg aaaaggagtt cgagcagatc
 121 gacaagtccg ggagctgggc ggccatttac caggatatcc gacatgaagc cagtgacttc
 181 ccatgtagag tggccaagct tcctaagaac aaaaaccgaa ataggtacag agacgtcagt
 241 ccctttgacc atagtcggat taaactacat caagaagata atgactatat caacgctagt
 301 ttgataaaaa tggaagaagc ccaaaggagt tacattctta cccagggccc tttgcctaac
 361 acatgcggtc actttttggga gatggtgtgg gagcagaaaa gcaggggtgt cgtcatgctc
 421 aacagagtga tggagaaagg ttcgttaaaa tgcgcacaat actggccaca aaaagaagaa
 481 aaagagatga tctttgaaga cacaaatttg aaattaacat tgatctctga agatatcaag
 541 tcatattata cagtgcgaca gctagaattg gaaaacctta caacccaaga aactcgagag
 601 atcttacatt tccactatac cacatggcct gactttggag tccctgaatc accagcctca
 661 ttcttgaact ttcttttcaa agtccgagag tcagggtcac tcagcccgga gcacgggccc
 721 gttgtggtgc actgcagtgc aggcatcggc aggtctggaa ccttctgtct ggctgatacc
 781 tgcctcctgc tgatggacaa gaggaaagac ccttcttccg ttgatatcaa gaaagtgctg
 841 ttagaaatga ggaagtttcg gatggggttg atccagacag ccgaccagct gcgcttctcc
 901 tacctggctg tgatcgaagg tgccaaattc atcatggggg actcttccgt gcaggatcag
 961 tggaaggagc tttcccacga ggacctggag cccccacccg agcatatccc cccacctccc
1021 cggccaccca aacgaatcct ggagccacac aatgggaaat gcagggagtt cttcccaaat
1081 caccagtggg tgaaggaaga gacccaggag gataaagact gccccatcaa ggaagaaaaa
1141 ggaagcccct taaatgccgc accctacggc atcgaaagca tgagtcaaga cactgaagtt
1201 agaagtcggg tcgtgggggg aagtcttcga ggtgcccagg ctgcctcccc agccaaaggg
```

-continued

```
1261 gagccgtcac tgcccgagaa ggacgaggac catgcactga gttactggaa gcccttcctg

1321 gtcaacatgt gcgtggctac ggtcctcacg gccggcgctt acctctgcta caggttcctg

1381 ttcaacagca acacatagcc tgaccctcct ccactccacc tccacccact gtccgcctct

1441 gcccgcagag cccacgcccg actagcaggc atgccgcggt aggtaagggc cgccggaccg

1501 cgtagagagc cgggccccgg acggacgttg gttctgcact aaaacccatc ttccccggat

1561 gtgtgtctca cccctcatcc ttttactttt tgccccttcc actttgagta ccaaatccac

1621 aagccatttt ttgaggagag tgaaagagag taccatgctg gcggcgcaga gggaaggggc

1681 ctacacccgt cttggggctc gccccaccca gggctccctc ctggagcatc ccaggcggcg

1741 cacgccaaca gcccccccct tgaatctgca gggagcaact ctccactcca tatttattta

1801 aacaattttt tccccaaagg catccatagt gcactagcat ttcttgaac caataatgta

1861 ttaaaatttt ttgatgtcag ccttgcatca agggctttat caaaaagtac aataataaat

1921 cctcaggtag tactgggaat ggaaggcttt gccatgggcc tgctgcgtca gaccagtact

1981 gggaaggagg acggttgtaa gcagttgtta tttagtgata ttgtgggtaa cgtgagaaga

2041 tagaacaatg ctataatata taatgaacac gtgggtattt aataagaaac atgatgtgag

2101 attactttgt cccgcttatt ctcctccctg ttatctgcta gatctagttc tcaatcactg

2161 ctcccccgtg tgtattagaa tgcatgtaag gtcttcttgt gtcctgatga aaaatatgtg

2221 cttgaaatga gaaactttga tctctgctta ctaatgtgcc ccatgtccaa gtccaacctg

2281 cctgtgcatg acctgatcat tacatggctg tggttcctaa gcctgttgct gaagtcattg

2341 tcgctcagca atagggtgca gttttccagg aataggcatt tgctaattcc tggcatgaca

2401 ctctagtgac ttcctggtga ggcccagcct gtcctggtac agcagggtct tgctgtaact

2461 cagacattcc aagggtatgg gaagccatat tcacacctca cgctctggac atgatttagg

2521 gaagcaggga cacccccgc cccccacctt tgggatcagc ctccgccatt ccaagtcaac

2581 actcttcttg agcagaccgt gatttggaag agaggcacct gctggaaacc acacttcttg

2641 aaacagcctg ggtgacggtc ctttaggcag cctgccgccg tctctgtccc ggttcacctt

2701 gccgagagag gcgcgtctgc ccccaccctca aaccctgtgg ggcctgatgg tgctcacgac

2761 tcttcctgca aagggaactg aagacctcca cattaagtgg ctttttaaca tgaaaaacac

2821 ggcagctgta gctcccgagc tactctcttg ccagcatttt cacattttgc ctttctcgtg

2881 gtagaagcca gtacagagaa attctgtggt gggaacattc gaggtgtcac cctgcagagc

2941 tatggtgagg tgtggataag gcttaggtgc caggctgtaa gcattctgag ctggcttgtt

3001 gtttttaagt cctgtatatg tatgtagtag tttgggtgtg tatatatagt agcatttcaa

3061 aatggacgta ctggtttaac ctcctatcct tggagagcag ctggctctcc accttgttac

3121 acattatgtt agagaggtag cgagctgctc tgctatatgc cttaagccaa tatttactca

3181 tcaggtcatt attttttaca atggccatgg aataaaccat ttttacaaaa ataaaaacaa

3241 aaaaagc
```

Human PTP-1B amino acid sequence
GenBank HUMPTPBX Accession no. M31724

SEQUENCE ID NO: 17

```
MEMEKEFEQIDKSGSWAAIYQDIRHEASDFPCRVAKLPKNKNRNRYRDVSPFDHSRIKLHQEDNDYINASLIKMEEAQRSYILTQGP

LPNTCGHFWEMVWEQKSRGVVMLNRVMEKGSLKCAQYWPQKEEKEMIFEDTNLKLTLISEDIKSYYTVRQLELENLTTQETREILHF

HYTTWPDFGVPESPASFLNFLFKVRESGSLSPEHGPVVVHCSAGIGRSGTFCLADTCLLLMDKRKDPSSVDIKKVLLEMRKFRMGLI

QTADQLRFSYLAVIEGAKFIMGDSSVQDQWKELSHEDLEPPPEHIPPPPRPPKRILEPHNGKCREFFPNHQWVKEETQEDKDCPIKE

EKGSPLNAAPYGIESMSQDTEVRSRVVGGSLRGAQAASPAKGEPSLPEKDEDHALSYWKPFLVNMCVATVLTAGAYLCYRFLFNSNT
```

TABLE 2

| | SEQ ID NO: | | |
|---|---|---|---|
| | cDNA | Amino Acid | GenBank Accession No: |
| Human Osteocalcin cDNA | 1 | 2 | NM_199173 |
| Mouse osteocalcin gene 1 | 3 | 5 | NM_007541 |
| Mouse osteocalcin gene 2 | 4 | 5 | NM_001032298 |
| Human Gamma-glutamyl carboxylase | 6 | 7 | NM_000821 |
| Mouse Gamma-glutamyl carboxylase | 8 | 9 | NM_019802 |
| Mouse Esp (OST-PTP, Ptprv) | 10 | 11 | NM_007955 |
| Rat (OST-PTP, Ptprv) | 14 | 15 | L36884 |
| Human PTP-1B | 16 | 17 | M31724 |

What is claimed is:

1. A method of treating or preventing anxiety, depression, or memory loss in a mammal comprising administering to a mammal in need thereof a pharmaceutical composition comprising a therapeutically effective amount of undercarboxylated/uncarboxylated osteocalcin and a pharmaceutically acceptable carrier or excipient, thereby treating or preventing the anxiety, depression, or memory loss.

2. The method of claim 1 wherein the mammal is a human and the osteocalcin is human osteocalcin.

3. The method of claim 2 wherein the cognitive disorder is anxiety due to aging, depression due to aging, or memory loss due to aging.

4. The method of claim 2 wherein the undercarboxylated/uncarboxylated osteocalcin is a preparation of undercarboxylated/uncarboxylated osteocalcin in which more than about 20% of the total Glu residues at the positions corresponding to positions 17, 21 and 24 of mature human osteocalcin in the preparation are not carboxylated.

5. The method of claim 4 wherein all three of the glutamic acids in the undercarboxylated/uncarboxylated osteocalcin at the positions corresponding to positions 17, 21 and 24 of mature human osteocalcin are not carboxylated.

6. The method of claim 2 wherein the undercarboxylated/uncarboxylated osteocalcin shares at least 80% amino acid sequence identity with mature human osteocalcin when the undercarboxylated/uncarboxylated osteocalcin and mature human osteocalcin are aligned for maximum sequence homology.

7. The method of claim 6 wherein the undercarboxylated/uncarboxylated osteocalcin shares about 98% amino acid sequence identity with mature human osteocalcin when the undercarboxylated/uncarboxylated osteocalcin and mature human osteocalcin are aligned for maximum sequence homology.

8. The method of claim 2 wherein the undercarboxylated/uncarboxylated osteocalcin is a polypeptide selected from the group consisting of:

(a) a fragment comprising mature human osteocalcin missing the last 10 amino acids from the C-terminal end;

(b) a fragment comprising mature human osteocalcin missing the first 10 amino acids from the N-terminal end;

(c) a fragment comprising amino acids 62-90 of SEQ ID NO:2;

(d) a fragment comprising amino acids 1-36 of mature human osteocalcin;

(e) a fragment comprising amino acids 13-26 of mature human osteocalcin; and (f) a fragment comprising amino acids 13-46 of mature human osteocalcin.

9. The method of claim 2 which is a method of treating or preventing anxiety.

10. The method of claim 2 which is a method of treating or preventing depression.

11. The method of claim 2 which is a method of treating or preventing memory loss.

* * * * *